US008518945B2

(12) United States Patent
Hendricks et al.

(10) Patent No.: US 8,518,945 B2
(45) Date of Patent: Aug. 27, 2013

(54) PYRROLOPYRAZINE KINASE INHIBITORS

(75) Inventors: Robert Than Hendricks, San Carlos, CA (US); Johannes Hermann, Jersey City, NJ (US); Rama Kondru, Morris Plains, NJ (US); Yan Lou, Glen Ridge, NJ (US); Stephen M. Lynch, Westfield, NJ (US); Timothy D. Owens, Jersey City, NJ (US); Michael Soth, Glen Rock, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 143 days.

(21) Appl. No.: 13/040,310

(22) Filed: Mar. 4, 2011

(65) Prior Publication Data
US 2011/0230462 A1 Sep. 22, 2011

Related U.S. Application Data

(60) Provisional application No. 61/315,998, filed on Mar. 22, 2010, provisional application No. 61/440,890, filed on Feb. 9, 2011.

(51) Int. Cl.
*A61K 31/495* (2006.01)

(52) U.S. Cl.
USPC ............. 514/249; 544/61; 544/117; 544/350; 544/373; 546/112; 546/114; 546/148; 546/199; 546/268.1; 548/202; 548/255; 548/335.1; 548/364.7; 548/469; 548/560; 548/579; 548/950; 549/59; 549/356

(58) Field of Classification Search
USPC ................... 514/249; 544/61, 117, 350, 373; 546/112, 114, 148, 199, 268.1; 548/202, 548/255, 335.1, 364.7, 469, 560, 579, 950; 549/59, 356
See application file for complete search history.

(56) References Cited

U.S. PATENT DOCUMENTS

| 7,902,197 | B2 | 3/2011 | Elworthy et al. |
| 7,932,254 | B2 | 4/2011 | DuBois et al. |
| 7,939,531 | B2 | 5/2011 | Bamberg et al. |
| 2006/0148801 | A1 | 7/2006 | Hsieh et al. |
| 2007/0049615 | A1 | 3/2007 | Ibrahim et al. |
| 2009/0215785 | A1 | 8/2009 | DuBois et al. |
| 2010/0267666 | A1 | 10/2010 | Bamberg et al. |

FOREIGN PATENT DOCUMENTS

| WO | 01/47922 | 7/2001 |
| WO | 03/000688 | 1/2003 |
| WO | 03/082868 | 10/2003 |
| WO | 2007/004557 | 7/2007 |
| WO | 2007/077949 | 7/2007 |
| WO | 2008/033798 | 3/2008 |
| WO | 2008/063888 | 5/2008 |
| WO | 2008/079903 | 7/2008 |
| WO | 2008/084861 | 7/2008 |
| WO | 2008/147800 | 12/2008 |
| WO | 2009/106441 | 9/2009 |
| WO | 2009/106442 | 9/2009 |
| WO | 2009/106443 | 9/2009 |
| WO | 2009/106444 | 9/2009 |
| WO | 2009/106445 | 9/2009 |

OTHER PUBLICATIONS

International Search Report for Corres. PCT/EP2011/054091 dated Jun. 9, 2011.
Catlett-Falcone, R. et al., Constitutive Activation of Stat3 Signaling Confers Resistance to Apoptosis in Human U266 Myeloma Cells, Immunity (1999) 10:105-115.
Changelian, P.S. et al., Prevention of Organ Allograft Rejection by a Specific Janus Kinase 3 Inhibitor, Science (2003) 302:875.
Cheng, A.M. et al., Syk tyrosine kinase required for mouse viability and B-cell development, Nature (1995) 378:303-306.
Costello, P.S. et al., Critical role for the tyrosine kinase Syk in signalling through the high affinity IgE receptor of mast cells, Oncogene (1996) 13:2595-2605.
Demoulin, J. et al., A Single Tyrosine of the Interleukin-9 (IL-9) Receptor is Required for STAT Activation, Antiapoptotic Activity, and Growth Regulation by IL-9, Molecular and Cellular Biology (1996) 16(9):4710-4716.
Horvath, C.M. et al., The state of the STATs: recent developments in the study of signal transduction to the nucleus, Current Opinion in Cell Biology (1997) 9:233-239.
Jurlander, J. et al., Characterization of Interleukin-10 Receptor Expression on B-Cell Chronic Lymphocytic Leukemia Cells, Blood (1997) 89(11):4146-4152.
Kaneko, S et al., Rescue by cytokines of apoptotic cell death induced by IL-2 deprivation of human antigen-specific T cell clones, Clin. Exp. Immunol. (1997) 109:185-193.
Kirken, R.A., Targeting JAK3 for Immune Suppress on and Allograft Acceptance, Transplantation Proceedings, (2001) 33:3208-3270.
Kudlacz, E. et al., The Novel JAK-3 Inhibitor CP-690550 Is a Potent Immunosuppressive Agent in Various Murine Models, American Journal of Transplantation (2004) 4:51-57.

(Continued)

*Primary Examiner* — Douglas M Willis

(57) ABSTRACT

The present invention relates to the use of novel pyrrolopyrazine derivatives of Formula I,

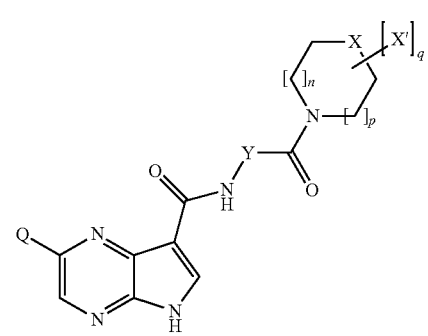

wherein the variables n, p, q, Q, X, X' and Y are defined as described herein, which inhibit JAK and SYK and are useful for the treatment of auto-immune and inflammatory diseases.

16 Claims, No Drawings

(56) References Cited

OTHER PUBLICATIONS

Lach-Trifilieff, et al., Syk-deficient eosinophils show normal interleukin-5-mediated differentiation, maturation, and survival but no longer respond to Fc γR activation; Blood (2000) 96(7):2506-2510.

Leonard, W.J. et al., JAKS and STATS: Biological Implications, Annu. Rev. Immunol. (1998) 16:293-322.

Leonard, W.J., et al., Cytokine receptor signaling pathways, J. Allergy Clin. Immunol (2000) 105:877-888.

Leonard, W.J., Dysfunctional Cytokine Receptor Signaling in Severe Combined Immunodeficiency, Journal of Investigative Medicine (1996) 44(5) 304-311.

Malaviya, R , et al., Genetic and Biochemical Evidence for a Critical Role of Janus Kinase (JAK)-3 in Mast Cell-Mediated Type I Hypersensitivity Reactions, Biochemical and Biophysical Research Communications (1999) 257:807-813.

Malavia, R., et al., Targeting Janus Kinase 3 in Mast Cells Prevents Immediate Hypersensitivity Reactions and Anaphylaxis, The Journal of Biological Chemistry (1999) 274(38):27028-27038.

Muller-Ladner, U. et al., Activation of the IL-4 STAT Pathway in Rheumatoid Synovium, Journal of Immunology (2000) 164:3894-3901.

Nakamura, N. et al., An Epidermal Growth Factor Receptor/Jak2 Tyrosine Kinase Domain Chimera Induces Tyrosine Phosphorylation of Stat5 and Transduces a Growth Signal in Hematopoietic Cells, Journal of Biological Chemistry (1996) 271(32):19483-19488.

Nielsen, M. et al., Constitutive Activation of a Slowly Migrating Isoform of Stat3 in Mycosis Fungoides: Tyrphostin AG490 Inhibits Stat3 Activation and Growth of Mycosis Fungoides Tumor Cell Lines, Proc. Natl. Acad. Sci. USA (1997) 94:6764-6769.

Rane, S.G. at al., Janus kinases: components of multiple signaling pathways, Oncogene (2000) 19:5662-5679.

Roberts, J.L. et al., Janus kinase 3 (JAK3) deficiency: clinical, immunologic, and molecular analyses of 10 patients and outcomes of stem cell transplantation, Blood (2004) 103(6)2009-2018.

Sablayrolles, et al., Methyl-6 5H-pyrrolo[2,3-b]pyrazinecarboxylate-7 d'ethyle: structure et mecanisme d'obtention a partir de l'amino-2 pyrazine, Bulletin de la Societe Chimique de France, Jul.-Aug. 1989, 467-471.

Stenton, G.R. et al., Inhibition of Allergic Inflammation in the Airways Using Aerosolized Antisense to Syk Kinase, J. Immunol (2002) 169:1028-1036.

Sudbeck, E.A. et al., Structure-based Design of Specific Inhibitors of Janus Kinase 3 as Apoptosis-inducing Antileukemic Agents, Clinical Cancer Research (1999) 5:1569-1582.

Suzuki, K. et al., Role of common cytokine receptor γ chain (γc)- and Jak3-dependent signaling in the proliferation and survival of murine mast cells, Blood (2000) 96(6):2172-2180.

Taylor, J.A., et al., Activation of the High-Affinity Immunoglobulin E Receptor FcεRl in RBL-2H3 Cells Is Inhibited by Syk SH2 Domains, Molecular and Cellular Biology (1995) 15(8):4149-4157.

Trieu, V.N., et al., A Specific Inhibitor of Janus Kinase-3 Increases Survival in a Transgenic Mouse Model of Amyotrophic Lateral Sclerosis, Biochemical and Biophysical Research Communications (2000) 267:22-25.

Turner, M. et al , Perinatal lethality and blocked B-cell development in mice lacking the tyrosine kinase Syk, Nature (1995) 378(16):298-302.

Verbsky, J.W. et al., Nonhematopoietic Expression of Janus Kinase 3 is Required for Efficient Recruitment of Th2 Lymphocytes and Eosinophils in OVA-Induced Airway Inflammation, Journal of Immunology (2002) 168:2475-2482.

Wong, B.R. et al., Targeting Syk as a treatment for allergic and autoimmune disorders, Expert Opin. Investig. Drugs (2004) 13(7):743-762.

Yamamoto, N. et al., The Orally Available Spleen Tyrosine Kinase Inhibitor 2-[7-(3,4-Dimethoxyphenyl)-imidazo[1,2-c]pyrimidin-5-ylamino]-nicotinamide Dihydrochloride (BAY 61-3606) Blocks Antigen-Induced Airway Inflammation in Rodents, Journal of Pharmacology and Experimental Therapeutics (2003) 306(3):1174-1181.

Yu, C. et al., Constitutive Activation of the Janus Kinase-STAT Pathway in T Lymphoma Overexpressing the Lck Protein Tyrosine Kinase, Journal of Immunology (1997) 159:5206-5210.

Rice, L.M. et al., Spiranes III.1a,b Azaspiranes and Intermediates; J. Med. Chem. (1963) 6:388-402.

International Search Report, PCT/EP2009/051761, May 8, 2009.

(International Search Report for PCT/EP2011/057911 Jul. 5, 2011).

(International Search Report for PCT/EP2011/057910 Jul. 4, 2011).

(International Search Report for PCT/EP2011/054171 Jun. 17, 2011).

(International Search Report PCT/EP2009/051761 May 8, 2009).

PYRROLOPYRAZINE KINASE INHIBITORS

CROSS-REFERENCE TO RELATED APPLICATIONS

This application is entitled to the benefit of U.S. provisional patent application Ser. No. 61/315,998 filed on Mar. 22, 2010 and U.S. provisional patent application Ser. No. 61/440,890, filed on Feb. 9, 2011, the disclosures of which are incorporated herein by reference.

This application is related to U.S. application Ser. No. 12/378,837, filed on Feb. 20, 2009, Ser. No. 12/378,869, filed on Feb. 20, 2009, Ser. No. 12/378,971, filed on Feb. 20, 2009, Ser. No. 12/378,977, filed on Feb. 20, 2009, and Ser. No. 12/378,978, filed on Feb. 20, 2009, the disclosures of which are incorporated herein by reference.

FIELD OF THE INVENTION

The present invention relates to the use of novel pyrrolopyrazine derivatives which are JAK and SYK inhibitors and selectively inhibit JAK3 and are useful for the treatment of auto-immune and inflammatory diseases.

Protein kinases constitute one of the largest families of human enzymes and regulate many different signaling processes by adding phosphate groups to proteins; particularly tyrosine kinases phosphorylate proteins on the alcohol moiety of tyrosine residues. The tyrosine kinase family includes members that control cell growth, migration, and differentiation. Abnormal kinase activity has been implicated in a variety of human diseases including cancers, autoimmune and inflammatory diseases. Since protein kinases are among the key regulators of cell signaling they provide a means to modulate cellular function with small molecule inhibitors of kinase activity and thus make good drug design targets. In addition to treatment of kinase-mediated disease processes, selective and efficacious inhibitors of kinase activity are also useful for investigation of cell signaling processes and identification of other cellular targets of therapeutic interest.

The JAKs (JAnus Kinases) are a family of cytoplasmic protein tyrosine kinases including JAK1, JAK2, JAK3 and TYK2. Each of the JAKs is preferentially associated with the intracytoplasmic portion of discrete cytokine receptors (*Annu. Rev. Immunol.* 16 (1998), pp. 293-322). The JAKs are activated following ligand binding and initiate signaling by phosphorylating cytokine receptors that, per se, are devoid of intrinsic kinase activity. This phosphorylation creates docking sites on the receptors for other molecules known as STAT proteins (signal transducers and activators of transcription) and the phosphorylated JAKs bind various STAT proteins. STAT proteins, or STATs, are DNA binding proteins activated by phosphorylation of tyrosine residues, and function both as signaling molecules and transcription factors and ultimately bind to specific DNA sequences present in the promoters of cytokine-responsive genes (Leonard et al., (2000), J. Allergy Clin. Immunol. 105:877-888).

JAK/STAT signaling has been implicated in the mediation of many abnormal immune responses such as allergies, asthma, autoimmune diseases such as transplant (allograft) rejection, rheumatoid arthritis, amyotrophic lateral sclerosis and multiple sclerosis, as well as in solid and hematologic malignancies such as leukemia and lymphomas.

Thus, the JAKs and STATs are components of multiple potentially intertwined signal-transduction pathways (*Oncogene* 19 (2000), pp. 5662-5679), which indicates the difficulty of specifically targeting one element of the JAK-STAT pathway without interfering with other signal transduction pathways.

The JAK kinases, including JAK3, are abundantly expressed in primary leukemic cells from children with acute lymphoblastic leukemia, the most common form of childhood cancer, and studies have correlated STAT activation in certain cells with signals regulating apoptosis (Demoulin et al., (1996), Mol. Cell. Biol. 16:4710-6; Jurlander et al., (1997), Blood. 89:4146-52; Kaneko et al., (1997), Clin. Exp. Immun. 109:185-193; and Nakamura et al., (1996), J. Biol. Chem. 271: 19483-8). They are also known to be important to lymphocyte differentiation, function and survival. JAK3 in particular plays an essential role in the function of lymphocytes, macrophages, and mast cells. Given the importance of this JAK kinase, compounds which modulate the JAK pathway, including those selective for JAK3, can be useful for treating diseases or conditions where the function of lymphocytes, macrophages, or mast cells is involved (Kudlacz et al., (2004) Am. J. Transplant 4:51-57; Changelian (2003) Science 302:875-878). Conditions in which targeting of the JAK pathway or modulation of the JAK kinases, particularly JAK3, are contemplated to be therapeutically useful include, leukemia, lymphoma, transplant rejection (e.g., pancreas islet transplant rejection, bone marrow transplant applications (e.g., graft-versus-host disease), autoimmune diseases (e.g., diabetes), and inflammation (e.g., asthma, allergic reactions). Conditions which can benefit for inhibition of JAK3 are discussed in greater detail below.

However, in contrast to the relatively ubiquitous expression of JAK1, JAK2 and Tyk2, JAK3 has a more restricted and regulated expression. Whereas some JAKs (JAK1, JAK2, Tyk2) are used by a variety of cytokine receptors, JAK3 is used only by cytokines that contain a γc in their receptor. JAK3, therefore, plays a role in cytokine signaling for cytokines which receptor was shown to date to use the common gamma chain; IL-2, IL-4, IL-7, IL-9, IL-15 and IL-21. JAK1 interacts with, among others, the receptors for cytokines IL-2, IL-4, IL-7, IL-9 and IL-21, while JAK2 interacts with, among others, the receptors for IL-9 and TNF-alpha. Upon the binding of certain cytokines to their receptors (e.g., IL-2, IL-4, IL-7, IL-9, IL-15 and IL-21), receptor oligomerization occurs, resulting in the cytoplasmic tails of associated JAK kinases being brought into proximity and facilitating the trans-phosphorylation of tyrosine residues on the JAK kinase. This trans-phosphorylation results in the activation of the JAK kinase.

Animal studies have suggested that JAK3 not only plays a critical role in B and T lymphocyte maturation, but that JAK3 is constitutively required to maintain T cell function. Modulation of immune activity through this novel mechanism can prove useful in the treatment of T cell proliferative disorders such as transplant rejection and autoimmune diseases.

In particular, JAK3 has been implicated in a variety of biological processes. For example, the proliferation and survival of murine mast cells induced by IL-4 and IL-9 have been shown to be dependent on JAK3- and gamma chain-signaling (Suzuki et al., (2000), Blood 96:2172-2180). JAK3 also plays a crucial role in IgE receptor-mediated mast cell degranulation responses (Malaviya et al., (1999), Biochem. Biophys. Res. Commun. 257:807-813), and inhibition of JAK3 kinase has been shown to prevent type I hypersensitivity reactions, including anaphylaxis (Malaviya et al., (1999), J. Biol. Chem. 274:27028-27038). JAK3 inhibition has also been shown to result in immune suppression for allograft rejection (Kirken, (2001), Transpl. Proc. 33:3268-3270). JAK3 kinases have also been implicated in the mechanism involved in early and late stages of rheumatoid arthritis (Muller-Ladner et al., (2000), J. Immunal. 164:3894-3901); familial amyotrophic lateral sclerosis (Trieu et al., (2000), Biochem Biophys. Res. Commun. 267:22-25); leukemia (Sudbeck et al., (1999), Clin. Cancer Res. 5:1569-1582); mycosis fungoides, a form of T-cell lymphoma (Nielsen et al., (1997), Prac. Natl. Acad. Sci. USA 94:6764-6769); and abnormal cell growth (Yu et al., (1997), J. Immunol. 159:5206-5210; Catlett-Falcone et al., (1999), Immunity 10:105-115).

JAK3 inhibitors are useful therapy as immunosuppressive agents for organ transplants, xeno transplantation, lupus, multiple sclerosis, rheumatoid arthritis, psoriasis, Type I diabetes and complications from diabetes, cancer, asthma, atopic dermatitis, autoimmune thyroid disorders, ulcerative colitis, Crohn's disease, Alzheimer's disease, Leukemia and other indications where immunosuppression would be desirable.

Non-hematopoietic expression of JAK3 has also been reported, although the functional significance of this has yet to be clarified (J. Immunol. 168 (2002), pp. 2475-2482). Because bone marrow transplants for SCID are curative (Blood 103 (2004), pp. 2009-2018), it seems unlikely that JAK3 has essential non-redundant functions in other tissues or organs. Hence, in contrast with other targets of immuno-suppressive drugs, the restricted distribution of JAK3 is appealing. Agents that act on molecular targets with expression limited to the immune system might lead to an optimal efficacy:toxicity ratio. Targeting JAK3 would, therefore, theoretically offer immune suppression where it is needed (i.e. on cells actively participating in immune responses) without resulting in any effects outside of these cell populations. Although defective immune responses have been described in various STAT$^{-/-}$ strains (J. Investig. Med. 44 (1996), pp. 304-311; Curr. Opin. Cell Biol. 9 (1997), pp. 233-239), the ubiquitous distribution of STATs and the fact that those molecules lack enzymatic activity that could be targeted with small-molecule inhibitors has contributed to their non-selection as key targets for immunosuppression.

SYK (Spleen Tyrosine Kinase) is a non-receptor tyrosine kinase that is essential for B-cell activation through BCR signaling. SYK become activated upon binding to phospho-ryated BCR and thus initiates the early signaling events following BCR activation. Mice deficient in SYK exhibit an early block in B-cell development (Cheng et al. Nature 378: 303, 1995; Turner et al. Nature 378:298, 1995). Therefore inhibition of SYK enzymatic activity in cells is proposed as a treatment for autoimmune disease through its effects on autoantibody production.

In addition to the role of SYK in BCR signaling and B-cell activation, it also plays a key role in FcεRI mediated mast cell degranulation and eosinophil activation. Thus, SYK is implicated in allergic disorders including asthma (reviewed in Wong et al. Expert Opin Investig Drugs 13:743, 2004). SYK binds to the phosphorylated gamma chain of FcδRI via its SH2 domains and is essential for downstream signaling (Taylor et al. Mol. Cell. Biol. 15:4149, 1995). SYK deficient mast cells demonstrate defective degranulation, arachidonic acid and cytokine secretion (Costello et al. Oncogene 13:2595, 1996). This also has been shown for pharmacologic agents that inhibit SYK activity in mast cells (Yamamoto et al. J Pharmacol Exp Ther 306:1174, 2003). Treatment with SYK antisense oligonucleotides inhibits antigen-induced infiltration of eosinophils and neutrophils in an animal model of asthma (Stenton et al. J Immunol 169:1028, 2002). SYK deficient eosinophils also show impaired activation in response to FcδR stimulation (Lach-Trifilieffe et al. Blood 96:2506, 2000). Therefore, small molecule inhibitors of SYK will be useful for treatment of allergy-induced inflammatory diseases including asthma.

In view of the numerous conditions that are contemplated to benefit by treatment involving modulation of the JAK and/or SYK pathways it is immediately apparent that new compounds that modulate JAK and/or SYK pathways and methods of using these compounds should provide substantial therapeutic benefits to a wide variety of patients. Provided herein are novel pyrrolopyrazine derivatives for use in the treatment of conditions in which targeting of the JAK and/or SYK pathways or inhibition of JAK or SYK kinases, particularly JAK3, and are therapeutically useful for the treatment of auto-immune and inflammatory diseases.

SUMMARY OF THE INVENTION

The novel pyrrolopyrazine derivatives provided herein selectively inhibit JAK3 and are useful for the treatment of auto-immune and inflammatory diseases. The compounds of the invention modulate the JAK and/or SYK pathways and are useful novel pyrrolopyrazine derivatives for the treatment of auto-immune and inflammatory diseases, wherein preferred compounds selectively inhibit JAK3. For example, the compounds of the invention may inhibit JAK3 and SYK, wherein preferred compounds are selective for JAK3 of the JAK kinases and are useful novel pyrrolopyrazine derivatives for the treatment of auto-immune and inflammatory diseases. Furthermore, the compounds of the invention may inhibit JAK3 and JAK2, wherein preferred compounds are selective for JAK3 of the JAK kinases, and are useful novel pyrrolopyrazine derivatives for the treatment of auto-immune and inflammatory diseases. Similarly, the compounds of the invention may inhibit JAK3 and JAK1, wherein preferred compounds are selective for JAK3 of the JAK kinases, and are useful novel pyrrolopyrazine derivatives for the treatment of auto-immune and inflammatory diseases.

The application provides a compound of Formula I

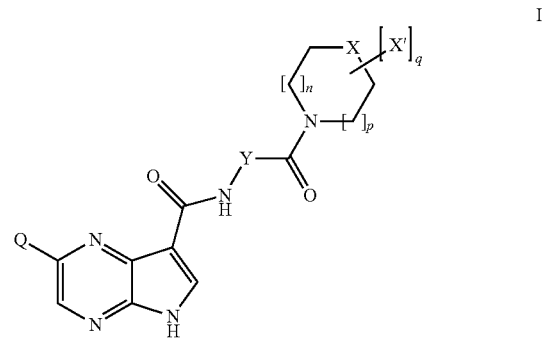

wherein:
Y is CH(R$^1$);
  R$^1$ is H or R$^{1a}$;
    R$^{1a}$ is lower alkyl, lower alkoxy, phenyl, benzyl, heteroaryl, cycloalkyl, heterocycloalkyl, or cycloalkylalkyl, optionally substituted with one or more R$^{1a'}$;
    R$^{1a'}$ is halogen, lower alkyl, lower haloalkyl, lower alkoxy, lower hydroxy alkyl, lower haloalkyl, oxo, hydroxy, or —CN;
X is C(R$^2$)(R$^3$), N(R$^2$), S(=O)$_2$, or O;
  each R$^2$ is independently H or R$^{2a}$;

each $R^{2a}$ is independently lower alkyl, lower haloalkyl, halogen, lower alkoxy, lower hydroxyalkyl, cyano, cyano lower alkyl, hydroxy, C(=O)$R^{2a'}$ or S(=O)$_2$$R^{2a'}$;

each $R^{a2'}$ is independently H or lower alkyl;

each X' is independently halogen, lower alkyl, cyano, hydroxy, lower haloalkyl, lower hydroxyalkyl, heteroaryl, spiroheterocycloalkyl, spirocycloalkyl, lower alkoxy, lower alkylamino, or lower dialkylamino;

or X' and $R^2$ come together to form a bicyclic ring system, optionally substituted with one or more $R^{2'}$;

$R^{2'}$ is halogen, lower alkyl, lower alkoxy, hydroxy, hydroxy lower alkyl, lower haloalkyl, lower hydroxyalkylcyano, or —S(O)$_2$CH$_3$;

$R^3$ is H, hydroxy, halogen or lower alkyl;

or $R^2$ and $R^3$ come together to form a spirocyclic ring system, optionally substituted with one or more $R^{2'}$;

q is 0, 1, 2, 3, or 4;

n is 0 or 1;

p is 0 or 1;

Q is H, halogen, hydroxy, cyano or Q';

Q' is lower alkyl, lower alkenyl, lower alkynyl, lower alkoxy, cycloalkyl, cycloalkyloxy, phenyl, phenyloxy, cycloalkenyl, heterocycloalkyl, or heteroaryl, optionally substituted with one or more $Q^a$;

$Q^a$ is $Q^b$ or $Q^c$;

$Q^b$ is halogen, oxo, hydroxy, —CN, —SCH$_3$, —S(O)$_2$CH$_3$, or —S(=O)CH$_3$;

$Q^c$ is $Q^d$ or $Q^{e'}$;

or two $Q^a$ come together to form a bicyclic ring system, optionally substituted with one or more $Q^b$ or $Q^c$;

$Q^d$ is —O($Q^e$), —S(=O)$_2$($Q^e$), —C(=O)N($Q^e$)$_2$, —S(O)$_2$($Q^e$), —C(=O)($Q^e$), —C(=O)O($Q^e$), —N($Q^e$)$_2$; —N($Q^e$)C(=O)($Q^e$), —N($Q^e$)C(=O)O($Q^e$), or —N($Q^e$)C(=O)N($Q^e$)$_2$;

each $Q^e$ is independently H or $Q^{e'}$;

each $Q^{e'}$ is independently lower alkyl, phenyl, benzyl, lower haloalkyl, lower alkoxy, cycloalkyl, cycloalkyl lower alkyl, cycloalkenyl, heterocycloalkyl, or heteroaryl, optionally substituted with one or more $Q^f$;

$Q^f$ is $Q^g$ or $Q^h$;

$Q^g$ is halogen, hydroxy, cyano, oxo, or —C(=O)($Q^h$);

$Q^h$ is lower alkyl, lower haloalkyl, lower alkoxy, amino, phenyl, benzyl, cycloalkyl, heterocycloalkyl, or heteroaryl, optionally substituted with one or more $Q^i$; and $Q^i$ is halogen, hydroxy, cyano, lower alkyl, lower haloalkyl, or lower alkoxy;

or a pharmaceutically acceptable salt thereof.

The application provides a compound of Formula I'

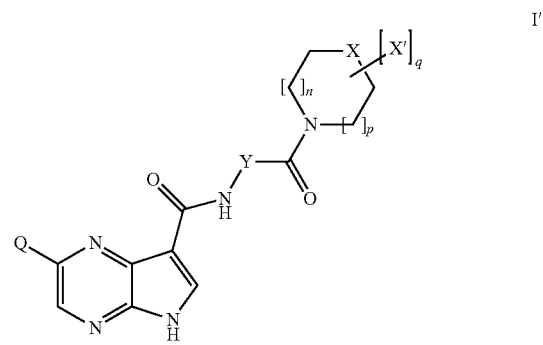

wherein:

Y is CH($R^1$);

$R^1$ is H or $R^{1a}$;

$R^{1a}$ is lower alkyl, lower alkoxy, phenyl, benzyl, heteroaryl, cycloalkyl, heterocycloalkyl, or cycloalkylalkyl, optionally substituted with one or more $R^{1a'}$;

$R^{1a'}$ is halogen, lower alkyl, lower haloalkyl, lower alkoxy, lower hydroxy alkyl, lower haloalkyl, oxo, hydroxy, or —CN;

X is C($R^2$)($R^3$), N($R^2$) or O;

each $R^2$ is independently H or $R^{2a}$;

each $R^{2a}$ is independently lower alkyl, lower haloalkyl, halogen, lower alkoxy, lower hydroxyalkyl, cyano, cyano lower alkyl, hydroxy, C(=O)$R^{2a'}$ or S(=O)$_2$$R^{2a'}$;

each $R^{a2'}$ is independently H or lower alkyl;

each X' is independently halogen, lower alkyl, cyano, hydroxy, lower haloalkyl, lower hydroxyalkyl, heteroaryl, spiroheterocycloalkyl, spirocycloalkyl, lower alkoxy, lower alkylamino, or lower dialkylamino;

or X' and $R^2$ come together to form a bicyclic ring system, optionally substituted with one or more $R^{2'}$;

$R^{2'}$ is halogen, lower alkyl, lower alkoxy, hydroxy, lower haloalkyl, lower hydroxyalkylcyano, or —S(O)$_2$CH$_3$;

$R^3$ is H, hydroxy, halogen or lower alkyl;

q is 0, 1, 2, 3, or 4;

n is 0 or 1;

p is 0 or 1;

Q is H, halogen, hydroxy, cyano or Q';

Q' is lower alkyl, lower alkenyl, lower alkynyl, cycloalkyl, phenyl, cycloalkenyl, heterocycloalkyl, or heteroaryl, optionally substituted with one or more $Q^a$;

$Q^a$ is $Q^b$ or $Q^c$;

$Q^b$ is halogen, oxo, hydroxy, —CN, —SCH$_3$, —S(O)$_2$CH$_3$, or —S(=O)CH$_3$;

$Q^c$ is $Q^d$ or $Q^{e'}$;

or two $Q^a$ come together to form a bicyclic ring system, optionally substituted with one or more $Q^b$ or $Q^c$;

$Q^d$ is —O($Q^e$), —S(=O)$_2$($Q^e$), —C(=O)N($Q^e$)$_2$, —S(O)$_2$($Q^e$), —C(=O)($Q^e$), —C(=O)O($Q^e$), —N($Q^e$)$_2$; —N($Q^e$)C(=O)($Q^e$), —N($Q^e$)C(=O)O($Q^e$), or —N($Q^e$)C(=O)N($Q^e$)$_2$;

each $Q^e$ is independently H or $Q^{e'}$;

each $Q^{e'}$ is independently lower alkyl, phenyl, benzyl, lower haloalkyl, lower alkoxy, cycloalkyl, cycloalkenyl, heterocycloalkyl, or heteroaryl, optionally substituted with one or more $Q^f$;

$Q^f$ is $Q^g$ or $Q^h$;

Qᵍ is halogen, hydroxy, cyano, oxo, or —C(=O)(Qʰ);

Qʰ is lower alkyl, lower haloalkyl, lower alkoxy, amino, phenyl, benzyl, cycloalkyl, heterocycloalkyl, or heteroaryl, optionally substituted with one or more Qⁱ; and Qⁱ is halogen, hydroxy, cyano, lower alkyl, lower haloalkyl, or lower alkoxy;

or a pharmaceutically acceptable salt thereof.

The application provides a method for treating an inflammatory or autoimmune condition comprising administering to a patient in need thereof a therapeutically effective amount of the compounds of the claimed invention.

The application provides a pharmaceutical composition comprising the compound of Formula I, admixed with at least one pharmaceutically acceptable carrier, excipient or diluent

DETAILED DESCRIPTION OF THE INVENTION

Definitions

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined herein above" refers to the broadest definition for each group as provided in the Summary of the Invention or the broadest claim. In all other embodiments provided below, substituents which can be present in each embodiment and which are not explicitly defined retain the broadest definition provided in the Summary of the Invention.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

As used herein, unless specifically indicated otherwise, the word "or" is used in the "inclusive" sense of "and/or" and not the "exclusive" sense of "either/or".

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

When any variable (e.g., X, X', or Q) occurs more than one time in any moiety or formula depicting and describing compounds employed or claimed in the present invention, its definition on each occurrence is independent of its definition at every other occurrence. Also, combinations of substituents and/or variables are permissible only if such compounds result in stable compounds.

The symbols "*" at the end of a bond or "_ _ _ _ _ _" drawn through a bond each refer to the point of attachment of a functional group or other chemical moiety to the rest of the molecule of which it is a part. Thus, for example:

MeC(=O)OR⁴ wherein

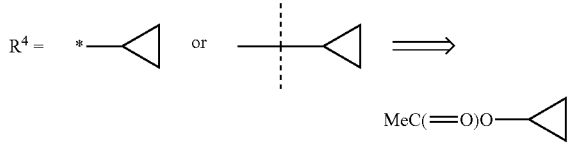

A bond drawn into ring system (as opposed to connected at a distinct vertex) indicates that the bond may be attached to any of the suitable ring atoms.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen or a substituent.

The phrase "come together to form a bicyclic ring system" as used herein means join to form a bicyclic ring system, wherein each ring may be made up of either 4-7 carbon atoms or 4-7 carbon and heteroatoms, and may be saturated or unsaturated.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

The definitions described herein may be appended to form chemically-relevant combinations, such as "heteroalkylaryl," "haloalkylheteroaryl," "arylalkylheterocyclyl," "alkylcarbonyl," "alkoxyalkyl," "cycloalkylalkyl" and the like. When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" refers to an alkyl group having one to two phenyl substituents, and thus includes benzyl, phenylethyl, and biphenyl. An "alkylaminoalkyl" is an alkyl group having one to two alkylamino substituents. "Hydroxyalkyl" includes 2-hydroxyethyl, 2-hydroxypropyl, 1-(hydroxymethyl)-2-methylpropyl, 2-hydroxybutyl, 2,3-dihydroxybutyl, 2-(hydroxymethyl), 3-hydroxypropyl, and so forth. Accordingly, as used herein, the term "hydroxyalkyl" is used to define a subset of heteroalkyl groups defined below. The term -(ar)alkyl refers to either an unsubstituted alkyl or an aralkyl group. The term (hetero)aryl or (het)aryl refers to either an aryl or a heteroaryl group.

Compounds of formula I may exhibit tautomerism. Tautomeric compounds can exist as two or more interconvertable species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(=O)—CH— ⇌ —C(—OH)=CH—), amide/imidic acid (—C(=O)—NH— ⇌ —C(—OH)=N—) and amidine (—C(=NR)—NH— ⇌ —C(—NHR)=N—) tautomers. The latter two are particularly common in heteroaryl and heterocyclic rings and the present invention encompasses all tautomeric forms of the compounds.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics*, 10$^{th}$ Ed., McGraw Hill Companies Inc., New York (2001). Any suitable materials and/or methods known to those of skill can be utilized in carrying out the present invention. However, preferred materials and methods are described. Materials, reagents and the like to which reference are made in the following description and examples are obtainable from commercial sources, unless otherwise noted.

The term "acyl" as used herein denotes a group of formula —C(=O)R wherein R is hydrogen or lower alkyl as defined herein. The term or "alkylcarbonyl" as used herein denotes a group of formula C(=O)R wherein R is alkyl as defined herein. The term $C_{1-6}$ acyl refers to a group —C(=O)R contain 6 carbon atoms. The term "arylcarbonyl" as used herein means a group of formula C(=O)R wherein R is an aryl group; the term "benzoyl" as used herein an "arylcarbonyl" group wherein R is phenyl.

The term "alkyl" as used herein denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "$C_{1-10}$ alkyl" as used herein refers to an alkyl composed of 1 to 10 carbons. Examples of alkyl groups include, but are not limited to, lower alkyl groups include methyl, ethyl, propyl, i-propyl, n-butyl, i-butyl, t-butyl or pentyl, isopentyl, neopentyl, hexyl, heptyl, and octyl.

When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" denotes the radical R'R"—, wherein R' is a phenyl radical, and R" is an alkylene radical as defined herein with the understanding that the attachment point of the phenylalkyl moiety will be on the alkylene radical. Examples of arylalkyl radicals include, but are not limited to, benzyl, phenylethyl, 3-phenylpropyl. The terms "arylalkyl", "aryl alkyl", or "aralkyl" are interpreted similarly except R' is an aryl radical. The terms "heteroaryl alkyl" or "heteroarylalkyl" are interpreted similarly except R' is optionally an aryl or a heteroaryl radical.

The term "haloalkyl" as used herein denotes a unbranched or branched chain alkyl group as defined above wherein 1, 2, 3 or more hydrogen atoms are substituted by a halogen. The term "lower haloalkyl" denotes a straight or branched chain hydrocarbon residue containing 1 to 6 carbon atoms, wherein 1, 2, 3 or more hydrogen atoms are substituted by a halogen. Examples are 1-fluoromethyl, 1-chloromethyl, 1-bromomethyl, 1-iodomethyl, difluoromethyl, trifluoromethyl, trichloromethyl, tribromomethyl, triiodomethyl, 1-fluoroethyl, 1-chloroethyl, 1-bromoethyl, 1-iodoethyl, 2-fluoroethyl, 2-chloroethyl, 2-bromoethyl, 2-iodoethyl, 2,2-dichloroethyl, 3-bromopropyl or 2,2,2-trifluoroethyl.

The term "alkylene" as used herein denotes a divalent saturated linear hydrocarbon radical of 1 to 10 carbon atoms (e.g., $(CH_2)_n$) or a branched saturated divalent hydrocarbon radical of 2 to 10 carbon atoms (e.g., —CHMe- or —CH$_2$CH(i-Pr)CH$_2$—), unless otherwise indicated. Except in the case of methylene, the open valences of an alkylene group are not attached to the same atom. Examples of alkylene radicals include, but are not limited to, methylene, ethylene, propylene, 2-methyl-propylene, 1,1-dimethyl-ethylene, butylene, 2-ethylbutylene.

The term "alkoxy" as used herein means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an alkoxy group with a "lower alkyl" group as previously defined. "$C_{1-10}$ alkoxy" as used herein refers to an —O-alkyl wherein alkyl is $C_{1-10}$.

The term "hydroxyalkyl" as used herein denotes an alkyl radical as herein defined wherein one to three hydrogen atoms on different carbon atoms is/are replaced by hydroxyl groups.

The term "cycloalkyl" as used herein refers to a saturated carbocyclic ring containing 3 to 8 carbon atoms, i.e. cyclopropyl, cyclobutyl, cyclopentyl, cyclohexyl, cycloheptyl or cyclooctyl. "$C_{3-7}$ cycloalkyl" as used herein refers to an cycloalkyl composed of 3 to 7 carbons in the carbocyclic ring.

The term "cycloalkenyl" refers to a partially unsaturated carbocyclic containing 5 to 7 carbon atoms unless otherwise specified and having a carbon-carbon double bond within the ring. For example, $C_{5-6}$ cycloalkenyl refers to a cycloalkenyl group having from 5 to 6 member atoms. In certain embodiments cycloalkenyl groups have one carbon-carbon double bond within the ring. In other embodiments, cycloalkenyl groups have more than one carbon-carbon double bond within the ring. However, cycloalkenyl rings are not aromatic. Cycloalkenyl groups may be optionally substituted with one or more substituent. Examples of cycloalkenyl include, but are not limited to, cyclopentenyl and cyclohexenyl.

The term "halogen" or "halo" as used herein means fluorine, chlorine, bromine, or iodine.

The term "amino" as used herein encompasses —NR$_2$, wherein each R group is independently H or lower alky, wherein lower alkyl is as defined herein. Examples of amino groups include dimethyl amino, methyl amino and NH$_2$.

As used herein, the term "aryl" means a monocyclic or bicyclic (also referred to as "biaryl"), substituted or unsubstituted carbocyclic aromatic group. Examples of aryl groups are phenyl, naphthyl and the like.

The term "heteroaryl" as used herein means a monocyclic, bicyclic ("heterobiaryl"), or tricyclic radical of 5 to 18 ring atoms having at least one aromatic ring containing four to eight atoms per ring, incorporating one or more N, O, or S heteroatoms, the remaining ring atoms being carbon, with the understanding that the attachment point of the heteroaryl radical will be on an aromatic ring. As well known to those skilled in the art, heteroaryl rings have less aromatic character than their all-carbon counter parts. Thus, for the purposes of the invention, a heteroaryl group need only have some degree of aromatic character. Examples of heteroaryl moieties include monocyclic aromatic heterocycles having 5 to 6 ring atoms and 1 to 3 heteroatoms include, but is not limited to, pyridinyl, pyrimidinyl, pyrazinyl, pyrrolyl, pyrazolyl, imidazolyl, indolyl oxazol, isoxazole, thiazole, isothiazole, triazoline, triazolyl, thiophenyl, furanyl, thiadiazole and oxadiaxoline which can optionally be substituted with one or more, preferably one or two substituents selected from hydroxy, cyano, alkyl, alkoxy, thio, lower haloalkoxy, alkylthio, halo, haloalkyl, alkylsulfinyl, alkylsulfonyl, halogen, amino, alkylamino, dialkylamino, aminoalkyl, alkylaminoalkyl, and dialkylaminoalkyl, nitro, alkoxycarbonyl and carbamoyl, alkylcarbamoyl, dialkylcarbamoyl, arylcarbamoyl, alkylcarbonylamino and arylcarbonylamino. Examples of bicyclic moieties include, but are not limited to, quinolinyl, indazolyl, isoquinolinyl, benzofuryl, benzothiophenyl, benzoxazole, benzisoxazole, benzothiazole, pyrrolopyridinyl, pyrrolopyrazinyl and benzisothiazole.

The term "heterocycloalkyl", "heterocyclyl" or "heterocycle" as used herein denotes a monovalent saturated cyclic radical, consisting of one or more rings, preferably one to two rings or three rings, of three to eight atoms per ring, incorporating one or more ring carbon atoms and one or more ring heteroatoms (chosen from N,O or $S(=O)_{0-2}$), wherein the point of attachment can be through either a carbon atom or a heteroatom, and which can optionally be independently substituted with one or more, preferably one or two or three substituents selected from hydroxy, oxo, cyano, lower alkyl, lower alkoxy, lower haloalkoxy, alkylthio, halo, haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino, arylcarbonylamino, unless otherwise indicated. Examples of heterocyclic radicals include, but are not limited to, azetidinyl, pyrrolidinyl, hexahydroazepinyl, oxetanyl, tetrahydrofuranyl, tetrahydrothiophenyl, oxazolidinyl, thiazolidinyl, isoxazolidinyl, pyrrolidinyl, morpholinyl, piperazinyl, piperidinyl, isoindolinyl, dihydroisoquinolinyle, tetrahydropyranyl, tetrahydrocarbolinyl, imidazolinyl, thiomorpholinyl, quinuclidinyl and imidazolinyl.

The phrase "organ rejection" includes acute allograft or xenograft rejection and chronic allograft or xenograft rejection in the setting of vascularized and/or non-vascularized (e.g. bone marrow, pancreatic islet cells) transplants.

The term "excipient" as used herein refers to a compound that is useful in preparing a pharmaceutical composition, generally safe, non-toxic and neither biologically nor otherwise undesirable, and includes excipients that are acceptable for veterinary use as well as human pharmaceutical use. The compounds of this invention can be administered alone but will generally be administered in admixture with one or more suitable pharmaceutical excipients, diluents or carriers selected with regard to the intended route of administration and standard pharmaceutical practice.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

A "pharmaceutically acceptable salt" form of an active ingredient may also initially confer a desirable pharmacokinetic property on the active ingredient which were absent in the non-salt form, and may even positively affect the pharmacodynamics of the active ingredient with respect to its therapeutic activity in the body. The phrase "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

Inhibitors of JAK3

The application provides a compound of Formula I

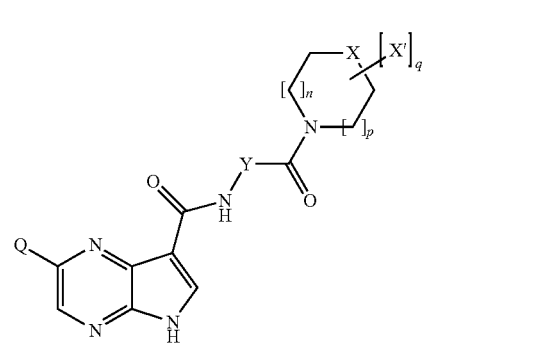

wherein:
Y is $CH(R^1)$;
  $R^1$ is H or $R^{1a}$;
    $R^{1a}$ is lower alkyl, lower alkoxy, phenyl, benzyl, heteroaryl, cycloalkyl, heterocycloalkyl, or cycloalkylalkyl, optionally substituted with one or more $R^{1a'}$;
    $R^{1a'}$ is halogen, lower alkyl, lower haloalkyl, lower alkoxy, lower hydroxy alkyl, lower haloalkyl, oxo, hydroxy, or —CN;
X is $C(R^2)(R^3)$, $N(R^2)$, $S(=O)_2$, or O;
  each $R^2$ is independently H or $R^{2a}$;
    each $R^{2a}$ is independently lower alkyl, lower haloalkyl, halogen, lower alkoxy, lower hydroxyalkyl, cyano, cyano lower alkyl, hydroxy, $C(=O)R^{2a'}$ or $S(=O)_2 R^{2a'}$;
    each $R^{a2'}$ is independently H or lower alkyl;
each X' is independently halogen, lower alkyl, cyano, hydroxy, lower haloalkyl, lower hydroxyalkyl, heteroaryl, spiroheterocycloalkyl, spirocycloalkyl, lower alkoxy, lower alkylamino, or lower dialkylamino;
  or X' and $R^2$ come together to form a bicyclic ring system, optionally substituted with one or more $R^{2'}$;
    $R^{2'}$ is halogen, lower alkyl, lower alkoxy, hydroxy, hydroxy lower alkyl, lower haloalkyl, lower hydroxyalkylcyano, or $—S(O)_2CH_3$;
  $R^3$ is H, hydroxy, halogen or lower alkyl;
  or $R^2$ and $R^3$ come together to form a spirocyclic ring system, optionally substituted with one or more $R^{2'}$;
q is 0, 1, 2, 3, or 4;
n is 0 or 1;
p is 0 or 1;
Q is H, halogen, hydroxy, cyano or Q';
  Q' is lower alkyl, lower alkenyl, lower alkynyl, lower alkoxy, cycloalkyl, cycloalkyloxy, phenyl, phenyloxy, cycloalkenyl, heterocycloalkyl, or heteroaryl, optionally substituted with one or more $Q^a$;
    $Q^a$ is $Q^b$ or $Q^c$;
      $Q^b$ is halogen, oxo, hydroxy, —CN, $—SCH_3$, $—S(O)_2 CH_3$, or $—S(=O)CH_3$;

$Q^c$ is $Q^d$ or $Q^{e'}$;
or two $Q^a$ come together to form a bicyclic ring system, optionally substituted with one or more $Q^b$ or $Q^c$;
$Q^d$ is —O($Q^e$), —S(=O)$_2$($Q^e$), —C(=O)N($Q^e$)$_2$, —S(O)$_2$($Q^e$), —C(=O)($Q^e$), —C(=O)O($Q^e$), —N($Q^e$)$_2$; —N($Q^e$)C(=O)($Q^e$), —N($Q^e$)C(=O)O($Q^e$), or —N($Q^e$)C(=O)N($Q^e$)$_2$;
each $Q^e$ is independently H or $Q^{e'}$;
each $Q^{e'}$ is independently lower alkyl, phenyl, benzyl, lower haloalkyl, lower alkoxy, cycloalkyl, cycloalkyl lower alkyl, cycloalkenyl, heterocycloalkyl, or heteroaryl, optionally substituted with one or more $Q^f$;
$Q^f$ is $Q^g$ or $Q^h$;
$Q^g$ is halogen, hydroxy, cyano, oxo, or —C(=O)($Q^h$);
$Q^h$ is lower alkyl, lower haloalkyl, lower alkoxy, amino, phenyl, benzyl, cycloalkyl, heterocycloalkyl, or heteroaryl, optionally substituted with one or more $Q^i$; and
$Q^i$ is halogen, hydroxy, cyano, lower alkyl, lower haloalkyl, or lower alkoxy;
or a pharmaceutically acceptable salt thereof.

The application provides a compound of Formula I'

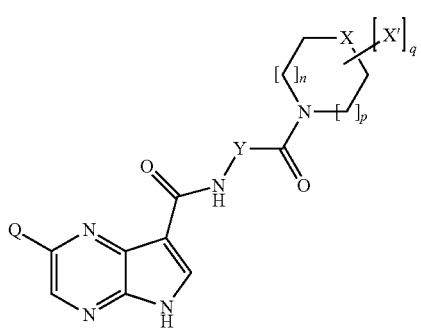

I' wherein:
Y is CH($R^1$);
$R^1$ is H or $R^{1a}$;
$R^{1a}$ is lower alkyl, lower alkoxy, phenyl, benzyl, heteroaryl, cycloalkyl, heterocycloalkyl, or cycloalkylalkyl, optionally substituted with one or more $R^{1a'}$;
$R^{1a'}$ is halogen, lower alkyl, lower haloalkyl, lower alkoxy, lower hydroxy alkyl, lower haloalkyl, oxo, hydroxy, or —CN;
X is C($R^2$)($R^3$), N($R^2$) or O;
each $R^2$ is independently H or $R^{2a}$;
each $R^{2a}$ is independently lower alkyl, lower haloalkyl, halogen, lower alkoxy, lower hydroxyalkyl, cyano, cyano lower alkyl, hydroxy, C(=O)$R^{2a'}$ or S(=O)$_2$$R^{2a'}$;
each $R^{a2'}$ is independently H or lower alkyl;
each X' is independently halogen, lower alkyl, cyano, hydroxy, lower haloalkyl, lower hydroxyalkyl, heteroaryl, spiroheterocycloalkyl, spirocycloalkyl, lower alkoxy, lower alkylamino, or lower dialkylamino;
or X' and $R^2$ come together to form a bicyclic ring system, optionally substituted with one or more $R^{2'}$;
$R^{2'}$ is halogen, lower alkyl, lower alkoxy, hydroxy, lower haloalkyl, lower hydroxyalkylcyano, or —S(O)$_2$CH$_3$;
$R^3$ is H, hydroxy, halogen or lower alkyl;
q is 0, 1, 2, 3, or 4;
n is 0 or 1;
p is 0 or 1;
Q is H, halogen, hydroxy, cyano or Q';
Q' is lower alkyl, lower alkenyl, lower alkynyl, cycloalkyl, phenyl, cycloalkenyl, heterocycloalkyl, or heteroaryl, optionally substituted with one or more $Q^a$;
$Q^a$ is $Q^b$ or $Q^c$;
$Q^b$ is halogen, oxo, hydroxy, —CN, —SCH$_3$, —S(O)$_2$CH$_3$, or —S(=O)CH$_3$;
$Q^c$ is $Q^d$ or $Q^{e'}$;
or two $Q^a$ come together to form a bicyclic ring system, optionally substituted with one or more $Q^b$ or $Q^c$;
$Q^d$ is —O($Q^e$), —S(=O)$_2$($Q^e$), —C(=O)N($Q^e$)$_2$, —S(O)$_2$($Q^e$), —C(=O)($Q^e$), —C(=O)O($Q^e$), —N($Q^e$)$_2$; —N($Q^e$)C(=O)($Q^e$), —N($Q^e$)C(=O)O($Q^e$), or —N($Q^e$)C(=O)N($Q^e$)$_2$;
each $Q^e$ is independently H or $Q^{e'}$;
each $Q^{e'}$ is independently lower alkyl, phenyl, benzyl, lower haloalkyl, lower alkoxy, cycloalkyl, cycloalkenyl, heterocycloalkyl, or heteroaryl, optionally substituted with one or more $Q^f$;
$Q^f$ is $Q^g$ or $Q^h$;
$Q^g$ is halogen, hydroxy, cyano, oxo, or —C(=O)($Q^h$);
$Q^h$ is lower alkyl, lower haloalkyl, lower alkoxy, amino, phenyl, benzyl, cycloalkyl, heterocycloalkyl, or heteroaryl, optionally substituted with one or more $Q^i$; and
Q is halogen, hydroxy, cyano, lower alkyl, lower haloalkyl, or lower alkoxy;
or a pharmaceutically acceptable salt thereof.

In one variation of Formula I, Q is cycloalkyl or heteroaryl, optionally substituted with lower alkyl.
In one variation of Formula I, X is C($R^2$)($R^3$).
In one variation of Formula I, $R^2$ is lower alkyl, cyano, halogen, lower alkoxy, lower haloalkyl, heteroaryl, or hydroxy.
In one variation of Formula I, n is 0 and p is 0.
In one variation of Formula I, n is 1 and p is 0.
In one variation of Formula I, n is 1 and p is 1.
In one variation of Formula I, n is 0 and p is 1.
In one variation of Formula I, q is 0.
In one variation of Formula I, q is 1.
In one variation of Formula I, q is 0 and $R^1$ is lower alkyl, lower alkoxy, cycloalkyl, lower haloalkyl, or lower haloalkyl cycloalkyl.
In one variation of Formula I, $R^1$ is lower alkyl or cycloalkyl.
In one variation of Formula I, $R^3$ is H.
In one variation of Formula I, $R^3$ is lower alkyl.
In one variation of Formula I, $R^3$ is halogen.
In one variation of Formula I, q is 0 and $R^1$ is lower alkyl or cycloalkyl.
In one variation of Formula I, q is 0 and $R^3$ is H.
In one variation of Formula I, q is 0 and $R^3$ is lower alkyl.
In one variation of Formula I, q is 0 and $R^3$ is halogen.
In one variation of Formula I, $R^1$ is lower alkyl, lower alkoxy, cycloalkyl, lower haloalkyl, or lower haloalkyl cycloalkyl.
In one variation of Formula I, n is 1, p is 1, and $R^1$ is lower alkyl, lower alkoxy, cycloalkyl, lower haloalkyl, or lower haloalkyl cycloalkyl.
In one variation of Formula I, n is 1, p is 1, and $R^1$ is lower alkyl or cycloalkyl.
In one variation of Formula I, $R^1$ is lower alkyl or cycloalkyl, n is 1, p is 1, and q is 0.

In one variation of Formula I, $R^1$ is lower alkyl or cycloalkyl, n is 1, p is 1, and $R^3$ is H.

In one variation of Formula I, $R^1$ is lower alkyl or cycloalkyl, n is 1, p is 1, and $R^3$ is lower alkyl.

In one variation of Formula I, $R^1$ is lower alkyl or cycloalkyl, n is 1, p is 1, and $R^3$ is halogen.

In one variation of Formula I, n is 0, p is 1, and $R^1$ is lower alkyl, lower alkoxy, cycloalkyl, lower haloalkyl, or lower haloalkyl cycloalkyl.

In one variation of Formula I, n is 0, p is 1, and $R^1$ is lower alkyl or cycloalkyl.

In one variation of Formula I, $R^1$ is lower alkyl or cycloalkyl, n is 0, p is 1, and q is 0.

In one variation of Formula I, $R^1$ is lower alkyl or cycloalkyl, n is 0, p is 1, and $R^3$ is H.

In one variation of Formula I, $R^1$ is lower alkyl or cycloalkyl, n is 0, p is 1, and $R^3$ is lower alkyl.

In one variation of Formula I, $R^1$ is lower alkyl or cycloalkyl, n is 0, p is 1, and $R^3$ is halogen.

In one variation of Formula I, n is 0, p is 0, and $R^1$ is lower alkyl, lower alkoxy, cycloalkyl, lower haloalkyl, or lower haloalkyl cycloalkyl.

In one variation of Formula I, n is 0, p is 0, and $R^1$ is lower alkyl or cycloalkyl.

In one variation of Formula I, $R^1$ is lower alkyl or cycloalkyl, n is 0, p is 0, and q is 0.

In one variation of Formula I, $R^1$ is lower alkyl or cycloalkyl, n is 0, p is 0, and $R^3$ is H.

In one variation of Formula I, $R^1$ is lower alkyl or cycloalkyl, n is 0, p is 0, and $R^3$ is lower alkyl.

In one variation of Formula I, $R^1$ is lower alkyl or cycloalkyl, n is 0, p is 0, and $R^3$ is halogen.

In one variation of Formula I, n is 1, p is 0, $R^1$ is lower alkyl, lower alkoxy, cycloalkyl, lower haloalkyl, or lower haloalkyl cycloalkyl.

In one variation of Formula I, n is 1, p is 0, $R^1$ is lower alkyl or cycloalkyl.

In one variation of Formula I, n is 1, p is 0, $R^1$ is lower alkyl or cycloalkyl, q is 0.

In one variation of Formula I, n is 1, p is 0, $R^1$ is lower alkyl or cycloalkyl, $R^3$ is H.

In one variation of Formula I, n is 1, p is 0, $R^1$ is lower alkyl or cycloalkyl, $R^3$ is lower alkyl.

In one variation of Formula I, n is 1, p is 0, $R^1$ is lower alkyl or cycloalkyl, $R^3$ is halogen.

In one variation of Formula I, Q is cycloalkyl, phenyl or heteroaryl, optionally substituted with one or more $Q^a$.

In one variation of Formula I, X is $C(R^2)(R^3)$ and Q is cycloalkyl, phenyl or heteroaryl, optionally substituted with one or more $Q^a$.

In one variation of Formula I, $R^2$ is lower alkyl, cyano, halogen, lower alkoxy, lower haloalkyl, heteroaryl, or hydroxy, X is $C(R^2)(R^3)$ and Q is cycloalkyl, phenyl or heteroaryl, optionally substituted with one or more $Q^a$.

In one variation of Formula I, n is 0, p is 0, $R^2$ is lower alkyl, cyano, halogen, lower alkoxy, lower haloalkyl, heteroaryl, or hydroxy, X is $C(R^2)(R^3)$ and Q is cycloalkyl, phenyl or heteroaryl, optionally substituted with one or more $Q^a$.

In one variation of Formula I, n is 1, p is 0, $R^2$ is lower alkyl, cyano, halogen, lower alkoxy, lower haloalkyl, heteroaryl, or hydroxy, X is $C(R^2)(R^3)$ and Q is cycloalkyl, phenyl or heteroaryl, optionally substituted with one or more $Q^a$.

In one variation of Formula I, n is 1, p is 1, $R^2$ is lower alkyl, cyano, halogen, lower alkoxy, lower haloalkyl, heteroaryl, or hydroxy, X is $C(R^2)(R^3)$ and Q is cycloalkyl, phenyl or heteroaryl, optionally substituted with one or more $Q^a$.

In one variation of Formula I, $R^2$ is cyano, X is $C(R^2)(R^3)$ and Q is cycloalkyl, phenyl or heteroaryl, optionally substituted with one or more $Q^a$.

In one variation of Formula I, q is 0, $R^2$ is lower alkyl, cyano, halogen, lower alkoxy, lower haloalkyl, heteroaryl, or hydroxy, X is $C(R^2)(R^3)$ and Q is cycloalkyl, phenyl or heteroaryl, optionally substituted with one or more $Q^a$.

In one variation of Formula I, q is 0, $R^2$ is cyano, X is $C(R^2)(R^3)$ and Q is cycloalkyl, phenyl or heteroaryl, optionally substituted with one or more $Q^a$.

In one variation of Formula I, $R^1$ is lower alkyl, lower alkoxy, cycloalkyl, lower haloalkyl, or lower haloalkyl cycloalkyl, q is 0, $R^2$ is cyano, X is $C(R^2)(R^3)$ and Q is cycloalkyl, phenyl or heteroaryl, optionally substituted with one or more $Q^a$.

In one variation of Formula I, $R^1$ is lower alkyl or cycloalkyl, q is 0, $R^2$ is cyano, X is $C(R^2)(R^3)$ and Q is cycloalkyl, phenyl or heteroaryl, optionally substituted with one or more $Q^a$.

In one variation of Formula I, $R^3$ is H, $R^1$ is lower alkyl or cycloalkyl, q is 0, $R^2$ is cyano, $R^2$ is lower alkyl, cyano, halogen, lower alkoxy, lower haloalkyl, heteroaryl, or hydroxy, X is $C(R^2)(R^3)$ and Q is cycloalkyl, phenyl or heteroaryl, optionally substituted with one or more $Q^a$.

In one variation of Formula I, $R^3$ is lower alkyl, $R^1$ is lower alkyl or cycloalkyl, q is 0, $R^2$ is cyano, $R^2$ is lower alkyl, cyano, halogen, lower alkoxy, lower haloalkyl, heteroaryl, or hydroxy, X is $C(R^2)(R^3)$ and Q is cycloalkyl, phenyl or heteroaryl, optionally substituted with one or more $Q^a$.

The application provides a compound selected from the group consisting of:

2-Cyclopropyl-5H-pyrrolo[2,3-b]pyrazine-7-carboxylic acid ((R)-1-methyl-2-oxo-2-pyrrolidin-1-yl-ethyl)-amide;

2-Cyclopropyl-5H-pyrrolo[2,3-b]pyrazine-7-carboxylic acid ((R)-1-methyl-2-oxo-2-piperidin-1-yl-ethyl)-amide;

2-Cyclopropyl-5H-pyrrolo[2,3-b]pyrazine-7-carboxylic acid [(R)-1-(pyrrolidine-1-carbonyl)-propyl]-amide;

2-Cyclopropyl-5H-pyrrolo[2,3-b]pyrazine-7-carboxylic acid [(R)-2-methyl-1-(pyrrolidine-1-carbonyl)-propyl]-amide;

2-Cyclopropyl-5H-pyrrolo[2,3-b]pyrazine-7-carboxylic acid ((R)-1-cyclopropyl-2-oxo-2-pyrrolidin-1-yl-ethyl)-amide;

2-Cyclopropyl-5H-pyrrolo[2,3-b]pyrazine-7-carboxylic acid ((S)-1-methyl-2-oxo-2-pyrrolidin-1-yl-ethyl)-amide;

2-Cyclopropyl-5H-pyrrolo[2,3-b]pyrazine-7-carboxylic acid [(R)-2-methyl-1-(piperidine-1-carbonyl)-propyl]-amide;

2-Cyclopropyl-5H-pyrrolo[2,3-b]pyrazine-7-carboxylic acid [(R)-2-methyl-1-(morpholine-4-carbonyl)-propyl]-amide;

2-Cyclopropyl-5H-pyrrolo[2,3-b]pyrazine-7-carboxylic acid [(R)-2-(3-methoxy-pyrrolidin-1-yl)-1-methyl-2-oxo-ethyl]-amide;

2-Cyclopropyl-5H-pyrrolo[2,3-b]pyrazine-7-carboxylic acid [(R)-2,2-dimethyl-1-(pyrrolidine-1-carbonyl)-propyl]-amide;

2-Cyclopropyl-5H-pyrrolo[2,3-b]pyrazine-7-carboxylic acid [(R)-2-(3-hydroxy-pyrrolidin-1-yl)-1-methyl-2-oxo-ethyl]-amide;

2-Cyclopropyl-5H-pyrrolo[2,3-b]pyrazine-7-carboxylic acid ((S)-1-methyl-2-oxo-2-piperidin-1-yl-ethyl)-amide;

2-(1-Ethyl-1H-pyrazol-4-yl)-5H-pyrrolo[2,3-b]pyrazine-7-carboxylic acid [(R)-2,2-dimethyl-1-(pyrrolidine-1-carbonyl)-propyl]-amide;

2-Cyclopropyl-5H-pyrrolo[2,3-b]pyrazine-7-carboxylic acid [(R)-2-(3-cyano-pyrrolidin-1-yl)-1-methyl-2-oxo-ethyl]-amide;
2-Cyclopropyl-5H-pyrrolo[2,3-b]pyrazine-7-carboxylic acid [(R)-1-methyl-2-(3-methyl-pyrrolidin-1-yl)-2-oxo-ethyl]-amide;
2-Cyclopropyl-5H-pyrrolo[2,3-b]pyrazine-7-carboxylic acid [(R)-1-methyl-2-(2-methyl-pyrrolidin-1-yl)-2-oxo-ethyl]-amide;
2-Cyclopropyl-5H-pyrrolo[2,3-b]pyrazine-7-carboxylic acid ((R)-2-azetidin-1-yl-1-methyl-2-oxo-ethyl)-amide;
2-Phenoxy-5H-pyrrolo[2,3-b]pyrazine-7-carboxylic acid [(R)-2-methyl-1-(pyrrolidine-1-carbonyl)-propyl]-amide;
2-Cyclopropyl-5H-pyrrolo[2,3-b]pyrazine-7-carboxylic acid [2,2,2-trifluoro-1-(pyrrolidine-1-carbonyl)-ethyl]-amide;
2-Cyclopropyl-5H-pyrrolo[2,3-b]pyrazine-7-carboxylic acid [(R)-2-(3-cyano-azetidin-1-yl)-1-methyl-2-oxo-ethyl]-amide;
2-Cyclopropyl-5H-pyrrolo[2,3-b]pyrazine-7-carboxylic acid [(R)-2-(3,3-difluoro-pyrrolidin-1-yl)-1-methyl-2-oxo-ethyl]-amide;
2-Cyclopropyl-5H-pyrrolo[2,3-b]pyrazine-7-carboxylic acid [(R)-2-((S)-3-fluoro-pyrrolidin-1-yl)-1-methyl-2-oxo-ethyl]-amide;
2-Cyclopropyl-5H-pyrrolo[2,3-b]pyrazine-7-carboxylic acid [(R)-2-((R)-3-fluoro-pyrrolidin-1-yl)-1-methyl-2-oxo-ethyl]-amide;
2-Cyclopropyl-5H-pyrrolo[2,3-b]pyrazine-7-carboxylic acid [(R)-1-methyl-2-(2-oxa-6-aza-spiro[3.3]hept-6-yl)-2-oxo-ethyl]-amide;
2-Cyclopropyl-5H-pyrrolo[2,3-b]pyrazine-7-carboxylic acid [(R)-1-methyl-2-oxo-2-(3-trifluoromethyl-pyrrolidin-1-yl)-ethyl]-amide;
2-Cyclopropyl-5H-pyrrolo[2,3-b]pyrazine-7-carboxylic acid ((R)-1-cyclopentyl-2-oxo-2-pyrrolidin-1-yl-ethyl)-amide;
2-(1-Ethyl-1H-pyrazol-4-yl)-5H-pyrrolo[2,3-b]pyrazine-7-carboxylic acid ((R)-1-cyclopropyl-2-oxo-2-pyrrolidin-1-yl-ethyl)-amide;
2-(1-Ethyl-1H-pyrazol-4-yl)-5H-pyrrolo[2,3-b]pyrazine-7-carboxylic acid [(R)-1-(3-cyano-3-methyl-pyrrolidine-1-carbonyl)-2,2-dimethyl-propyl]-amide;
2-Cyclopropyl-5H-pyrrolo[2,3-b]pyrazine-7-carboxylic acid [(R)-1-(3-cyano-piperidine-1-carbonyl)-2,2-dimethyl-propyl]-amide;
2-Cyclopropyl-5H-pyrrolo[2,3-b]pyrazine-7-carboxylic acid [(R)-1-((S)-3-cyano-pyrrolidine-1-carbonyl)-2,2-dimethyl-propyl]-amide;
2-Cyclopropyl-5H-pyrrolo[2,3-b]pyrazine-7-carboxylic acid [(R)-1-((R)-3-cyano-pyrrolidine-1-carbonyl)-2,2-dimethyl-propyl]-amide;
2-Cyclopropyl-5H-pyrrolo[2,3-b]pyrazine-7-carboxylic acid [(R)-2,2-dimethyl-1-(piperidine-1-carbonyl)-propyl]-amide;
2-Cyclopropyl-5H-pyrrolo[2,3-b]pyrazine-7-carboxylic acid [(R)-1-(3-cyano-azetidine-1-carbonyl)-2,2-dimethyl-propyl]-amide;
2-(1-Ethyl-1H-pyrazol-4-yl)-5H-pyrrolo[2,3-b]pyrazine-7-carboxylic acid [(R)-1-(1-methyl-cyclopropyl)-2-oxo-2-pyrrolidin-1-yl-ethyl]-amide;
2-Cyclopropyl-5H-pyrrolo[2,3-b]pyrazine-7-carboxylic acid [(R)-1-(4-cyano-piperidine-1-carbonyl)-2,2-dimethyl-propyl]-amide;
2-(1-Ethyl-1H-pyrazol-4-yl)-5H-pyrrolo[2,3-b]pyrazine-7-carboxylic acid [(R)-1-(3-cyano-3-fluoro-pyrrolidine-1-carbonyl)-2,2-dimethyl-propyl]-amide;
2-Cyclopropyl-5H-pyrrolo[2,3-b]pyrazine-7-carboxylic acid ((R)-1-cyclohexyl-2-oxo-2-pyrrolidin-1-yl-ethyl)-amide;
2-(1-Ethyl-1H-pyrazol-4-yl)-5H-pyrrolo[2,3-b]pyrazine-7-carboxylic acid {(R)-1-[3-(4,5-dihydro-1H-imidazol-2-yl)-3-fluoro-pyrrolidine-1-carbonyl]-2,2-dimethyl-propyl}-amide;
2-Cyclopropyl-5H-pyrrolo[2,3-b]pyrazine-7-carboxylic acid [(R)-1-(3-cyano-3-methyl-azetidine-1-carbonyl)-2,2-dimethyl-propyl]-amide;
2-Cyclopropyl-5H-pyrrolo[2,3-b]pyrazine-7-carboxylic acid [(R)-2-(3-cyano-azetidin-1-yl)-1-cyclopentyl-2-oxo-ethyl]-amide;
2-Cyclopropyl-5H-pyrrolo[2,3-b]pyrazine-7-carboxylic acid [(R)-1-(3,3-difluoro-pyrrolidine-1-carbonyl)-2,2-dimethyl-propyl]-amide;
2-Cyclopropyl-5H-pyrrolo[2,3-b]pyrazine-7-carboxylic acid [(R)-1-(3,4-dihydro-1H-isoquinoline-2-carbonyl)-2,2-dimethyl-propyl]-amide;
2-Cyclopropyl-5H-pyrrolo[2,3-b]pyrazine-7-carboxylic acid [(R)-1-(4-cyano-piperidine-1-carbonyl)-3-methyl-butyl]-amide;
2-Cyclopropyl-5H-pyrrolo[2,3-b]pyrazine-7-carboxylic acid [(R)-1-(4-cyano-4-methyl-piperidine-1-carbonyl)-2,2-dimethyl-propyl]-amide;
2-Cyclopropyl-5H-pyrrolo[2,3-b]pyrazine-7-carboxylic acid [(R)-2-(4-cyano-piperidin-1-yl)-1-cyclopentyl-2-oxo-ethyl]-amide;
2-Cyclopropyl-5H-pyrrolo[2,3-b]pyrazine-7-carboxylic acid [(S)-2-(4-cyano-piperidin-1-yl)-2-oxo-1-(1-trifluoromethyl-cyclopropyl)-ethyl]-amide;
2-Cyclopropyl-5H-pyrrolo[2,3-b]pyrazine-7-carboxylic acid [(R)-2-(4-cyano-piperidin-1-yl)-2-oxo-1-(1-trifluoromethyl-cyclopropyl)-ethyl]-amide;
2-Cyclopropyl-5H-pyrrolo[2,3-b]pyrazine-7-carboxylic acid [(R)-1-benzyl-2-(4-cyano-piperidin-1-yl)-2-oxo-ethyl]-amide;
2-Cyclopropyl-5H-pyrrolo[2,3-b]pyrazine-7-carboxylic acid [(R)-1-(4-cyano-piperidine-1-carbonyl)-3,3-dimethyl-butyl]-amide;
2-(3,5-Bis-trifluoromethyl-phenyl)-5H-pyrrolo[2,3-b]pyrazine-7-carboxylic acid [(R)-1-(4-cyano-piperidine-1-carbonyl)-2,2-dimethyl-propyl]-amide;
2-(3-Pyrrolidin-1-yl-phenyl)-5H-pyrrolo[2,3-b]pyrazine-7-carboxylic acid [(R)-1-(4-cyano-piperidine-1-carbonyl)-2,2-dimethyl-propyl]-amide;
2-Cyclopropyl-5H-pyrrolo[2,3-b]pyrazine-7-carboxylic acid [(R)-1-(4,4-difluoro-piperidine-1-carbonyl)-2,2-dimethyl-propyl]-amide;
2-(1-Methyl-1H-pyrazol-4-yl)-5H-pyrrolo[2,3-b]pyrazine-7-carboxylic acid [(R)-1-(3-cyano-azetidine-1-carbonyl)-2,2-dimethyl-propyl]-amide;
2-(1H-Pyrazol-4-yl)-5H-pyrrolo[2,3-b]pyrazine-7-carboxylic acid [(R)-1-(4-cyano-piperidine-1-carbonyl)-2,2-dimethyl-propyl]-amide;
2-(1-Methyl-1H-pyrazol-4-yl)-5H-pyrrolo[2,3-b]pyrazine-7-carboxylic acid [(R)-1-(4-cyano-piperidine-1-carbonyl)-2,2-dimethyl-propyl]-amide;
2-(1-Ethyl-1H-pyrazol-4-yl)-5H-pyrrolo[2,3-b]pyrazine-7-carboxylic acid [(R)-1-(4-cyano-piperidine-1-carbonyl)-2,2-dimethyl-propyl]-amide;
2-Cyclopropyl-5H-pyrrolo[2,3-b]pyrazine-7-carboxylic acid [(R)-1-(4-acetyl-piperazine-1-carbonyl)-2,2-dimethyl-propyl]-amide;
2-Cyclopropyl-5H-pyrrolo[2,3-b]pyrazine-7-carboxylic acid [(R)-2,2-dimethyl-1-(4-trifluoromethyl-piperidine-1-carbonyl)-propyl]-amide;

2-(1-Methyl-1H-pyrazol-4-yl)-5H-pyrrolo[2,3-b]pyrazine-7-carboxylic acid [(R)-1-((S)-3-cyano-pyrrolidine-1-carbonyl)-2,2-dimethyl-propyl]-amide;

2-(1-Methyl-1H-pyrazol-4-yl)-5H-pyrrolo[2,3-b]pyrazine-7-carboxylic acid [(R)-1-((R)-3-cyano-pyrrolidine-1-carbonyl)-2,2-dimethyl-propyl]-amide;

2-Cyclopropyl-5H-pyrrolo[2,3-b]pyrazine-7-carboxylic acid [(R)-2-(4-cyano-piperidin-1-yl)-1-cyclopropyl-2-oxo-ethyl]-amide;

2-(1-Ethyl-1H-pyrazol-4-yl)-5H-pyrrolo[2,3-b]pyrazine-7-carboxylic acid [(R)-2-(3-cyano-azetidin-1-yl)-1-methyl-2-oxo-ethyl]-amide;

2-(1-Methyl-1H-pyrazol-4-yl)-5H-pyrrolo[2,3-b]pyrazine-7-carboxylic acid [(R)-2-(4-cyano-piperidin-1-yl)-1-cyclopropyl-2-oxo-ethyl]-amide;

2-(3,4,5-Trimethoxy-phenyl)-5H-pyrrolo[2,3-b]pyrazine-7-carboxylic acid [(R)-1-(4-cyano-piperidine-1-carbonyl)-2,2-dimethyl-propyl]-amide;

2-Cyclopropyl-5H-pyrrolo[2,3-b]pyrazine-7-carboxylic acid [(R)-1-(4-hydroxy-4-phenyl-piperidine-1-carbonyl)-2,2-dimethyl-propyl]-amide;

2-(2,5-Dimethoxy-phenyl)-5H-pyrrolo[2,3-b]pyrazine-7-carboxylic acid [(R)-1-(4-cyano-piperidine-1-carbonyl)-2,2-dimethyl-propyl]-amide;

2-(1-Ethyl-1H-pyrazol-4-yl)-5H-pyrrolo[2,3-b]pyrazine-7-carboxylic acid [(R)-2-(4-cyano-piperidin-1-yl)-1-methyl-2-oxo-ethyl]-amide;

2-Cyclopropyl-5H-pyrrolo[2,3-b]pyrazine-7-carboxylic acid [(R)-2-(3-cyano-azetidin-1-yl)-1-cyclopropyl-2-oxo-ethyl]-amide;

2-(1-Methyl-1H-pyrazol-4-yl)-5H-pyrrolo[2,3-b]pyrazine-7-carboxylic acid [(R)-1-(3-cyano-azetidine-1-carbonyl)-3-methyl-butyl]-amide;

2-(1-Methyl-1H-pyrazol-4-yl)-5H-pyrrolo[2,3-b]pyrazine-7-carboxylic acid [(R)-2-(3-cyano-azetidin-1-yl)-1-cyclopropyl-2-oxo-ethyl]-amide;

2-(1-Ethyl-1H-pyrazol-4-yl)-5H-pyrrolo[2,3-b]pyrazine-7-carboxylic acid [(R)-2-(4-cyano-piperidin-1-yl)-1-cyclopropyl-2-oxo-ethyl]-amide;

2-Cyclopropyl-5H-pyrrolo[2,3-b]pyrazine-7-carboxylic acid [(R)-1-(4-hydroxy-4-trifluoromethyl-piperidine-1-carbonyl)-2,2-dimethyl-propyl]-amide;

2-Cyclopropyl-5H-pyrrolo[2,3-b]pyrazine-7-carboxylic acid [(R)-1-(4-hydroxy-4-methyl-piperidine-1-carbonyl)-2,2-dimethyl-propyl]-amide;

2-(1-Ethyl-1H-pyrazol-4-yl)-5H-pyrrolo[2,3-b]pyrazine-7-carboxylic acid [(S)-2-(4-cyano-piperidin-1-yl)-2-oxo-1-(1-trifluoromethyl-cyclopropyl)-ethyl]-amide;

2-(1-Ethyl-1H-pyrazol-4-yl)-5H-pyrrolo[2,3-b]pyrazine-7-carboxylic acid [(R)-2-(4-cyano-piperidin-1-yl)-2-oxo-1-(1-trifluoromethyl-cyclopropyl)-ethyl]-amide;

2-(1-Methyl-1H-pyrazol-4-yl)-5H-pyrrolo[2,3-b]pyrazine-7-carboxylic acid [(R)-2-(3-cyano-azetidin-1-yl)-1-cyclohexyl-2-oxo-ethyl]-amide;

2-(1-Methyl-1H-imidazol-4-yl)-5H-pyrrolo[2,3-b]pyrazine-7-carboxylic acid [(R)-1-(4-cyano-piperidine-1-carbonyl)-2,2-dimethyl-propyl]-amide;

2-(1-Cyclopropyl-1H-pyrazol-4-yl)-5H-pyrrolo[2,3-b]pyrazine-7-carboxylic acid [(R)-1-(4-cyano-piperidine-1-carbonyl)-2,2-dimethyl-propyl]-amide;

2-[1-(2,2,2-Trifluoro-ethyl)-1H-pyrazol-4-yl]-5H-pyrrolo[2,3-b]pyrazine-7-carboxylic acid [(R)-1-(4-cyano-piperidine-1-carbonyl)-2,2-dimethyl-propyl]-amide;

2-Cyclopropyl-5H-pyrrolo[2,3-b]pyrazine-7-carboxylic acid [(R)-2-((S)-3-cyano-pyrrolidin-1-yl)-1-cyclopropyl-2-oxo-ethyl]-amide;

2-(1-Methyl-1H-pyrazol-4-yl)-5H-pyrrolo[2,3-b]pyrazine-7-carboxylic acid [(R)-2-((S)-3-cyano-pyrrolidin-1-yl)-1-cyclopropyl-2-oxo-ethyl]-amide;

2-(1-Methyl-1H-pyrazol-4-yl)-5H-pyrrolo[2,3-b]pyrazine-7-carboxylic acid [(R)-2-((R)-3-cyano-pyrrolidin-1-yl)-1-cyclopropyl-2-oxo-ethyl]-amide;

2-Cyclopropyl-5H-pyrrolo[2,3-b]pyrazine-7-carboxylic acid [(R)-2-((R)-3-cyano-pyrrolidin-1-yl)-1-cyclopropyl-2-oxo-ethyl]-amide;

2-Cyclopropyl-5H-pyrrolo[2,3-b]pyrazine-7-carboxylic acid [(R)-1-cyclopropyl-2-(2-oxa-6-aza-spiro[3.3]hept-6-yl)-2-oxo-ethyl]-amide;

2-(1-Methyl-1H-pyrazol-4-yl)-5H-pyrrolo[2,3-b]pyrazine-7-carboxylic acid [(R)-1-cyclopropyl-2-(2-oxa-6-aza-spiro[3.3]hept-6-yl)-2-oxo-ethyl]-amide;

2-Cyclopropyl-5H-pyrrolo[2,3-b]pyrazine-7-carboxylic acid [(R)-1-cyclopropyl-2-((1S,5R,6R)-6-hydroxymethyl-3-aza-bicyclo[3.1.0]hex-3-yl)-2-oxo-ethyl]-amide;

2-(1-Methyl-1H-pyrazol-4-yl)-5H-pyrrolo[2,3-b]pyrazine-7-carboxylic acid [(R)-1-cyclopropyl-2-((1S,5R,6R)-6-hydroxymethyl-3-aza-bicyclo[3.1.0]hex-3-yl)-2-oxo-ethyl]-amide;

2-Cyclopropyl-5H-pyrrolo[2,3-b]pyrazine-7-carboxylic acid [(R)-1-cyclopropyl-2-(1,1-dioxo-1$\lambda^6$-thiomorpholin-4-yl)-2-oxo-ethyl]-amide;

2-(1-Methyl-1H-pyrazol-4-yl)-5H-pyrrolo[2,3-b]pyrazine-7-carboxylic acid [(R)-1-cyclopropyl-2-(1,1-dioxo-1$\lambda^6$-thiomorpholin-4-yl)-2-oxo-ethyl]-amide;

2-Cyclohexyloxy-5H-pyrrolo[2,3-b]pyrazine-7-carboxylic acid [(R)-1-(4-cyano-piperidine-1-carbonyl)-2,2-dimethyl-propyl]-amide;

2-(3,3,3-Trifluoro-propoxy)-5H-pyrrolo[2,3-b]pyrazine-7-carboxylic acid [(R)-1-(4-cyano-piperidine-1-carbonyl)-2,2-dimethyl-propyl]-amide;

2-Cyclopentyloxy-5H-pyrrolo[2,3-b]pyrazine-7-carboxylic acid [(R)-1-(4-cyano-piperidine-1-carbonyl)-2,2-dimethyl-propyl]-amide;

2-(2,2,2-Trifluoro-ethoxy)-5H-pyrrolo[2,3-b]pyrazine-7-carboxylic acid [(R)-1-(4-cyano-piperidine-1-carbonyl)-2,2-dimethyl-propyl]-amide;

2-Isopropoxy-5H-pyrrolo[2,3-b]pyrazine-7-carboxylic acid [(R)-1-(4-cyano-piperidine-1-carbonyl)-2,2-dimethyl-propyl]-amide;

2-(4-Chloro-1-oxo-1,3-dihydro-isoindol-2-yl)-5H-pyrrolo[2,3-b]pyrazine-7-carboxylic acid [(R)-2-(3-cyano-azetidin-1-yl)-1-cyclopropyl-2-oxo-ethyl]-amide;

2-(7-Chloro-thieno[3,2-b]pyridin-2-yl)-5H-pyrrolo[2,3-b]pyrazine-7-carboxylic acid [(R)-2-(3-cyano-azetidin-1-yl)-1-cyclopropyl-2-oxo-ethyl]-amide;

2-(7-Pyrrolidin-1-yl-thieno[3,2-b]pyridin-2-yl)-5H-pyrrolo[2,3-b]pyrazine-7-carboxylic acid [(R)-2-(3-cyano-azetidin-1-yl)-1-cyclopropyl-2-oxo-ethyl]-amide;

2-[7-(2,2,2-Trifluoro-ethoxy)-thieno[3,2-b]pyridin-2-yl]-5H-pyrrolo[2,3-b]pyrazine-7-carboxylic acid [(R)-2-(3-cyano-azetidin-1-yl)-1-cyclopropyl-2-oxo-ethyl]-amide;

2-(7-Methoxy-thieno[3,2-b]pyridin-2-yl)-5H-pyrrolo[2,3-b]pyrazine-7-carboxylic acid [(R)-2-(3-cyano-azetidin-1-yl)-1-cyclopropyl-2-oxo-ethyl]-amide;

2-(7-Chloro-thieno[3,2-b]pyridin-2-yl)-5H-pyrrolo[2,3-b]pyrazine-7-carboxylic acid [(R)-2-(3-cyano-azetidin-1-yl)-1-methyl-2-oxo-ethyl]-amide;

2-(7-Pyrrolidin-1-yl-thieno[3,2-b]pyridin-2-yl)-5H-pyrrolo[2,3-b]pyrazine-7-carboxylic acid [(R)-2-(3-cyano-azetidin-1-yl)-1-methyl-2-oxo-ethyl]-amide;

2-[7-(2,2,2-Trifluoro-ethoxy)-thieno[3,2-b]pyridin-2-yl]-5H-pyrrolo[2,3-b]pyrazine-7-carboxylic acid [(R)-2-(3-cyano-azetidin-1-yl)-1-methyl-2-oxo-ethyl]-amide;

2-(7-Methoxy-thieno[3,2-b]pyridin-2-yl)-5H-pyrrolo[2,3-b]pyrazine-7-carboxylic acid [(R)-2-(3-cyano-azetidin-1-yl)-1-methyl-2-oxo-ethyl]-amide;

2-(1,3-Dimethyl-1H-pyrazol-4-yl)-5H-pyrrolo[2,3-b]pyrazine-7-carboxylic acid [(R)-2-(3-cyano-azetidin-1-yl)-1-methyl-2-oxo-ethyl]-amide;

2-(1-Ethyl-1H-pyrazol-4-yl)-5H-pyrrolo[2,3-b]pyrazine-7-carboxylic acid [(S)-1-(4-cyano-piperidine-1-carbonyl)-3,3,3-trifluoro-propyl]-amide;

2-(1-Ethyl-1H-pyrazol-4-yl)-5H-pyrrolo[2,3-b]pyrazine-7-carboxylic acid [(R)-1-(4-cyano-piperidine-1-carbonyl)-3,3,3-trifluoro-propyl]-amide;

2-(1-Cyclopentyl-1H-[1,2,3]triazol-4-yl)-5H-pyrrolo[2,3-b]pyrazine-7-carboxylic acid [(R)-2-(4-cyano-piperidin-1-yl)-1-cyclopropyl-2-oxo-ethyl]-amide;

2-(1-Phenyl-1H-[1,2,3]triazol-4-yl)-5H-pyrrolo[2,3-b]pyrazine-7-carboxylic acid [(R)-2-(4-cyano-piperidin-1-yl)-1-cyclopropyl-2-oxo-ethyl]-amide;

2-(3-Pyrrolidin-1-yl-phenyl)-5H-pyrrolo[2,3-b]pyrazine-7-carboxylic acid [(R)-2-(3-cyano-azetidin-1-yl)-1-methyl-2-oxo-ethyl]-amide;

2-(3-Methylcarbamoyl-phenyl)-5H-pyrrolo[2,3-b]pyrazine-7-carboxylic acid [(R)-2-(3-cyano-azetidin-1-yl)-1-methyl-2-oxo-ethyl]-amide;

2-(3-Isopropylcarbamoyl-phenyl)-5H-pyrrolo[2,3-b]pyrazine-7-carboxylic acid [(R)-2-(3-cyano-azetidin-1-yl)-1-methyl-2-oxo-ethyl]-amide;

2-[3-(Cyclopropylmethyl-carbamoyl)-phenyl]-5H-pyrrolo[2,3-b]pyrazine-7-carboxylic acid [(R)-2-(3-cyano-azetidin-1-yl)-1-methyl-2-oxo-ethyl]-amide;

2-(4-Cyclopent-1-enyl-pyridin-2-yl)-5H-pyrrolo[2,3-b]pyrazine-7-carboxylic acid [(R)-2-(3-cyano-azetidin-1-yl)-1-methyl-2-oxo-ethyl]-amide;

2-Cyclopropyl-5H-pyrrolo[2,3-b]pyrazine-7-carboxylic acid [(R)-2-(4-cyano-piperidin-1-yl)-2-oxo-1-phenyl-ethyl]-amide;

2-Pyridin-2-yl-5H-pyrrolo[2,3-b]pyrazine-7-carboxylic acid [(R)-1-(4-cyano-piperidine-1-carbonyl)-2,2-dimethyl-propyl]-amide;

2-Cyclopropyl-5H-pyrrolo[2,3-b]pyrazine-7-carboxylic acid [(R)-2-(4-cyano-piperidin-1-yl)-1-cyclopropylmethyl-2-oxo-ethyl]-amide;

2-[1-(4-Fluoro-phenyl)-1H-pyrazol-4-yl]-5H-pyrrolo[2,3-b]pyrazine-7-carboxylic acid [(R)-1-(4-cyano-piperidine-1-carbonyl)-2,2-dimethyl-propyl]-amide;

2-(4-Trifluoromethyl-pyridin-2-yl)-5H-pyrrolo[2,3-b]pyrazine-7-carboxylic acid [(R)-1-(4-cyano-piperidine-1-carbonyl)-2,2-dimethyl-propyl]-amide;

2-(1-Cyclopropylmethyl-1H-imidazol-4-yl)-5H-pyrrolo[2,3-b]pyrazine-7-carboxylic acid [(R)-1-(4-cyano-piperidine-1-carbonyl)-2,2-dimethyl-propyl]-amide;

2-(1-Cyclopentyl-1H-imidazol-4-yl)-5H-pyrrolo[2,3-b]pyrazine-7-carboxylic acid [(R)-1-(4-cyano-piperidine-1-carbonyl)-2,2-dimethyl-propyl]-amide;

2-(1-Cyclopentyl-1H-imidazol-4-yl)-5H-pyrrolo[2,3-b]pyrazine-7-carboxylic acid [(R)-2-(4-cyano-piperidin-1-yl)-1-cyclopropyl-2-oxo-ethyl]-amide;

2-[1-(2,2,2-Trifluoro-ethyl)-1H-imidazol-4-yl]-5H-pyrrolo[2,3-b]pyrazine-7-carboxylic acid [(R)-1-(4-cyano-piperidine-1-carbonyl)-2,2-dimethyl-propyl]-amide;

2-[3-(3,3-Dimethyl-pyrrolidin-1-yl)-phenyl]-5H-pyrrolo[2,3-b]pyrazine-7-carboxylic acid [(R)-2-(3-cyano-azetidin-1-yl)-1-methyl-2-oxo-ethyl]-amide;

2-Cyclopropyl-5H-pyrrolo[2,3-b]pyrazine-7-carboxylic acid [(1R,2S)-1-(4-cyano-piperidine-1-carbonyl)-2-methyl-butyl]-amide;

2-(3,4,5-Trimethoxy-phenyl)-5H-pyrrolo[2,3-b]pyrazine-7-carboxylic acid [(R)-2-(3-cyano-azetidin-1-yl)-1-methyl-2-oxo-ethyl]-amide;

2-[(1S,5R)-3-(3-Aza-bicyclo[3.1.0]hex-3-yl)-phenyl]-5H-pyrrolo[2,3-b]pyrazine-7-carboxylic acid [(R)-2-(3-cyano-azetidin-1-yl)-1-methyl-2-oxo-ethyl]-amide;

2-(4-Methoxy-pyridin-2-yl)-5H-pyrrolo[2,3-b]pyrazine-7-carboxylic acid [(R)-1-(4-cyano-piperidine-1-carbonyl)-2,2-dimethyl-propyl]-amide;

2-(4-Trifluoromethyl-phenyl)-5H-pyrrolo[2,3-b]pyrazine-7-carboxylic acid [(R)-1-(4-cyano-piperidine-1-carbonyl)-2,2-dimethyl-propyl]-amide;

2-(4-Cyclopropylmethoxy-pyridin-2-yl)-5H-pyrrolo[2,3-b]pyrazine-7-carboxylic acid [(R)-2-(4-cyano-piperidin-1-yl)-1-cyclopropyl-2-oxo-ethyl]-amide;

2-(4-Cyclopentyloxy-pyridin-2-yl)-5H-pyrrolo[2,3-b]pyrazine-7-carboxylic acid [(R)-1-(4-cyano-piperidine-1-carbonyl)-2,2-dimethyl-propyl]-amide;

2-(4-Cyclopropylmethoxy-pyridin-2-yl)-5H-pyrrolo[2,3-b]pyrazine-7-carboxylic acid [(R)-2-(3-cyano-azetidin-1-yl)-1-methyl-2-oxo-ethyl]-amide;

2-[1-(2,5-Difluoro-phenyl)-1H-imidazol-4-yl]-5H-pyrrolo[2,3-b]pyrazine-7-carboxylic acid [(R)-2-(3-cyano-azetidin-1-yl)-1-cyclopropyl-2-oxo-ethyl]-amide;

2-[1-(2,3,5-Trifluoro-phenyl)-1H-imidazol-4-yl]-5H-pyrrolo[2,3-b]pyrazine-7-carboxylic acid [(R)-2-(3-cyano-azetidin-1-yl)-1-cyclopropyl-2-oxo-ethyl]-amide;

2-(1-Ethyl-1H-pyrazol-4-yl)-5H-pyrrolo[2,3-b]pyrazine-7-carboxylic acid [(R)-1-(4,4-difluoro-piperidine-1-carbonyl)-2,2-dimethyl-propyl]-amide;

2-Cyclopropyl-5H-pyrrolo[2,3-b]pyrazine-7-carboxylic acid [(R)-1-(7,8-dihydro-5H-[1,6]naphthyridine-6-carbonyl)-2,2-dimethyl-propyl]-amide;

2-Cyclopropyl-5H-pyrrolo[2,3-b]pyrazine-7-carboxylic acid [(R)-2-(3-cyano-azetidin-1-yl)-2-oxo-1-(tetrahydro-pyran-4-yl)-ethyl]-amide;

2-Cyclopropyl-5H-pyrrolo[2,3-b]pyrazine-7-carboxylic acid [(S)-2-(3-cyano-azetidin-1-yl)-2-oxo-1-(tetrahydro-pyran-4-yl)-ethyl]-amide;

2-Cyclopropyl-5H-pyrrolo[2,3-b]pyrazine-7-carboxylic acid [(R)-1-(2,3-dihydro-indole-1-carbonyl)-2,2-dimethyl-propyl]-amide;

2-(1-Ethyl-1H-pyrazol-4-yl)-5H-pyrrolo[2,3-b]pyrazine-7-carboxylic acid [(R)-1-cyclopropyl-2-(3,3-difluoro-pyrrolidin-1-yl)-2-oxo-ethyl]-amide;

2-(1-Ethyl-1H-pyrazol-4-yl)-5H-pyrrolo[2,3-b]pyrazine-7-carboxylic acid [(R)-1-(4-hydroxy-4-methyl-piperidine-1-carbonyl)-2,2-dimethyl-propyl]-amide;

2-Cyclopropyl-5H-pyrrolo[2,3-b]pyrazine-7-carboxylic acid [(R)-2-(3-cyano-3-methyl-azetidin-1-yl)-1-cyclopropyl-2-oxo-ethyl]-amide;

2-(1-Methyl-1H-pyrazol-4-yl)-5H-pyrrolo[2,3-b]pyrazine-7-carboxylic acid [(R)-2-(3-cyano-3-methyl-azetidin-1-yl)-1-cyclopropyl-2-oxo-ethyl]-amide;

2-(1-Methyl-1H-pyrazol-4-yl)-5H-pyrrolo[2,3-b]pyrazine-7-carboxylic acid [(R)-1-(3-cyano-3-methyl-azetidine-1-carbonyl)-2,2-dimethyl-propyl]-amide;

2-(1-Ethyl-1H-pyrazol-4-yl)-5H-pyrrolo[2,3-b]pyrazine-7-carboxylic acid [(R)-1-cyclopropyl-2-(4,4-difluoro-piperidin-1-yl)-2-oxo-ethyl]-amide;

2-(4-tert-Butyl-pyridin-2-yl)-5H-pyrrolo[2,3-b]pyrazine-7-carboxylic acid [(R)-2-(4-cyano-piperidin-1-yl)-1-cyclopropyl-2-oxo-ethyl]-amide;

2-(1-Ethyl-1H-pyrazol-4-yl)-5H-pyrrolo[2,3-b]pyrazine-7-carboxylic acid [(R)-1-cyclopropyl-2-(4-hydroxy-4-trifluoromethyl-piperidin-1-yl)-2-oxo-ethyl]-amide;

2-(4-Phenyl-pyridin-2-yl)-5H-pyrrolo[2,3-b]pyrazine-7-carboxylic acid [(R)-2-(4-cyano-piperidin-1-yl)-1-cyclopropyl-2-oxo-ethyl]-amide;

2-(1-Ethyl-1H-pyrazol-4-yl)-5H-pyrrolo[2,3-b]pyrazine-7-carboxylic acid [(R)-1-cyclopropyl-2-(3-hydroxy-3-methyl-azetidin-1-yl)-2-oxo-ethyl]-amide;

2-Cyclopropyl-5H-pyrrolo[2,3-b]pyrazine-7-carboxylic acid [(1R,2R)-1-(4-cyano-piperidine-1-carbonyl)-2-methyl-butyl]-amide;

2-(1-Methyl-1H-pyrazol-4-yl)-5H-pyrrolo[2,3-b]pyrazine-7-carboxylic acid [(R)-1-cyclopropyl-2-(3,3-difluoro-azetidin-1-yl)-2-oxo-ethyl]-amide;

2-(1-Methyl-1H-pyrazol-4-yl)-5H-pyrrolo[2,3-b]pyrazine-7-carboxylic acid [(R)-2-(3-cyano-3-ethyl-azetidin-1-yl)-1-cyclopropyl-2-oxo-ethyl]-amide;

2-(4-Pyrazol-1-yl-pyridin-2-yl)-5H-pyrrolo[2,3-b]pyrazine-7-carboxylic acid [(R)-2-(3-cyano-azetidin-1-yl)-1-methyl-2-oxo-ethyl]-amide;

2-(4-Pyrrol-1-yl-pyridin-2-yl)-5H-pyrrolo[2,3-b]pyrazine-7-carboxylic acid [(R)-2-(3-cyano-azetidin-1-yl)-1-methyl-2-oxo-ethyl]-amide;

2-(4-Thiophen-2-yl-pyridin-2-yl)-5H-pyrrolo[2,3-b]pyrazine-7-carboxylic acid [(R)-2-(4-cyano-piperidin-1-yl)-1-cyclopropyl-2-oxo-ethyl]-amide;

2-(4-Methylcarbamoyl-pyridin-2-yl)-5H-pyrrolo[2,3-b]pyrazine-7-carboxylic acid [(R)-2-(3-cyano-azetidin-1-yl)-1-methyl-2-oxo-ethyl]-amide;

2-(2-Chloro-thiazol-5-yl)-5H-pyrrolo[2,3-b]pyrazine-7-carboxylic acid [(R)-1-(4-cyano-piperidine-1-carbonyl)-2,2-dimethyl-propyl]-amide;

2-[1-(3,5-Difluoro-phenyl)-2-methyl-1H-imidazol-4-yl]-5H-pyrrolo[2,3-b]pyrazine-7-carboxylic acid [(R)-1-(3-cyano-azetidine-1-carbonyl)-2,2-dimethyl-propyl]-amide;

2-[1-(3-Fluoro-phenyl)-2-methyl-1H-imidazol-4-yl]-5H-pyrrolo[2,3-b]pyrazine-7-carboxylic acid [(R)-1-(3-cyano-azetidine-1-carbonyl)-2,2-dimethyl-propyl]-amide;

2-(2-Methyl-1-phenyl-1H-imidazol-4-yl)-5H-pyrrolo[2,3-b]pyrazine-7-carboxylic acid [(R)-2-(3-cyano-azetidin-1-yl)-1-cyclopropyl-2-oxo-ethyl]-amide;

2-(4-Trifluoromethyl-phenyl)-5H-pyrrolo[2,3-b]pyrazine-7-carboxylic acid [(R)-2-(3-cyano-azetidin-1-yl)-1-cyclopropyl-2-oxo-ethyl]-amide;

2-[4-(4-Acetyl-piperazin-1-yl)-phenyl]-5H-pyrrolo[2,3-b]pyrazine-7-carboxylic acid [(R)-2-(3-cyano-azetidin-1-yl)-1-cyclopropyl-2-oxo-ethyl]-amide;

2-[4-(4-Methyl-piperazin-1-yl)-phenyl]-5H-pyrrolo[2,3-b]pyrazine-7-carboxylic acid [(R)-2-(3-cyano-azetidin-1-yl)-1-cyclopropyl-2-oxo-ethyl]-amide;

2-(4-Morpholin-4-yl-phenyl)-5H-pyrrolo[2,3-b]pyrazine-7-carboxylic acid [(R)-2-(3-cyano-azetidin-1-yl)-1-cyclopropyl-2-oxo-ethyl]-amide;

2-(4-Dimethylamino-phenyl)-5H-pyrrolo[2,3-b]pyrazine-7-carboxylic acid [(R)-2-(3-cyano-azetidin-1-yl)-1-cyclopropyl-2-oxo-ethyl]-amide;

2-[2-Methyl-1-(2,2,2-trifluoro-ethyl)-1H-imidazol-4-yl]-5H-pyrrolo[2,3-b]pyrazine-7-carboxylic acid [(R)-2-(3-cyano-azetidin-1-yl)-1-cyclopropyl-2-oxo-ethyl]-amide; and 2-Phenyl-5H-pyrrolo[2,3-b]pyrazine-7-carboxylic acid [(R)-2-(3-cyano-azetidin-1-yl)-1-cyclopropyl-2-oxo-ethyl]-amide.

The application provides a method for treating an inflammatory or autoimmune condition comprising administering to a patient in need thereof a therapeutically effective amount of the compound of Formula I.

The application provides the above method, further comprising administering an additional therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating diabetes, or an agent for treating immunodeficiency disorders.

The application provides a method for treating rheumatoid arthritis comprising administering to a patient in need thereof a therapeutically effective amount of the compound of Formula I.

The application provides a method for treating asthma comprising administering to a patient in need thereof a therapeutically effective amount of the compound of Formula I.

The application provides a method for treating an inflammatory condition comprising administering to a patient in need thereof a therapeutically effective amount of the compound of Formula I.

The application provides a method for inhibiting T-cell proliferative disorder comprising administering to a patient in need thereof a therapeutically effective amount of the compound of Formula I.

The application provides a method for inhibiting T-cell proliferative disorder comprising administering to a patient in need thereof a therapeutically effective amount of the compound of Formula I The application provides the above method, wherein the proliferative disorder is cancer.

The application provides a method for treating a B-cell proliferative disorder comprising administering to a patient in need thereof a therapeutically effective amount of the compound of Formula I.

The application provides a method for treating an immune disorder including lupus, multiple sclerosis, rheumatoid arthritis, psoriasis, Type I diabetes, complications from organ transplants, xeno transplantation, diabetes, cancer, asthma, atopic dermatitis, autoimmune thyroid disorders, ulcerative colitis, Crohn's disease, Alzheimer's disease, and Leukemia, comprising administering to a patient in need thereof a therapeutically effective amount of the compound of Formula I.

The application provides a method for preventing or treating all forms of organ rejection, including acute allograft or xenograft rejection and chronic allograft or xenograft rejection, of vascularized or non-vascularized transplants, comprising administering to a patient in need thereof the compound of Formula I.

The application provides a method for inhibiting JAK3 activity comprising administering the compound of Formula I, wherein the compound exhibits an $IC_{50}$ of 50 micromolar or less in an in vitro biochemical assay of JAK3 activity.

The application provides the above method, wherein the compound exhibits an $IC_{50}$ of 100 nanomolar or less in an in vitro biochemical assay of JAK3 activity.

The application provides the above method, wherein the compound exhibits an $IC_{50}$ of 10 nanomolar or less in an in vitro biochemical assay of JAK3 activity.

A method for inhibiting SYK activity comprising administering the compound of Formula I, wherein the compound exhibits an $IC_{50}$ of 50 micromolar or less in an in vitro biochemical assay of SYK activity.

The application provides the above method, wherein the compound exhibits an $IC_{50}$ of 100 nanomolar or less in an in vitro biochemical assay of SYK activity.

The application provides the above method, wherein the compound exhibits an $IC_{50}$ of 10 nanomolar or less in an in vitro biochemical assay of SYK activity.

The application provides a method for treating an inflammatory condition comprising co-administering to a patient in need thereof a therapeutically effective amount of an anti-inflammatory compound in combination with the compound of Formula I.

The application provides a method for treating an immune disorder comprising co-administering to a patient in need thereof a therapeutically effective amount of an immunosuppressant compound in combination with the compound of Formula I.

The application provides a pharmaceutical composition comprising the compound of Formula I, admixed with at least one pharmaceutically acceptable carrier, excipient or diluent.

The application provides the above composition, further comprising an additional therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating diabetes, and an agent for treating immunodeficiency disorders.

The application provides a process for preparing the compound of Formula I.

The application provides a use of the compound of Formula I in the manufacture of a medicament for the treatment of an inflammatory disorder.

The application provides a use of the compound of Formula I in the manufacture of a medicament for the treatment of an autoimmune disorder.

The application provides the invention as hereinbefore described.

Compounds

Examples of representative compounds encompassed by the present invention and within the scope of the invention are provided in the following Table. These examples and preparations which follow are provided to enable those skilled in the art to more clearly understand and to practice the present invention. They should not be considered as limiting the scope of the invention, but merely as being illustrative and representative thereof.

In general, the nomenclature used in this Application is based on AUTONOM™ v.4.0, a Beilstein Institute computerized system for the generation of IUPAC systematic nomenclature. If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

TABLE I depicts exemplified compounds according to Formula I.

TABLE I

| COMPOUND | STRUCTURE | SYSTEMATIC NAME | MP |
|---|---|---|---|
| I-1 | 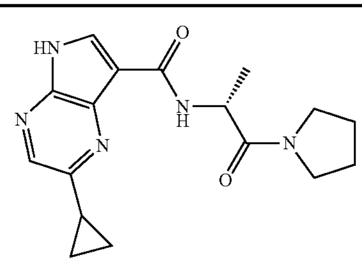 | 2-Cyclopropyl-5H-pyrrolo[2,3-b]pyrazine-7-carboxylic acid ((R)-1-methyl-2-oxo-2-pyrrolidin-1-yl-ethyl)-amide | 237.0-239.0 |
| I-2 | 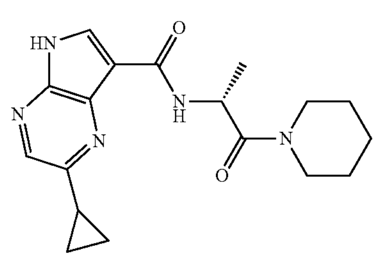 [SMILES: C[C@@H](NC(=O)c1c[nH]c2ncc(C3CC3)nc12)C(=O)N1CCCCC1] | 2-Cyclopropyl-5H-pyrrolo[2,3-b]pyrazine-7-carboxylic acid ((R)-1-methyl-2-oxo-2-piperidin-1-yl-ethyl)-amide | 190.0-192.0 |
| I-3 | 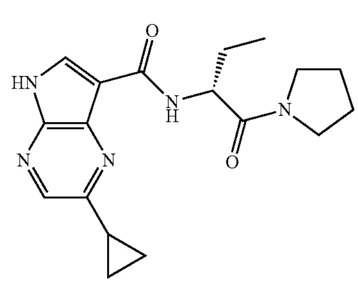 [SMILES: CC[C@@H](NC(=O)c1c[nH]c2ncc(C3CC3)nc12)C(=O)N1CCCC1] | 2-Cyclopropyl-5H-pyrrolo[2,3-b]pyrazine-7-carboxylic acid [(R)-1-(pyrrolidine-1-carbonyl)-propyl]-amide | 240.9-242.5 |

TABLE I-continued

| COMPOUND | STRUCTURE | SYSTEMATIC NAME | MP |
|---|---|---|---|
| I-4 | 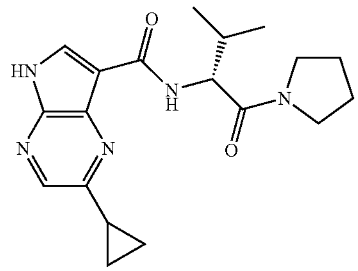 [SMILES: CC(C)[C@@H](NC(=O)c1c[nH]c2ncc(C3CC3)nc12)C(=O)N1CCCC1] | 2-Cyclopropyl-5H-pyrrolo[2,3-b]pyrazine-7-carboxylic acid [(R)-2-methyl-1-(pyrrolidine-1-carbonyl)-propyl]-amide | 171.0-172.1 |
| I-5 | 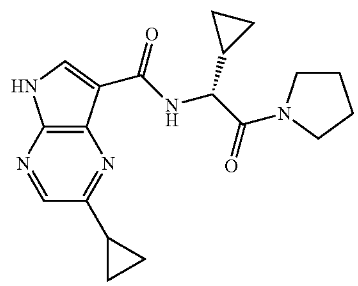 [SMILES: O=C(N[C@@H](C(=O)N1CCCC1)C1CC1)c1c[nH]c2ncc(C3CC3)nc12] | 2-Cyclopropyl-5H-pyrrolo[2,3-b]pyrazine-7-carboxylic acid ((R)-1-cyclopropyl-2-oxo-2-pyrrolidin-1-yl-ethyl)-amide | 254.0-256.0 |
| I-6 | 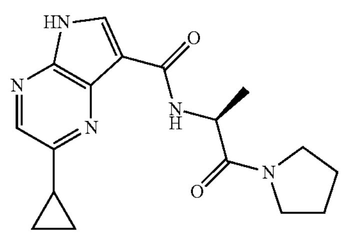 [SMILES: C[C@H](NC(=O)c1c[nH]c2ncc(C3CC3)nc12)C(=O)N1CCCC1] | 2-Cyclopropyl-5H-pyrrolo[2,3-b]pyrazine-7-carboxylic acid ((S)-1-methyl-2-oxo-2-pyrrolidin-1-yl-ethyl)-amide | |
| I-7 | 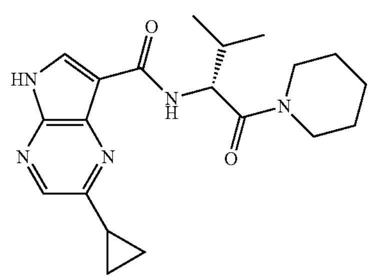 [SMILES: CC(C)[C@@H](NC(=O)c1c[nH]c2ncc(C3CC3)nc12)C(=O)N1CCCCC1] | 2-Cyclopropyl-5H-pyrrolo[2,3-b]pyrazine-7-carboxylic acid [(R)-2-methyl-1-(piperidine-1-carbonyl)-propyl]-amide | 183.0-185.0 |
| I-8 | 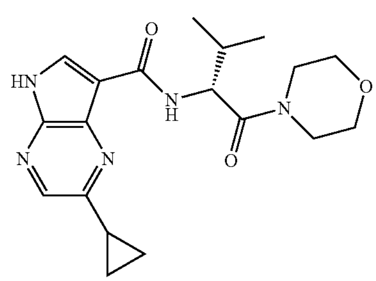 [SMILES: CC(C)[C@@H](NC(=O)c1c[nH]c2ncc(C3CC3)nc12)C(=O)N1CCOCC1] | 2-Cyclopropyl-5H-pyrrolo[2,3-b]pyrazine-7-carboxylic acid [(R)-2-methyl-1-(morpholine-4-carbonyl)-propyl]-amide | 154.0-156.0 |

TABLE I-continued

| COMPOUND | STRUCTURE | SYSTEMATIC NAME | MP |
|---|---|---|---|
| I-9 | 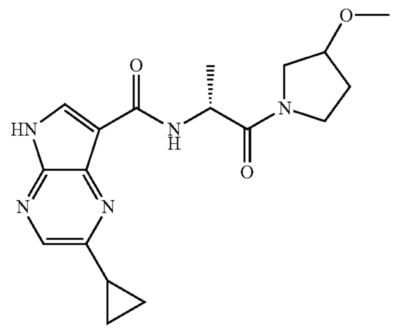 [SMILES: COC1CCN(C(=O)[C@@H](C)NC(=O)c2c[nH]c3ncc(C4CC4)nc23)C1] | 2-Cyclopropyl-5H-pyrrolo[2,3-b]pyrazine-7-carboxylic acid [(R)-2-(3-methoxy-pyrrolidin-1-yl)-1-methyl-2-oxo-ethyl]-amide | |
| I-10 | 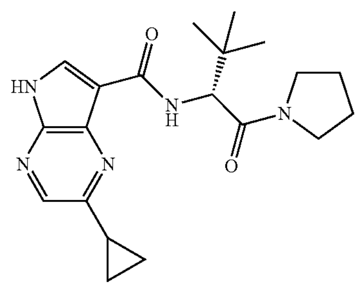 [SMILES: CC(C)(C)[C@@H](NC(=O)c1c[nH]c2ncc(C3CC3)nc12)C(=O)N1CCCC1] | 2-Cyclopropyl-5H-pyrrolo[2,3-b]pyrazine-7-carboxylic acid [(R)-2,2-dimethyl-1-(pyrrolidine-1-carbonyl)-propyl]-amide | 201.0-203.0 |
| I-11 | 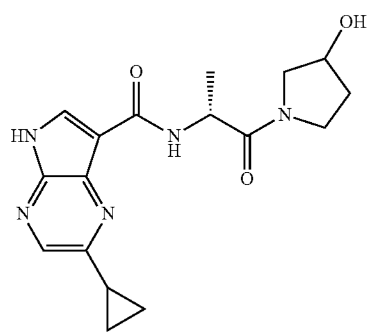 | 2-Cyclopropyl-5H-pyrrolo[2,3-b]pyrazine-7-carboxylic acid [(R)-2-(3-hydroxy-pyrrolidin-1-yl)-1-methyl-2-oxo-ethyl]-amide | |
| I-12 | 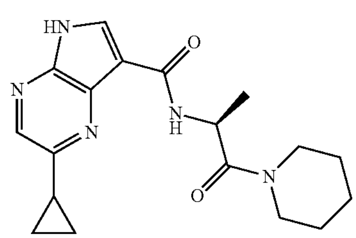 [SMILES: C[C@H](NC(=O)c1c[nH]c2ncc(C3CC3)nc12)C(=O)N1CCCCC1] | 2-Cyclopropyl-5H-pyrrolo[2,3-b]pyrazine-7-carboxylic acid ((S)-1-methyl-2-oxo-2-piperidin-1-yl-ethyl)-amide | |
| I-13 | 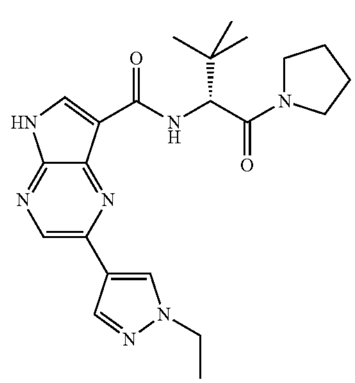 [SMILES: CCn1cc(-c2cnc3[nH]cc(C(=O)N[C@@H](C(=O)N4CCCC4)C(C)(C)C)c3n2)cn1] | 2-(1-Ethyl-1H-pyrazol-4-yl)-5H-pyrrolo[2,3-b]pyrazine-7-carboxylic acid [(R)-2,2-dimethyl-1-(pyrrolidine-1-carbonyl)-propyl]-amide | |

TABLE I-continued

| COMPOUND | STRUCTURE | SYSTEMATIC NAME | MP |
|---|---|---|---|
| I-14 | 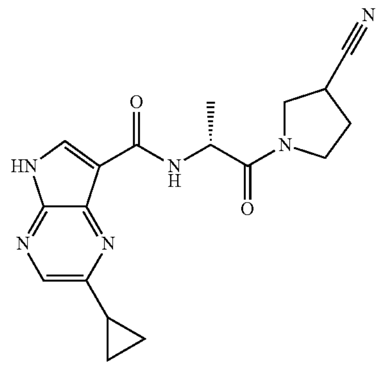 [SMILES: C[C@@H](NC(=O)c1c[nH]c2ncc(C3CC3)nc12)C(=O)N1CCC(C#N)C1] | 2-Cyclopropyl-5H-pyrrolo[2,3-b]pyrazine-7-carboxylic acid [(R)-2-(3-cyano-pyrrolidin-1-yl)-1-methyl-2-oxo-ethyl]-amide | |
| I-15 | 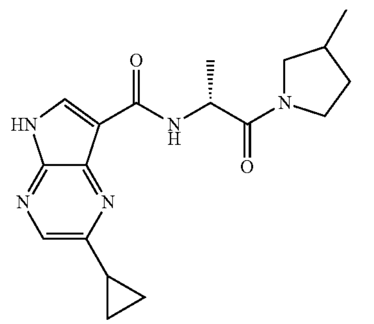 [SMILES: CC1CCN(C(=O)[C@@H](C)NC(=O)c2c[nH]c3ncc(C4CC4)nc23)C1] | 2-Cyclopropyl-5H-pyrrolo[2,3-b]pyrazine-7-carboxylic acid [(R)-1-methyl-2-(3-methyl-pyrrolidin-1-yl)-2-oxo-ethyl]-amide | |
| I-16 | 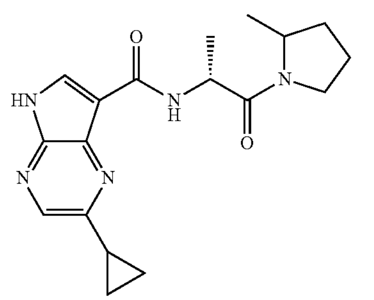 [SMILES: CC1CCCN1C(=O)[C@@H](C)NC(=O)c1c[nH]c2ncc(C3CC3)nc12] | 2-Cyclopropyl-5H-pyrrolo[2,3-b]pyrazine-7-carboxylic acid [(R)-1-methyl-2-(2-methyl-pyrrolidin-1-yl)-2-oxo-ethyl]-amide | |
| I-17 | 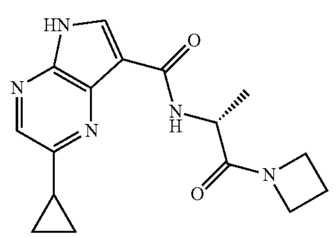 [SMILES: C[C@@H](NC(=O)c1c[nH]c2ncc(C3CC3)nc12)C(=O)N1CCC1] | 2-Cyclopropyl-5H-pyrrolo[2,3-b]pyrazine-7-carboxylic acid ((R)-2-azetidin-1-yl-1-methyl-2-oxo-ethyl)-amide | |
| I-18 | 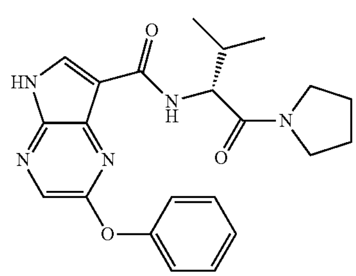 [SMILES: CC(C)[C@@H](NC(=O)c1c[nH]c2ncc(Oc3ccccc3)nc12)C(=O)N1CCCC1] | 2-Phenoxy-5H-pyrrolo[2,3-b]pyrazine-7-carboxylic acid [(R)-2-methyl-1-(pyrrolidine-1-carbonyl)-propyl]-amide | |

TABLE I-continued

| COMPOUND | STRUCTURE | SYSTEMATIC NAME | MP |
|---|---|---|---|
| I-19 | 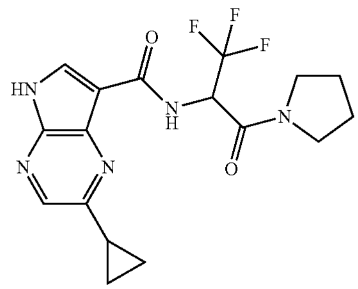 [SMILES: O=C(NC(C(=O)N1CCCC1)C(F)(F)F)c1c[nH]c2ncc(C3CC3)nc12] | 2-Cyclopropyl-5H-pyrrolo[2,3-b]pyrazine-7-carboxylic acid [2,2,2-trifluoro-1-(pyrrolidine-1-carbonyl)-ethyl]-amide | |
| I-20 | 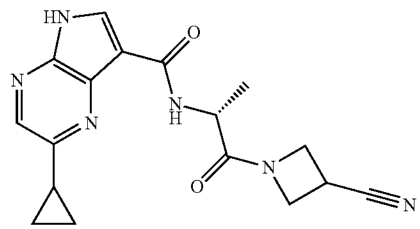 [SMILES: C[C@@H](NC(=O)c1c[nH]c2ncc(C3CC3)nc12)C(=O)N1CC(C#N)C1] | 2-Cyclopropyl-5H-pyrrolo[2,3-b]pyrazine-7-carboxylic acid [(R)-2-(3-cyano-azetidin-1-yl)-1-methyl-2-oxo-ethyl]-amide | |
| I-21 | 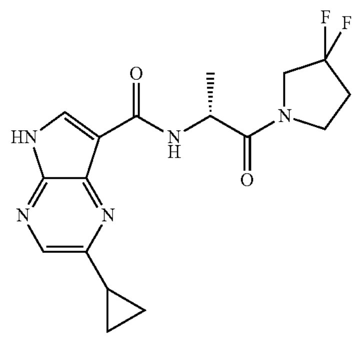 [SMILES: C[C@@H](NC(=O)c1c[nH]c2ncc(C3CC3)nc12)C(=O)N1CCC(F)(F)C1] | 2-Cyclopropyl-5H-pyrrolo[2,3-b]pyrazine-7-carboxylic acid [(R)-2-(3,3-difluoro-pyrrolidin-1-yl)-1-methyl-2-oxo-ethyl]-amide | |
| I-22 | 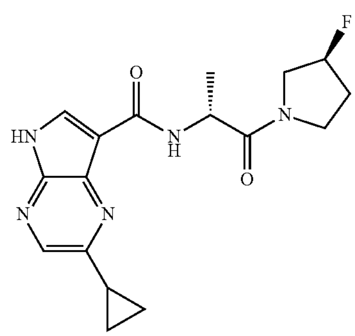 [SMILES: C[C@@H](NC(=O)c1c[nH]c2ncc(C3CC3)nc12)C(=O)N1CC[C@H](F)C1] | 2-Cyclopropyl-5H-pyrrolo[2,3-b]pyrazine-7-carboxylic acid [(R)-2-((S)-3-fluoro-pyrrolidin-1-yl)-1-methyl-2-oxo-ethyl]-amide | |
| I-23 | 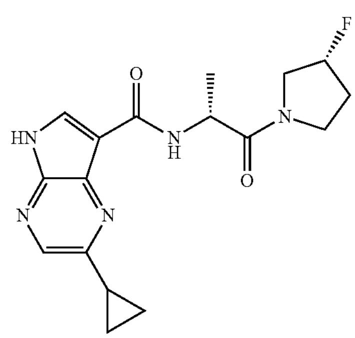 [SMILES: C[C@@H](NC(=O)c1c[nH]c2ncc(C3CC3)nc12)C(=O)N1CC[C@@H](F)C1] | 2-Cyclopropyl-5H-pyrrolo[2,3-b]pyrazine-7-carboxylic acid [(R)-2-((R)-3-fluoro-pyrrolidin-1-yl)-1-methyl-2-oxo-ethyl]-amide | |

TABLE I-continued

| COMPOUND | STRUCTURE | SYSTEMATIC NAME | MP |
|---|---|---|---|
| I-24 | 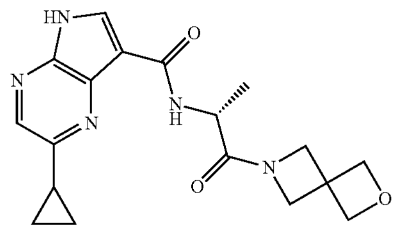 [SMILES: C[C@@H](NC(=O)c1c[nH]c2ncc(C3CC3)nc12)C(=O)N1CC2(COC2)C1] | 2-Cyclopropyl-5H-pyrrolo[2,3-b]pyrazine-7-carboxylic acid [(R)-1-methyl-2-(2-oxa-6-aza-spiro[3.3]hept-6-yl)-2-oxo-ethyl]-amide | |
| I-25 | 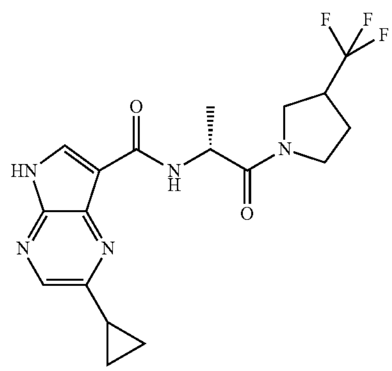 [SMILES: C[C@@H](NC(=O)c1c[nH]c2ncc(C3CC3)nc12)C(=O)N1CCC(C(F)(F)F)C1] | 2-Cyclopropyl-5H-pyrrolo[2,3-b]pyrazine-7-carboxylic acid [(R)-1-methyl-2-oxo-2-(3-trifluoromethyl-pyrrolidin-1-yl)-ethyl]-amide | |
| I-26 | 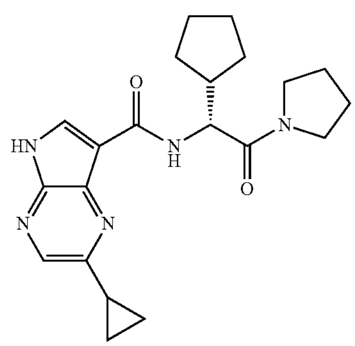 [SMILES: O=C(N[C@@H](C(=O)N1CCCC1)C1CCCC1)c1c[nH]c2ncc(C3CC3)nc12] | 2-Cyclopropyl-5H-pyrrolo[2,3-b]pyrazine-7-carboxylic acid ((R)-1-cyclopentyl-2-oxo-2-pyrrolidin-1-yl-ethyl)-amide | |
| I-27 | 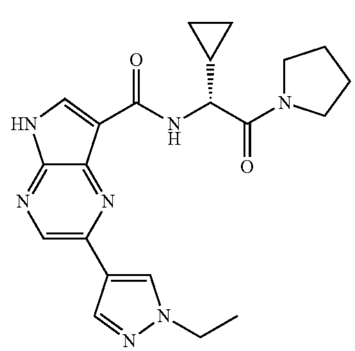 [SMILES: CCn1cc(-c2cnc3[nH]cc(C(=O)N[C@@H](C(=O)N4CCCC4)C4CC4)c3n2)cn1] | 2-(1-Ethyl-1H-pyrazol-4-yl)-5H-pyrrolo[2,3-b]pyrazine-7-carboxylic acid ((R)-1-cyclopropyl-2-oxo-2-pyrrolidin-1-yl-ethyl)-amide | 210-212 |

TABLE I-continued

| COMPOUND | STRUCTURE | SYSTEMATIC NAME | MP |
|---|---|---|---|
| I-28 | 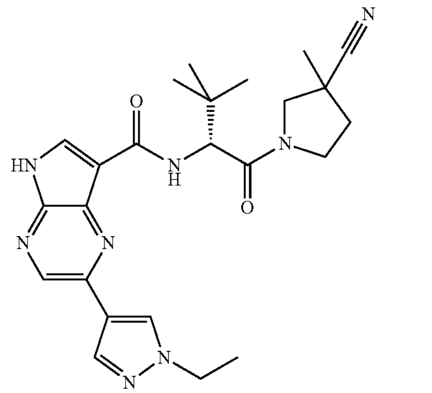 [SMILES: CCn1cc(-c2cnc3[nH]cc(C(=O)N[C@@H](C(=O)N4CCC(C)(C#N)C4)C(C)(C)C)c3n2)cn1] | 2-(1-Ethyl-1H-pyrazol-4-yl)-5H-pyrrolo[2,3-b]pyrazine-7-carboxylic acid [(R)-1-(3-cyano-3-methyl-pyrrolidine-1-carbonyl)-2,2-dimethyl-propyl]-amide | 228-230 |
| I-29 | 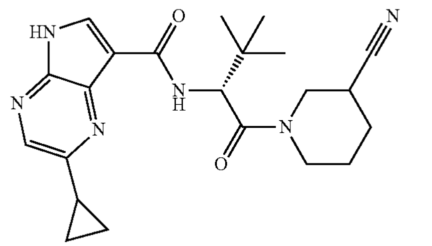 [SMILES: CC(C)(C)[C@@H](NC(=O)c1c[nH]c2ncc(C3CC3)nc12)C(=O)N1CCCC(C#N)C1] | 2-Cyclopropyl-5H-pyrrolo[2,3-b]pyrazine-7-carboxylic acid [(R)-1-(3-cyano-piperidine-1-carbonyl)-2,2-dimethyl-propyl]-amide | |
| I-30 | 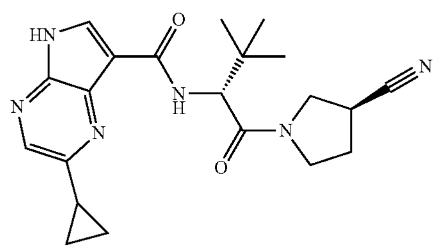 [SMILES: CC(C)(C)[C@@H](NC(=O)c1c[nH]c2ncc(C3CC3)nc12)C(=O)N1CC[C@H](C#N)C1] | 2-Cyclopropyl-5H-pyrrolo[2,3-b]pyrazine-7-carboxylic acid [(R)-1-((S)-3-cyano-pyrrolidine-1-carbonyl)-2,2-dimethyl-propyl]-amide | |
| I-31 | 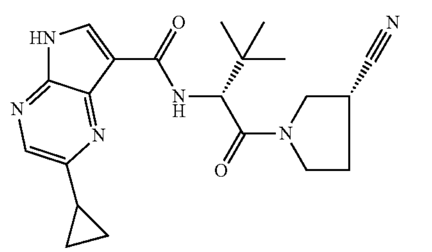 [SMILES: CC(C)(C)[C@@H](NC(=O)c1c[nH]c2ncc(C3CC3)nc12)C(=O)N1CC[C@@H](C#N)C1] | 2-Cyclopropyl-5H-pyrrolo[2,3-b]pyrazine-7-carboxylic acid [(R)-1-((R)-3-cyano-pyrrolidine-1-carbonyl)-2,2-dimethyl-propyl]-amide | |
| I-32 | 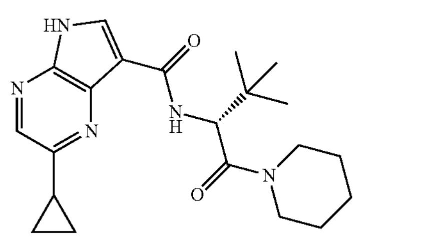 [SMILES: CC(C)(C)[C@@H](NC(=O)c1c[nH]c2ncc(C3CC3)nc12)C(=O)N1CCCCC1] | 2-Cyclopropyl-5H-pyrrolo[2,3-b]pyrazine-7-carboxylic acid [(R)-2,2-dimethyl-1-(piperidine-1-carbonyl)-propyl]-amide | |

TABLE I-continued

| COMPOUND | STRUCTURE | SYSTEMATIC NAME | MP |
|---|---|---|---|
| I-33 | 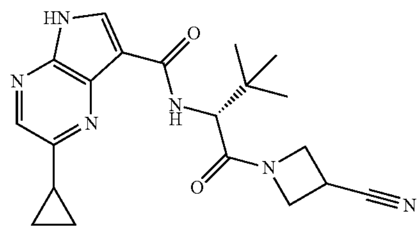 [SMILES: CC(C)(C)[C@@H](NC(=O)c1c[nH]c2ncc(C3CC3)nc12)C(=O)N1CC(C#N)C1] | 2-Cyclopropyl-5H-pyrrolo[2,3-b]pyrazine-7-carboxylic acid [(R)-1-(3-cyano-azetidine-1-carbonyl)-2,2-dimethyl-propyl]-amide | |
| I-34 | 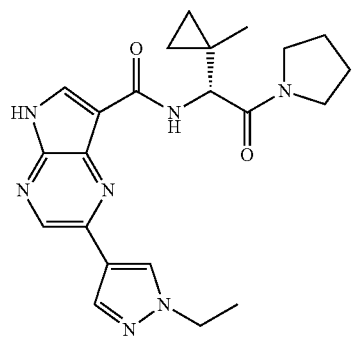 [SMILES: CCn1cc(-c2cnc3[nH]cc(C(=O)N[C@@H](C(=O)N4CCCC4)C4(C)CC4)c3n2)cn1] | 2-(1-Ethyl-1H-pyrazol-4-yl)-5H-pyrrolo[2,3-b]pyrazine-7-carboxylic acid [(R)-1-(1-methyl-cyclopropyl)-2-oxo-2-pyrrolidin-1-yl-ethyl]-amide | 218-220 |
| I-35 | 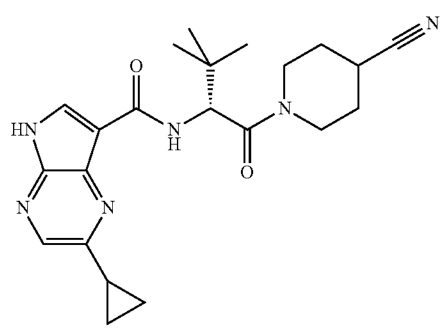 [SMILES: CC(C)(C)[C@@H](NC(=O)c1c[nH]c2ncc(C3CC3)nc12)C(=O)N1CCC(C#N)CC1] | 2-Cyclopropyl-5H-pyrrolo[2,3-b]pyrazine-7-carboxylic acid [(R)-1-(4-cyano-piperidine-1-carbonyl)-2,2-dimethyl-propyl]-amide | 249-251 |
| I-36 | 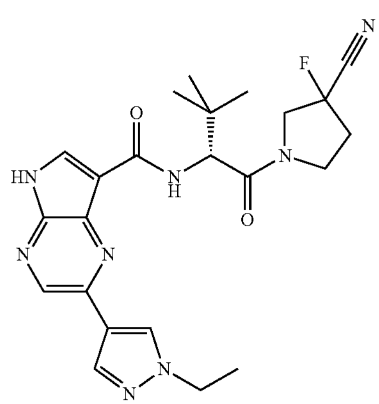 [SMILES: CCn1cc(-c2cnc3[nH]cc(C(=O)N[C@@H](C(=O)N4CCC(F)(C#N)C4)C(C)(C)C)c3n2)cn1] | 2-(1-Ethyl-1H-pyrazol-4-yl)-5H-pyrrolo[2,3-b]pyrazine-7-carboxylic acid [(R)-1-(3-cyano-3-fluoro-pyrrolidine-1-carbonyl)-2,2-dimethyl-propyl]-amide | |

TABLE I-continued

| COMPOUND | STRUCTURE | SYSTEMATIC NAME | MP |
|---|---|---|---|
| I-37 | 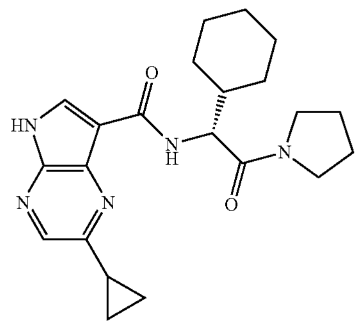 [SMILES: O=C(N[C@@H](C(=O)N1CCCC1)C1CCCCC1)c1c[nH]c2ncc(C3CC3)nc12] | 2-Cyclopropyl-5H-pyrrolo[2,3-b]pyrazine-7-carboxylic acid ((R)-1-cyclohexyl-2-oxo-2-pyrrolidin-1-yl-ethyl)-amide | |
| I-38 | 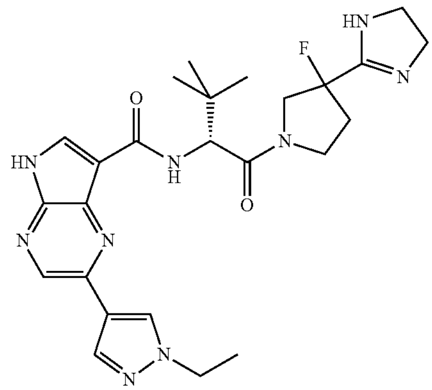 [SMILES: CCn1cc(-c2cnc3[nH]cc(C(=O)N[C@@H](C(=O)N4CCC(F)(C5=NCCN5)C4)C(C)(C)C)c3n2)cn1] | 2-(1-Ethyl-1H-pyrazol-4-yl)-5H-pyrrolo[2,3-b]pyrazine-7-carboxylic acid {(R)-1-[3-(4,5-dihydro-1H-imidazol-2-yl)-3-fluoro-pyrrolidine-1-carbonyl]-2,2-dimethyl-propyl}-amide | |
| I-39 | 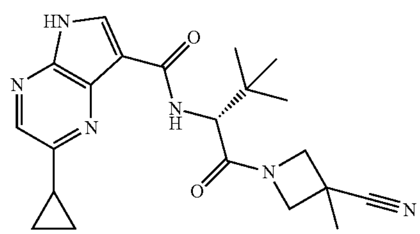 [SMILES: CC1(C#N)CN(C(=O)[C@H](NC(=O)c2c[nH]c3ncc(C4CC4)nc23)C(C)(C)C)C1] | 2-Cyclopropyl-5H-pyrrolo[2,3-b]pyrazine-7-carboxylic acid [(R)-1-(3-cyano-3-methyl-azetidine-1-carbonyl)-2,2-dimethyl-propyl]-amide | |
| I-40 | 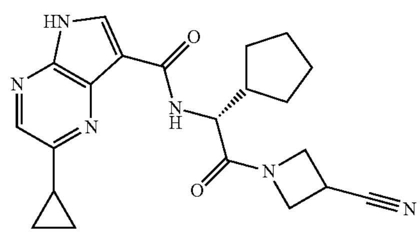 [SMILES: N#CC1CN(C(=O)[C@H](NC(=O)c2c[nH]c3ncc(C4CC4)nc23)C2CCCC2)C1] | 2-Cyclopropyl-5H-pyrrolo[2,3-b]pyrazine-7-carboxylic acid [(R)-2-(3-cyano-azetidin-1-yl)-1-cyclopentyl-2-oxo-ethyl]-amide | |
| I-41 | 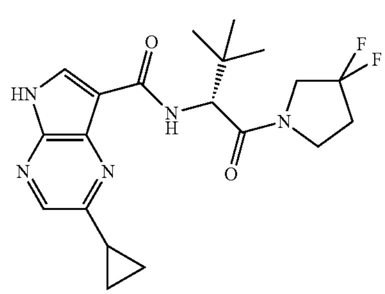 [SMILES: CC(C)(C)[C@@H](NC(=O)c1c[nH]c2ncc(C3CC3)nc12)C(=O)N1CCC(F)(F)C1] | 2-Cyclopropyl-5H-pyrrolo[2,3-b]pyrazine-7-carboxylic acid [(R)-1-(3,3-difluoro-pyrrolidine-1-carbonyl)-2,2-dimethyl-propyl]-amide | |

TABLE I-continued

| COMPOUND | STRUCTURE | SYSTEMATIC NAME | MP |
|---|---|---|---|
| I-42 | 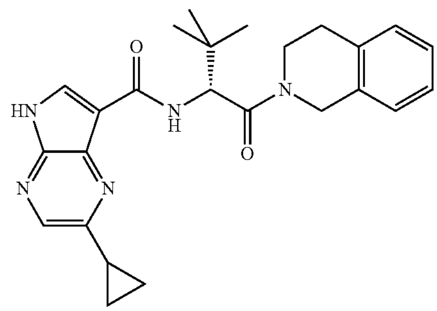 [SMILES: CC(C)(C)[C@@H](NC(=O)c1c[nH]c2ncc(C3CC3)nc12)C(=O)N1CCc2ccccc2C1] | 2-Cyclopropyl-5H-pyrrolo[2,3-b]pyrazine-7-carboxylic acid [(R)-1-(3,4-dihydro-1H-isoquinoline-2-carbonyl)-2,2-dimethyl-propyl]-amide | |
| I-43 | 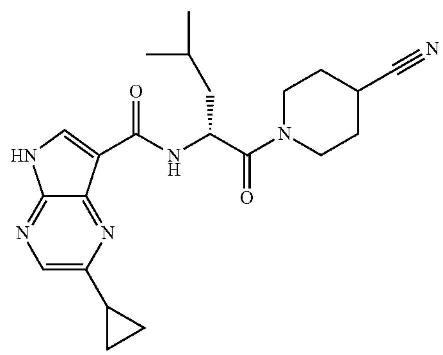 [SMILES: CC(C)C[C@@H](NC(=O)c1c[nH]c2ncc(C3CC3)nc12)C(=O)N1CCC(C#N)CC1] | 2-Cyclopropyl-5H-pyrrolo[2,3-b]pyrazine-7-carboxylic acid [(R)-1-(4-cyano-piperidine-1-carbonyl)-3-methyl-butyl]-amide | |
| I-44 | 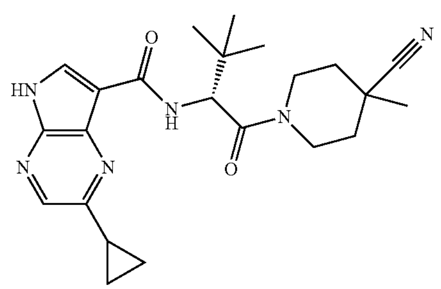 [SMILES: CC1(C#N)CCN(C(=O)[C@H](NC(=O)c2c[nH]c3ncc(C4CC4)nc23)C(C)(C)C)CC1] | 2-Cyclopropyl-5H-pyrrolo[2,3-b]pyrazine-7-carboxylic acid [(R)-1-(4-cyano-4-methyl-piperidine-1-carbonyl)-2,2-dimethyl-propyl]-amide | |
| I-45 | 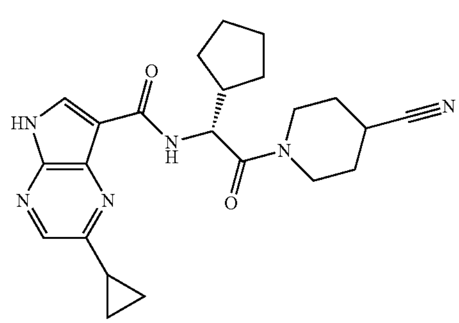 [SMILES: N#CC1CCN(C(=O)[C@H](NC(=O)c2c[nH]c3ncc(C4CC4)nc23)C2CCCC2)CC1] | 2-Cyclopropyl-5H-pyrrolo[2,3-b]pyrazine-7-carboxylic acid [(R)-2-(4-cyano-piperidin-1-yl)-1-cyclopentyl-2-oxo-ethyl]-amide | |

TABLE I-continued

| COMPOUND | STRUCTURE | SYSTEMATIC NAME | MP |
|---|---|---|---|
| I-46 | 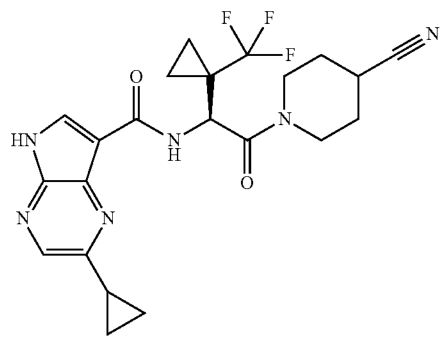 [SMILES: N#CC1CCN(C(=O)[C@@H](NC(=O)c2c[nH]c3ncc(C4CC4)nc23)C2(C(F)(F)F)CC2)CC1] | 2-Cyclopropyl-5H-pyrrolo[2,3-b]pyrazine-7-carboxylic acid [(S)-2-(4-cyano-piperidin-1-yl)-2-oxo-1-(1-trifluoromethyl-cyclopropyl)-ethyl]-amide | |
| I-47 | 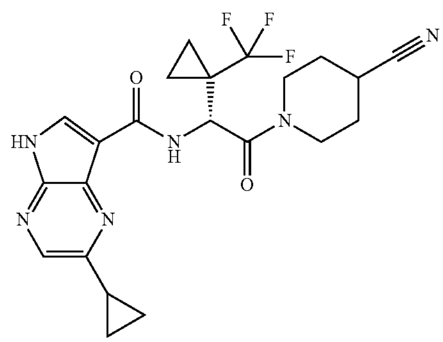 [SMILES: N#CC1CCN(C(=O)[C@H](NC(=O)c2c[nH]c3ncc(C4CC4)nc23)C2(C(F)(F)F)CC2)CC1] | 2-Cyclopropyl-5H-pyrrolo[2,3-b]pyrazine-7-carboxylic acid [(R)-2-(4-cyano-piperidin-1-yl)-2-oxo-1-(1-trifluoromethyl-cyclopropyl)-ethyl]-amide | |
| I-48 | 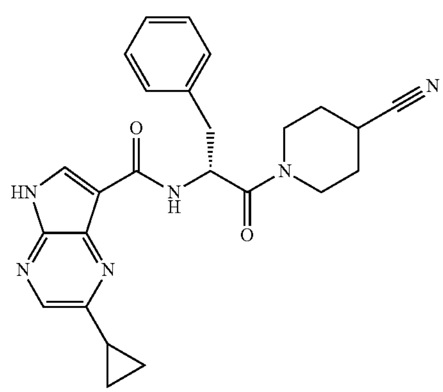 [SMILES: N#CC1CCN(C(=O)[C@@H](Cc2ccccc2)NC(=O)c2c[nH]c3ncc(C4CC4)nc23)CC1] | 2-Cyclopropyl-5H-pyrrolo[2,3-b]pyrazine-7-carboxylic acid [(R)-1-benzyl-2-(4-cyano-piperidin-1-yl)-2-oxo-ethyl]-amide | |
| I-49 | 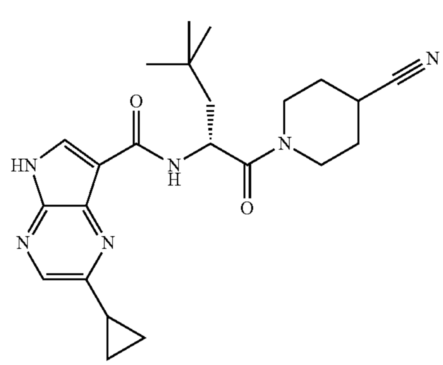 [SMILES: CC(C)(C)C[C@@H](NC(=O)c1c[nH]c2ncc(C3CC3)nc12)C(=O)N1CCC(C#N)CC1] | 2-Cyclopropyl-5H-pyrrolo[2,3-b]pyrazine-7-carboxylic acid [(R)-1-(4-cyano-piperidine-1-carbonyl)-3,3-dimethyl-butyl]-amide | |

TABLE I-continued

| COMPOUND | STRUCTURE | SYSTEMATIC NAME | MP |
|---|---|---|---|
| I-50 | 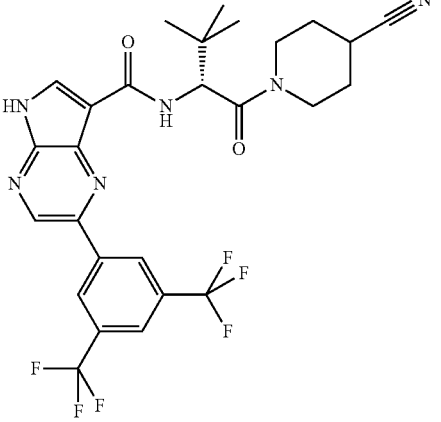 | 2-(3,5-Bis-trifluoromethyl-phenyl)-5H-pyrrolo[2,3-b]pyrazine-7-carboxylic acid [(R)-1-(4-cyano-piperidine-1-carbonyl)-2,2-dimethyl-propyl]-amide | |
| I-51 | 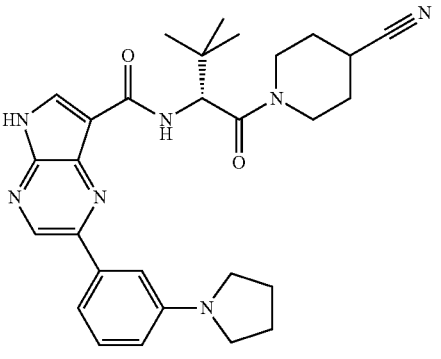 [SMILES: CC(C)(C)[C@@H](NC(=O)c1c[nH]c2ncc(-c3cccc(N4CCCC4)c3)nc12)C(=O)N1CCC(C#N)CC1] | 2-(3-Pyrrolidin-1-yl-phenyl)-5H-pyrrolo[2,3-b]pyrazine-7-carboxylic acid [(R)-1-(4-cyano-piperidine-1-carbonyl)-2,2-dimethyl-propyl]-amide | |
| I-52 | 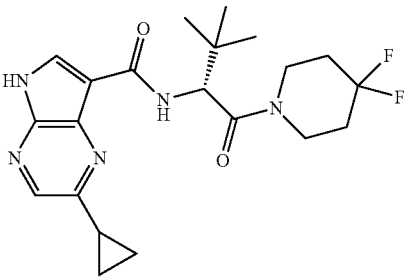 [SMILES: CC(C)(C)[C@@H](NC(=O)c1c[nH]c2ncc(C3CC3)nc12)C(=O)N1CCC(F)(F)CC1] | 2-Cyclopropyl-5H-pyrrolo[2,3-b]pyrazine-7-carboxylic acid [(R)-1-(4,4-difluoro-piperidine-1-carbonyl)-2,2-dimethyl-propyl]-amide | |
| I-53 | 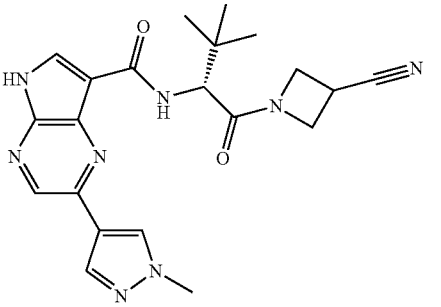 [SMILES: Cn1cc(-c2cnc3[nH]cc(C(=O)N[C@@H](C(=O)N4CC(C#N)C4)C(C)(C)C)c3n2)cn1] | 2-(1-Methyl-1H-pyrazol-4-yl)-5H-pyrrolo[2,3-b]pyrazine-7-carboxylic acid [(R)-1-(3-cyano-azetidine-1-carbonyl)-2,2-dimethyl-propyl]-amide | |

TABLE I-continued

| COMPOUND | STRUCTURE | SYSTEMATIC NAME | MP |
|---|---|---|---|
| I-54 | 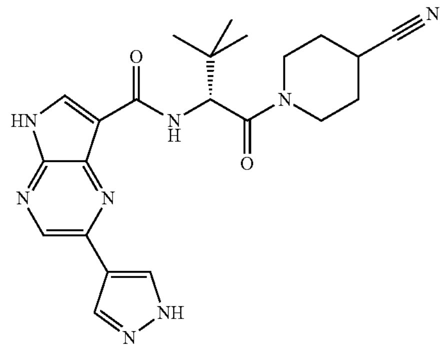 [SMILES: CC(C)(C)[C@@H](NC(=O)c1c[nH]c2ncc(-c3cn[nH]c3)nc12)C(=O)N1CCC(C#N)CC1] | 2-(1H-Pyrazol-4-yl)-5H-pyrrolo[2,3-b]pyrazine-7-carboxylic acid [(R)-1-(4-cyano-piperidine-1-carbonyl)-2,2-dimethyl-propyl]-amide | |
| I-55 | 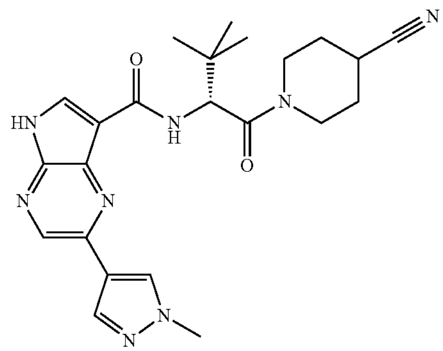 [SMILES: Cn1cc(-c2cnc3[nH]cc(C(=O)N[C@@H](C(=O)N4CCC(C#N)CC4)C(C)(C)C)c3n2)cn1] | 2-(1-Methyl-1H-pyrazol-4-yl)-5H-pyrrolo[2,3-b]pyrazine-7-carboxylic acid [(R)-1-(4-cyano-piperidine-1-carbonyl)-2,2-dimethyl-propyl]-amide | |
| I-56 | 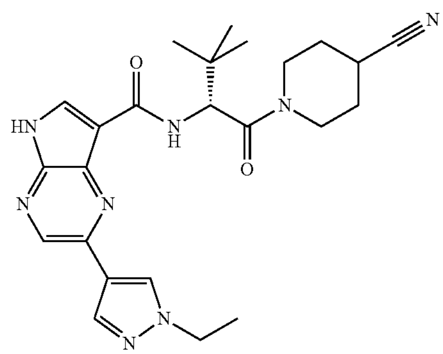 [SMILES: CCn1cc(-c2cnc3[nH]cc(C(=O)N[C@@H](C(=O)N4CCC(C#N)CC4)C(C)(C)C)c3n2)cn1] | 2-(1-Ethyl-1H-pyrazol-4-yl)-5H-pyrrolo[2,3-b]pyrazine-7-carboxylic acid [(R)-1-(4-cyano-piperidine-1-carbonyl)-2,2-dimethyl-propyl]-amide | |
| I-57 | 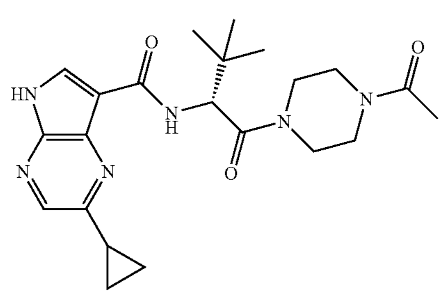 [SMILES: CC(=O)N1CCN(C(=O)[C@H](NC(=O)c2c[nH]c3ncc(C4CC4)nc23)C(C)(C)C)CC1] | 2-Cyclopropyl-5H-pyrrolo[2,3-b]pyrazine-7-carboxylic acid [(R)-1-(4-acetyl-piperazine-1-carbonyl)-2,2-dimethyl-propyl]-amide | |

TABLE I-continued

| COMPOUND | STRUCTURE | SYSTEMATIC NAME | MP |
|---|---|---|---|
| I-58 | 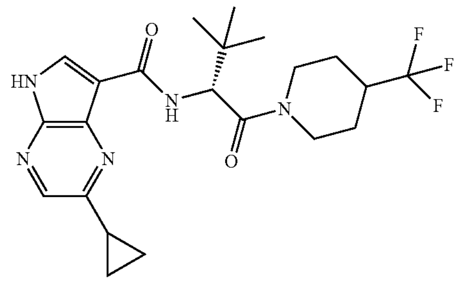 [SMILES: CC(C)(C)[C@@H](NC(=O)c1c[nH]c2ncc(C3CC3)nc12)C(=O)N1CCC(C(F)(F)F)CC1] | 2-Cyclopropyl-5H-pyrrolo[2,3-b]pyrazine-7-carboxylic acid [(R)-2,2-dimethyl-1-(4-trifluoromethyl-piperidine-1-carbonyl)-propyl]-amide | |
| I-59 | 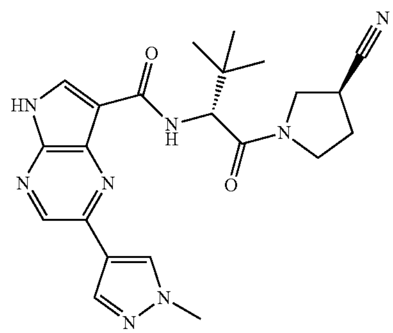 [SMILES: Cn1cc(-c2cnc3[nH]cc(C(=O)N[C@@H](C(=O)N4CC[C@H](C#N)C4)C(C)(C)C)c3n2)cn1] | 2-(1-Methyl-1H-pyrazol-4-yl)-5H-pyrrolo[2,3-b]pyrazine-7-carboxylic acid [(R)-1-((S)-3-cyano-pyrrolidine-1-carbonyl)-2,2-dimethyl-propyl]-amide | |
| I-60 | 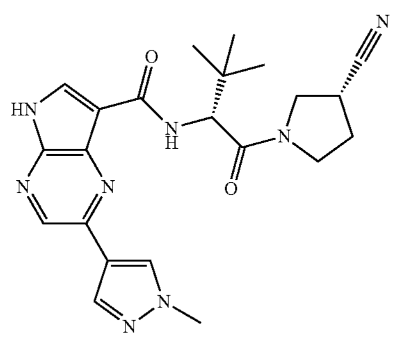 [SMILES: Cn1cc(-c2cnc3[nH]cc(C(=O)N[C@@H](C(=O)N4CC[C@@H](C#N)C4)C(C)(C)C)c3n2)cn1] | 2-(1-Methyl-1H-pyrazol-4-yl)-5H-pyrrolo[2,3-b]pyrazine-7-carboxylic acid [(R)-1-((R)-3-cyano-pyrrolidine-1-carbonyl)-2,2-dimethyl-propyl]-amide | |
| I-61 | 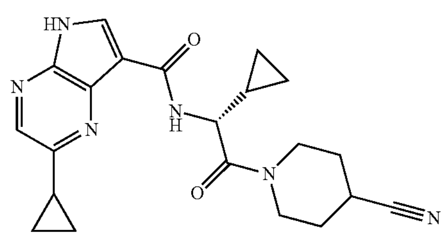 [SMILES: N#CC1CCN(C(=O)[C@H](NC(=O)c2c[nH]c3ncc(C4CC4)nc23)C2CC2)CC1] | 2-Cyclopropyl-5H-pyrrolo[2,3-b]pyrazine-7-carboxylic acid [(R)-2-(4-cyano-piperidin-1-yl)-1-cyclopropyl-2-oxo-ethyl]-amide | |
| I-62 | 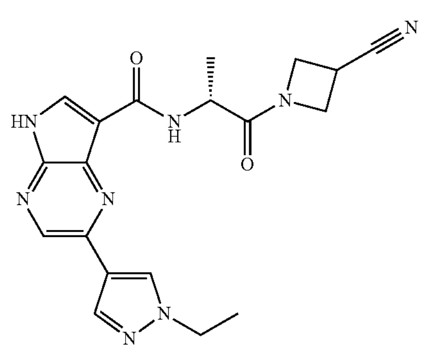 [SMILES: CCn1cc(-c2cnc3[nH]cc(C(=O)N[C@H](C)C(=O)N4CC(C#N)C4)c3n2)cn1] | 2-(1-Ethyl-1H-pyrazol-4-yl)-5H-pyrrolo[2,3-b]pyrazine-7-carboxylic acid [(R)-2-(3-cyano-azetidin-1-yl)-1-methyl-2-oxo-ethyl]-amide | |

TABLE I-continued

| COMPOUND | STRUCTURE | SYSTEMATIC NAME | MP |
|---|---|---|---|
| I-63 | 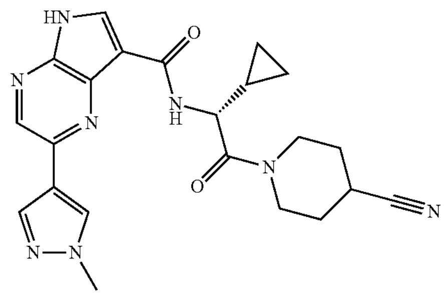 [SMILES: Cn1cc(-c2cnc3[nH]cc(C(=O)N[C@@H](C(=O)N4CCC(C#N)CC4)C4CC4)c3n2)cn1] | 2-(1-Methyl-1H-pyrazol-4-yl)-5H-pyrrolo[2,3-b]pyrazine-7-carboxylic acid [(R)-2-(4-cyano-piperidin-1-yl)-1-cyclopropyl-2-oxo-ethyl]-amide | |
| I-64 | 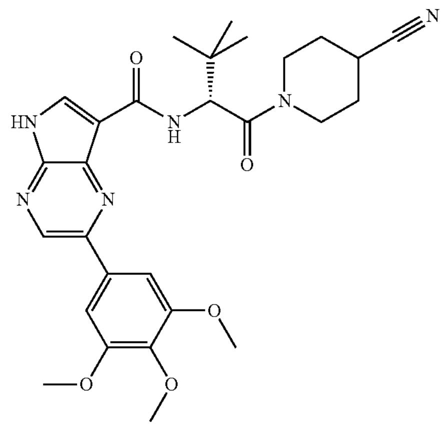 [SMILES: COc1cc(-c2cnc3[nH]cc(C(=O)N[C@@H](C(=O)N4CCC(C#N)CC4)C(C)(C)C)c3n2)cc(OC)c1OC] | 2-(3,4,5-Trimethoxy-phenyl)-5H-pyrrolo[2,3-b]pyrazine-7-carboxylic acid [(R)-1-(4-cyano-piperidine-1-carbonyl)-2,2-dimethyl-propyl]-amide | |
| I-65 | 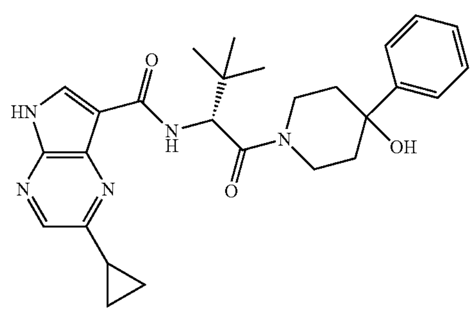 [SMILES: CC(C)(C)[C@@H](NC(=O)c1c[nH]c2ncc(C3CC3)nc12)C(=O)N1CCC(O)(c2ccccc2)CC1] | 2-Cyclopropyl-5H-pyrrolo[2,3-b]pyrazine-7-carboxylic acid [(R)-1-(4-hydroxy-4-phenyl-piperidine-1-carbonyl)-2,2-dimethyl-propyl]-amide | |
| I-66 | 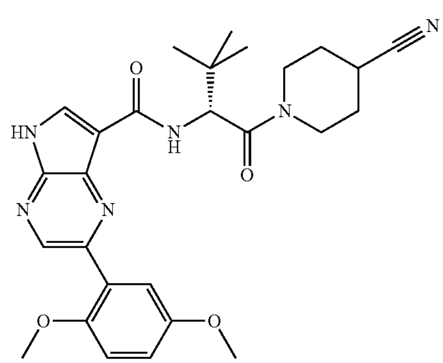 [SMILES: COc1ccc(OC)c(-c2cnc3[nH]cc(C(=O)N[C@@H](C(=O)N4CCC(C#N)CC4)C(C)(C)C)c3n2)c1] | 2-(2,5-Dimethoxy-phenyl)-5H-pyrrolo[2,3-b]pyrazine-7-carboxylic acid [(R)-1-(4-cyano-piperidine-1-carbonyl)-2,2-dimethyl-propyl]-amide | |

TABLE I-continued

| COMPOUND | STRUCTURE | SYSTEMATIC NAME | MP |
|---|---|---|---|
| I-67 | 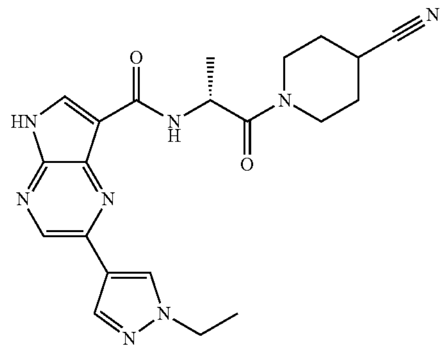 [SMILES: CCn1cc(-c2cnc3[nH]cc(C(=O)N[C@H](C)C(=O)N4CCC(C#N)CC4)c3n2)cn1] | 2-(1-Ethyl-1H-pyrazol-4-yl)-5H-pyrrolo[2,3-b]pyrazine-7-carboxylic acid [(R)-2-(4-cyano-piperidin-1-yl)-1-methyl-2-oxo-ethyl]-amide | |
| I-68 | 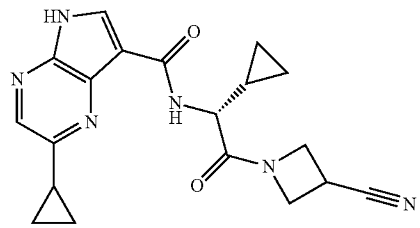 [SMILES: N#CC1CN(C(=O)[C@H](NC(=O)c2c[nH]c3ncc(C4CC4)nc23)C2CC2)C1] | 2-Cyclopropyl-5H-pyrrolo[2,3-b]pyrazine-7-carboxylic acid [(R)-2-(3-cyano-azetidin-1-yl)-1-cyclopropyl-2-oxo-ethyl]-amide | |
| I-69 | 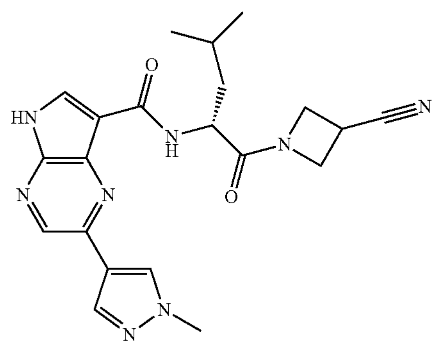 [SMILES: CC(C)C[C@@H](NC(=O)c1c[nH]c2ncc(-c3cnn(C)c3)nc12)C(=O)N1CC(C#N)C1] | 2-(1-Methyl-1H-pyrazol-4-yl)-5H-pyrrolo[2,3-b]pyrazine-7-carboxylic acid [(R)-1-(3-cyano-azetidine-1-carbonyl)-3-methyl-butyl]-amide | |
| I-70 | 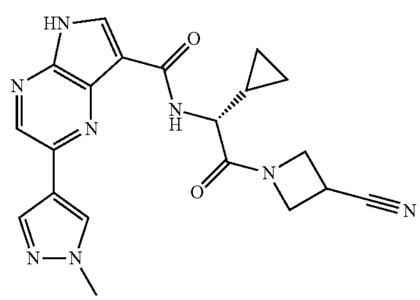 [SMILES: Cn1cc(-c2cnc3[nH]cc(C(=O)N[C@@H](C(=O)N4CC(C#N)C4)C4CC4)c3n2)cn1] | 2-(1-Methyl-1H-pyrazol-4-yl)-5H-pyrrolo[2,3-b]pyrazine-7-carboxylic acid [(R)-2-(3-cyano-azetidin-1-yl)-1-cyclopropyl-2-oxo-ethyl]-amide | |
| I-71 | 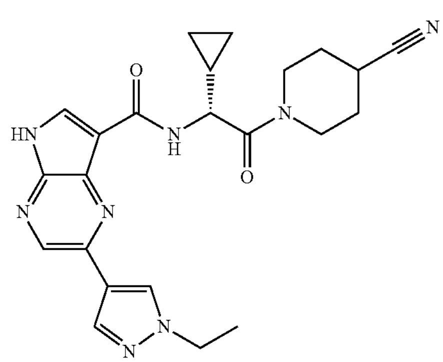 [SMILES: CCn1cc(-c2cnc3[nH]cc(C(=O)N[C@@H](C(=O)N4CCC(C#N)CC4)C4CC4)c3n2)cn1] | 2-(1-Ethyl-1H-pyrazol-4-yl)-5H-pyrrolo[2,3-b]pyrazine-7-carboxylic acid [(R)-2-(4-cyano-piperidin-1-yl)-1-cyclopropyl-2-oxo-ethyl]-amide | |

TABLE I-continued

| COMPOUND | STRUCTURE | SYSTEMATIC NAME | MP |
|---|---|---|---|
| I-72 | 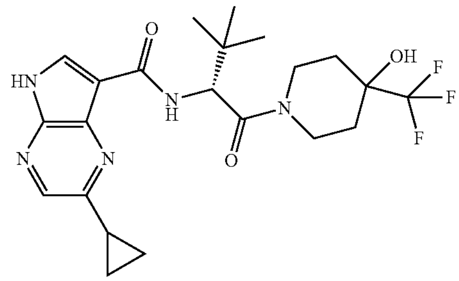 [SMILES: CC(C)(C)[C@@H](NC(=O)c1c[nH]c2ncc(C3CC3)nc12)C(=O)N1CCC(O)(C(F)(F)F)CC1] | 2-Cyclopropyl-5H-pyrrolo[2,3-b]pyrazine-7-carboxylic acid [(R)-1-(4-hydroxy-4-trifluoromethyl-piperidine-1-carbonyl)-2,2-dimethyl-propyl]-amide | |
| I-73 | 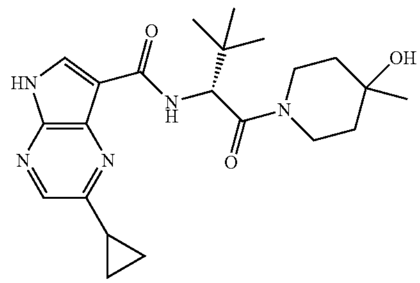 [SMILES: CC1(O)CCN(C(=O)[C@H](NC(=O)c2c[nH]c3ncc(C4CC4)nc23)C(C)(C)C)CC1] | 2-Cyclopropyl-5H-pyrrolo[2,3-b]pyrazine-7-carboxylic acid [(R)-1-(4-hydroxy-4-methyl-piperidine-1-carbonyl)-2,2-dimethyl-propyl]-amide | |
| I-74 | 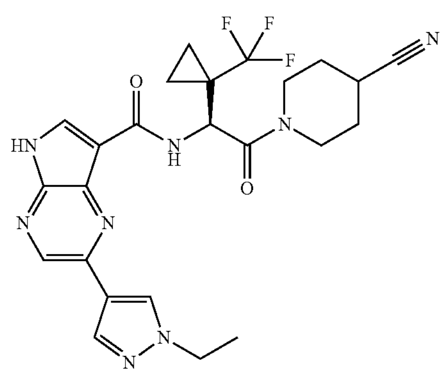 [SMILES: CCn1cc(-c2cnc3[nH]cc(C(=O)N[C@H](C(=O)N4CCC(C#N)CC4)C4(C(F)(F)F)CC4)c3n2)cn1] | 2-(1-Ethyl-1H-pyrazol-4-yl)-5H-pyrrolo[2,3-b]pyrazine-7-carboxylic acid [(S)-2-(4-cyano-piperidin-1-yl)-2-oxo-1-(1-trifluoromethyl-cyclopropyl)-ethyl]-amide | |
| I-75 | 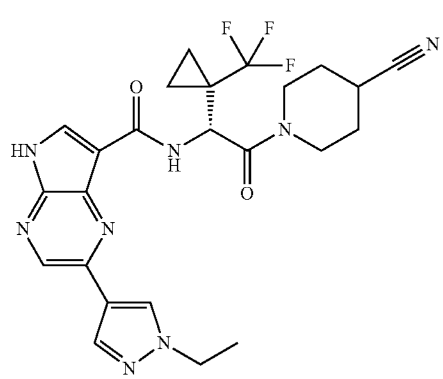 [SMILES: CCn1cc(-c2cnc3[nH]cc(C(=O)N[C@@H](C(=O)N4CCC(C#N)CC4)C4(C(F)(F)F)CC4)c3n2)cn1] | 2-(1-Ethyl-1H-pyrazol-4-yl)-5H-pyrrolo[2,3-b]pyrazine-7-carboxylic acid [(R)-2-(4-cyano-piperidin-1-yl)-2-oxo-1-(1-trifluoromethyl-cyclopropyl)-ethyl]-amide | |

TABLE I-continued

| COMPOUND | STRUCTURE | SYSTEMATIC NAME | MP |
|---|---|---|---|
| I-76 | 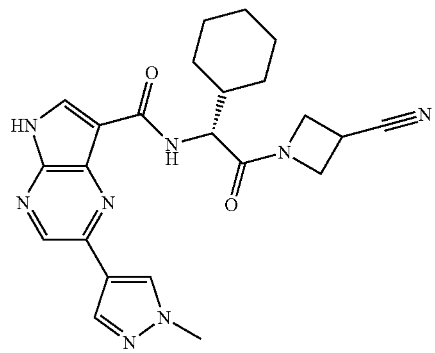 [SMILES: Cn1cc(-c2cnc3[nH]cc(C(=O)N[C@@H](C(=O)N4CC(C#N)C4)C4CCCCC4)c3n2)cn1] | 2-(1-Methyl-1H-pyrazol-4-yl)-5H-pyrrolo[2,3-b]pyrazine-7-carboxylic acid [(R)-2-(3-cyano-azetidin-1-yl)-1-cyclohexyl-2-oxo-ethyl]-amide | |
| I-77 | 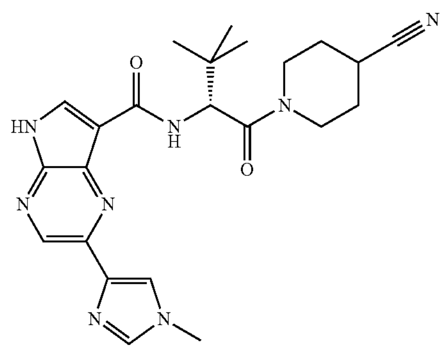 [SMILES: Cn1cnc(-c2cnc3[nH]cc(C(=O)N[C@@H](C(=O)N4CCC(C#N)CC4)C(C)(C)C)c3n2)c1] | 2-(1-Methyl-1H-imidazol-4-yl)-5H-pyrrolo[2,3-b]pyrazine-7-carboxylic acid [(R)-1-(4-cyano-piperidine-1-carbonyl)-2,2-dimethyl-propyl]-amide | |
| I-78 | 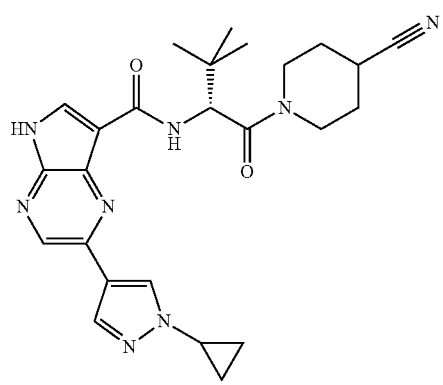 [SMILES: CC(C)(C)[C@@H](NC(=O)c1c[nH]c2ncc(-c3cnn(C4CC4)c3)nc12)C(=O)N1CCC(C#N)CC1] | 2-(1-Cyclopropyl-1H-pyrazol-4-yl)-5H-pyrrolo[2,3-b]pyrazine-7-carboxylic acid [(R)-1-(4-cyano-piperidine-1-carbonyl)-2,2-dimethyl-propyl]-amide | |
| I-79 | 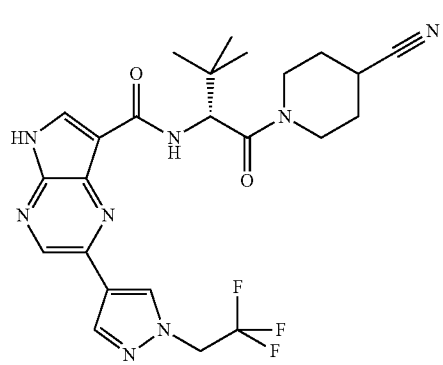 [SMILES: CC(C)(C)[C@@H](NC(=O)c1c[nH]c2ncc(-c3cnn(CC(F)(F)F)c3)nc12)C(=O)N1CCC(C#N)CC1] | 2-[1-(2,2,2-Trifluoro-ethyl)-1H-pyrazol-4-yl]-5H-pyrrolo[2,3-b]pyrazine-7-carboxylic acid [(R)-1-(4-cyano-piperidine-1-carbonyl)-2,2-dimethyl-propyl]-amide | |

TABLE I-continued

| COMPOUND | STRUCTURE | SYSTEMATIC NAME | MP |
|---|---|---|---|
| I-80 | 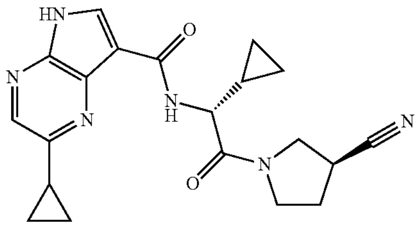 [SMILES: N#C[C@H]1CCN(C(=O)[C@H](NC(=O)c2c[nH]c3ncc(C4CC4)nc23)C2CC2)C1] | 2-Cyclopropyl-5H-pyrrolo[2,3-b]pyrazine-7-carboxylic acid [(R)-2-((S)-3-cyano-pyrrolidin-1-yl)-1-cyclopropyl-2-oxo-ethyl]-amide | |
| I-81 | 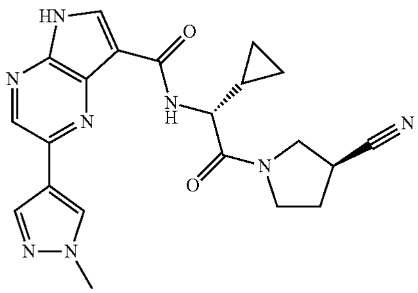 [SMILES: Cn1cc(-c2cnc3[nH]cc(C(=O)N[C@@H](C(=O)N4CC[C@H](C#N)C4)C4CC4)c3n2)cn1] | 2-(1-Methyl-1H-pyrazol-4-yl)-5H-pyrrolo[2,3-b]pyrazine-7-carboxylic acid [(R)-2-((S)-3-cyano-pyrrolidin-1-yl)-1-cyclopropyl-2-oxo-ethyl]-amide | |
| I-82 | 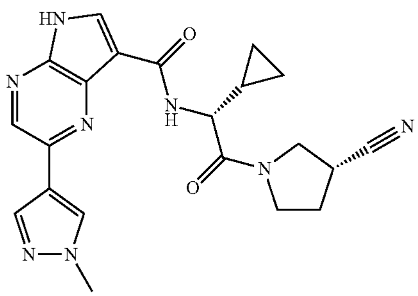 [SMILES: Cn1cc(-c2cnc3[nH]cc(C(=O)N[C@@H](C(=O)N4CC[C@@H](C#N)C4)C4CC4)c3n2)cn1] | 2-(1-Methyl-1H-pyrazol-4-yl)-5H-pyrrolo[2,3-b]pyrazine-7-carboxylic acid [(R)-2-((R)-3-cyano-pyrrolidin-1-yl)-1-cyclopropyl-2-oxo-ethyl]-amide | |
| I-83 | 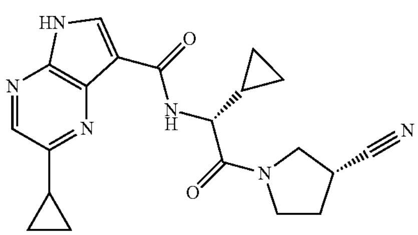 [SMILES: N#C[C@@H]1CCN(C(=O)[C@H](NC(=O)c2c[nH]c3ncc(C4CC4)nc23)C2CC2)C1] | 2-Cyclopropyl-5H-pyrrolo[2,3-b]pyrazine-7-carboxylic acid [(R)-2-((R)-3-cyano-pyrrolidin-1-yl)-1-cyclopropyl-2-oxo-ethyl]-amide | |
| I-84 | 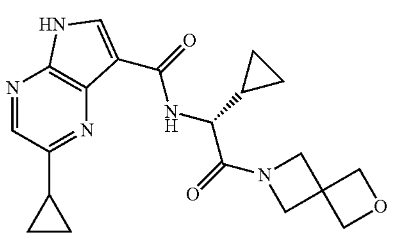 [SMILES: O=C(N[C@@H](C(=O)N1CC2(COC2)C1)C1CC1)c1c[nH]c2ncc(C3CC3)nc12] | 2-Cyclopropyl-5H-pyrrolo[2,3-b]pyrazine-7-carboxylic acid [(R)-1-cyclopropyl-2-(2-oxa-6-aza-spiro[3.3]hept-6-yl)-2-oxo-ethyl]-amide | |
| I-85 | 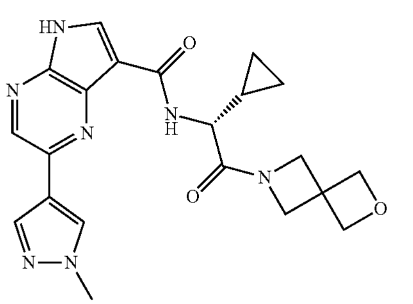 [SMILES: Cn1cc(-c2cnc3[nH]cc(C(=O)N[C@@H](C(=O)N4CC5(COC5)C4)C4CC4)c3n2)cn1] | 2-(1-Methyl-1H-pyrazol-4-yl)-5H-pyrrolo[2,3-b]pyrazine-7-carboxylic acid [(R)-1-cyclopropyl-2-(2-oxa-6-aza-spiro[3.3]hept-6-yl)-2-oxo-ethyl]-amide | |

TABLE I-continued

| COMPOUND | STRUCTURE | SYSTEMATIC NAME | MP |
|---|---|---|---|
| I-86 | 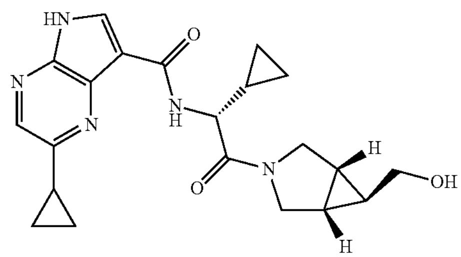 [SMILES: O=C(N[C@@H](C(=O)N1C[C@@H]2[C@@H](CO)[C@@H]2C1)C1CC1)c1c[nH]c2ncc(C3CC3)nc12] | 2-Cyclopropyl-5H-pyrrolo[2,3-b]pyrazine-7-carboxylic acid [(R)-1-cyclopropyl-2-((1S,5R,6R)-6-hydroxymethyl-3-azabicyclo[3.1.0]hex-3-yl)-2-oxo-ethyl]-amide | |
| I-87 | 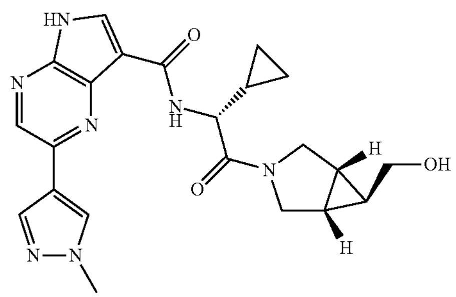 [SMILES: Cn1cc(-c2cnc3[nH]cc(C(=O)N[C@@H](C(=O)N4C[C@@H]5[C@@H](CO)[C@@H]5C4)C4CC4)c3n2)cn1] | 2-(1-Methyl-1H-pyrazol-4-yl)-5H-pyrrolo[2,3-b]pyrazine-7-carboxylic acid [(R)-1-cyclopropyl-2-((1S,5R,6R)-6-hydroxymethyl-3-azabicyclo[3.1.0]hex-3-yl)-2-oxo-ethyl]-amide | |
| I-88 | 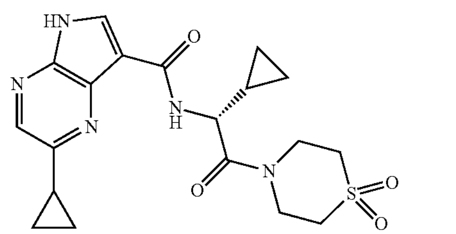 [SMILES: O=C(N[C@@H](C(=O)N1CCS(=O)(=O)CC1)C1CC1)c1c[nH]c2ncc(C3CC3)nc12] | 2-Cyclopropyl-5H-pyrrolo[2,3-b]pyrazine-7-carboxylic acid [(R)-1-cyclopropyl-2-(1,1-dioxo-1$\lambda^6$-thiomorpholin-4-yl)-2-oxo-ethyl]-amide | |
| I-89 | 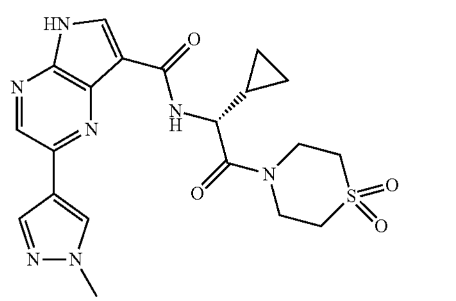 [SMILES: Cn1cc(-c2cnc3[nH]cc(C(=O)N[C@@H](C(=O)N4CCS(=O)(=O)CC4)C4CC4)c3n2)cn1] | 2-(1-Methyl-1H-pyrazol-4-yl)-5H-pyrrolo[2,3-b]pyrazine-7-carboxylic acid [(R)-1-cyclopropyl-2-(1,1-dioxo-1$\lambda^6$-thiomorpholin-4-yl)-2-oxo-ethyl]-amide | |
| I-90 | 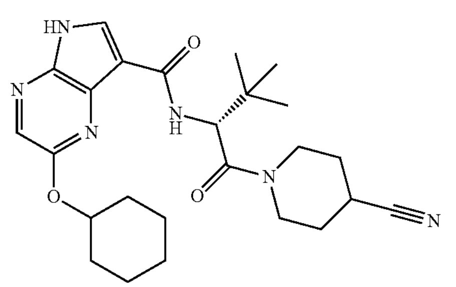 [SMILES: CC(C)(C)[C@@H](NC(=O)c1c[nH]c2ncc(OC3CCCCC3)nc12)C(=O)N1CCC(C#N)CC1] | 2-Cyclohexyloxy-5H-pyrrolo[2,3-b]pyrazine-7-carboxylic acid [(R)-1-(4-cyano-piperidine-1-carbonyl)-2,2-dimethyl-propyl]-amide | |

TABLE I-continued

| COMPOUND | STRUCTURE | SYSTEMATIC NAME | MP |
|---|---|---|---|
| I-91 | 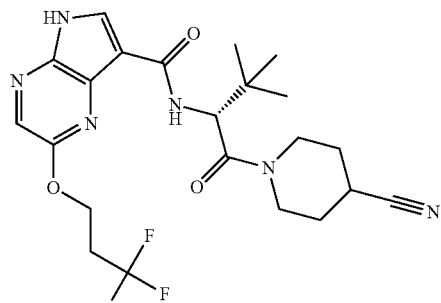 | 2-(3,3,3-Trifluoro-propoxy)-5H-pyrrolo[2,3-b]pyrazine-7-carboxylic acid [(R)-1-(4-cyano-piperidine-1-carbonyl)-2,2-dimethyl-propyl]-amide | |
| I-92 | 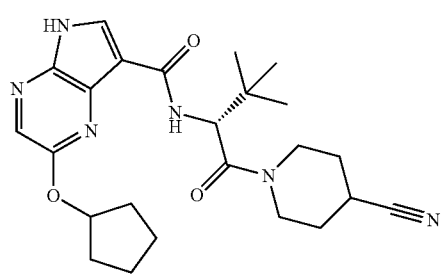 [SMILES: CC(C)(C)[C@@H](NC(=O)c1c[nH]c2ncc(OC3CCCC3)nc12)C(=O)N1CCC(C#N)CC1] | 2-Cyclopentyloxy-5H-pyrrolo[2,3-b]pyrazine-7-carboxylic acid [(R)-1-(4-cyano-piperidine-1-carbonyl)-2,2-dimethyl-propyl]-amide | |
| I-93 | 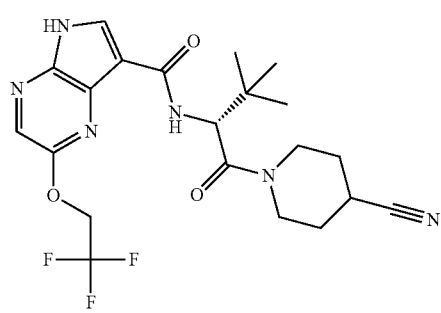 [SMILES: CC(C)(C)[C@@H](NC(=O)c1c[nH]c2ncc(OCC(F)(F)F)nc12)C(=O)N1CCC(C#N)CC1] | 2-(2,2,2-Trifluoro-ethoxy)-5H-pyrrolo[2,3-b]pyrazine-7-carboxylic acid [(R)-1-(4-cyano-piperidine-1-carbonyl)-2,2-dimethyl-propyl]-amide | |
| I-94 | 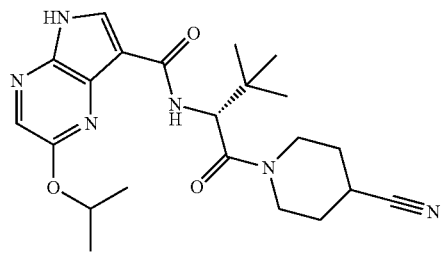 [SMILES: CC(C)Oc1cnc2[nH]cc(C(=O)N[C@@H](C(=O)N3CCC(C#N)CC3)C(C)(C)C)c2n1] | 2-Isopropoxy-5H-pyrrolo[2,3-b]pyrazine-7-carboxylic acid [(R)-1-(4-cyano-piperidine-1-carbonyl)-2,2-dimethyl-propyl]-amide | |
| I-95 | 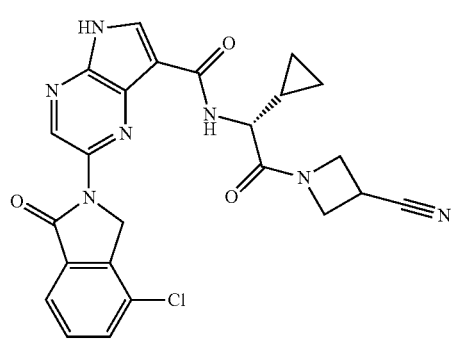 [SMILES: N#CC1CN(C(=O)[C@H](NC(=O)c2c[nH]c3ncc(N4Cc5c(Cl)cccc5C4=O)nc23)C2CC2)C1] | 2-(4-Chloro-1-oxo-1,3-dihydro-isoindol-2-yl)-5H-pyrrolo[2,3-b]pyrazine-7-carboxylic acid [(R)-2-(3-cyano-azetidin-1-yl)-1-cyclopropyl-2-oxo-ethyl]-amide | |

TABLE I-continued

| COMPOUND | STRUCTURE | SYSTEMATIC NAME | MP |
|---|---|---|---|
| I-96 | 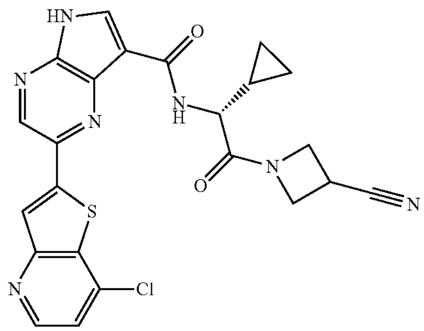 [SMILES: N#CC1CN(C(=O)[C@H](NC(=O)c2c[nH]c3ncc(-c4cc5nccc(Cl)c5s4)nc23)C2CC2)C1] | 2-(7-Chloro-thieno[3,2-b]pyridin-2-yl)-5H-pyrrolo[2,3-b]pyrazine-7-carboxylic acid [(R)-2-(3-cyano-azetidin-1-yl)-1-cyclopropyl-2-oxo-ethyl]-amide | |
| I-97 | 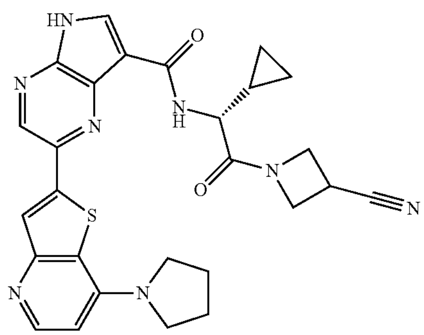 [SMILES: N#CC1CN(C(=O)[C@H](NC(=O)c2c[nH]c3ncc(-c4cc5nccc(N6CCCC6)c5s4)nc23)C2CC2)C1] | 2-(7-Pyrrolidin-1-yl-thieno[3,2-b]pyridin-2-yl)-5H-pyrrolo[2,3-b]pyrazine-7-carboxylic acid [(R)-2-(3-cyano-azetidin-1-yl)-1-cyclopropyl-2-oxo-ethyl]-amide | |
| I-98 | 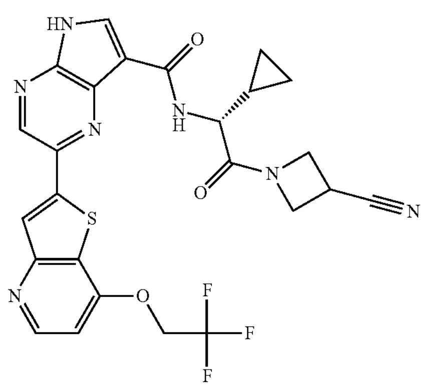 [SMILES: N#CC1CN(C(=O)[C@H](NC(=O)c2c[nH]c3ncc(-c4cc5nccc(OCC(F)(F)F)c5s4)nc23)C2CC2)C1] | 2-[7-(2,2,2-Trifluoro-ethoxy)-thieno[3,2-b]pyridin-2-yl]-5H-pyrrolo[2,3-b]pyrazine-7-carboxylic acid [(R)-2-(3-cyano-azetidin-1-yl)-1-cyclopropyl-2-oxo-ethyl]-amide | |
| I-99 | 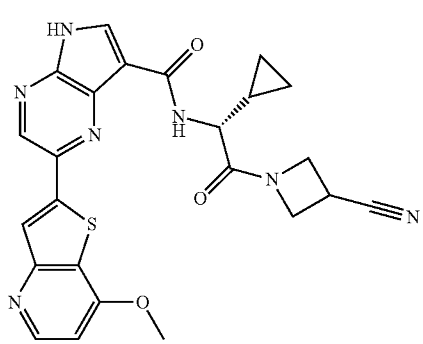 [SMILES: COc1ccnc2cc(-c3cnc4[nH]cc(C(=O)N[C@@H](C(=O)N5CC(C#N)C5)C5CC5)c4n3)sc12] | 2-(7-Methoxy-thieno[3,2-b]pyridin-2-yl)-5H-pyrrolo[2,3-b]pyrazine-7-carboxylic acid [(R)-2-(3-cyano-azetidin-1-yl)-1-cyclopropyl-2-oxo-ethyl]-amide | |

TABLE I-continued

| COMPOUND | STRUCTURE | SYSTEMATIC NAME | MP |
|---|---|---|---|
| I-100 | 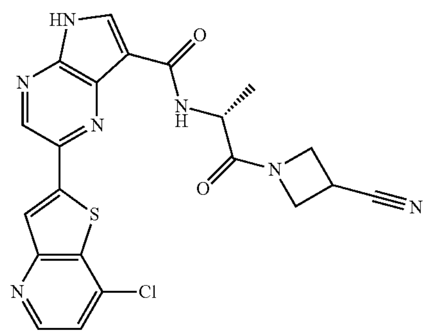 [SMILES: C[C@@H](NC(=O)c1c[nH]c2ncc(-c3cc4nccc(Cl)c4s3)nc12)C(=O)N1CC(C#N)C1] | 2-(7-Chloro-thieno[3,2-b]pyridin-2-yl)-5H-pyrrolo[2,3-b]pyrazine-7-carboxylic acid [(R)-2-(3-cyano-azetidin-1-yl)-1-methyl-2-oxo-ethyl]-amide | |
| I-101 | 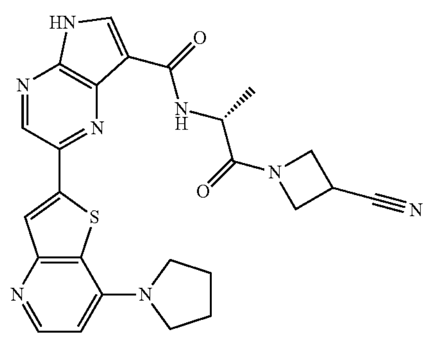 [SMILES: C[C@@H](NC(=O)c1c[nH]c2ncc(-c3cc4nccc(N5CCCC5)c4s3)nc12)C(=O)N1CC(C#N)C1] | 2-(7-Pyrrolidin-1-yl-thieno[3,2-b]pyridin-2-yl)-5H-pyrrolo[2,3-b]pyrazine-7-carboxylic acid [(R)-2-(3-cyano-azetidin-1-yl)-1-methyl-2-oxo-ethyl]-amide | |
| I-102 | 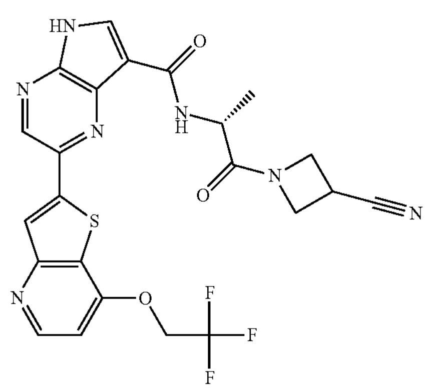 [SMILES: C[C@@H](NC(=O)c1c[nH]c2ncc(-c3cc4nccc(OCC(F)(F)F)c4s3)nc12)C(=O)N1CC(C#N)C1] | 2-[7-(2,2,2-Trifluoro-ethoxy)-thieno[3,2-b]pyridin-2-yl]-5H-pyrrolo[2,3-b]pyrazine-7-carboxylic acid [(R)-2-(3-cyano-azetidin-1-yl)-1-methyl-2-oxo-ethyl]-amide | |
| I-103 | 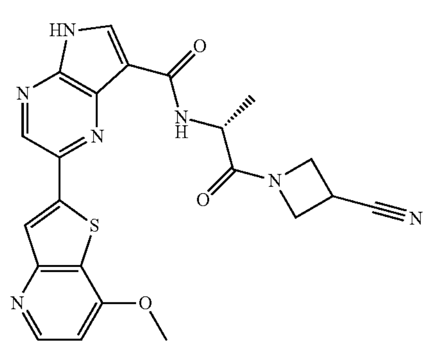 [SMILES: COc1ccnc2cc(-c3cnc4[nH]cc(C(=O)N[C@H](C)C(=O)N5CC(C#N)C5)c4n3)sc12] | 2-(7-Methoxy-thieno[3,2-b]pyridin-2-yl)-5H-pyrrolo[2,3-b]pyrazine-7-carboxylic acid [(R)-2-(3-cyano-azetidin-1-yl)-1-methyl-2-oxo-ethyl]-amide | |

TABLE I-continued

| COMPOUND | STRUCTURE | SYSTEMATIC NAME | MP |
|---|---|---|---|
| I-104 | 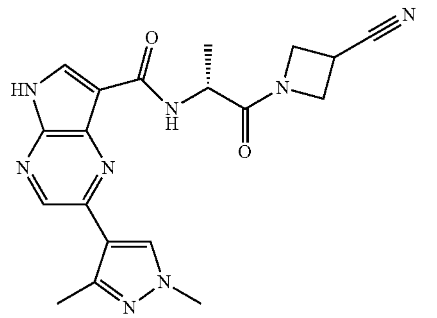 [SMILES: Cc1nn(C)cc1-c1cnc2[nH]cc(C(=O)N[C@H](C)C(=O)N3CC(C#N)C3)c2n1] | 2-(1,3-Dimethyl-1H-pyrazol-4-yl)-5H-pyrrolo[2,3-b]pyrazine-7-carboxylic acid [(R)-2-(3-cyano-azetidin-1-yl)-1-methyl-2-oxo-ethyl]-amide | |
| I-105 | 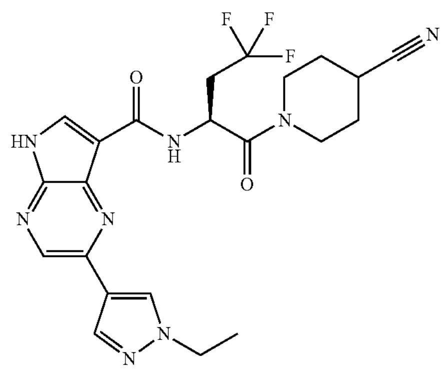 [SMILES: CCn1cc(-c2cnc3[nH]cc(C(=O)N[C@@H](CC(F)(F)F)C(=O)N4CCC(C#N)CC4)c3n2)cn1] | 2-(1-Ethyl-1H-pyrazol-4-yl)-5H-pyrrolo[2,3-b]pyrazine-7-carboxylic acid [(S)-1-(4-cyano-piperidine-1-carbonyl)-3,3,3-trifluoro-propyl]-amide | |
| I-106 | 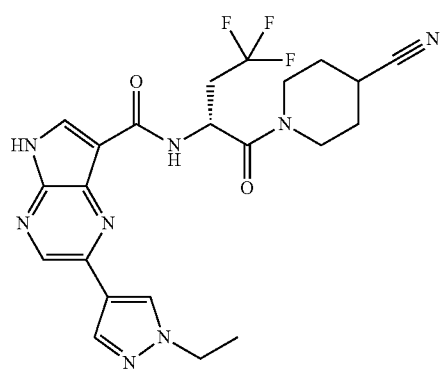 [SMILES: CCn1cc(-c2cnc3[nH]cc(C(=O)N[C@H](CC(F)(F)F)C(=O)N4CCC(C#N)CC4)c3n2)cn1] | 2-(1-Ethyl-1H-pyrazol-4-yl)-5H-pyrrolo[2,3-b]pyrazine-7-carboxylic acid [(R)-1-(4-cyano-piperidine-1-carbonyl)-3,3,3-trifluoro-propyl]-amide | |
| I-107 | 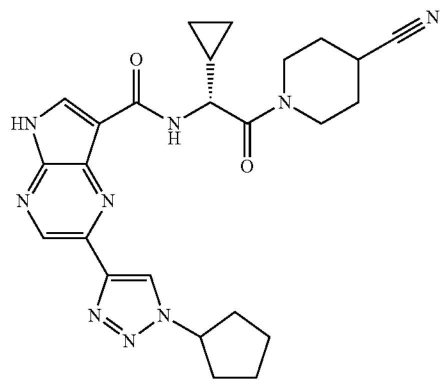 [SMILES: N#CC1CCN(C(=O)[C@H](NC(=O)c2c[nH]c3ncc(-c4cn(C5CCCC5)nn4)nc23)C2CC2)CC1] | 2-(1-Cyclopentyl-1H-[1,2,3]triazol-4-yl)-5H-pyrrolo[2,3-b]pyrazine-7-carboxylic acid [(R)-2-(4-cyano-piperidin-1-yl)-1-cyclopropyl-2-oxo-ethyl]-amide | |

TABLE I-continued

| COMPOUND | STRUCTURE | SYSTEMATIC NAME | MP |
|---|---|---|---|
| I-108 | 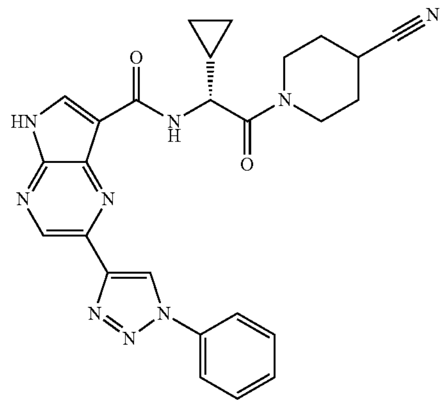 [SMILES: N#CC1CCN(C(=O)[C@H](NC(=O)c2c[nH]c3ncc(-c4cn(-c5ccccc5)nn4)nc23)C2CC2)CC1] | 2-(1-Phenyl-1H-[1,2,3]triazol-4-yl)-5H-pyrrolo[2,3-b]pyrazine-7-carboxylic acid [(R)-2-(4-cyano-piperidin-1-yl)-1-cyclopropyl-2-oxo-ethyl]-amide | |
| I-109 | 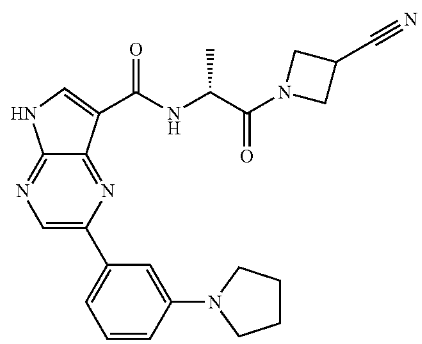 [SMILES: C[C@@H](NC(=O)c1c[nH]c2ncc(-c3cccc(N4CCCC4)c3)nc12)C(=O)N1CC(C#N)C1] | 2-(3-Pyrrolidin-1-yl-phenyl)-5H-pyrrolo[2,3-b]pyrazine-7-carboxylic acid [(R)-2-(3-cyano-azetidin-1-yl)-1-methyl-2-oxo-ethyl]-amide | |
| I-110 | 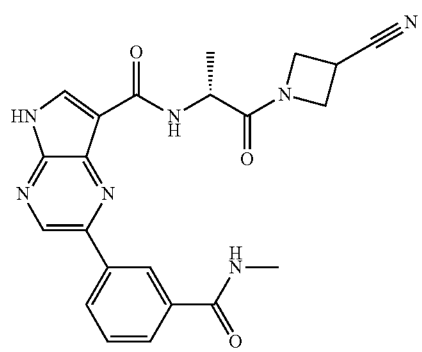 [SMILES: CNC(=O)c1cccc(-c2cnc3[nH]cc(C(=O)N[C@H](C)C(=O)N4CC(C#N)C4)c3n2)c1] | 2-(3-Methylcarbamoyl-phenyl)-5H-pyrrolo[2,3-b]pyrazine-7-carboxylic acid [(R)-2-(3-cyano-azetidin-1-yl)-1-methyl-2-oxo-ethyl]-amide | |
| I-111 | 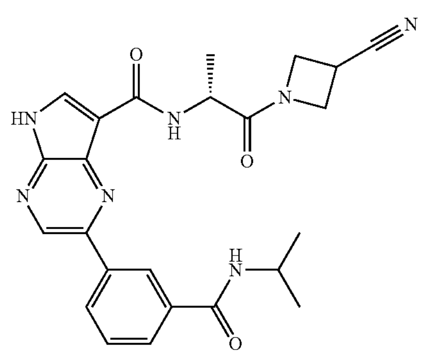 [SMILES: CC(C)NC(=O)c1cccc(-c2cnc3[nH]cc(C(=O)N[C@H](C)C(=O)N4CC(C#N)C4)c3n2)c1] | 2-(3-Isopropylcarbamoyl-phenyl)-5H-pyrrolo[2,3-b]pyrazine-7-carboxylic acid [(R)-2-(3-cyano-azetidin-1-yl)-1-methyl-2-oxo-ethyl]-amide | |

TABLE I-continued

| COMPOUND | STRUCTURE | SYSTEMATIC NAME | MP |
|---|---|---|---|
| I-112 | 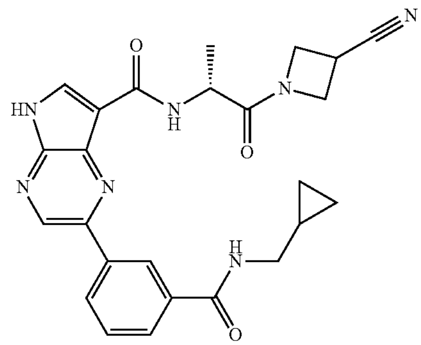 [SMILES: C[C@@H](NC(=O)c1c[nH]c2ncc(-c3cccc(C(=O)NCC4CC4)c3)nc12)C(=O)N1CC(C#N)C1] | 2-[3-(Cyclopropylmethyl-carbamoyl)-phenyl]-5H-pyrrolo[2,3-b]pyrazine-7-carboxylic acid [(R)-2-(3-cyano-azetidin-1-yl)-1-methyl-2-oxo-ethyl]-amide | |
| I-113 | 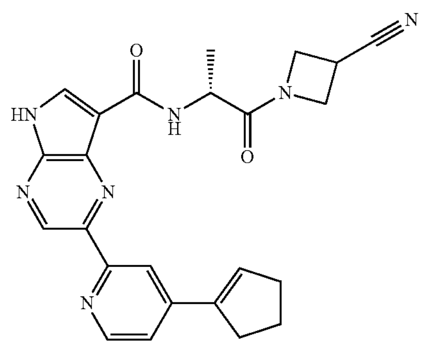 [SMILES: C[C@@H](NC(=O)c1c[nH]c2ncc(-c3cc(C4=CCCC4)ccn3)nc12)C(=O)N1CC(C#N)C1] | 2-(4-Cyclopent-1-enyl-pyridin-2-yl)-5H-pyrrolo[2,3-b]pyrazine-7-carboxylic acid [(R)-2-(3-cyano-azetidin-1-yl)-1-methyl-2-oxo-ethyl]-amide | |
| I-114 | 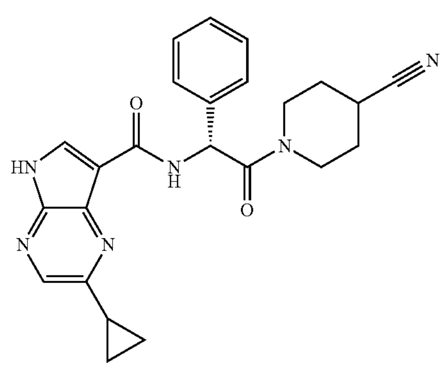 [SMILES: N#CC1CCN(C(=O)[C@H](NC(=O)c2c[nH]c3ncc(C4CC4)nc23)c2ccccc2)CC1] | 2-Cyclopropyl-5H-pyrrolo[2,3-b]pyrazine-7-carboxylic acid [(R)-2-(4-cyano-piperidin-1-yl)-2-oxo-1-phenyl-ethyl]-amide | |
| I-115 | 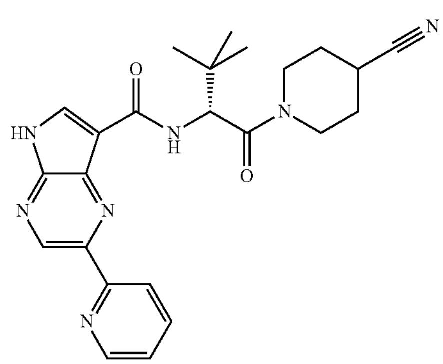 [SMILES: CC(C)(C)[C@@H](NC(=O)c1c[nH]c2ncc(-c3ccccn3)nc12)C(=O)N1CCC(C#N)CC1] | 2-Pyridin-2-yl-5H-pyrrolo[2,3-b]pyrazine-7-carboxylic acid [(R)-1-(4-cyano-piperidine-1-carbonyl)-2,2-dimethyl-propyl]-amide | |

TABLE I-continued

| COMPOUND | STRUCTURE | SYSTEMATIC NAME | MP |
|---|---|---|---|
| I-116 | 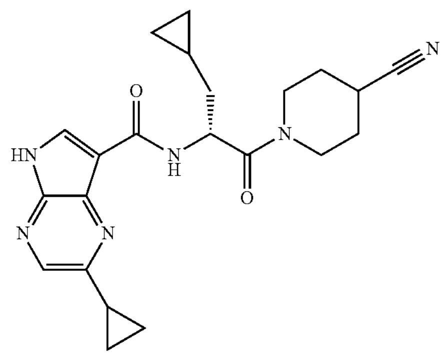 [SMILES: N#CC1CCN(C(=O)[C@@H](CC2CC2)NC(=O)c2c[nH]c3ncc(C4CC4)nc23)CC1] | 2-Cyclopropyl-5H-pyrrolo[2,3-b]pyrazine-7-carboxylic acid [(R)-2-(4-cyano-piperidin-1-yl)-1-cyclopropylmethyl-2-oxo-ethyl]-amide | |
| I-117 | 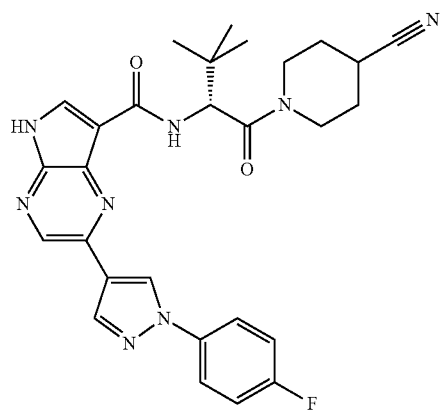 [SMILES: CC(C)(C)[C@@H](NC(=O)c1c[nH]c2ncc(-c3cnn(-c4ccc(F)cc4)c3)nc12)C(=O)N1CCC(C#N)CC1] | 2-[1-(4-Fluoro-phenyl)-1H-pyrazol-4-yl]-5H-pyrrolo[2,3-b]pyrazine-7-carboxylic acid [(R)-1-(4-cyano-piperidine-1-carbonyl)-2,2-dimethyl-propyl]-amide | |
| I-118 | 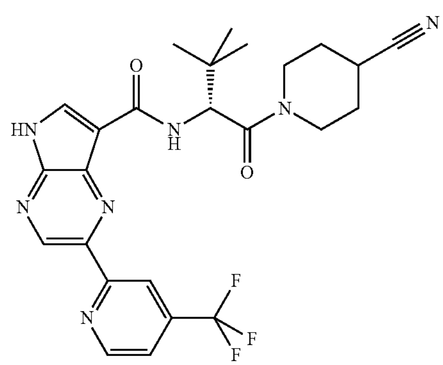 [SMILES: CC(C)(C)[C@@H](NC(=O)c1c[nH]c2ncc(-c3cc(C(F)(F)F)ccn3)nc12)C(=O)N1CCC(C#N)CC1] | 2-(4-Trifluoromethyl-pyridin-2-yl)-5H-pyrrolo[2,3-b]pyrazine-7-carboxylic acid [(R)-1-(4-cyano-piperidine-1-carbonyl)-2,2-dimethyl-propyl]-amide | |
| I-119 | 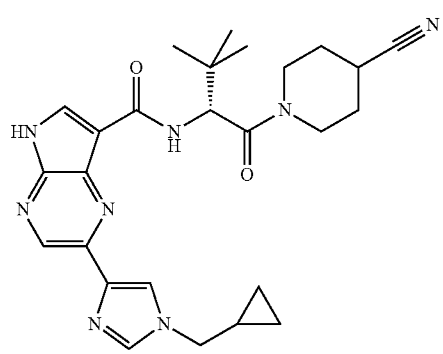 [SMILES: CC(C)(C)[C@@H](NC(=O)c1c[nH]c2ncc(-c3cn(CC4CC4)cn3)nc12)C(=O)N1CCC(C#N)CC1] | 2-(1-Cyclopropylmethyl-1H-imidazol-4-yl)-5H-pyrrolo[2,3-b]pyrazine-7-carboxylic acid [(R)-1-(4-cyano-piperidine-1-carbonyl)-2,2-dimethyl-propyl]-amide | |

TABLE I-continued

| COMPOUND | STRUCTURE | SYSTEMATIC NAME | MP |
|---|---|---|---|
| I-120 | 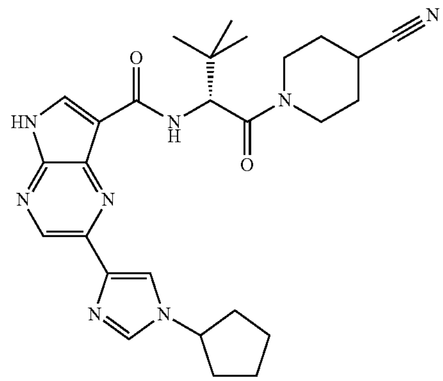 [SMILES: CC(C)(C)[C@@H](NC(=O)c1c[nH]c2ncc(-c3cn(C4CCCC4)cn3)nc12)C(=O)N1CCC(C#N)CC1] | 2-(1-Cyclopentyl-1H-imidazol-4-yl)-5H-pyrrolo[2,3-b]pyrazine-7-carboxylic acid [(R)-1-(4-cyano-piperidine-1-carbonyl)-2,2-dimethyl-propyl]-amide | |
| I-121 | 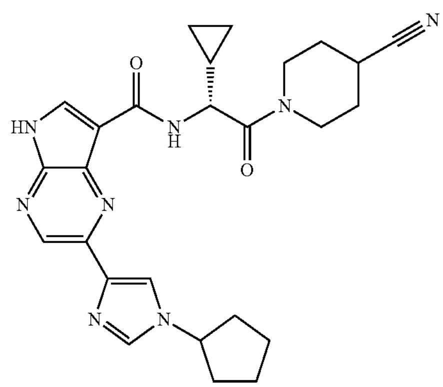 [SMILES: N#CC1CCN(C(=O)[C@H](NC(=O)c2c[nH]c3ncc(-c4cn(C5CCCC5)cn4)nc23)C2CC2)CC1] | 2-(1-Cyclopentyl-1H-imidazol-4-yl)-5H-pyrrolo[2,3-b]pyrazine-7-carboxylic acid [(R)-2-(4-cyano-piperidin-1-yl)-1-cyclopropyl-2-oxo-ethyl]-amide | |
| I-122 | 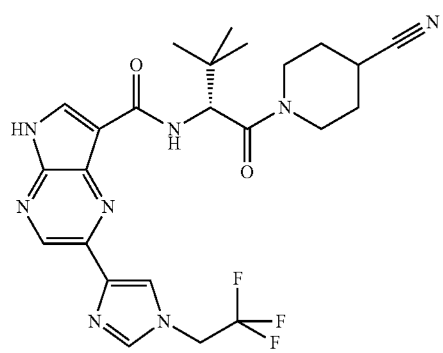 [SMILES: CC(C)(C)[C@@H](NC(=O)c1c[nH]c2ncc(-c3cn(CC(F)(F)F)cn3)nc12)C(=O)N1CCC(C#N)CC1] | 2-[1-(2,2,2-Trifluoro-ethyl)-1H-imidazol-4-yl]-5H-pyrrolo[2,3-b]pyrazine-7-carboxylic acid [(R)-1-(4-cyano-piperidine-1-carbonyl)-2,2-dimethyl-propyl]-amide | |
| I-123 | 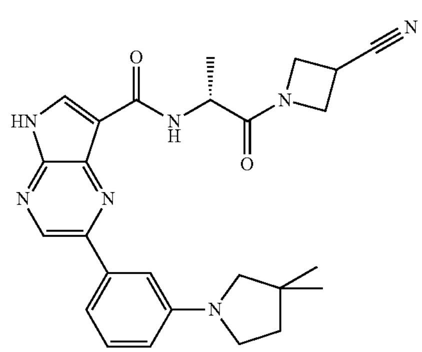 [SMILES: C[C@@H](NC(=O)c1c[nH]c2ncc(-c3cccc(N4CCC(C)(C)C4)c3)nc12)C(=O)N1CC(C#N)C1] | 2-[3-(3,3-Dimethyl-pyrrolidin-1-yl)-phenyl]-5H-pyrrolo[2,3-b]pyrazine-7-carboxylic acid [(R)-2-(3-cyano-azetidin-1-yl)-1-methyl-2-oxo-ethyl]-amide | |

TABLE I-continued

| COMPOUND | STRUCTURE | SYSTEMATIC NAME | MP |
|---|---|---|---|
| I-124 | 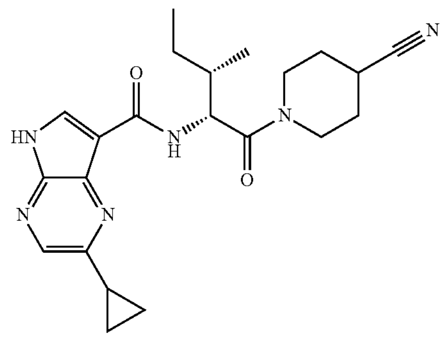 [SMILES: CC[C@H](C)[C@@H](NC(=O)c1c[nH]c2ncc(C3CC3)nc12)C(=O)N1CCC(C#N)CC1] | 2-Cyclopropyl-5H-pyrrolo[2,3-b]pyrazine-7-carboxylic acid [(1R,2S)-1-(4-cyano-piperidine-1-carbonyl)-2-methyl-butyl]-amide | |
| I-125 | 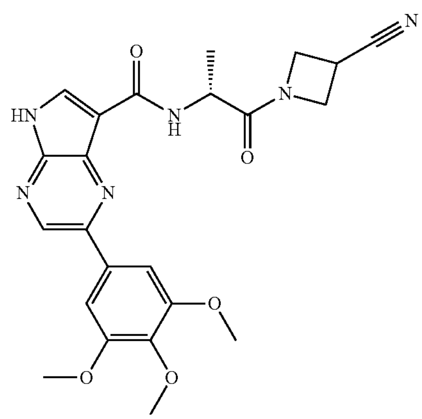 [SMILES: COc1cc(-c2cnc3[nH]cc(C(=O)N[C@H](C)C(=O)N4CC(C#N)C4)c3n2)cc(OC)c1OC] | 2-(3,4,5-Trimethoxy-phenyl)-5H-pyrrolo[2,3-b]pyrazine-7-carboxylic acid [(R)-2-(3-cyano-azetidin-1-yl)-1-methyl-2-oxo-ethyl]-amide | |
| I-126 | 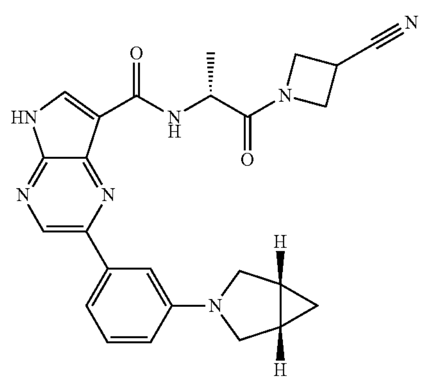 [SMILES: C[C@@H](NC(=O)c1c[nH]c2ncc(-c3cccc(N4C[C@H]5C[C@H]5C4)c3)nc12)C(=O)N1CC(C#N)C1] | 2-[(1S,5R)-3-(3-Aza-bicyclo[3.1.0]hex-3-yl)-phenyl]-5H-pyrrolo[2,3-b]pyrazine-7-carboxylic acid [(R)-2-(3-cyano-azetidin-1-yl)-1-methyl-2-oxo-ethyl]-amide | |
| I-127 | 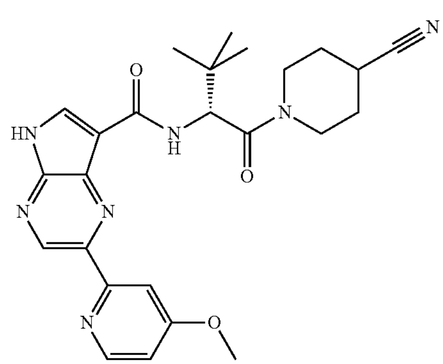 [SMILES: COc1ccnc(-c2cnc3[nH]cc(C(=O)N[C@@H](C(=O)N4CCC(C#N)CC4)C(C)(C)C)c3n2)c1] | 2-(4-Methoxy-pyridin-2-yl)-5H-pyrrolo[2,3-b]pyrazine-7-carboxylic acid [(R)-1-(4-cyano-piperidine-1-carbonyl)-2,2-dimethyl-propyl]-amide | |

TABLE I-continued

| COMPOUND | STRUCTURE | SYSTEMATIC NAME | MP |
|---|---|---|---|
| I-128 | 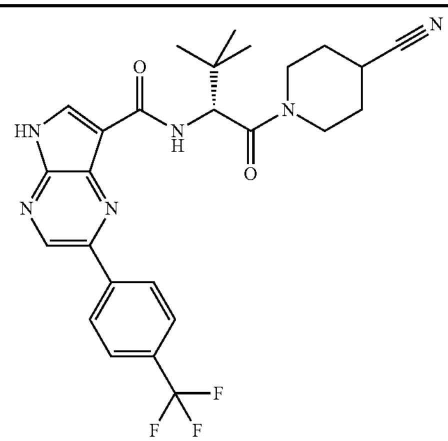 | 2-(4-Trifluoromethyl-phenyl)-5H-pyrrolo[2,3-b]pyrazine-7-carboxylic acid [(R)-1-(4-cyano-piperidine-1-carbonyl)-2,2-dimethyl-propyl]-amide | |
| I-129 | 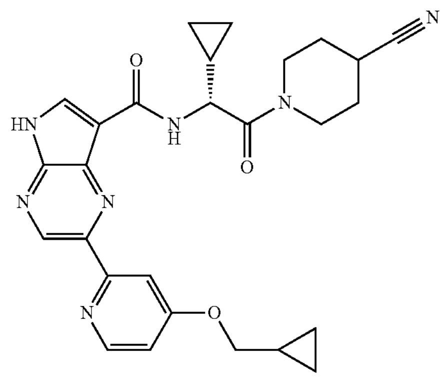 [SMILES: N#CC1CCN(C(=O)[C@H](NC(=O)c2c[nH]c3ncc(-c4cc(OCC5CC5)ccn4)nc23)C2CC2)CC1] | 2-(4-Cyclopropylmethoxy-pyridin-2-yl)-5H-pyrrolo[2,3-b]pyrazine-7-carboxylic acid [(R)-2-(4-cyano-piperidin-1-yl)-1-cyclopropyl-2-oxo-ethyl]-amide | |
| I-130 | 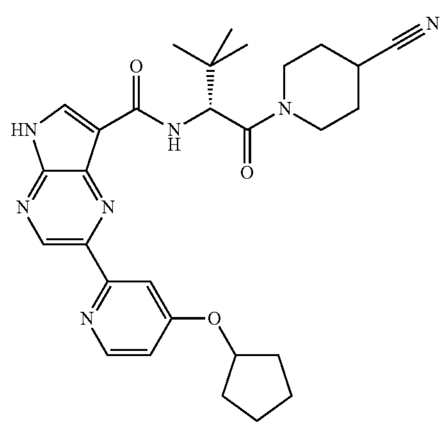 [SMILES: CC(C)(C)[C@@H](NC(=O)c1c[nH]c2ncc(-c3cc(OC4CCCC4)ccn3)nc12)C(=O)N1CCC(C#N)CC1] | 2-(4-Cyclopentyloxy-pyridin-2-yl)-5H-pyrrolo[2,3-b]pyrazine-7-carboxylic acid [(R)-1-(4-cyano-piperidine-1-carbonyl)-2,2-dimethyl-propyl]-amide | |
| I-131 | 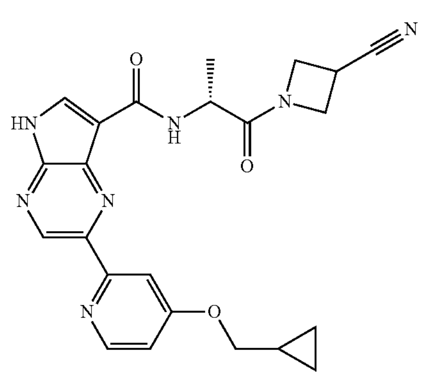 [SMILES: C[C@@H](NC(=O)c1c[nH]c2ncc(-c3cc(OCC4CC4)ccn3)nc12)C(=O)N1CC(C#N)C1] | 2-(4-Cyclopropylmethoxy-pyridin-2-yl)-5H-pyrrolo[2,3-b]pyrazine-7-carboxylic acid [(R)-2-(3-cyano-azetidin-1-yl)-1-methyl-2-oxo-ethyl]-amide | |

TABLE I-continued

| COMPOUND | STRUCTURE | SYSTEMATIC NAME | MP |
|---|---|---|---|
| I-132 | 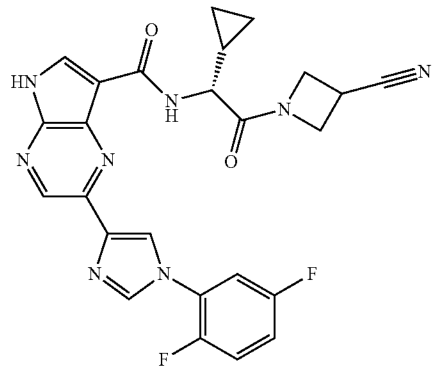 [SMILES: N#CC1CN(C(=O)[C@H](NC(=O)c2c[nH]c3ncc(-c4cn(-c5cc(F)ccc5F)cn4)nc23)C2CC2)C1] | 2-[1-(2,5-Difluoro-phenyl)-1H-imidazol-4-yl]-5H-pyrrolo[2,3-b]pyrazine-7-carboxylic acid [(R)-2-(3-cyano-azetidin-1-yl)-1-cyclopropyl-2-oxo-ethyl]-amide | |
| I-133 | 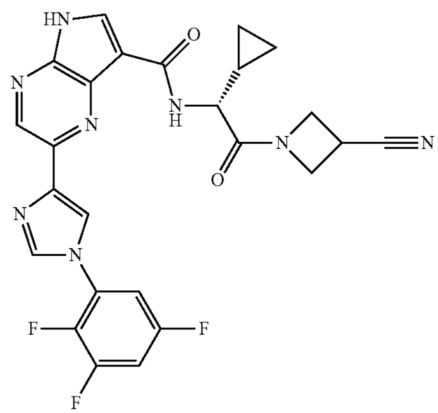 [SMILES: N#CC1CN(C(=O)[C@H](NC(=O)c2c[nH]c3ncc(-c4cn(-c5cc(F)cc(F)c5F)cn4)nc23)C2CC2)C1] | 2-[1-(2,3,5-Trifluoro-phenyl)-1H-imidazol-4-yl]-5H-pyrrolo[2,3-b]pyrazine-7-carboxylic acid [(R)-2-(3-cyano-azetidin-1-yl)-1-cyclopropyl-2-oxo-ethyl]-amide | |
| I-134 | 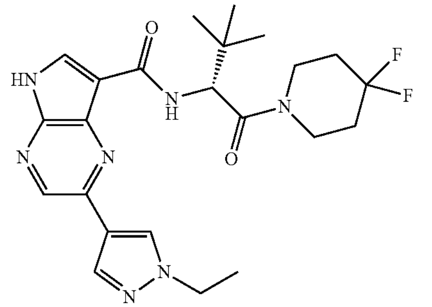 [SMILES: CCn1cc(-c2cnc3[nH]cc(C(=O)N[C@@H](C(=O)N4CCC(F)(F)CC4)C(C)(C)C)c3n2)cn1] | 2-(1-Ethyl-1H-pyrazol-4-yl)-5H-pyrrolo[2,3-b]pyrazine-7-carboxylic acid [(R)-1-(4,4-difluoro-piperidine-1-carbonyl)-2,2-dimethyl-propyl]-amide | |
| I-135 | 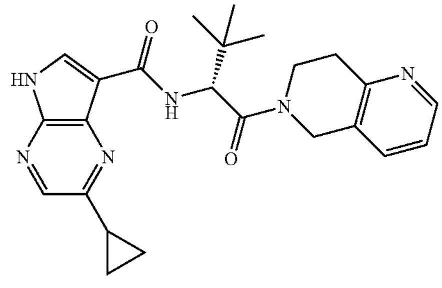 [SMILES: CC(C)(C)[C@@H](NC(=O)c1c[nH]c2ncc(C3CC3)nc12)C(=O)N1CCc2ncccc2C1] | 2-Cyclopropyl-5H-pyrrolo[2,3-b]pyrazine-7-carboxylic acid [(R)-1-(7,8-dihydro-5H-[1,6]naphthyridine-6-carbonyl)-2,2-dimethyl-propyl]-amide | |

TABLE I-continued

| COMPOUND | STRUCTURE | SYSTEMATIC NAME | MP |
|---|---|---|---|
| I-136 | 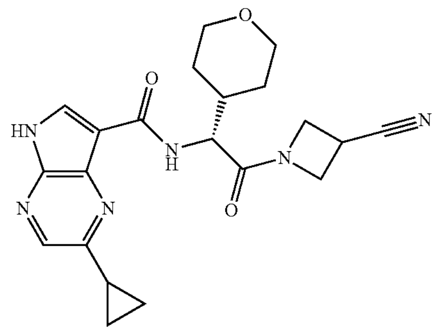 [SMILES: N#CC1CN(C(=O)[C@H](NC(=O)c2c[nH]c3ncc(C4CC4)nc23)C2CCOCC2)C1] | 2-Cyclopropyl-5H-pyrrolo[2,3-b]pyrazine-7-carboxylic acid [(R)-2-(3-cyano-azetidin-1-yl)-2-oxo-1-(tetrahydro-pyran-4-yl)-ethyl]-amide | |
| I-137 | 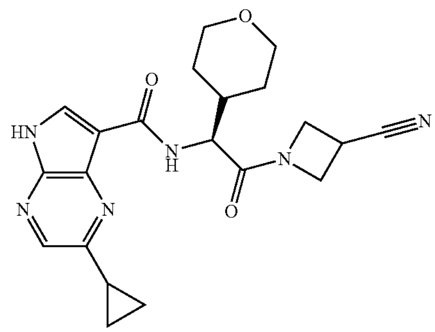 [SMILES: N#CC1CN(C(=O)[C@@H](NC(=O)c2c[nH]c3ncc(C4CC4)nc23)C2CCOCC2)C1] | 2-Cyclopropyl-5H-pyrrolo[2,3-b]pyrazine-7-carboxylic acid [(S)-2-(3-cyano-azetidin-1-yl)-2-oxo-1-(tetrahydro-pyran-4-yl)-ethyl]-amide | |
| I-138 | 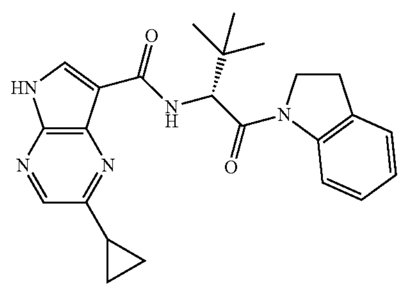 [SMILES: CC(C)(C)[C@@H](NC(=O)c1c[nH]c2ncc(C3CC3)nc12)C(=O)N1CCc2ccccc21] | 2-Cyclopropyl-5H-pyrrolo[2,3-b]pyrazine-7-carboxylic acid [(R)-1-(2,3-dihydro-indole-1-carbonyl)-2,2-dimethyl-propyl]-amide | |
| I-139 | 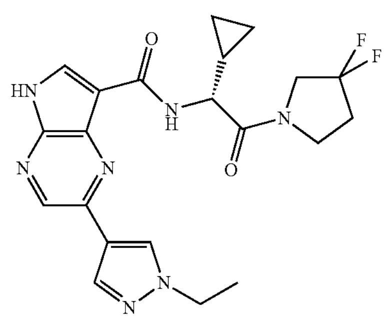 [SMILES: CCn1cc(-c2cnc3[nH]cc(C(=O)N[C@@H](C(=O)N4CCC(F)(F)C4)C4CC4)c3n2)cn1] | 2-(1-Ethyl-1H-pyrazol-4-yl)-5H-pyrrolo[2,3-b]pyrazine-7-carboxylic acid [(R)-1-cyclopropyl-2-(3,3-difluoro-pyrrolidin-1-yl)-2-oxo-ethyl]-amide | |
| I-140 | 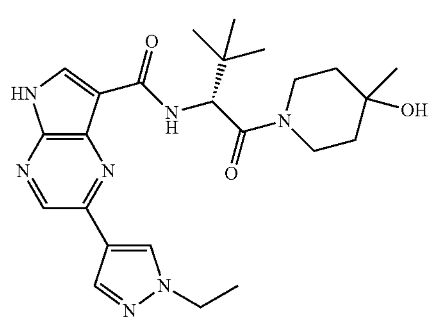 [SMILES: CCn1cc(-c2cnc3[nH]cc(C(=O)N[C@@H](C(=O)N4CCC(C)(O)CC4)C(C)(C)C)c3n2)cn1] | 2-(1-Ethyl-1H-pyrazol-4-yl)-5H-pyrrolo[2,3-b]pyrazine-7-carboxylic acid [(R)-1-(4-hydroxy-4-methyl-piperidine-1-carbonyl)-2,2-dimethyl-propyl]-amide | |

TABLE I-continued

| COMPOUND | STRUCTURE | SYSTEMATIC NAME | MP |
|---|---|---|---|
| I-141 | 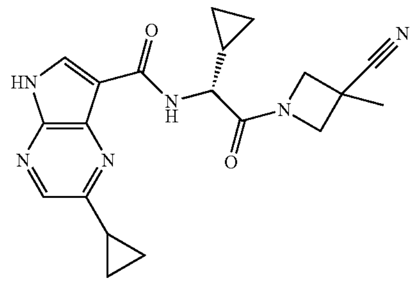 [SMILES: CC1(C#N)CN(C(=O)[C@H](NC(=O)c2c[nH]c3ncc(C4CC4)nc23)C2CC2)C1] | 2-Cyclopropyl-5H-pyrrolo[2,3-b]pyrazine-7-carboxylic acid [(R)-2-(3-cyano-3-methyl-azetidin-1-yl)-1-cyclopropyl-2-oxo-ethyl]-amide | |
| I-142 | 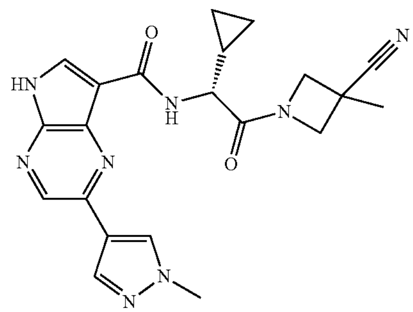 [SMILES: Cn1cc(-c2cnc3[nH]cc(C(=O)N[C@@H](C(=O)N4CC(C)(C#N)C4)C4CC4)c3n2)cn1] | 2-(1-Methyl-1H-pyrazol-4-yl)-5H-pyrrolo[2,3-b]pyrazine-7-carboxylic acid [(R)-2-(3-cyano-3-methyl-azetidin-1-yl)-1-cyclopropyl-2-oxo-ethyl]-amide | |
| I-143 | 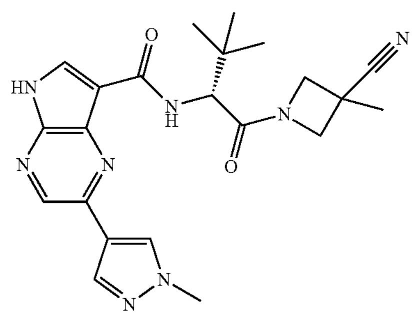 [SMILES: Cn1cc(-c2cnc3[nH]cc(C(=O)N[C@@H](C(=O)N4CC(C)(C#N)C4)C(C)(C)C)c3n2)cn1] | 2-(1-Methyl-1H-pyrazol-4-yl)-5H-pyrrolo[2,3-b]pyrazine-7-carboxylic acid [(R)-1-(3-cyano-3-methyl-azetidine-1-carbonyl)-2,2-dimethyl-propyl]-amide | |
| I-144 | 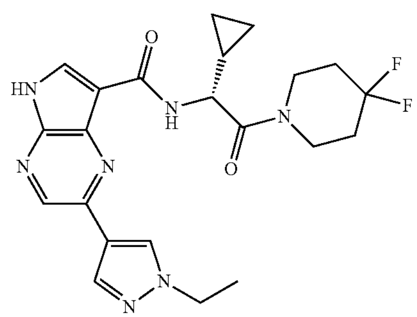 [SMILES: CCn1cc(-c2cnc3[nH]cc(C(=O)N[C@@H](C(=O)N4CCC(F)(F)CC4)C4CC4)c3n2)cn1] | 2-(1-Ethyl-1H-pyrazol-4-yl)-5H-pyrrolo[2,3-b]pyrazine-7-carboxylic acid [(R)-1-cyclopropyl-2-(4,4-difluoro-piperidin-1-yl)-2-oxo-ethyl]-amide | |
| I-145 | 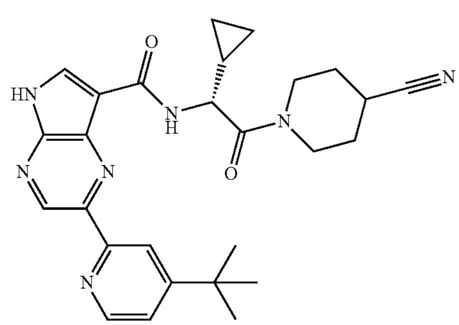 [SMILES: CC(C)(C)c1ccnc(-c2cnc3[nH]cc(C(=O)N[C@@H](C(=O)N4CCC(C#N)CC4)C4CC4)c3n2)c1] | 2-(4-tert-Butyl-pyridin-2-yl)-5H-pyrrolo[2,3-b]pyrazine-7-carboxylic acid [(R)-2-(4-cyano-piperidin-1-yl)-1-cyclopropyl-2-oxo-ethyl]-amide | |

TABLE I-continued

| COMPOUND | STRUCTURE | SYSTEMATIC NAME | MP |
|---|---|---|---|
| I-146 | 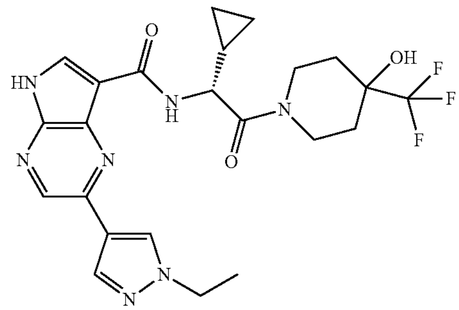 [SMILES: CCn1cc(-c2cnc3[nH]cc(C(=O)N[C@@H](C(=O)N4CCC(O)(C(F)(F)F)CC4)C4CC4)c3n2)cn1] | 2-(1-Ethyl-1H-pyrazol-4-yl)-5H-pyrrolo[2,3-b]pyrazine-7-carboxylic acid [(R)-1-cyclopropyl-2-(4-hydroxy-4-trifluoromethyl-piperidin-1-yl)-2-oxo-ethyl]-amide | |
| I-147 | 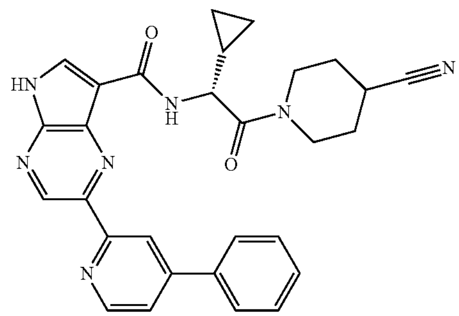 [SMILES: N#CC1CCN(C(=O)[C@H](NC(=O)c2c[nH]c3ncc(-c4cc(-c5ccccc5)ccn4)nc23)C2CC2)CC1] | 2-(4-Phenyl-pyridin-2-yl)-5H-pyrrolo[2,3-b]pyrazine-7-carboxylic acid [(R)-2-(4-cyano-piperidin-1-yl)-1-cyclopropyl-2-oxo-ethyl]-amide | |
| I-148 | 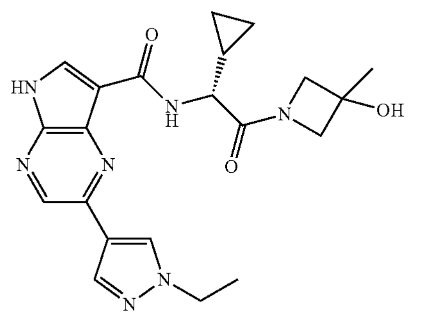 [SMILES: CCn1cc(-c2cnc3[nH]cc(C(=O)N[C@@H](C(=O)N4CC(C)(O)C4)C4CC4)c3n2)cn1] | 2-(1-Ethyl-1H-pyrazol-4-yl)-5H-pyrrolo[2,3-b]pyrazine-7-carboxylic acid [(R)-1-cyclopropyl-2-(3-hydroxy-3-methyl-azetidin-1-yl)-2-oxo-ethyl]-amide | |
| I-149 | 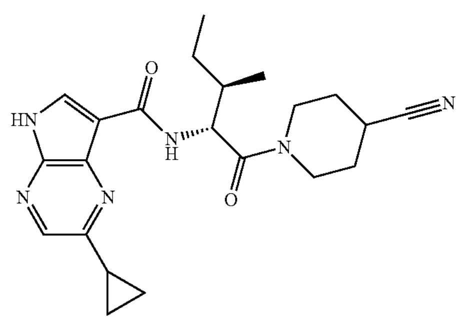 [SMILES: CC[C@@H](C)[C@@H](NC(=O)c1c[nH]c2ncc(C3CC3)nc12)C(=O)N1CCC(C#N)CC1] | 2-Cyclopropyl-5H-pyrrolo[2,3-b]pyrazine-7-carboxylic acid [(1R,2R)-1-(4-cyano-piperidine-1-carbonyl)-2-methyl-butyl]-amide | |
| I-150 | 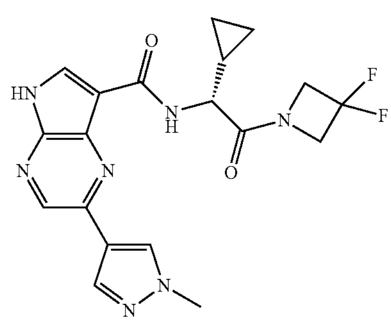 [SMILES: Cn1cc(-c2cnc3[nH]cc(C(=O)N[C@@H](C(=O)N4CC(F)(F)C4)C4CC4)c3n2)cn1] | 2-(1-Methyl-1H-pyrazol-4-yl)-5H-pyrrolo[2,3-b]pyrazine-7-carboxylic acid [(R)-1-cyclopropyl-2-(3,3-difluoro-azetidin-1-yl)-2-oxo-ethyl]-amide | |

TABLE I-continued

| COMPOUND | STRUCTURE | SYSTEMATIC NAME | MP |
|---|---|---|---|
| I-151 | 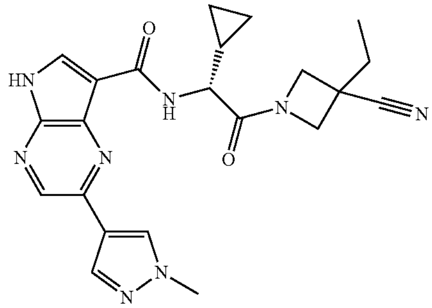 [SMILES: CCC1(C#N)CN(C(=O)[C@H](NC(=O)c2c[nH]c3ncc(-c4cnn(C)c4)nc23)C2CC2)C1] | 2-(1-Methyl-1H-pyrazol-4-yl)-5H-pyrrolo[2,3-b]pyrazine-7-carboxylic acid [(R)-2-(3-cyano-3-ethyl-azetidin-1-yl)-1-cyclopropyl-2-oxo-ethyl]-amide | |
| I-152 | 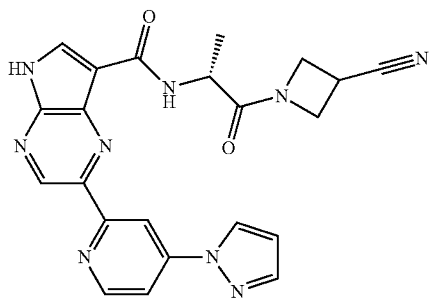 [SMILES: C[C@@H](NC(=O)c1c[nH]c2ncc(-c3cc(-n4cccn4)ccn3)nc12)C(=O)N1CC(C#N)C1] | 2-(4-Pyrazol-1-yl-pyridin-2-yl)-5H-pyrrolo[2,3-b]pyrazine-7-carboxylic acid [(R)-2-(3-cyano-azetidin-1-yl)-1-methyl-2-oxo-ethyl]-amide | |
| I-153 | 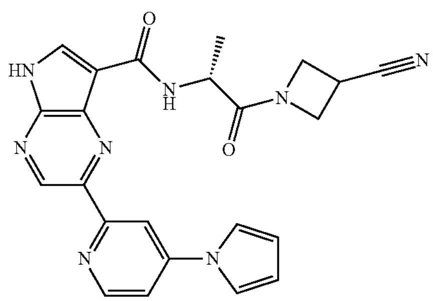 [SMILES: C[C@@H](NC(=O)c1c[nH]c2ncc(-c3cc(-n4cccc4)ccn3)nc12)C(=O)N1CC(C#N)C1] | 2-(4-Pyrrol-1-yl-pyridin-2-yl)-5H-pyrrolo[2,3-b]pyrazine-7-carboxylic acid [(R)-2-(3-cyano-azetidin-1-yl)-1-methyl-2-oxo-ethyl]-amide | |
| I-154 | 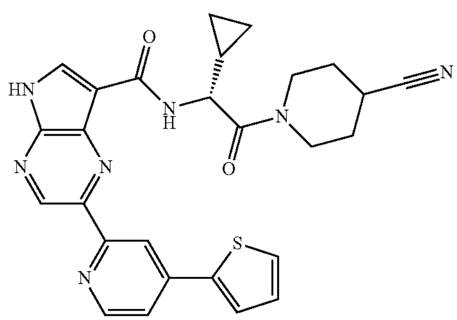 [SMILES: N#CC1CCN(C(=O)[C@H](NC(=O)c2c[nH]c3ncc(-c4cc(-c5cccs5)ccn4)nc23)C2CC2)CC1] | 2-(4-Thiophen-2-yl-pyridin-2-yl)-5H-pyrrolo[2,3-b]pyrazine-7-carboxylic acid [(R)-2-(4-cyano-piperidin-1-yl)-1-cyclopropyl-2-oxo-ethyl]-amide | |
| I-155 | 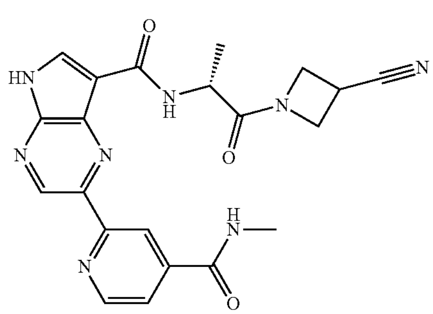 [SMILES: CNC(=O)c1ccnc(-c2cnc3[nH]cc(C(=O)N[C@H](C)C(=O)N4CC(C#N)C4)c3n2)c1] | 2-(4-Methylcarbamoyl-pyridin-2-yl)-5H-pyrrolo[2,3-b]pyrazine-7-carboxylic acid [(R)-2-(3-cyano-azetidin-1-yl)-1-methyl-2-oxo-ethyl]-amide | |

TABLE I-continued

| COMPOUND | STRUCTURE | SYSTEMATIC NAME | MP |
|---|---|---|---|
| I-156 | 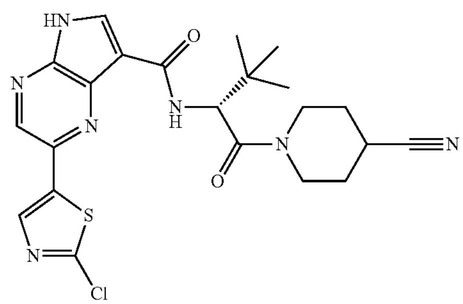 [SMILES: CC(C)(C)[C@@H](NC(=O)c1c[nH]c2ncc(-c3cnc(Cl)s3)nc12)C(=O)N1CCC(C#N)CC1] | 2-(2-Chloro-thiazol-5-yl)-5H-pyrrolo[2,3-b]pyrazine-7-carboxylic acid [(R)-1-(4-cyano-piperidine-1-carbonyl)-2,2-dimethyl-propyl]-amide | |
| I-157 | 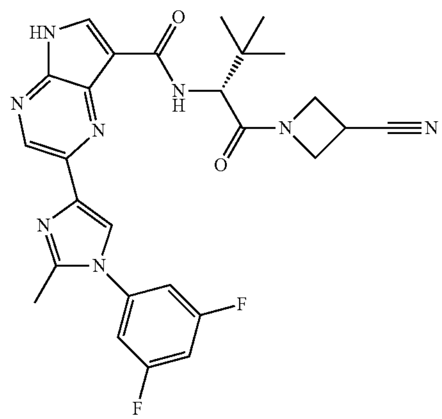 [SMILES: Cc1nc(-c2cnc3[nH]cc(C(=O)N[C@@H](C(=O)N4CC(C#N)C4)C(C)(C)C)c3n2)cn1-c1cc(F)cc(F)c1] | 2-[1-(3,5-Difluoro-phenyl)-2-methyl-1H-imidazol-4-yl]-5H-pyrrolo[2,3-b]pyrazine-7-carboxylic acid [(R)-1-(3-cyano-azetidine-1-carbonyl)-2,2-dimethyl-propyl]-amide | |
| I-158 | 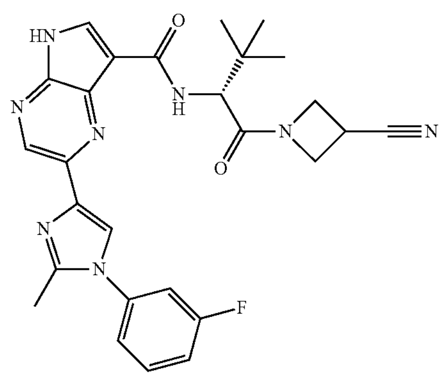 [SMILES: Cc1nc(-c2cnc3[nH]cc(C(=O)N[C@@H](C(=O)N4CC(C#N)C4)C(C)(C)C)c3n2)cn1-c1cccc(F)c1] | 2-[1-(3-Fluoro-phenyl)-2-methyl-1H-imidazol-4-yl]-5H-pyrrolo[2,3-b]pyrazine-7-carboxylic acid [(R)-1-(3-cyano-azetidine-1-carbonyl)-2,2-dimethyl-propyl]-amide | |
| I-159 | 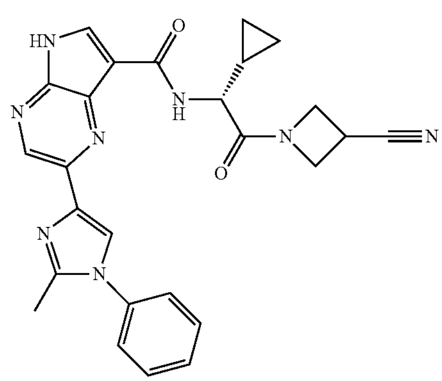 [SMILES: Cc1nc(-c2cnc3[nH]cc(C(=O)N[C@@H](C(=O)N4CC(C#N)C4)C4CC4)c3n2)cn1-c1ccccc1] | 2-(2-Methyl-1-phenyl-1H-imidazol-4-yl)-5H-pyrrolo[2,3-b]pyrazine-7-carboxylic acid [(R)-2-(3-cyano-azetidin-1-yl)-1-cyclopropyl-2-oxo-ethyl]-amide | |

TABLE I-continued

| COMPOUND | STRUCTURE | SYSTEMATIC NAME | MP |
|---|---|---|---|
| I-160 | 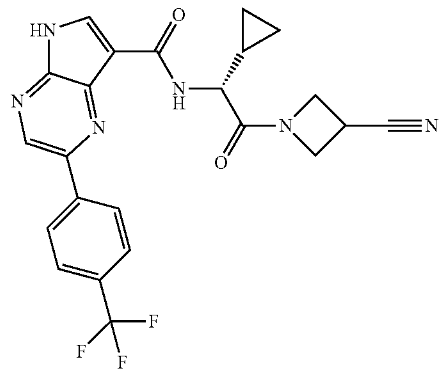 [SMILES: N#CC1CN(C(=O)[C@H](NC(=O)c2c[nH]c3ncc(-c4ccc(C(F)(F)F)cc4)nc23)C2CC2)C1] | 2-(4-Trifluoromethyl-phenyl)-5H-pyrrolo[2,3-b]pyrazine-7-carboxylic acid [(R)-2-(3-cyano-azetidin-1-yl)-1-cyclopropyl-2-oxo-ethyl]-amide | |
| I-161 | 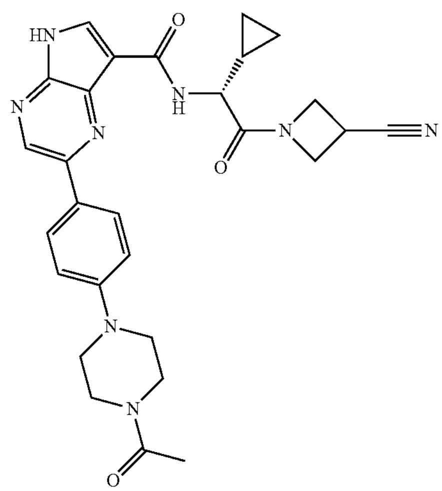 [SMILES: CC(=O)N1CCN(c2ccc(-c3cnc4[nH]cc(C(=O)N[C@@H](C(=O)N5CC(C#N)C5)C5CC5)c4n3)cc2)CC1] | 2-[4-(4-Acetyl-piperazin-1-yl)-phenyl]-5H-pyrrolo[2,3-b]pyrazine-7-carboxylic acid [(R)-2-(3-cyano-azetidin-1-yl)-1-cyclopropyl-2-oxo-ethyl]-amide | |
| I-162 | 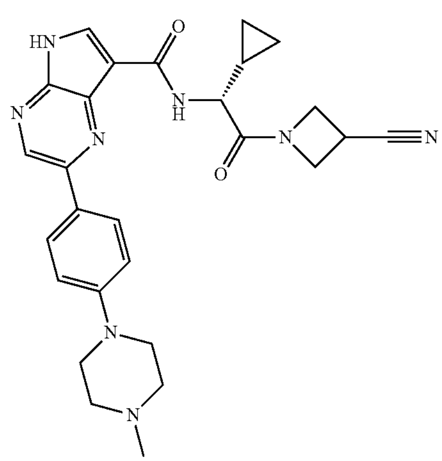 [SMILES: CN1CCN(c2ccc(-c3cnc4[nH]cc(C(=O)N[C@@H](C(=O)N5CC(C#N)C5)C5CC5)c4n3)cc2)CC1] | 2-[4-(4-Methyl-piperazin-1-yl)-phenyl]-5H-pyrrolo[2,3-b]pyrazine-7-carboxylic acid [(R)-2-(3-cyano-azetidin-1-yl)-1-cyclopropyl-2-oxo-ethyl]-amide | |

TABLE I-continued

| COMPOUND | STRUCTURE | SYSTEMATIC NAME | MP |
|---|---|---|---|
| I-163 | 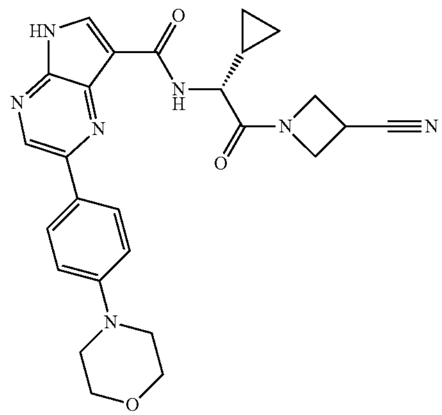 [SMILES: N#CC1CN(C(=O)[C@H](NC(=O)c2c[nH]c3ncc(-c4ccc(N5CCOCC5)cc4)nc23)C2CC2)C1] | 2-(4-Morpholin-4-yl-phenyl)-5H-pyrrolo[2,3-b]pyrazine-7-carboxylic acid [(R)-2-(3-cyano-azetidin-1-yl)-1-cyclopropyl-2-oxo-ethyl]-amide | |
| I-164 | 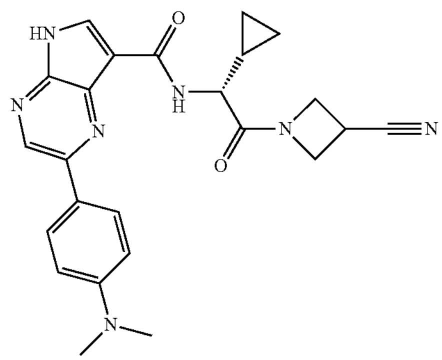 [SMILES: CN(C)c1ccc(-c2cnc3[nH]cc(C(=O)N[C@@H](C(=O)N4CC(C#N)C4)C4CC4)c3n2)cc1] | 2-(4-Dimethylamino-phenyl)-5H-pyrrolo[2,3-b]pyrazine-7-carboxylic acid [(R)-2-(3-cyano-azetidin-1-yl)-1-cyclopropyl-2-oxo-ethyl]-amide | |
| I-165 | 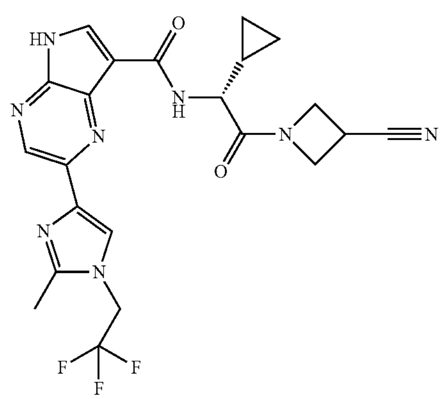 [SMILES: Cc1nc(-c2cnc3[nH]cc(C(=O)N[C@@H](C(=O)N4CC(C#N)C4)C4CC4)c3n2)cn1CC(F)(F)F] | 2-[2-Methyl-1-(2,2,2-trifluoro-ethyl)-1H-imidazol-4-yl]-5H-pyrrolo[2,3-b]pyrazine-7-carboxylic acid [(R)-2-(3-cyano-azetidin-1-yl)-1-cyclopropyl-2-oxo-ethyl]-amide | |
| I-166 | 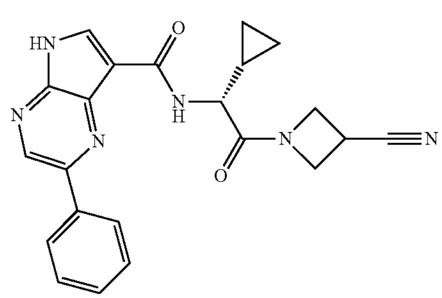 [SMILES: N#CC1CN(C(=O)[C@H](NC(=O)c2c[nH]c3ncc(-c4ccccc4)nc23)C2CC2)C1] | 2-Phenyl-5H-pyrrolo[2,3-b]pyrazine-7-carboxylic acid [(R)-2-(3-cyano-azetidin-1-yl)-1-cyclopropyl-2-oxo-ethyl]-amide | |

SYNTHESIS
General Scheme for Preparation of Pyrrolopyrazinyl Starting Material
Scheme 1
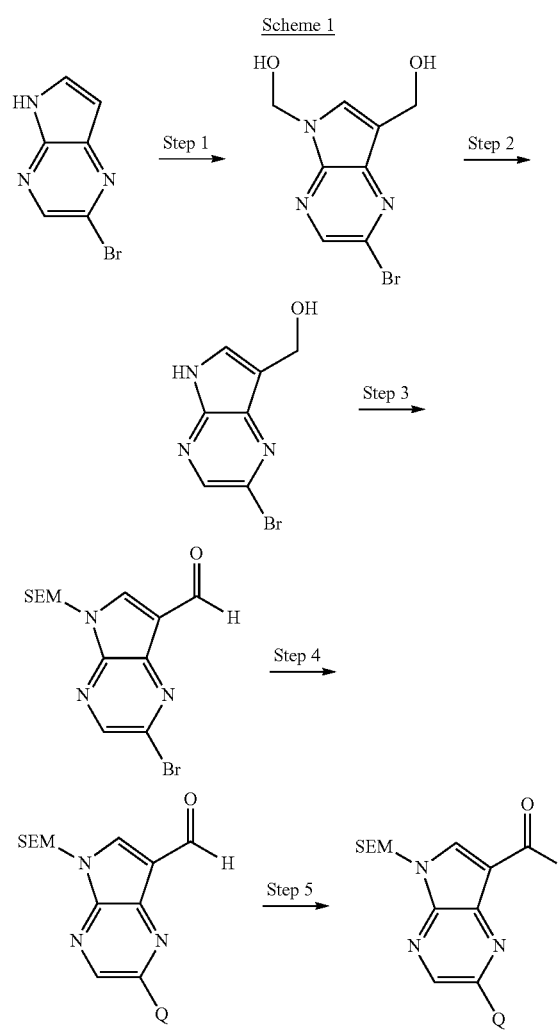
Scheme 2
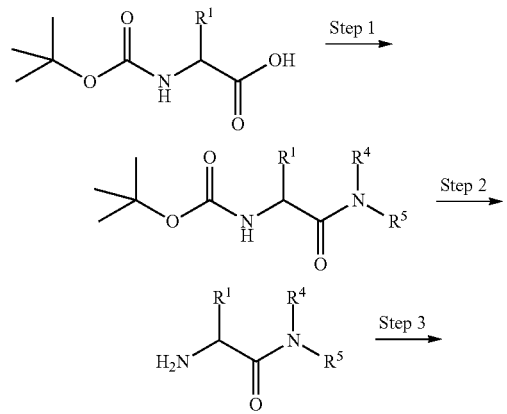
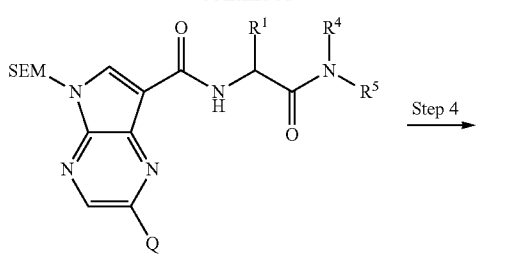
Scheme 3
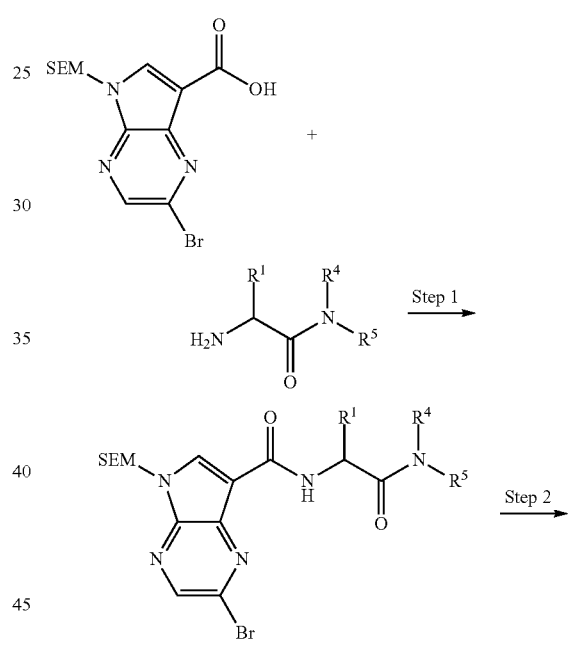
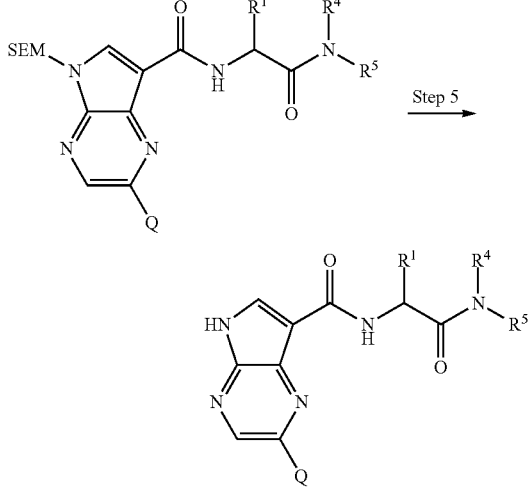

Description of the General Schemes

In the above general schemes, Q can be H, halogen, hydroxy, cyano or Q', Q' can be lower alkyl, lower alkenyl, lower alkynyl, lower alkoxy, cycloalkyl, cycloalkyloxy, phenyl, cycloalkenyl, heterocycloalkyl, or heteroaryl, optionally substituted with one or more $Q^a$, $Q^a$ can be $Q^b$ or $Q^c$, $Q^b$ can be halogen, oxo, hydroxy, —CN, —SCH$_3$, —S(O)$_2$CH$_3$, or —S(=O)CH$_3$, $Q^c$ can be $Q^d$ or $Q^{e'}$, or two $Q^a$ come together to form a bicyclic ring system, optionally substituted with one or more $Q^b$ or $Q^c$, $Q^d$ can be —O($Q^e$), —S(=O)$_2$($Q^e$), —C(=O)N($Q^e$)$_2$, —S(O)$_2$($Q^e$), —C(=O)($Q^e$), —C(=O)O ($Q^e$), —N($Q^e$)$_2$; —N($Q^e$)C(=O)($Q^e$), —N($Q^e$)C(=O)O ($Q^e$), or —N($Q^e$)C(=O)N($Q^e$)$_2$, each $Q^e$ can be independently H or $Q^{e'}$, each $Q^{e'}$ can be independently lower alkyl, phenyl, benzyl, lower haloalkyl, lower alkoxy, cycloalkyl, cycloalkyl lower alkyl, cycloalkenyl, heterocycloalkyl, or heteroaryl, optionally substituted with one or more $Q^f$, $Q^f$ can be $Q^g$ or $Q^h$, $Q^g$ can be halogen, hydroxy, cyano, oxo, or —C(=O)($Q^h$), $Q^h$ can be lower alkyl, lower haloalkyl, lower alkoxy, amino, phenyl, benzyl, cycloalkyl, heterocycloalkyl, or heteroaryl, optionally substituted with one or more $Q^i$, and $Q^i$ can be halogen, hydroxy, cyano, lower alkyl, lower haloalkyl, or lower alkoxy.

In the above general schemes, $R^1$ can be H or $R^{1a}$, $R^{1a}$ can be lower alkyl, lower alkoxy, phenyl, benzyl, heteroaryl, cycloalkyl, heterocycloalkyl, or cycloalkylalkyl, optionally substituted with one or more $R^{1a'}$, and $R^{1a'}$ can be halogen, lower alkyl, lower haloalkyl, lower alkoxy, lower hydroxy alkyl, lower haloalkyl, oxo, hydroxy, or —CN.

In the above general schemes, $R^4$ and $R^5$ together can form heterocyclic moieties as herein defined in formula I":

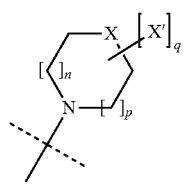

I"

X can be C($R^2$)($R^3$), N($R^2$), S(=O)$_2$, or O, each $R^2$ can be independently H or $R^{2a}$, each $R^{2a}$ can be independently lower alkyl, lower haloalkyl, halogen, lower alkoxy, lower hydroxyalkyl, cyano, cyano lower alkyl, hydroxy, C(=O)$R^{2a'}$ or S(=O)$_2R^{2a'}$, each $R^{a2'}$ can be independently H or lower alkyl, each X' can be independently halogen, lower alkyl, cyano, hydroxy, lower haloalkyl, lower hydroxyalkyl, heteroaryl, spiroheterocycloalkyl, spirocycloalkyl, lower alkoxy, lower alkylamino, or lower dialkylamino, or X' and $R^2$ come together to form a bicyclic ring system, optionally substituted with one or more $R^{2'}$, $R^{2'}$ can be halogen, lower alkyl, lower alkoxy, hydroxy, hydroxy lower alkyl, lower haloalkyl, lower hydroxyalkylcyano, or —S(O)$_2$CH$_3$, $R^3$ can be H, hydroxy, halogen or lower alkyl, or $R^2$ and $R^3$ come together to form a bicyclic ring system, optionally substituted with one or more $R^{2'}$, q can be 0, 1, 2, 3, or 4, n can be 0 or 1, and p can be 0 or 1.

Procedure 1

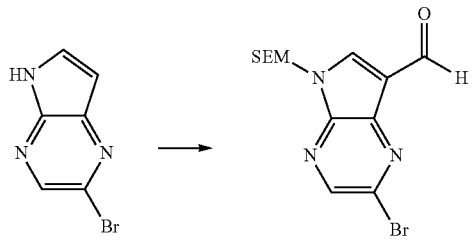 [SMILES: Brc1cnc2[nH]ccc2n1 ; C[Si](C)(C)CCOCn1cc(C=O)c2nc(Br)cnc21]

Method A

Step 1

To a partial suspension of 2-bromo-5H-pyrrolo[2,3-b] pyrazine (5.0 g, 25.2 mmol) in 1,4-dioxane (100 mL) was added 2.0 M aqueous NaOH (25 mL, 50.0 mmol) and 37% aqueous formaldehyde (19 mL, 252 mmol). The dark homogenous reaction mixture was stirred at room temperature overnight. The organics were evaporated under reduced pressure. The aqueous layer was neutralized with 1.0 M HCl and extracted with EtOAc (2×). The combined organics were concentrated to afford 2.6 g of an orange solid. Upon standing, a thick brown precipitate formed in the aqueous layer. The precipitate was collected by filtration and dried. The brown solid was extracted with hot 10% MeOH/EtOAC (3×200 mL). The extracts were combined and evaporated to provide an additional 3.05 g of orange solid. Overall yield was 5.65 g (87%) of (2-bromo-7-hydroxymethyl-pyrrolo[2,3-b]pyrazin-5-yl)-methanol.

Step 2

To a suspension of (2-bromo-7-hydroxymethyl-pyrrolo[2,3-b]pyrazin-5-yl)-methanol (5.65 g, 21.9 mmol) in THF (150 mL) was added a solution of 2.0 M aqueous NaOH (33 mL, 66 mmol). The homogeneous reaction mixture was stirred overnight then the organics were removed under reduced pressure. The aqueous residue was brought to pH 4 with 1.0 M aqueous HCl. The resulting precipitate was collected via filtration and rinsed with H$_2$O to afford 3.68 g of a yellow solid. The filtrate was extracted with EtOAc (2×) and the organics were concentrated under reduced pressure to provide an additional 0.92 g of yellow solid. Overall yield was 4.60 g (92%) of (2-bromo-5H-pyrrolo[2,3-b]pyrazin-7-yl)-methanol.

Step 3

A stock solution of Jones reagent (2.67 M) was prepared by carefully adding concentrated H$_2$SO$_4$ (2.3 mL) to CrO$_3$ (2.67 g) then diluting to 10 mL with H$_2$O. To a partial suspension of (2-bromo-5H-pyrrolo[2,3-b]pyrazin-7-yl)-methanol (4.6 g, 20.1 mmol) in acetone (300 mL) was slowly added Jones reagent (9 mL, 24.0 mmol). During the addition the starting material gradually dissolved and a thick green precipitate was formed. The reaction mixture was stirred for 15 min then quenched with i-PrOH (2 mL) and filtered over Celite, rinsing with acetone. The filtrate was concentrated to provide 4.76 g of 2-bromo-5H-pyrrolo[2,3-b]pyrazine-7-carbaldehyde as a yellow-orange solid that was used without further purification. To a solution of this solid in DMF (50 mL) at 0° C. was added NaH (60% in mineral oil, 1.2 g, 30.1 mmol). The reaction mixture was stirred at room temperature for 30 min then cooled back to 0° C. and 2-(trimethylsilyl)ethoxymethyl chloride (4.3 mL, 24.1 mmol) was slowly added. The reaction mixture was warmed to room temperature and stirred for 1 h then quenched with H$_2$O and extracted with EtOAc (3×). The combined organics were washed with H$_2$O (3×) and brine then dried over MgSO$_4$ and concentrated. The residue was purified by SiO$_2$ chromatography (20% to 30% EtOAc/hexanes) to isolate 3.82 g (53%) of 2-bromo-5-(2-trimethylsilanyl-ethoxymethyl)-5H-pyrrolo[2,3-b]pyrazine-7-carbaldehyde as a yellow solid.

Method B

Step 1

In a dry round-bottomed flask, 2-bromo-5H-pyrrolo[2,3-b]pyrazine (5.0 g, 25.2 mmol) was dissolved in DMF (50 mL). The reaction mixture was cooled to 0° C. and sodium hydride (60% dispersion in mineral oil, 1.22 g, 30.6 mmol). The reaction mixture was warmed to room temperature and stirred for 15 min then cooled back to 0° C. and SEM-Cl (5.4 mL, 30.4 mmol) was slowly added. After the addition was complete, the ice bath was removed and the reaction mixture was stirred at room temperature for 1.5 h. The reaction mixture was quenched with 50 mL water and extracted with 150 mL diethyl ether (2×). The combined organic layers were washed twice with 30 mL water and once with 30 mL brine then dried over sodium sulfate, filtered and concentrated. The residue was absorbed on ~20 g SiO$_2$ and chromatographed over 200 g SiO$_2$ with EtOAc/Hexanes (gradient: 0-15% EtOAc). All fractions containing product were combined and concentrated to afford 6.61 g (80%) of 2-bromo-5-(2-trimethylsilanyl-ethoxymethyl)-5H-pyrrolo[2,3-b]pyrazine as a pale yellow oil which gradually solidified.

Step 2

In a round-bottomed flask, 2-bromo-5-(2-trimethylsilanyl-ethoxymethyl)-5H-pyrrolo[2,3-b]pyrazine (6.58 g, 20.0 mmol) was dissolved in chloroform (pentene stabilized, 120 mL) and chloromethylenedimethyliminium chloride (10.3 g, 80.2 mmol) was added. The reaction mixture was stirred at reflux for 8 h as a steady stream of nitrogen gas was bubbled through the reaction mixture. The dark brown solution was cooled to room temperature and stirred overnight. The reaction mixture was carefully quenched with ~100 mL saturated NaHCO$_3$-solution (caution: exothermic) and then extracted twice with 200 mL diethyl ether. The organic layers were combined, dried over sodium sulfate, filtered and concentrated. The residue was absorbed on ~20 g SiO$_2$ and chromatographed over 200 g SiO$_2$ with EtOAc/Hexanes (gradient: 0-25% EtOAc). All fractions containing product were combined and concentrated to afford 5.92 g (83%) of an approx 3:1 mixture of 2-bromo-5-(2-trimethylsilanyl-ethoxymethyl)-5H-pyrrolo[2,3-b]pyrazine-7-carbaldehyde and 2-chloro-5-(2-trimethylsilanyl-ethoxymethyl)-5H-pyrrolo[2,3-b]pyrazine-7-carbaldehyde as a yellow solid.

Procedure 2

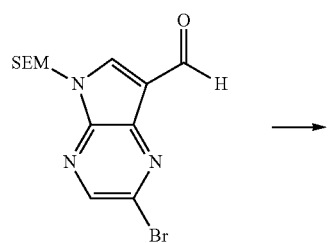

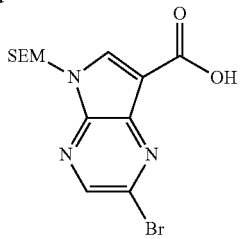

In a flask 2-bromo-5-(2-trimethylsilanylethoxymethyl)-5H-pyrrolo[2,3-b]pyrazine-7-carbaldehyde (3.11 g, 8.74 mmol) was dissolved in dioxane (120 mL) and H$_2$O (30 mL) and the mixture cooled at 0° C. Sulfamic acid (5.09 g, 52.4 mmol) was added, followed by a solution of sodium chlorite (1.28 g, 11.4 mmol) and potassium dihydrogen phosphate (14.3 g, 104.9 mmol) in H$_2$O (75 mL) via an addition funnel over 15 min. The mixture was allowed to warm to room temperature over 2 h. The resulting yellow solid was filtered off, washed with H$_2$O and hexane and dried. The filtrate was then extracted with EtOAc, and the combined organics washed with brine, dried over MgSO$_4$ and concentrated to give additional product. In total 3.71 g of 2-bromo-5-(2-trimethylsilanylethoxymethyl)-5H-pyrrolo[2,3-b]pyrazine-7-carboxylic acid was obtained as a yellow solid.

Procedure 3

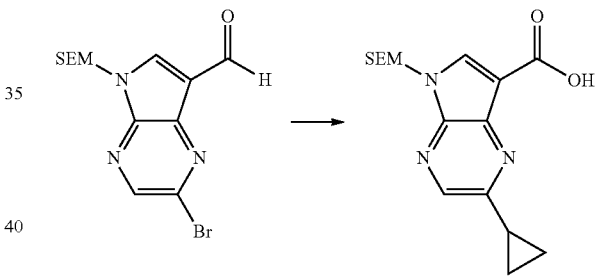

Step 1

A mixture of 2-bromo-5-(2-trimethylsilanyl-ethoxymethyl)-5H-pyrrolo[2,3-b]pyrazine-7-carbaldehyde (0.33 g, 0.93 mmol), cyclopropyl boronic acid (0.12 g, 1.39 mmol), tricyclohexyl phosphine (0.026 g, 0.09 mmol), palladium(II) acetate (0.01 g, 0.046 mmol) and potassium phosphate tribasic (0.63 g, 2.97 mmol) in 4 mL of toluene and 0.5 mL of water was flushed with Argon for 5 min then heated at 100° C. for 18 h. The cooled mixture was filtered through a pad of Celite, washed with EtOAc, and concentrated under reduced pressure. The residue was purified by silica gel chromatography eluting with 10% EtOAc/hexanes to afford 0.24 g (81%) of 2-cyclopropyl-5-(2-trimethylsilanyl-ethoxymethyl)-5H-pyrrolo[2,3-b]pyrazine-7-carbaldehyde as a yellow powder.

Step 2

To a solution of 2-cyclopropyl-5-(2-trimethylsilanyl-ethoxymethyl)-5H-pyrrolo[2,3-b]pyrazine-7-carbaldehyde (0.24 g, 0.75 mmol) in 1,4-dioxane (10 mL) and water (2 mL) at 0° C. was added sulfamic acid (0.44 g, 4.54 mmol). Then added dropwise a solution of sodium chlorite (0.09 g, 0.98 mmol) and potassium dihydrogen phosphate (1.22 g, 9.0 mmol) in 6 mL of water. After the addition, the reaction mixture was warmed to room temperature and stirred for 2 h then partitioned between water and ethyl acetate. The organic layer was washed with brine, dried over sodium sulfate and concentrated under reduced pressure. The residue was triturated with hexanes to obtain 0.22 g (87%) of 2-cyclopropyl-5-(2-trimethylsilanyl-ethoxymethyl)-5H-pyrrolo[2,3-b]pyrazine-7-carboxylic acid as a light yellow powder.

Procedure 4

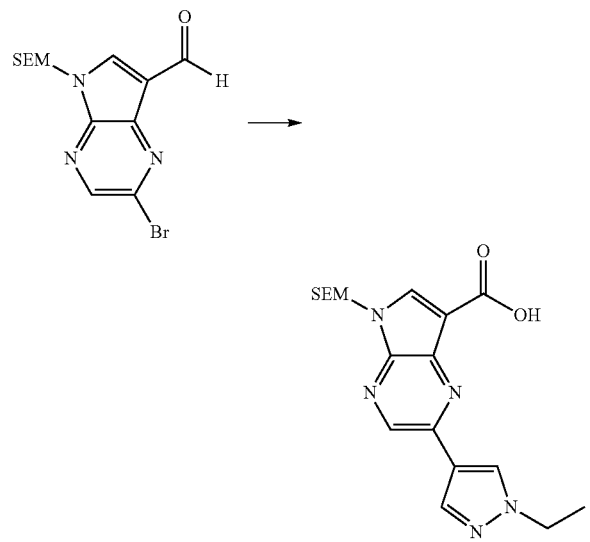

Step 1

To a solution of 2-bromo-5-((2-(trimethylsilyl)ethoxy)methyl)-5H-pyrrolo[2,3-b]pyrazine-7-carbaldehyde (1.33 g, 3.73 mmol) and 1-ethyl-4-(4,4,5,5-tetramethyl-1,3,2-dioxaborolan-2-yl)-1H-pyrazole (995 mg, 4.48 mmol) in 1,2-DME (20 mL) were added Pd(Ph$_3$P)$_4$ (0.22 g, 0.19 mmol) and 2.0 M aqueous K$_2$CO$_3$ (5.6 ml, 11.2 mmol). The reaction mixture was degassed by bubbling N$_2$ for 15 min then heated at 100° C. overnight. The resultant maroon reaction mixture was cooled and diluted with H$_2$O then extracted with EtOAc (2×). The combined organics were dried over MgSO$_4$ and concentrated. The crude residue was purified by SiO$_2$ chromatography (30% to 80% EtOAc/hexanes) to afford 1.12 g (81%) of 2-(1-ethyl-1H-pyrazol-4-yl)-5-((2-(trimethylsilyl)ethoxy)methyl)-5H-pyrrolo[2,3-b]pyrazine-7-carbaldehyde as a light orange-brown solid.

Step 2

To a solution of 2-(1-ethyl-1H-pyrazol-4-yl)-5-((2-(trimethylsilyl)ethoxy)methyl)-5H-pyrrolo[2,3-b]pyrazine-7-carbaldehyde (1.12 g, 3.01 mmol) in 1,4-dioxane (50 mL) and H$_2$O (10 mL) at 0° C. was added sulfamic acid (1.76 g, 18.1 mmol). Then added a solution of NaClO$_2$ (0.44 g, 3.92 mmol) and KH$_2$PO$_4$ (4.92 g, 36.2 mmol) in H$_2$O (30 mL) via dropping funnel over 15 min. The ice bath was removed and the yellow cloudy reaction mixture was stirred at room temperature for 2.5 h. The reaction mixture was diluted with H$_2$O and extracted with EtOAc (2×). The combined organic layers were dried over MgSO$_4$ and concentrated to an oily yellow solid which was triturated with 5% EtOAc/hexanes to afford 1.05 g (90%) of 2-(1-ethyl-1H-pyrazol-4-yl)-5-((2-(trimethylsilyl)ethoxy)methyl)-5H-pyrrolo[3,2-b]pyrazine-7-carboxylic acid as a light yellow solid.

Pharmaceutical Compositions and Administration

The compounds of the present invention may be formulated in a wide variety of oral administration dosage forms and carriers. Oral administration can be in the form of tablets, coated tablets, dragées, hard and soft gelatin capsules, solutions, emulsions, syrups, or suspensions. Compounds of the present invention are efficacious when administered by other routes of administration including continuous (intravenous drip) topical parenteral, intramuscular, intravenous, subcutaneous, transdermal (which may include a penetration enhancement agent), buccal, nasal, inhalation and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia.

Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polyactic acid.

Suitable formulations along with pharmaceutical carriers, diluents and excipients are described in *Remington: The Science and Practice of Pharmacy* 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 1000 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Indications and Method of Treatment

The application provides a method for treating an inflammatory or autoimmune condition comprising administering to a patient in need thereof a therapeutically effective amount of the compound of Formula I.

The application provides the above method, further comprising administering an additional therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating diabetes, or an agent for treating immunodeficiency disorders.

The application provides a method for treating rheumatoid arthritis comprising administering to a patient in need thereof a therapeutically effective amount of the compound of Formula I.

The application provides a method for treating asthma comprising administering to a patient in need thereof a therapeutically effective amount of the compound of Formula I.

The application provides a method for treating an inflammatory condition comprising administering to a patient in need thereof a therapeutically effective amount of the compound of Formula I.

The application provides a method for inhibiting T-cell proliferative disorder comprising administering to a patient in need thereof a therapeutically effective amount of the compound of Formula I.

The application provides a method for inhibiting T-cell proliferative disorder comprising administering to a patient in need thereof a therapeutically effective amount of the compound of Formula I The application provides the above method, wherein the proliferative disorder is cancer.

The application provides a method for treating a B-cell proliferative disorder comprising administering to a patient in need thereof a therapeutically effective amount of the compound of Formula I.

The application provides a method for treating an immune disorder including lupus, multiple sclerosis, rheumatoid arthritis, psoriasis, Type I diabetes, complications from organ transplants, xeno transplantation, diabetes, cancer, asthma, atopic dermatitis, autoimmune thyroid disorders, ulcerative colitis, Crohn's disease, Alzheimer's disease, and Leukemia, comprising administering to a patient in need thereof a therapeutically effective amount of the compound of Formula I.

The application provides a method for preventing or treating all forms of organ rejection, including acute allograft or xenograft rejection and chronic allograft or xenograft rejection, of vascularized or non-vascularized transplants, comprising administering to a patient in need thereof the compound of Formula I.

The application provides a method for inhibiting JAK3 activity comprising administering the compound of Formula I, wherein the compound exhibits an $IC_{50}$ of 50 micromolar or less in an in vitro biochemical assay of JAK3 activity.

The application provides the above method, wherein the compound exhibits an $IC_{50}$ of 100 nanomolar or less in an in vitro biochemical assay of JAK3 activity.

The application provides the above method, wherein the compound exhibits an $IC_{50}$ of 10 nanomolar or less in an in vitro biochemical assay of JAK3 activity.

A method for inhibiting SYK activity comprising administering the compound of Formula I, wherein the compound exhibits an $IC_{50}$ of 50 micromolar or less in an in vitro biochemical assay of SYK activity.

The application provides the above method, wherein the compound exhibits an $IC_{50}$ of 100 nanomolar or less in an in vitro biochemical assay of SYK activity.

The application provides the above method, wherein the compound exhibits an $IC_{50}$ of 10 nanomolar or less in an in vitro biochemical assay of SYK activity.

The application provides a method for treating an inflammatory condition comprising co-administering to a patient in need thereof a therapeutically effective amount of an anti-inflammatory compound in combination with the compound of Formula I.

The application provides a method for treating an immune disorder comprising co-administering to a patient in need thereof a therapeutically effective amount of an immunosuppressant compound in combination with the compound of Formula I.

EXAMPLES

The following examples illustrate the preparation and biological evaluation of compounds within the scope of the invention. These examples and preparations which follow are provided to enable those skilled in the art to more clearly understand and to practice the present invention. They should not be considered as limiting the scope of the invention, but merely as being illustrative and representative thereof.

Abbreviations

Commonly used abbreviations include: acetyl (Ac), azo-bis-isobutyrylnitrile (AIBN), atmospheres (Atm), 9-borabicyclo[3.3.1]nonane (9-BBN or BBN), tert-butoxycarbonyl (Boc), di-tert-butyl pyrocarbonate or boc anhydride ($BOC_2O$), benzyl (Bn), butyl (Bu), Chemical Abstracts Registration Number (CASRN), benzyloxycarbonyl (CBZ or Z), carbonyl diimidazole (CDI), 1,4-diazabicyclo[2.2.2]octane (DABCO), diethylaminosulfur trifluoride (DAST), dibenzylideneacetone (dba), 1,5-diazabicyclo[4.3.0]non-5-ene (DBN), 1,8-diazabicyclo[5.4.0]undec-7-ene (DBU), N,N'-dicyclohexylcarbodiimide (DCC), 1,2-dichloroethane (DCE), dichloromethane (DCM), diethyl azodicarboxylate (DEAD), di-iso-propylazodicarboxylate (DIAD), di-iso-butylaluminumhydride (DIBAL or DIBAL-H), di-iso-propylethylamine (DIPEA), N,N-dimethyl acetamide (DMA), 4-N,N-dimethylaminopyridine (DMAP), N,N-dimethylformamide (DMF), dimethyl sulfoxide (DMSO), 1,1'-bis-(diphenylphosphino)ethane (dppe), 1,1'-bis-(diphenylphosphino)ferrocene (dppf), 1-(3-dimethylaminopropyl)-3-ethylcarbodiimide hydrochloride (EDCI), ethyl (Et), ethyl acetate (EtOAc), ethanol (EtOH), 2-ethoxy-2H-quinoline-1-carboxylic acid ethyl ester (EEDQ), diethyl ether (Et$_2$O), O-(7-azabenzotriazole-1-yl)-N,N,N'N'-tetramethyluronium hexafluorophosphate acetic acid (HATU), acetic acid (HOAc), 1-N-hydroxybenzotriazole (HOBt), high pressure liquid chromatography (HPLC), iso-propanol (IPA), lithium hexamethyl disilazane (LiHMDS), methanol (MeOH), melting point (mp or MP), MeSO$_2$— (mesyl or Ms), methyl (Me), acetonitrile (MeCN), m-chloroperbenzoic acid (MCPBA), mass spectrum (ms or MS), methyl t-butyl ether (MTBE), N-bromosuccinimide (NBS), N-carboxyanhydride (NCA), N-chlorosuccinimide (NCS), N-methylmorpholine (NMM), N-methylpyrrolidone (NMP), pyridinium chlorochromate (PCC), pyridinium dichromate (PDC), phenyl (Ph), propyl (Pr), iso-propyl (i-Pr), pounds per square inch (psi), pyridine (pyr), room temperature (rt or RT), 2-(trimethylsilyl) ethoxymethyl chloride (SEMCl), tert-butyldimethylsilyl or t-BuMe$_2$Si (TBDMS), triethylamine (TEA or Et$_3$N), 2,2,6,6-tetramethylpiperidine 1-oxyl (TEMPO), triflate or CF$_3$SO$_2$— (TO, trifluoroacetic acid (TFA), 1,1'-bis-2,2,6,6-tetramethyl-heptane-2,6-dione (TMHD), O-benzotriazol-1-yl-N,N,N', N'-tetramethyluronium tetrafluoroborate (TBTU), thin layer chromatography (TLC), tetrahydrofuran (THF), trimethylsilyl or Me$_3$Si (TMS), p-toluenesulfonic acid monohydrate (TsOH or pTsOH), 4-Me-C$_6$H$_4$SO$_2$— or tosyl (Ts), N-urethane-N-carboxyanhydride (UNCA). Conventional nomenclature including the prefixes normal (n), iso (i-), secondary (sec-), tertiary (tert-) and neo have their customary meaning when used with an alkyl moiety. (J. Rigaudy and D. P. Klesney, *Nomenclature in Organic Chemistry*, IUPAC 1979 Pergamon Press, Oxford.).

Preparative Examples

Example 1

2-Cyclopropyl-5H-pyrrolo[2,3-b]pyrazine-7-carboxylic acid [(R)-2,2-dimethyl-1-(pyrrolidine-1-carbonyl)-propyl]-amide

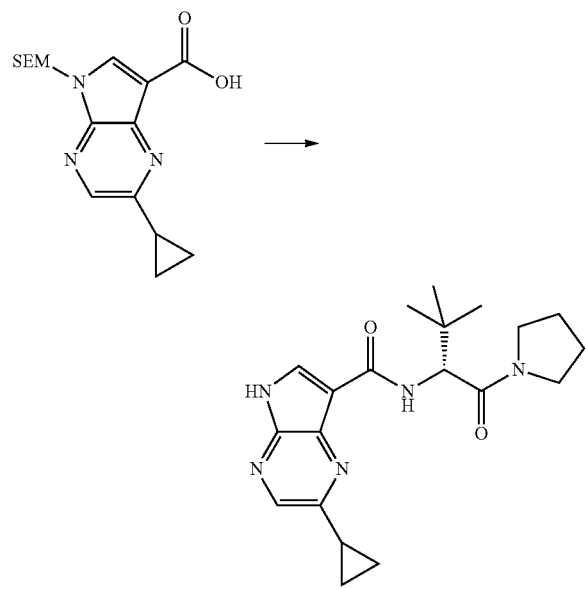 [SMILES: C[Si](C)(C)CCOCn1cc(C(=O)O)c2nc(C3CC3)cnc21 ; CC(C)(C)[C@@H](NC(=O)c1c[nH]c2ncc(C3CC3)nc12)C(=O)N1CCCC1]

Step 1

A 50 mL round-bottomed flask was charged with Boc-D-tert-leucine (1.00 g, 4.32 mmol), HOBT (728 mg, 4.76 mmol), EDC (912 mg, 4.76 mmol) and pyrrolidine (0.57 mL, 6.89 mmol). Then added DMF (18 mL) followed by N,N-diisopropylethylamine (1.1 ml, 6.3 mmol). The yellow reaction mixture was stirred at room temperature overnight then quenched with H$_2$O and extracted with Et$_2$O (2×). The combined organic layers were washed twice with H$_2$O and once with brine then dried over Na$_2$SO$_4$, filtered and concentrated. The residue was purified by chromatography over 40 g SiO$_2$ with EtOAc/hexanes (gradient: 0-30% EtOAc) to afford 1.0 g (83%) of (R)-tert-butyl 3,3-dimethyl-1-oxo-1-(pyrrolidin-1-yl)butan-2-ylcarbamate as an off-white solid.

Step 2

In a 10 mL round-bottomed flask, (R)-tert-butyl 3,3-dimethyl-1-oxo-1-(pyrrolidin-1-yl)butan-2-ylcarbamate (0.160 g, 0.56 mmol) was dissolved in 1.0 M hydrogen chloride solution in MeOH (3.6 ml, 3.6 mmol). The reaction mixture was stirred at room temperature overnight the concentrated to afford 140 mg of (R)-2-amino-3,3-dimethyl-1-(pyrrolidin-1-yl)butan-1-one hydrochloride as a hydroscopic off-white foam which was used without further purification.

Step 3

A 10 mL round-bottomed flask was charged with 2-cyclopropyl-5-((2-(trimethylsilyl)ethoxy)methyl)-5H-pyrrolo[2,3-b]pyrazine-7-carboxylic acid (0.12 g, 0.36 mmol), (R)-2-amino-3,3-dimethyl-1-(pyrrolidin-1-yl)butan-1-one hydrochloride (137 mg, 0.53 mmol), HOBt (61 mg, 0.40 mmol) and EDC (76 mg, 0.40 mmol). Then added DMF (1.6 mL) followed by N,N-diisopropylethylamine (0.16 mL, 0.92 mmol). The light yellow reaction mixture was stirred at room temperature overnight then quenched with water and extracted with diethyl ether (2×50 mL). The combined organic layers were washed twice with water and once with brine then dried over sodium sulfate, filtered and concentrated. The residue was purified by chromatography over 8 g SiO$_2$ with EtOAc/hexanes (gradient: 0-60% EtOAc) to afford 195 mg of (R)-2-cyclopropyl-N-(3,3-dimethyl-1-oxo-1-(pyrrolidin-1-yl)butan-2-yl)-5-((2-(trimethylsilyl)ethoxy)methyl)-5H-pyrrolo[2,3-b]pyrazine-7-carboxamide as a viscous yellow oil.

Step 4

In a 10 mL round-bottomed flask, (R)-2-cyclopropyl-N-(3,3-dimethyl-1-oxo-1-(pyrrolidin-1-yl)butan-2-yl)-5-((2-(trimethylsilyl)ethoxy)methyl)-5H-pyrrolo[2,3-b]pyrazine-7-carboxamide (0.19 g, 0.34 mmol) was dissolved in dichloromethane (1.4 mL). Trifluoroacetic acid (1.05 mL, 13.7 mmol) was added and the light yellow reaction mixture was stirred at room temperature for 2 h then concentrated under reduced pressure. The residue was dissolved in toluene (3 mL), concentrated and then placed under high vacuum for 30 min. The resultant foam was dissolved in dichloromethane (1.4 mL) and ethylenediamine (1.40 mL, 20.7 mmol) was added. The light yellow reaction mixture was stirred at room temperature for 2 h then quenched with water and extracted with EtOAc (2×50 mL). The combined organic layers were washed with water and brine then dried over sodium sulfate, filtered and concentrated. The residue was purified by chromatography over 8 g SiO$_2$ with MeOH/CH$_2$Cl$_2$ (gradient: 0-10% MeOH) to afford a yellow solid. Trituration with EtOAc provided 63 mg (50%) of 2-cyclopropyl-5H-pyrrolo[2,3-b]pyrazine-7-carboxylic acid [(R)-2,2-dimethyl-1-(pyrrolidine-1-carbonyl)-propyl]-amide as a white powder. MS: (M+H)⁺=370; mp=201.0-203.0.

Example 2

2-(1-Ethyl-1H-pyrazol-4-yl)-5H-pyrrolo[2,3-b]pyrazine-7-carboxylic acid [(R)-2,2-dimethyl-1-(pyrrolidine-1-carbonyl)-propyl]-amide

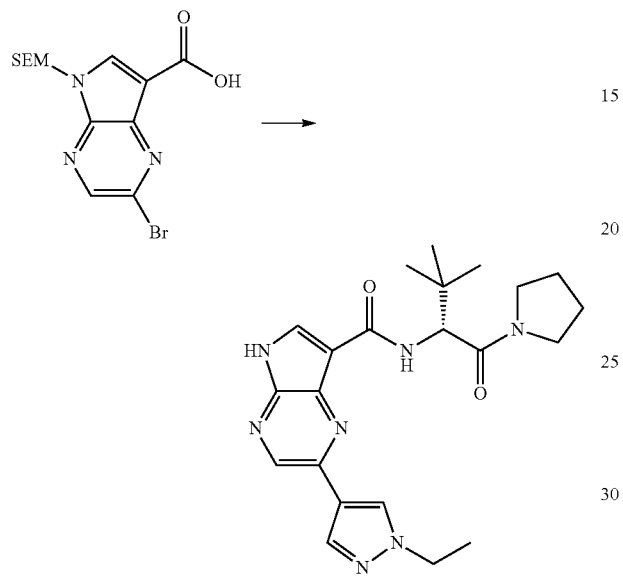

Step 1

In a flask were combined 2-bromo-5-(2-trimethylsilanylethoxymethyl)-5H-pyrrolo[2,3-b]pyrazine-7-carboxylic acid (125 mg, 0.34 mmol), (R)-2-amino-3,3-dimethyl-1-pyrrolidin-1-yl-butan-1-one hydrochloride (155 mg, 0.70 mmol), EDC (148 mg, 0.77 mmol) and HOBt (104 mg, 0.772 mmol). DMF (4.0 mL) was added followed by i-Pr₂NEt (0.19 mL, 1.07 mmol). The reaction mixture was stirred at room temperature for 1 h and then concentrated. The residue was taken up in EtOAc and 10% citric acid and the organic layer washed with 10% citric acid, sat. NaHCO₃, sat LiCl and brine, dried over MgSO₄, and concentrated to give 162 mg (90%) of 2-bromo-5-(2-trimethylsilanyl-ethoxymethyl)-5H-pyrrolo[2,3-b]pyrazine-7-carboxylic acid [(R)-2,2-dimethyl-1-(pyrrolidine-1-carbonyl)-propyl]-amide as a viscous brown oil.

Step 2

In a pressure tube 2-bromo-5-(2-trimethylsilanyl-ethoxymethyl)-5H-pyrrolo[2,3-b]pyrazine-7-carboxylic acid [(R)-2,2-dimethyl-1-(pyrrolidine-1-carbonyl)-propyl]-amide (162 mg, 0.30 mmol) and 1-ethyl-1H-pyrazole-4-boronic acid pinacol ester (80 mg, 0.36 mmol) were dissolved in DME (3.0 mL). Aqueous K₂CO₃ (2.0 M, 0.45 mL, 0.90 mmol) and Pd(PPh₃)₄ (17 mg, 0.015 mmol) were added and the mixture degassed with a gentle stream of N₂ for 15 min. The vial was then sealed and heated at 90° C. for 6 h. The reaction mixture was cooled to room temperature, quenched with H₂O and extracted with EtOAc. The organic extracts were washed with brine, dried over MgSO₄, and concentrated. The residue was purified by SiO₂ chromatography (20-100% EtOAc/hexane) to afford 125 mg (75%) of 2-(1-ethyl-1H-pyrazol-4-yl)-5-(2-trimethylsilanyl-ethoxymethyl)-5H-pyrrolo[2,3-b]pyrazine-7-carboxylic acid [(R)-2,2-dimethyl-1-(pyrrolidine-1-carbonyl)-propyl]-amide as a light brown foam.

Step 3

To a solution of 2-(1-ethyl-1H-pyrazol-4-yl)-5-(2-trimethylsilanyl-ethoxymethyl)-5H-pyrrolo[2,3-b]pyrazine-7-carboxylic acid [(R)-2,2-dimethyl-1-(pyrrolidine-1-carbonyl)-propyl]-amide in CH₂Cl₂ (2.25 mL) was added TFA (0.75 mL). The reaction mixture was stirred overnight and concentrated. The residue was dissolved in a mixture of ammonium hydroxide, MeOH and CH₂Cl₂ (1:10:60, 3.0 ml) and stirred at room temperature for 90 min. The reaction mixture was then concentrated and the residue purified by SiO₂ chromatography (0-10% MeOH/CH₂Cl₂) to afford 85 mg (89%) of 2-(1-ethyl-1H-pyrazol-4-yl)-5H-pyrrolo[2,3-b]pyrazine-7-carboxylic acid [(R)-2,2-dimethyl-1-(pyrrolidine-1-carbonyl)-propyl]-amide as a yellow powder. MS: (M+H)⁺=424.

Example 3

2-Cyclopropyl-5H-pyrrolo[2,3-b]pyrazine-7-carboxylic acid ((R)-1-cyclopentyl-2-oxo-2-pyrrolidin-1-yl-ethyl)-amide

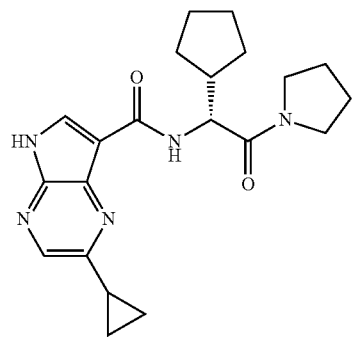

Prepared according to the procedure outlined in Example 1 substituting Boc-D-cyclopentyl glycine for Boc-D-tert-leucine. MS: (M+H)⁺=382.

Example 4

2-(1-Ethyl-1H-pyrazol-4-yl)-5H-pyrrolo[2,3-b]pyrazine-7-carboxylic acid ((R)-1-cyclopropyl-2-oxo-2-pyrrolidin-1-yl-ethyl)-amide

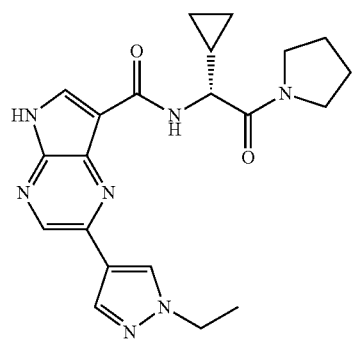

Prepared according to the procedure outlined in Example 1 substituting Boc-D-cyclopropyl glycine for Boc-D-tert-leucine and 2-(1-ethyl-1H-pyrazol-4-yl)-5-((2-(trimethylsilyl)ethoxy)methyl)-5H-pyrrolo[3,2-b]pyrazine-7-carboxylic acid for 2-cyclopropyl-5-(2-trimethylsilanyl-ethoxymethyl)-5H-pyrrolo[2, 3-1)]pyrazine-7-carboxylic acid. MS: (M+H)+= 408; mp=210.0-212.0.

Example 5

2-Cyclopropyl-5H-pyrrolo[2,3-b]pyrazine-7-carboxylic acid [(R)-2-(3,3-difluoro-pyrrolidin-1-yl)-1-methyl-2-oxo-ethyl]-amide

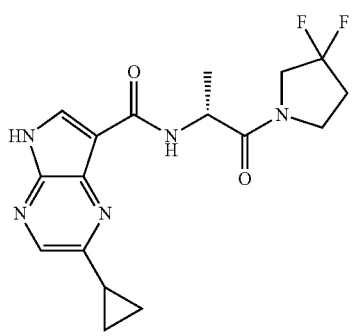 [SMILES: C[C@@H](NC(=O)c1c[nH]c2ncc(C3CC3)nc12)C(=O)N1CCC(F)(F)C1]

Prepared according to the procedure outlined in Example 1 substituting Boc-D-alanine for Boc-D-tert-leucine and 3,3-difluoropyrrolidine hydrochloride for pyrrolidine. MS: (M+H)+=364.

Example 6

2-Cyclopropyl-5H-pyrrolo[2,3-b]pyrazine-7-carboxylic acid [(R)-2-(3-cyano-pyrrolidin-1-yl)-1-methyl-2-oxo-ethyl]-amide

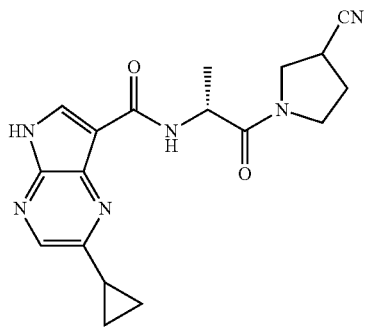 [SMILES: C[C@@H](NC(=O)c1c[nH]c2ncc(C3CC3)nc12)C(=O)N1CCC(C#N)C1]

Prepared according to the procedure outlined in Example 1 substituting Boc-D-alanine for Boc-D-tert-leucine and pyrrolidine-3-carbonitrile hydrochloride for pyrrolidine. MS: (M+H)+=353.

Example 7

2-(1-Ethyl-1H-pyrazol-4-yl)-5H-pyrrolo[2,3-b]pyrazine-7-carboxylic acid [(R)-2-(3-cyano-3-methyl-pyrrolidin-1-yl)-1-methyl-2-oxo-ethyl]-amide

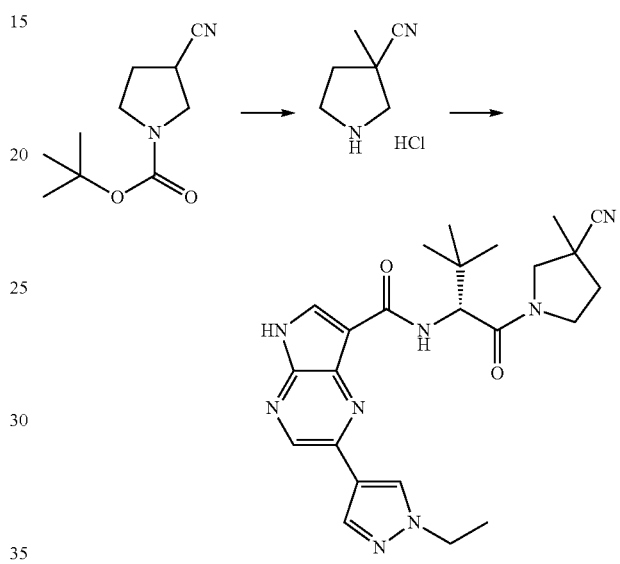

Step 1

To a solution of tert-butyl 3-cyanopyrrolidine-1-carboxylate (1.0 g, 5.1 mmol) in THF (20 mL) at −78° C. was slowly added LiHMDS (1.0 M in THF, 5.6 mL, 5.6 mmol). The reaction mixture was stirred at −78° C. for 30 min then iodomethane (0.48 mL, 7.64 mmol) was slowly added. The reaction mixture was stirred at −78° C. for 30 min then warmed to room temperature and quenched with saturated aqueous NH$_4$Cl. Diluted with H$_2$O and extracted with EtOAc (2×) then dried over MgSO$_4$ and concentrated. The residue was purified by SiO$_2$ chromatography (20% to 40% EtOAc/hexanes) to afford 0.95 g (89%) of tert-butyl 3-cyano-3-methylpyrrolidine-1-carboxylate as a pale yellow solid.

Step 2

A sample of tert-butyl 3-cyano-3-methylpyrrolidine-1-carboxylate (0.50 g, 2.38 mmol) was dissolved in 1.0 M HCl in MeOH (12 mL). The reaction mixture was stirred at room temperature overnight then concentrated to afford 0.38 g of 3-methylpyrrolidine-3-carbonitrile hydrochloride as a hydroscopic white foamy solid which was used without further purification.

Step 3

2-(1-Ethyl-1H-pyrazol-4-yl)-5H-pyrrolo[2,3-b]pyrazine-7-carboxylic acid [(R)-2-(3-cyano-3-methyl-pyrrolidin-1-yl)-1-methyl-2-oxo-ethyl]-amide. Prepared according to the procedure outlined in Example 1 substituting 3-methylpyrrolidine-3-carbonitrile hydrochloride for pyrrolidine and 2-(1-ethyl-1H-pyrazol-4-yl)-5-((2-(trimethylsilyl)ethoxy)methyl)-5H-pyrrolo[3,2-b]pyrazine-7-carboxylic acid for 2-cyclopropyl-5-(2-trimethylsilanyl-ethoxymethyl)-5H-pyrrolo[2,3-b]pyrazine-7-carboxylic acid. MS: (M+H)$^+$=463; mp=228.0-230.0.

Example 8

2-Cyclopropyl-5H-pyrrolo[2,3-b]pyrazine-7-carboxylic acid [(R)-2-(3-cyano-azetidin-1-yl)-1-methyl-2-oxo-ethyl]-amide

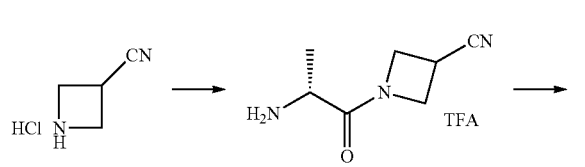

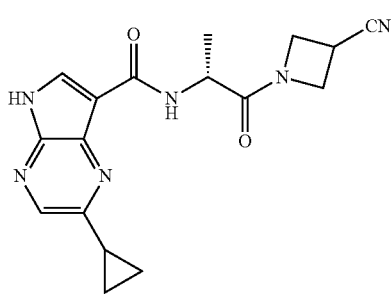

Step 1

Boc-D-alanine (1.0 g, 5.29 mmol) and O-benzotriazol-1-yl-N,N,N',N'-tetramethyluronium tetrafluoroborate (1.87 g, 5.81 mmol) were dissolved in dichloromethane. 3-Cyanoazetidine hydrochloride (0.94 g, 7.93 mmol) and then N,N-diisopropylethylamine (2.3 mL, 13.2 mmol) were added and the mixture was stirred at room temperature for 16 h. Water and ethyl acetate were added and the layers were separated. The aqueous layer was extracted once more with ethyl acetate. The combined organic layers were washed with sodium chloride solution, dried over sodium sulfate and concentrated. The residue was purified by silica gel chromatography (ethyl acetate/hexanes) to provide 0.91 g (68%) of [(R)-2-(3-cyano-azetidin-1-yl)-1-methyl-2-oxo-ethyl]-carbamic acid tert-butyl ester.

Step 2

[(R)-2-(3-Cyano-azetidin-1-yl)-1-methyl-2-oxo-ethyl]-carbamic acid tert-butyl ester (1.05 g, 3.27 mmol) was dissolved in 4 mL of dichloromethane. The solution was cooled in an ice bath and 1.2 mL of trifluoroacetic acid was added slowly. After 1.5 h the reaction was concentrated to afford 1-((R)-2-amino-propionyl)-azetidine-3-carbonitrile trifluoroacetate which was used without further purification.

Step 3

2-Cyclopropyl-5H-pyrrolo[2, 3-1)]pyrazine-7-carboxylic acid [(R)-2-(3-cyano-azetidin-1-yl)-1-methyl-2-oxo-ethyl]-amide. Prepared according to the procedure outlined in Example 1, steps 3-4 substituting 1-((R)-2-amino-propionyl)-azetidine-3-carbonitrile trifluoroacetate for (R)-2-amino-3,3-dimethyl-1-(pyrrolidin-1-yl)butan-1-one hydrochloride. MS: (M+H)$^+$=339.

Example 9

2-Cyclopropyl-5H-pyrrolo[2,3-b]pyrazine-7-carboxylic acid [(R)-1-(3-cyano-azetidine-1-carbonyl)-2,2-dimethyl-propyl]-amide

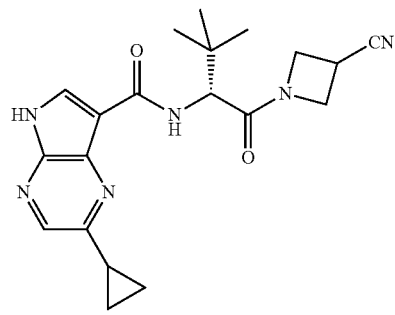 [SMILES: CC(C)(C)[C@@H](NC(=O)c1c[nH]c2ncc(C3CC3)nc12)C(=O)N1CC(C#N)C1]

Prepared according to the procedure outlined in Example 8 substituting Boc-D-tert-leucine for Boc-D-alanine MS: (M+H)$^+$=381.

Example 10

2-Cyclopropyl-5H-pyrrolo[2,3-b]pyrazine-7-carboxylic acid [(R)-1-(3-cyano-3-methyl-azetidine-1-carbonyl)-2,2-dimethyl-propyl]-amide

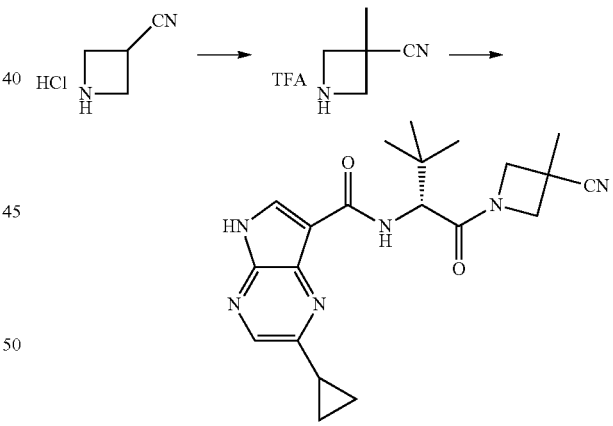

Step 1

3-Cyanoazetidine hydrochloride (3.64 g, 30.7 mmol) was suspended in 77 mL of dichloromethane. Triethylamine (4.3 mL, 30.7 mmol) was added, followed by portionwise addition of di-tert-butyl dicarbonate (8.0 g, 36.8 mmol). The reaction mixture was stirred for 16 h then diluted with aqueous hydrochloric acid and dichloromethane. The layers were separated and the aqueous layer was extracted with dichloromethane. The combined organic layers were washed with sodium chloride solution, dried over magnesium sulfate, and evaporated. The residue was purified by silica gel chromatography (ethyl acetate/hexanes) to give 5.5 g (98%) of tert-butyl 3-cyanoazetidine-1-carboxylate.

Step 2 tert-Butyl 3-cyanoazetidine-1-carboxylate (0.5 g, 2.74 mmol) was dissolved in 11 mL of THF and the reaction was cooled to −78° C. Sodium bis(trimethylsilyl)amide (3.02 mL of a 1M THF solution, 3.02 mmol) was added slowly. After 30 min, iodomethane (0.26 mL, 4.12 mmol) was added. The reaction mixture was stirred at −78° C. for 30 min then warmed to room temperature over 16 h. Water and ethyl acetate were added to the reaction, the layers were separated and the aqueous layer was extracted twice more with ethyl acetate. The combined organic layers were washed with sodium chloride solution, dried over magnesium sulfate, and evaporated. The residue was purified by silica gel chromatography (ethyl acetate/hexanes) to give 0.23 g (42%) 3-cyano-3-methyl-azetidine-1-carboxylic acid tert-butyl ester.

Step 3

3-Cyano-3-methyl-azetidine-1-carboxylic acid tert-butyl ester (0.23 g, 1.17 mmol) was dissolved in 12 mL of dichloromethane and the reaction was then stirred in an ice bath. Trifluoroacetic acid (3.6 mL) was added slowly and the solution was warmed to room temperature. After 3 h the reaction mixture was evaporated to afford 3-cyano-3-methyl-azetidine trifluoroacetate which was used without further purification.

Step 4

2-Cyclopropyl-5H-pyrrolo[2,3-b]pyrazine-7-carboxylic acid [(R)-1-(3-cyano-3-methyl-azetidine-1-carbonyl)-2,2-dimethyl-propyl]-amide. Prepared according to the procedure outlined in Example 8 substituting 3-cyano-3-methyl-azetidine trifluoroacetate for 3-cyanoazetidine hydrochloride and Boc-D-tert-leucine for Boc-D-alanine MS: (M+H)$^+$= 395.

Example 11

2-Cyclopropyl-5H-pyrrolo[2,3-b]pyrazine-7-carboxylic acid [(R)-1-(4-cyano-piperidine-1-carbonyl)-2,2-dimethyl-propyl]-amide

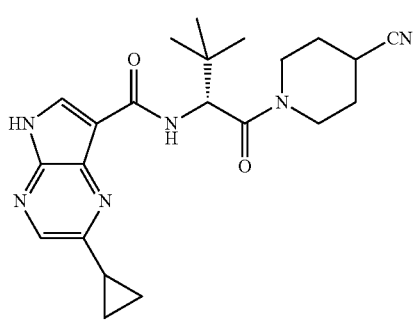 [SMILES: CC(C)(C)[C@@H](NC(=O)c1c[nH]c2ncc(C3CC3)nc12)C(=O)N1CCC(C#N)CC1]

Prepared according to the procedure outlined in Example 1 substituting piperidine-4-carbonitrile for pyrrolidine and using trifluoroacetic acid instead of hydrochloric acid for all N-Boc deprotection steps. MS: (M+H)$^+$=409; mp=249.0-251.0.

Example 12

2-(1-Ethyl-1H-pyrazol-4-yl)-5H-pyrrolo[2,3-b]pyrazine-7-carboxylic acid [(R)-1-(3-cyano-3-fluoro-pyrrolidine-1-carbonyl)-2,2-dimethyl-propyl]-amide

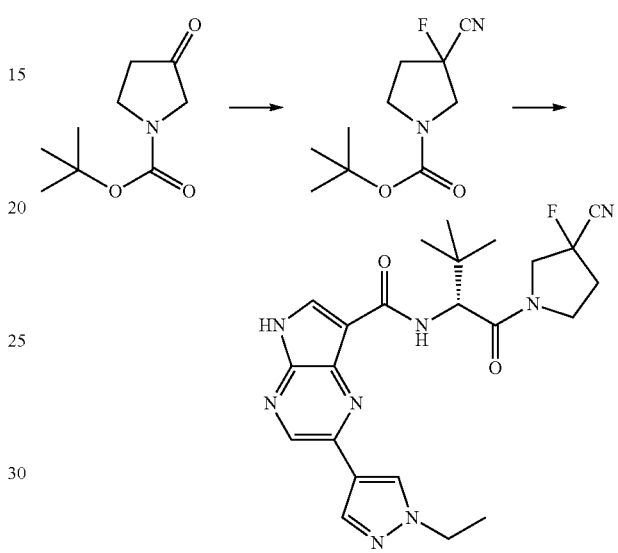

Step 1

To a solution of tert-butyl 3-oxopyrrolidine-1-carboxylate (2.0 g, 10.8 mmol) in THF (10 mL) at 0° C. was added KCN (1.05 g, 16.2 mmol) followed by H$_2$O (10 mL). To the homogeneous orange-brown reaction mixture was added a solution of sodium bisulfite (1.69 g, 16.2 mmol) in H$_2$O (10 mL). The cloudy reaction mixture was stirred at 0° C. for 1 h then extracted with CHCl$_3$ (3×). The combined organic layers were dried over MgSO$_4$ and concentrated. The resultant light brown oil was dissolved in CH$_2$Cl$_2$ (30 mL) and cooled to −78° C. then DAST (90%) (1.74 ml, 11.9 mmol) was slowly added. The reaction mixture was stirred at −78° C. for 10 min then warmed to 0° C. and stirred for 1 h. Carefully quenched with saturated aqueous NaHCO$_3$ then diluted with H$_2$O and extracted with CH$_2$Cl$_2$. The combined organics were dried over MgSO$_4$ and concentrated to a brown oil which was purified by SiO$_2$ chromatography (10% to 25% EtOAc/hexanes) to afford 0.45 g (20%) of tert-butyl 3-cyano-3-fluoro-pyrrolidine-1-carboxylate as a white solid.

Step 2

To a solution of tert-butyl 3-cyano-3-fluoropyrrolidine-1-carboxylate (240 mg, 1.12 mmol) in CH$_2$Cl$_2$ (5 mL) was added TFA (2.0 mL, 26.0 mmol). The pale yellow reaction mixture was stirred at room temperature for 4 h then concentrated to a yellow oil and dried under high vacuum. In a 50 mL flask were combined the above oil (237 mg, 1.04 mmol), (R)-2-(tert-butoxycarbonylamino)-3,3-dimethylbutanoic acid (200 mg, 0.87 mmol), and HOBT (146 mg, 0.95 mmol). Then added DMF (4 mL) followed by HATU (362 mg, 0.95 mmol) and N,N-diisopropylethylamine (0.45 mL, 2.59 mmol). The yellow reaction mixture was stirred at room temperature overnight then quenched with H$_2$O and extracted with EtOAc (3×). The combined organics were washed with H₂O (3×) then dried over MgSO₄ and concentrated. The crude residue was purified by SiO₂ chromatography (20% to 50% EtOAc/hexanes) to isolate 234 mg (83%) of tert-butyl (2R)-1-(3-cyano-3-fluoropyrrolidin-1-yl)-3,3-dimethyl-1-oxobutan-2-ylcarbamate as a viscous colorless oil.

Step 3

To a solution of tert-butyl (2R)-1-(3-cyano-3-fluoropyrrolidin-1-yl)-3,3-dimethyl-1-oxobutan-2-ylcarbamate (234 mg, 0.72 mmol) in CH₂Cl₂ (5 mL) was added TFA (2.0 mL, 26.0 mmol). The reaction mixture was stirred at room temperature for 3 h then concentrated and dried under high vacuum to provide 1-((R)-2-amino-3,3-dimethylbutanoyl)-3-fluoropyrrolidine-3-carbonitrile trifluoroacetate as a pale yellow oil which was used without further purification.

Step 4

2-(1-Ethyl-1H-pyrazol-4-yl)-5H-pyrrolo[2,3-b]pyrazine-7-carboxylic acid [(R)-1-(3-cyano-3-fluoro-pyrrolidine-1-carbonyl)-2,2-dimethyl-propyl]-amide. Prepared according to the procedure outlined in Example 1, steps 3-4 substituting 1-((R)-2-amino-3,3-dimethylbutanoyl)-3-fluoropyrrolidine-3-carbonitrile trifluoroacetate for (R)-2-amino-3,3-dimethyl-1-(pyrrolidin-1-yl)butan-1-one hydrochloride and 2-(1-ethyl-1H-pyrazol-4-yl)-5-((2-(trimethylsilyl)ethoxy)methyl)-5H-pyrrolo[3,2-b]pyrazine-7-carboxylic acid for 2-cyclopropyl-5-(2-trimethylsilanyl-ethoxymethyl)-5H-pyrrolo[2, 3-1)]pyrazine-7-carboxylic acid. MS: (M+H)⁺=467.

Example 13

2-Cyclopropyl-5H-pyrrolo[2,3-b]pyrazine-7-carboxylic acid [(R)-1-((S)-3-cyano-piperidine-1-carbonyl)-2,2-dimethyl-propyl]-amide and 2-Cyclopropyl-5H-pyrrolo[2,3-b]pyrazine-7-carboxylic acid [(R)-1-((R)-3-cyano-piperidine-1-carbonyl)-2,2-dimethyl-propyl]-amide

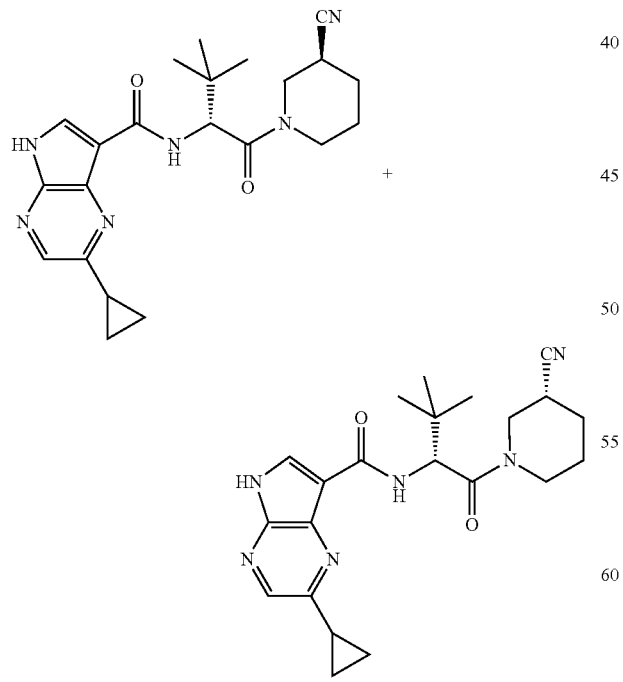

Prepared according to the procedure outlined in Example 1 substituting piperidine-3-carbonitrile trifluoroacetate for pyrrolidine and using trifluoroacetic acid instead of hydrochloric acid for all N-Boc deprotection steps. Diastereomers were separated at Step 3 via SiO₂ chromatography. R,S diastereomer, MS: (M+H)⁺=409; R,R diastereomer, MS: (M+H)⁺=409.

Example 14

2-Cyclopropyl-5H-pyrrolo[2,3-b]pyrazine-7-carboxylic acid [(R)-1-((S)-3-cyano-pyrrolidine-1-carbonyl)-2,2-dimethyl-propyl]-amide

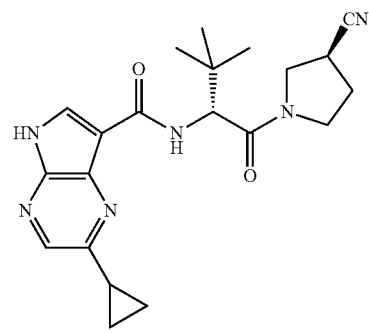 [SMILES: CC(C)(C)[C@@H](NC(=O)c1c[nH]c2ncc(C3CC3)nc12)C(=O)N1CC[C@H](C#N)C1]

Prepared according to the procedure outlined in Example 1 substituting (S)-pyrrolidine-3-carbonitrile trifluoroacetate for pyrrolidine and Fmoc-D-tert-leucine for Boc-D-tert-leucine. Trisamine-polystyrene resin was used for FMOC deprotection in Step 2. MS: (M+H)⁺=395.

Example 15

2-Cyclopropyl-5H-pyrrolo[2,3-b]pyrazine-7-carboxylic acid [(R)-1-((R)-3-cyano-pyrrolidine-1-carbonyl)-2,2-dimethyl-propyl]-amide

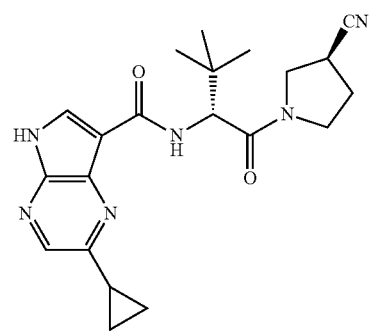

Prepared according to the procedure outlined in Example 1 substituting (R)-pyrrolidine-3-carbonitrile trifluoroacetate for pyrrolidine and Fmoc-D-tert-leucine for Boc-D-tert-leucine. Trisamine-polystyrene resin was used for FMOC deprotection in Step 2. MS: (M+H)$^+$=395.

Example 16

2-Cyclopropyl-5H-pyrrolo[2,3-b]pyrazine-7-carboxylic acid [(R)-2-(4-cyano-piperidin-1-yl)-2-oxo-1-(1-trifluoromethyl-cyclopropyl)-ethyl]-amide and 2-Cyclopropyl-5H-pyrrolo[2,3-b]pyrazine-7-carboxylic acid [(S)-2-(4-cyano-piperidin-1-yl)-2-oxo-1-(1-trifluoromethyl-cyclopropyl)-ethyl]-amide

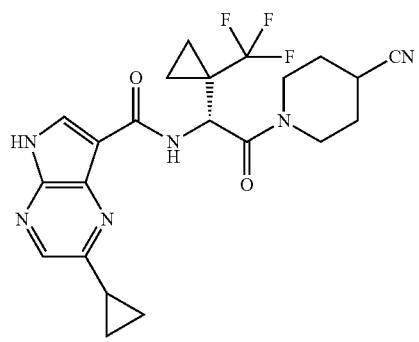

+

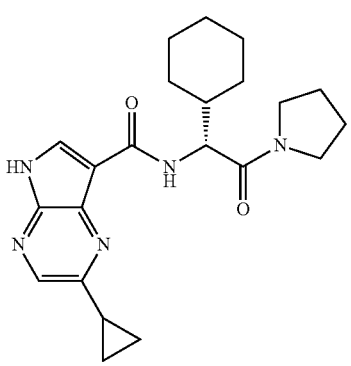 [SMILES: O=C(N[C@@H](C(=O)N1CCCC1)C1CCCCC1)c1c[nH]c2ncc(C3CC3)nc12]

Prepared according to the procedure outlined in Example 1 substituting piperidine-4-carbonitrile for pyrrolidine and N-Boc-2-(1-trifluoromethylcyclopropyl)-DL-glycine for Boc-D-tert-leucine and using trifluoroacetic acid instead of hydrochloric acid for all N-Boc deprotection steps. The R and S enantiomers were separated at Step 3 via chiral preparative SFC chromatography. R enantiomer, (M+H)$^+$=461; S enantiomer, (M+H)$^+$=461.

Example 17

2-Cyclopropyl-5H-pyrrolo[2,3-b]pyrazine-7-carboxylic acid ((R)-1-cyclohexyl-2-oxo-2-pyrrolidin-1-yl-ethyl)-amide

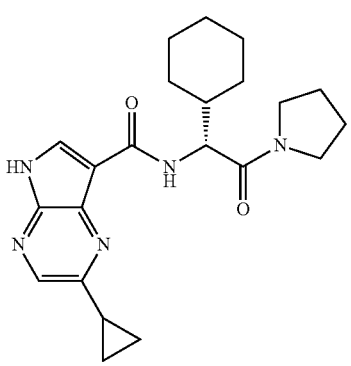 [SMILES: O=C(N[C@@H](C(=O)N1CCCC1)C1CCCCC1)c1c[nH]c2ncc(C3CC3)nc12]

Prepared according to the procedure outlined in Example 1 substituting Boc-D-cyclohexyl glycine for Boc-D-tert-leucine. MS: (M+H)$^+$=396.

Example 18

2-Cyclopropyl-5H-pyrrolo[2,3-b]pyrazine-7-carboxylic acid [(R)-1-(4,4-difluoro-piperidine-1-carbonyl)-2,2-dimethyl-propyl]-amide

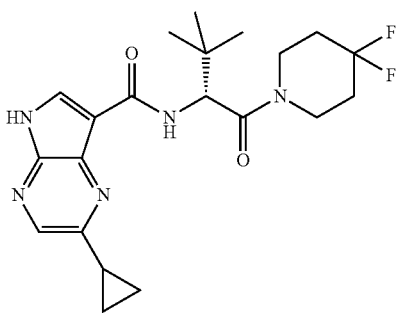 [SMILES: CC(C)(C)[C@@H](NC(=O)c1c[nH]c2ncc(C3CC3)nc12)C(=O)N1CCC(F)(F)CC1]

Prepared according to the procedure outlined in Example 1 substituting 4,4-difluoropiperidine hydrochloride for pyrrolidine. MS: (M+H)+=420.

Example 19

2-Cyclopropyl-5H-pyrrolo[2,3-b]pyrazine-7-carboxylic acid [(R)-2,2-dimethyl-1-(4-trifluoromethyl-piperidine-1-carbonyl)-propyl]-amide

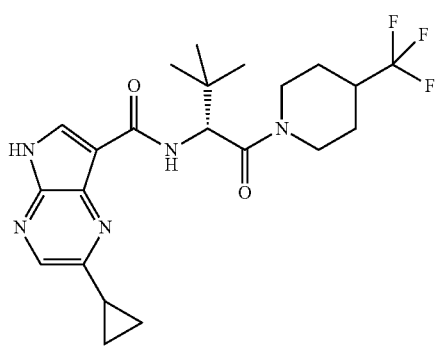 [SMILES: CC(C)(C)[C@@H](NC(=O)c1c[nH]c2ncc(C3CC3)nc12)C(=O)N1CCC(C(F)(F)F)CC1]

Prepared according to the procedure outlined in Example 1 substituting 4-(trifluoromethyl)piperidine hydrochloride for pyrrolidine. MS: (M+H)+=452.

Example 20

2-Cyclopropyl-5H-pyrrolo[2,3-b]pyrazine-7-carboxylic acid [(R)-1-(4-cyano-piperidine-1-carbonyl)-3-methyl-butyl]-amide

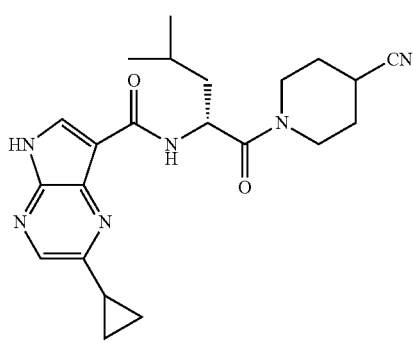 [SMILES: CC(C)C[C@@H](NC(=O)c1c[nH]c2ncc(C3CC3)nc12)C(=O)N1CCC(C#N)CC1]

Prepared according to the procedure outlined in Example 1 substituting Boc-D-leucine for Boc-D-tert-leucine and piperidine-4-carbonitrile for pyrrolidine. Trifluoroacetic acid was used for all N-Boc deprotection steps. MS: (M+H)+=409.

Example 21

2-Cyclopropyl-5H-pyrrolo[2,3-b]pyrazine-7-carboxylic acid ((R)-1-methyl-2-oxo-2-pyrrolidin-1-yl-ethyl)-amide

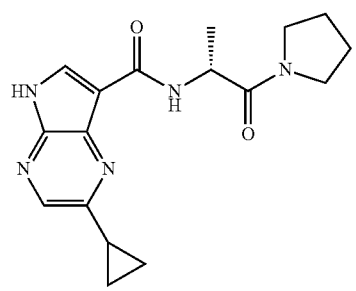 [SMILES: C[C@@H](NC(=O)c1c[nH]c2ncc(C3CC3)nc12)C(=O)N1CCCC1]

Prepared according to the procedure outlined in Example 1 substituting Boc-D-alanine for Boc-D-tert-leucine. MS: (M+H)+=328; mp=237.0-239.0.

Example 22

2-Cyclopropyl-5H-pyrrolo[2,3-b]pyrazine-7-carboxylic acid ((R)-1-methyl-2-oxo-2-piperidin-1-yl-ethyl)-amide

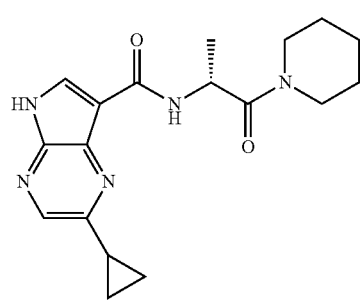 [SMILES: C[C@@H](NC(=O)c1c[nH]c2ncc(C3CC3)nc12)C(=O)N1CCCCC1]

Prepared according to the procedure outlined in Example 1 substituting piperidine for pyrrolidine and Boc-D-alanine for Boc-D-tert-leucine. MS: (M+H)⁺=342; mp=190.0-192.0.

Example 23

2-Cyclopropyl-5H-pyrrolo[2,3-b]pyrazine-7-carboxylic acid [(R)-1-(pyrrolidine-1-carbonyl)-propyl]-amide

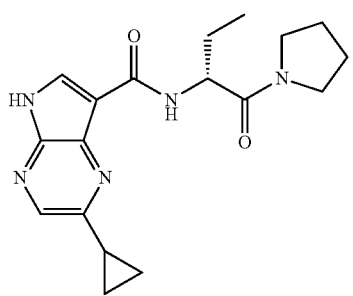 [SMILES: CC[C@@H](NC(=O)c1c[nH]c2ncc(C3CC3)nc12)C(=O)N1CCCC1]

Prepared according to the procedure outlined in Example 1 substituting Boc-D-aminobutyric acid for Boc-D-tert-leucine. MS: (M+H)⁺=342; mp=240.9-242.5.

Example 24

2-Cyclopropyl-5H-pyrrolo[2,3-b]pyrazine-7-carboxylic acid [(R)-2-methyl-1-(pyrrolidine-1-carbonyl)-propyl]-amide

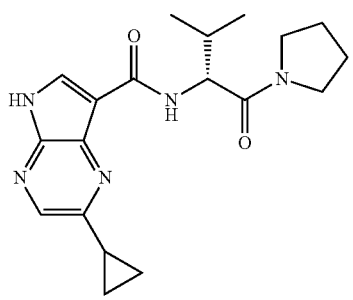 [SMILES: CC(C)[C@@H](NC(=O)c1c[nH]c2ncc(C3CC3)nc12)C(=O)N1CCCC1]

Prepared according to the procedure outlined in Example 1 substituting Boc-D-valine for Boc-D-tert-leucine. MS: (M+H)⁺=356; mp=171.0-172.1.

Example 25

2-Cyclopropyl-5H-pyrrolo[2,3-b]pyrazine-7-carboxylic acid ((R)-1-cyclopropyl-2-oxo-2-pyrrolidin-1-yl-ethyl)-amide

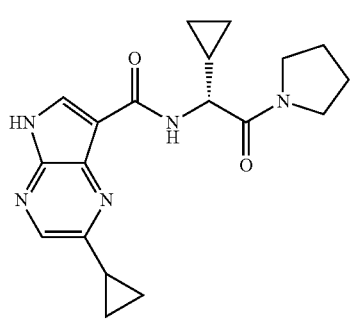 [SMILES: O=C(N[C@@H](C(=O)N1CCCC1)C1CC1)c1c[nH]c2ncc(C3CC3)nc12]

Prepared according to the procedure outlined in Example 1 substituting Boc-D-cyclopropyl glycine for Boc-D-tert-leucine. MS: (M+H)⁺=354; mp=254.0-256.0.

Example 26

2-Cyclopropyl-5H-pyrrolo[2,3-b]pyrazine-7-carboxylic acid [(R)-2-methyl-1-(piperidine-1-carbonyl)-propyl]-amide

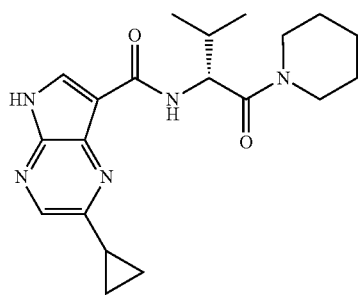 [SMILES: CC(C)[C@@H](NC(=O)c1c[nH]c2ncc(C3CC3)nc12)C(=O)N1CCCCC1]

Prepared according to the procedure outlined in Example 1 substituting piperidine for pyrrolidine and Boc-D-valine for Boc-D-tert-leucine. MS: (M+H)$^+$=370; mp=183.0-185.0.

Example 27

2-Cyclopropyl-5H-pyrrolo[2,3-b]pyrazine-7-carboxylic acid [(R)-2-methyl-1-(morpholine-4-carbonyl)-propyl]-amide

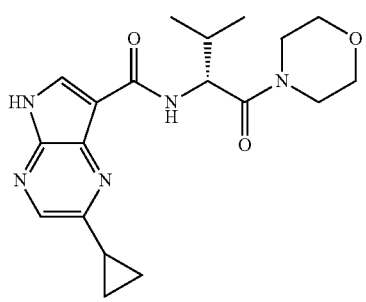 [SMILES: CC(C)[C@@H](NC(=O)c1c[nH]c2ncc(C3CC3)nc12)C(=O)N1CCOCC1]

Prepared according to the procedure outlined in Example 1 substituting morpholine for pyrrolidine and Boc-D-valine for Boc-D-tert-leucine. MS: (M+H)$^+$=372; mp=154.0-156.0.

Example 28

2-Cyclopropyl-5H-pyrrolo[2,3-b]pyrazine-7-carboxylic acid [(R)-2-(3-methoxy-pyrrolidin-1-yl)-1-methyl-2-oxo-ethyl]-amide

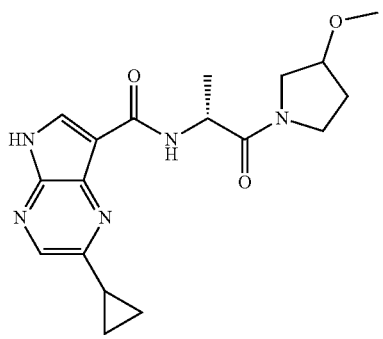 [SMILES: COC1CCN(C(=O)[C@@H](C)NC(=O)c2c[nH]c3ncc(C4CC4)nc23)C1]

Prepared according to the procedure outlined in Example 1 substituting 3-methoxypyrrolidine hydrochloride for pyrrolidine and Boc-D-alanine for Boc-D-tert-leucine. MS: (M+H)$^+$= 358.

Example 29

2-Cyclopropyl-5H-pyrrolo[2,3-b]pyrazine-7-carboxylic acid [(R)-2-(3-hydroxy-pyrrolidin-1-yl)-1-methyl-2-oxo-ethyl]-amide

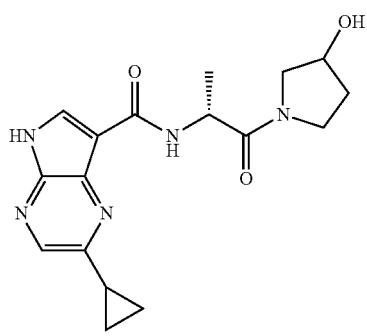

Prepared according to the procedure outlined in Example 1 substituting 3-hydroxypyrrolidine for pyrrolidine and Boc-D-alanine for Boc-D-tert-leucine. MS: (M+H)$^+$=344.

Example 30

2-Cyclopropyl-5H-pyrrolo[2,3-b]pyrazine-7-carboxylic acid [(R)-1-methyl-2-(3-methyl-pyrrolidin-1-yl)-2-oxo-ethyl]-amide

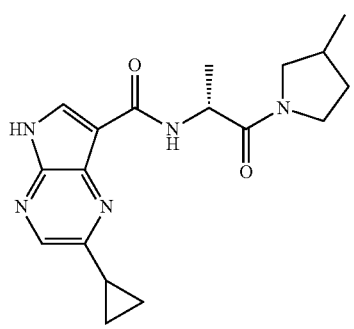 [SMILES: CC1CCN(C(=O)[C@@H](C)NC(=O)c2c[nH]c3ncc(C4CC4)nc23)C1]

Prepared according to the procedure outlined in Example 1 substituting 3-methylpyrrolidine for pyrrolidine and Boc-D-alanine for Boc-D-tert-leucine. MS: (M+H)$^+$=342.

Example 31

2-Cyclopropyl-5H-pyrrolo[2,3-b]pyrazine-7-carboxylic acid [(R)-1-methyl-2-(2-methyl-pyrrolidin-1-yl)-2-oxo-ethyl]-amide

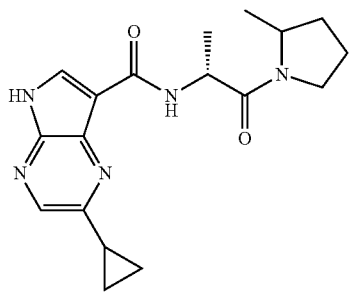 [SMILES: CC1CCCN1C(=O)[C@@H](C)NC(=O)c1c[nH]c2ncc(C3CC3)nc12]

Prepared according to the procedure outlined in Example 1 substituting 2-methylpyrrolidine for pyrrolidine and Boc-D-alanine for Boc-D-tert-leucine. MS: (M+H)$^+$=342.

Example 32

2-Cyclopropyl-5H-pyrrolo[2,3-b]pyrazine-7-carboxylic acid [2,2,2-trifluoro-1-(pyrrolidine-1-carbonyl)-ethyl]-amide

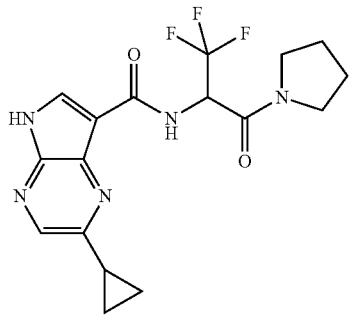 [SMILES: O=C(NC(C(=O)N1CCCC1)C(F)(F)F)c1c[nH]c2ncc(C3CC3)nc12]

Step 1

In a 50 mL round-bottomed flask, 3,3,3-trifluoro-DL-alanine (0.60 g, 4.2 mmol) was suspended in acetonitrile (10 mL). Triethylamine (0.70 mL, 5.0 mmol) was added followed by di-tert-butyl dicarbonate (1.0 g, 4.6 mmol). The pale yellow solution was stirred at room temperature over the weekend. The reaction mixture was diluted with ~100 mL dichloromethane and washed with ~15 mL 1.0 M aqueous HCl. The aqueous layer was extracted with ~100 mL dichloromethane. The organic layers were combined, dried over sodium sulfate, filtered and concentrated to afford 1.07 g of 2-tert-butoxycarbonylamino-3,3,3-trifluoro-propionic acid as a light yellow solid which was used without further purification.

Step 2

2-Cyclopropyl-5H-pyrrolo[2,3-b]pyrazine-7-carboxylic acid [2,2,2-trifluoro-1-(pyrrolidine-1-carbonyl)-ethyl]-amide. Prepared according to the procedure outlined in Example 1 substituting 2-tert-butoxycarbonylamino-3,3,3-trifluoro-propionic acid for Boc-D-tert-leucine. MS: (M+H)$^+$= 382.

Example 33

2-Cyclopropyl-5H-pyrrolo[2,3-b]pyrazine-7-carboxylic acid [(R)-2-((S)-3-fluoro-pyrrolidin-1-yl)-1-methyl-2-oxo-ethyl]-amide

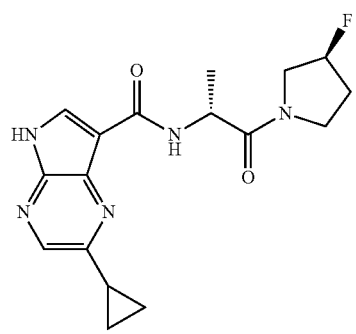 [SMILES: C[C@@H](NC(=O)c1c[nH]c2ncc(C3CC3)nc12)C(=O)N1CC[C@H](F)C1]

Prepared according to the procedure outlined in Example 1 substituting (S)-3-fluoropyrrolidine hydrochloride for pyrrolidine and Boc-D-alanine for Boc-D-tert-leucine. MS: (M+H)$^+$=346.

Example 34

2-Cyclopropyl-5H-pyrrolo[2,3-b]pyrazine-7-carboxylic acid [(R)-2-((R)-3-fluoro-pyrrolidin-1-yl)-1-methyl-2-oxo-ethyl]-amide

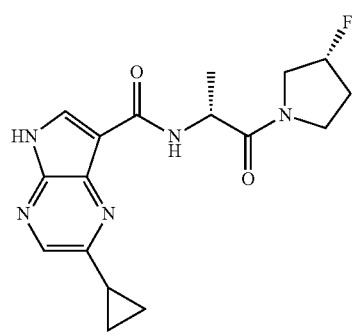 [SMILES: C[C@@H](NC(=O)c1c[nH]c2ncc(C3CC3)nc12)C(=O)N1CC[C@@H](F)C1]

Prepared according to the procedure outlined in Example 1 substituting (R)-3-fluoropyrrolidine hydrochloride for pyrrolidine and Boc-D-alanine for Boc-D-tert-leucine. MS: (M+H)+=346.

Example 35

2-Cyclopropyl-5H-pyrrolo[2,3-b]pyrazine-7-carboxylic acid [(R)-1-methyl-2-oxo-2-(3-trifluoromethyl-pyrrolidin-1-yl)-ethyl]-amide

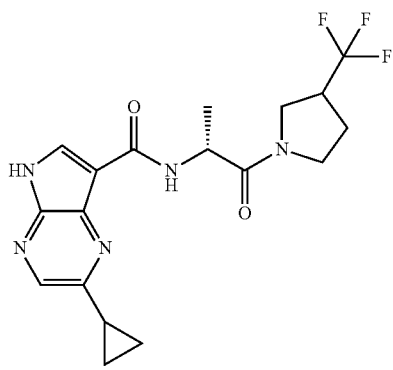 [SMILES: C[C@@H](NC(=O)c1c[nH]c2ncc(C3CC3)nc12)C(=O)N1CCC(C(F)(F)F)C1]

Prepared according to the procedure outlined in Example 1 substituting 3-(trifluoromethyl)pyrrolidine hydrochloride for pyrrolidine and Boc-D-alanine for Boc-D-tert-leucine. MS: (M+H)+=396.

Example 36

2-Cyclopropyl-5H-pyrrolo[2,3-b]pyrazine-7-carboxylic acid [(R)-2,2-dimethyl-1-(piperidine-1-carbonyl)-propyl]-amide

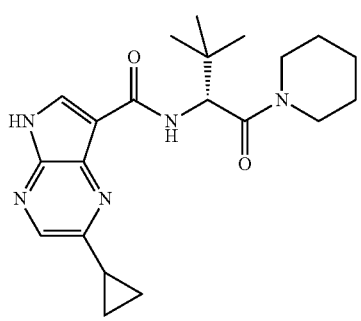 [SMILES: CC(C)(C)[C@@H](NC(=O)c1c[nH]c2ncc(C3CC3)nc12)C(=O)N1CCCCC1]

Prepared according to the procedure outlined in Example 1 substituting piperidine for pyrrolidine. MS: (M+H)+=384.

Example 37

2-Cyclopropyl-5H-pyrrolo[2,3-b]pyrazine-7-carboxylic acid [(R)-2-(3-cyano-azetidin-1-yl)-1-cyclopentyl-2-oxo-ethyl]-amide

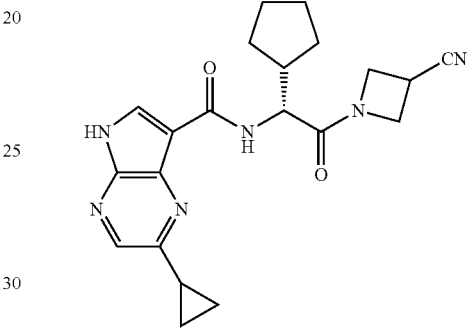

Prepared according to the procedure outlined in Example 12 substituting Boc-D-cyclopentyl glycine for Boc-D-alanine MS: (M+H)+=393.

Example 38

2-Cyclopropyl-5H-pyrrolo[2,3-b]pyrazine-7-carboxylic acid [(R)-1-(3,3-difluoro-pyrrolidine-1-carbonyl)-2,2-dimethyl-propyl]-amide

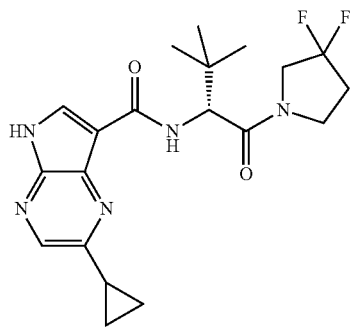 [SMILES: CC(C)(C)[C@@H](NC(=O)c1c[nH]c2ncc(C3CC3)nc12)C(=O)N1CCC(F)(F)C1]

Prepared according to the procedure outlined in Example 1 substituting 3,3-difluoropyrrolidine hydrochloride for pyrrolidine. MS: (M+H)+=406.

Example 39

2-Cyclopropyl-5H-pyrrolo[2,3-b]pyrazine-7-carboxylic acid [(R)-1-(3,4-dihydro-1H-isoquinoline-2-carbonyl)-2,2-dimethyl-propyl]-amide

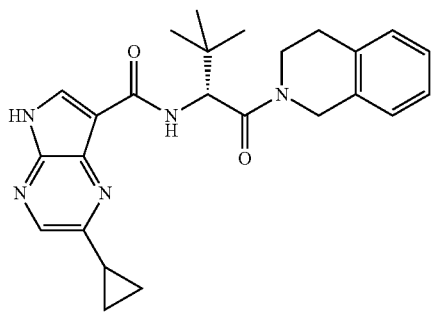 [SMILES: CC(C)(C)[C@@H](NC(=O)c1c[nH]c2ncc(C3CC3)nc12)C(=O)N1CCc2ccccc2C1]

Prepared according to the procedure outlined in Example 1 substituting 1,2,3,4-tetrahydroisoquinoline for pyrrolidine. MS: (M+H)+=432.

Example 40

2-Cyclopropyl-5H-pyrrolo[2,3-b]pyrazine-7-carboxylic acid [(R)-1-(4-cyano-4-methyl-piperidine-1-carbonyl)-2,2-dimethyl-propyl]-amide

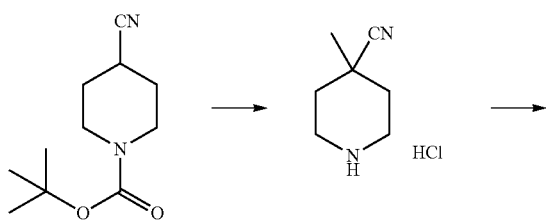

Step 1

In a round-bottomed flask, tert-butyl 4-cyanopiperidine-1-carboxylate (0.70 g, 3.3 mmol) was dissolved in THF (14 mL). The solution was cooled to −76° C. and lithium bis(trimethylsilyl)amide (1.0 M solution in THF, 3.7 mL, 3.7 mmol) was added dropwise over 15 min. The yellow solution was stirred at −76° C. for 30 min then iodomethane (0.32 mL, 5.1 mmol) was slowly added. The reaction mixture was stirred at −76° C. for 30 min and then warmed to room temperature over 1 h. The reaction mixture was quenched with 10 mL saturated aqueous NH4Cl, diluted with water and extracted with EtOAc (2×). The organic layers were washed with water and brine then dried over sodium sulfate, filtered and concentrated. The residue was purified by SiO2 chromatography with 0% to 20% EtOAc/hexanes to afford 0.71 g (95%) of 4-cyano-4-methyl-piperidine-1-carboxylic acid tert-butyl ester as a pale yellow oil.

Step 2

In a round-bottomed flask, 4-cyano-4-methyl-piperidine-1-carboxylic acid tert-butyl ester (0.35 g, 1.56 mmol) was dissolved in hydrogen chloride, 1.0 M solution in methanol (9.0 mL, 9.00 mmol). The reaction mixture was stirred at room temperature overnight then concentrated to give 0.27 g of 4-methyl-piperidine-4-carbonitrile hydrochloride as an off-white foam which was used without further purification.

Step 3

2-Cyclopropyl-5H-pyrrolo[2,3-b]pyrazine-7-carboxylic acid [(R)-1-(4-cyano-4-methyl-piperidine-1-carbonyl)-2,2-dimethyl-propyl]-amide. Prepared according to the procedure outlined in Example 1 substituting 4-methyl-piperidine-4-carbonitrile hydrochloride for pyrrolidine. MS: (M+H)+=423.

Example 41

2-Cyclopropyl-5H-pyrrolo[2,3-b]pyrazine-7-carboxylic acid [(R)-2-(4-cyano-piperidin-1-yl)-1-cyclopentyl-2-oxo-ethyl]-amide

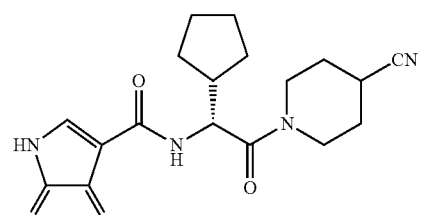

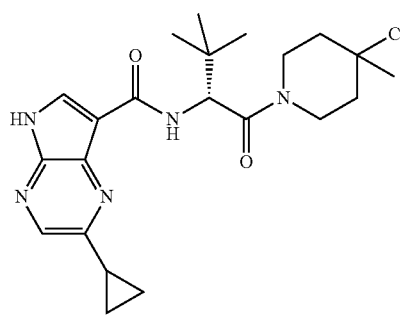

Prepared according to the procedure outlined in Example 1 substituting piperidine-4-carbonitrile for pyrrolidine and Boc-D-cyclopentyl glycine for Boc-D-tert-leucine and using trifluoroacetic acid instead of hydrochloric acid for all N-Boc deprotection steps. MS: (M+H)+=421.

Example 42

2-Cyclopropyl-5H-pyrrolo[2,3-b]pyrazine-7-carboxylic acid [(R)-1-benzyl-2-(4-cyano-piperidin-1-yl)-2-oxo-ethyl]-amide

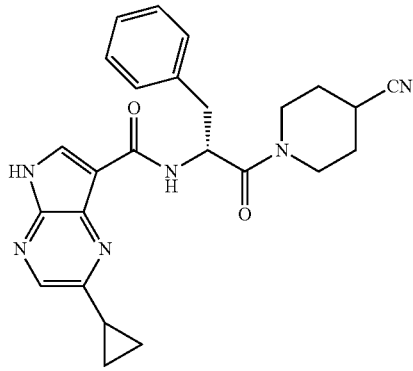 [SMILES: N#CC1CCN(C(=O)[C@@H](Cc2ccccc2)NC(=O)c2c[nH]c3ncc(C4CC4)nc23)CC1]

Prepared according to the procedure outlined in Example 1 substituting piperidine-4-carbonitrile for pyrrolidine and Boc-D-phenylalanine for Boc-D-tert-leucine and using trifluoroacetic acid instead of hydrochloric acid for all N-Boc deprotection steps. MS: (M+H)+=443.

Example 43

2-Cyclopropyl-5H-pyrrolo[2,3-b]pyrazine-7-carboxylic acid [(R)-1-(4-cyano-piperidine-1-carbonyl)-3,3-dimethyl-butyl]-amide

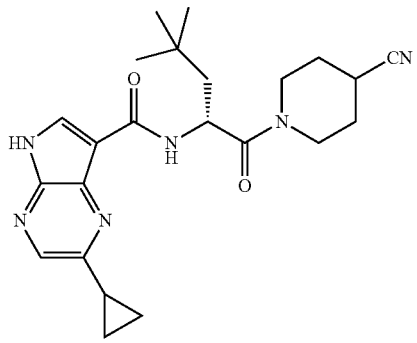 [SMILES: CC(C)(C)C[C@@H](NC(=O)c1c[nH]c2ncc(C3CC3)nc12)C(=O)N1CCC(C#N)CC1]

Prepared according to the procedure outlined in Example 1 substituting piperidine-4-carbonitrile for pyrrolidine and Boc-beta-tert-butyl-D-alanine for Boc-D-tert-leucine and using trifluoroacetic acid instead of hydrochloric acid for all N-Boc deprotection steps. MS: (M+H)+=423.

Example 44

2-(3,5-Bis-trifluoromethyl-phenyl)-5H-pyrrolo[2,3-b]pyrazine-7-carboxylic acid [(R)-1-(4-cyano-piperidine-1-carbonyl)-2,2-dimethyl-propyl]-amide

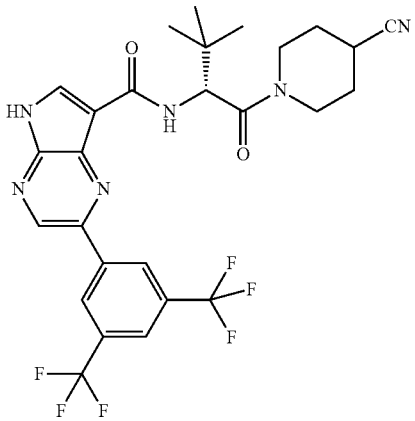 [SMILES: CC(C)(C)[C@@H](NC(=O)c1c[nH]c2ncc(-c3cc(C(F)(F)F)cc(C(F)(F)F)c3)nc12)C(=O)N1CCC(C#N)CC1]

Prepared according to the procedure outlined in Example 2 substituting 1-((R)-2-amino-3,3-dimethyl-butyryl)-piperidine-4-carbonitrile trifluoroacetate for (R)-2-amino-3,3-dimethyl-1-pyrrolidin-1-yl-butan-1-one hydrochloride in Step 1 and 3,5-bis-trifluoromethyl-phenylboronic acid for 1-ethyl-1H-pyrazole-4-boronic acid pinacol ester in Step 2. MS: (M+H)+=581.

Example 45

2-(3-Pyrrolidin-1-yl-phenyl)-5H-pyrrolo[2,3-b]pyrazine-7-carboxylic acid [(R)-1-(4-cyano-piperidine-1-carbonyl)-2,2-dimethyl-propyl]-amide

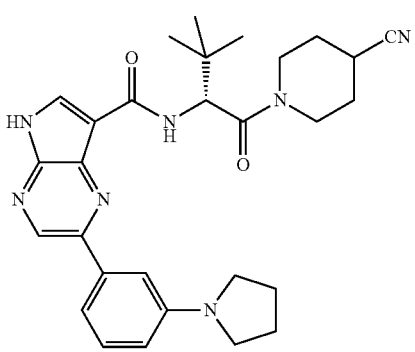 [SMILES: CC(C)(C)[C@@H](NC(=O)c1c[nH]c2ncc(-c3cccc(N4CCCC4)c3)nc12)C(=O)N1CCC(C#N)CC1]

Prepared according to the procedure outlined in Example 2 substituting 1-((R)-2-amino-3,3-dimethyl-butyryl)-piperidine-4-carbonitrile trifluoroacetate for (R)-2-amino-3,3-dimethyl-1-pyrrolidin-1-yl-butan-1-one hydrochloride in Step 1 and 3-(1-pyrrolidinyl)phenylboronic acid hydrochloride for 1-ethyl-1H-pyrazole-4-boronic acid pinacol ester in Step 2. MS: (M+H)+=514.

Example 46

2-(1-Methyl-1H-pyrazol-4-yl)-5H-pyrrolo[2,3-b]pyrazine-7-carboxylic acid [(R)-1-(3-cyano-azetidine-1-carbonyl)-2,2-dimethyl-propyl]-amide

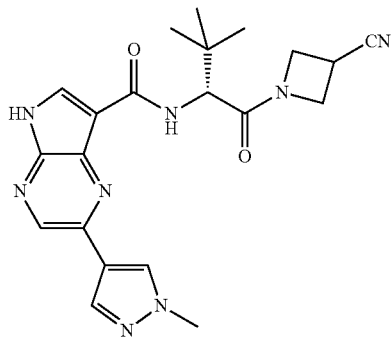 [SMILES: Cn1cc(-c2cnc3[nH]cc(C(=O)N[C@@H](C(=O)N4CC(C#N)C4)C(C)(C)C)c3n2)cn1]

Prepared according to the procedure outlined in Example 1 substituting 3-cyanoazetidine hydrochloride for pyrrolidine and 2-(1-methyl-1H-pyrazol-4-yl)-5-((2-(trimethylsilyl)ethoxy)methyl)-5H-pyrrolo[3,2-b]pyrazine-7-carboxylic acid for 2-cyclopropyl-5-(2-trimethylsilanyl-ethoxymethyl)-5H-pyrrolo[2,3-b]pyrazine-7-carboxylic acid. Trifluoroacetic acid was used in place of hydrochloric acid for all N-Boc deprotection steps. MS: (M+H)+=421.

Example 47

2-(1H-Pyrazol-4-yl)-5H-pyrrolo[2,3-b]pyrazine-7-carboxylic acid [(R)-1-(4-cyano-piperidine-1-carbonyl)-2,2-dimethyl-propyl]-amide

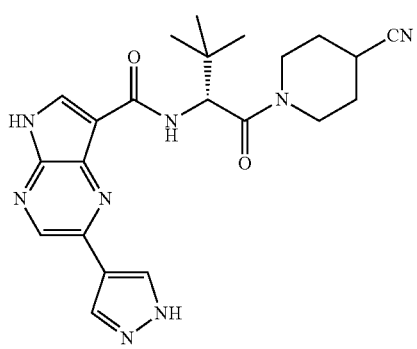 [SMILES: CC(C)(C)[C@@H](NC(=O)c1c[nH]c2ncc(-c3cn[nH]c3)nc12)C(=O)N1CCC(C#N)CC1]

Prepared according to the procedure outlined in Example 2 substituting 1-((R)-2-amino-3,3-dimethyl-butyryl)-piperidine-4-carbonitrile trifluoroacetate for (R)-2-amino-3,3-dimethyl-1-pyrrolidin-1-yl-butan-1-one hydrochloride in Step 1 and 1-Boc-pyrazole-4-boronic acid pinacol ester for 1-ethyl-1H-pyrazole-4-boronic acid pinacol ester in Step 2. MS: (M+H)+=435.

Example 48

2-(1-Methyl-1H-pyrazol-4-yl)-5H-pyrrolo[2,3-b]pyrazine-7-carboxylic acid [(R)-1-(4-cyano-piperidine-1-carbonyl)-2,2-dimethyl-propyl]-amide

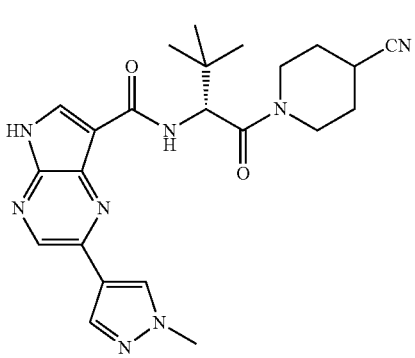 [SMILES: Cn1cc(-c2cnc3[nH]cc(C(=O)N[C@@H](C(=O)N4CCC(C#N)CC4)C(C)(C)C)c3n2)cn1]

Prepared according to the procedure outlined in Example 2 substituting 1-((R)-2-amino-3,3-dimethyl-butyryl)-piperidine-4-carbonitrile trifluoroacetate for (R)-2-amino-3,3-dimethyl-1-pyrrolidin-1-yl-butan-1-one hydrochloride in Step 1 and 1-methyl-1H-pyrazole-4-boronic acid pinacol ester for 1-ethyl-1H-pyrazole-4-boronic acid pinacol ester in Step 2. MS: (M+H)+=449.

Example 49

2-(1-Ethyl-1H-pyrazol-4-yl)-5H-pyrrolo[2,3-b]pyrazine-7-carboxylic acid [(R)-1-(4-cyano-piperidine-1-carbonyl)-2,2-dimethyl-propyl]-amide

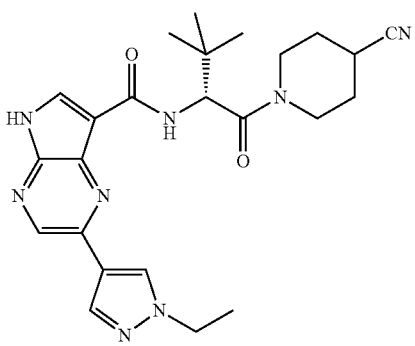 [SMILES: CCn1cc(-c2cnc3[nH]cc(C(=O)N[C@@H](C(=O)N4CCC(C#N)CC4)C(C)(C)C)c3n2)cn1]

Prepared according to the procedure outlined in Example 2 substituting 1-((R)-2-amino-3,3-dimethyl-butyryl)-piperidine-4-carbonitrile trifluoroacetate for (R)-2-amino-3,3-dimethyl-1-pyrrolidin-1-yl-butan-1-one hydrochloride in Step 1. MS: (M+H)⁺=463.

Example 50

2-(3,4,5-Trimethoxy-phenyl)-5H-pyrrolo[2,3-b]pyrazine-7-carboxylic acid [(R)-1-(4-cyano-piperidine-1-carbonyl)-2,2-dimethyl-propyl]-amide

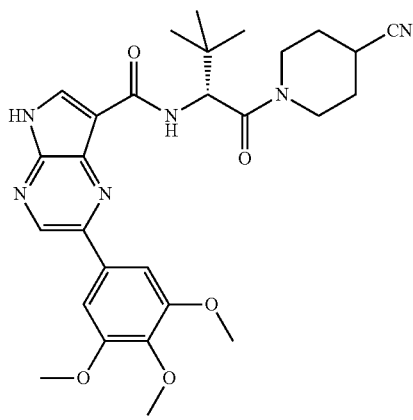 [SMILES: COc1cc(-c2cnc3[nH]cc(C(=O)N[C@@H](C(=O)N4CCC(C#N)CC4)C(C)(C)C)c3n2)cc(OC)c1OC]

Prepared according to the procedure outlined in Example 2 substituting 1-((R)-2-amino-3,3-dimethyl-butyryl)-piperidine-4-carbonitrile trifluoroacetate for (R)-2-amino-3,3-dimethyl-1-pyrrolidin-1-yl-butan-1-one hydrochloride in Step 1 and 3,4,5-trimethoxyphenylboronic acid for 1-ethyl-1H-pyrazole-4-boronic acid pinacol ester in Step 2. MS: (M+H)⁺= 535.

Example 51

2-(2,5-Dimethoxy-phenyl)-5H-pyrrolo[2,3-b]pyrazine-7-carboxylic acid [(R)-1-(4-cyano-piperidine-1-carbonyl)-2,2-dimethyl-propyl]-amide

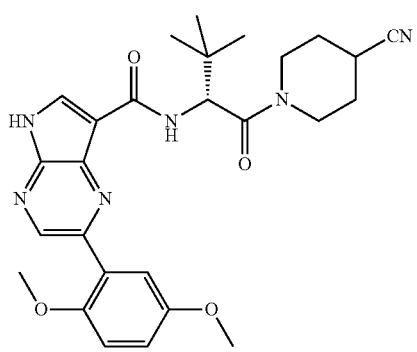 [SMILES: COc1ccc(OC)c(-c2cnc3[nH]cc(C(=O)N[C@@H](C(=O)N4CCC(C#N)CC4)C(C)(C)C)c3n2)c1]

Prepared according to the procedure outlined in Example 2 substituting 1-((R)-2-amino-3,3-dimethyl-butyryl)-piperidine-4-carbonitrile trifluoroacetate for (R)-2-amino-3,3-dimethyl-1-pyrrolidin-1-yl-butan-1-one hydrochloride in Step 1 and 2,5-dimethoxyphenylboronic acid for 1-ethyl-1H-pyrazole-4-boronic acid pinacol ester in Step 2. MS: (M+H)⁺= 505.

Example 52

2-Cyclopropyl-5H-pyrrolo[2,3-b]pyrazine-7-carboxylic acid [(R)-1-(4-acetyl-piperazine-1-carbonyl)-2,2-dimethyl-propyl]-amide

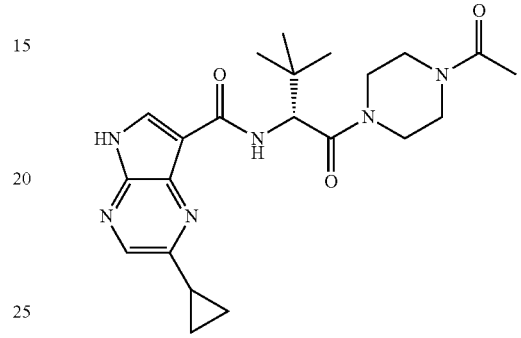

Prepared according to the procedure outlined in Example 1 substituting 1-acetylpiperazine for pyrrolidine. MS: (M+H)⁺= 427.

Example 53

2-(1-Methyl-1H-pyrazol-4-yl)-5H-pyrrolo[3,2-b]pyrazine-7-carboxylic acid [(R)-1-((S)-3-cyano-pyrrolidine-1-carbonyl)-2,2-dimethyl-propyl]-amide

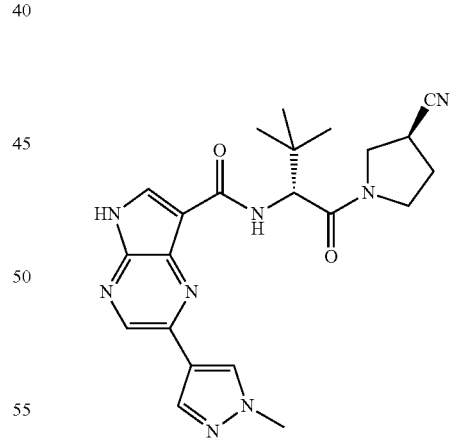

Prepared according to the procedure outlined in Example 1 substituting (S)-pyrrolidine-3-carbonitrile trifluoroacetate for pyrrolidine and 2-(1-methyl-1H-pyrazol-4-yl)-5-((2-(trimethylsilyl)ethoxy)methyl)-5H-pyrrolo[3,2-b]pyrazine-7-carboxylic acid for 2-cyclopropyl-5-(2-trimethylsilanyl-ethoxymethyl)-5H-pyrrolo[2,3-b]pyrazine-7-carboxylic

Example 54

2-(1-Methyl-1H-pyrazol-4-yl)-5H-pyrrolo[2,3-b]pyrazine-7-carboxylic acid [(R)-1-((R)-3-cyano-pyrrolidine-1-carbonyl)-2,2-dimethyl-propyl]-amide

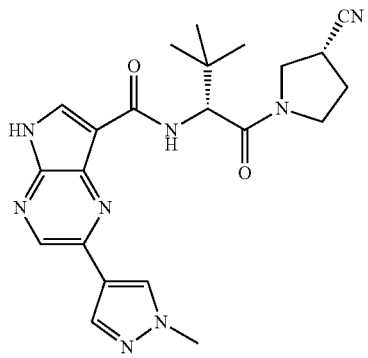 [SMILES: Cn1cc(-c2cnc3[nH]cc(C(=O)N[C@@H](C(=O)N4CC[C@@H](C#N)C4)C(C)(C)C)c3n2)cn1]

Prepared according to the procedure outlined in Example 1 substituting (R)-pyrrolidine-3-carbonitrile trifluoroacetate for pyrrolidine and 2-(1-methyl-1H-pyrazol-4-yl)-5-((2-(trimethylsilyl)ethoxy)methyl)-5H-pyrrolo[3,2-b]pyrazine-7-carboxylic acid for 2-cyclopropyl-5-(2-trimethylsilanyl-ethoxymethyl)-5H-pyrrolo[2,3-b]pyrazine-7-carboxylic acid. Trifluoroacetic acid was used in place of hydrochloric acid for all N-Boc deprotection steps. MS: (M+H)$^+$=435.

Example 55

2-Cyclopropyl-5H-pyrrolo[2,3-b]pyrazine-7-carboxylic acid [(R)-2-(4-cyano-piperidin-1-yl)-1-cyclopropyl-2-oxo-ethyl]-amide

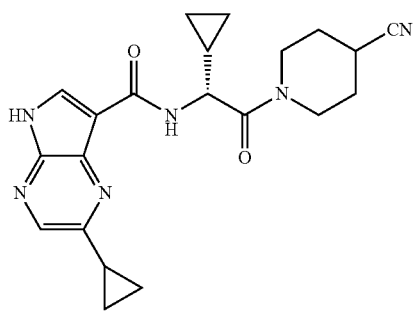 [SMILES: N#CC1CCN(C(=O)[C@H](NC(=O)c2c[nH]c3ncc(C4CC4)nc23)C2CC2)CC1]

Prepared according to the procedure outlined in Example 1 substituting piperidine-4-carbonitrile for pyrrolidine and Boc-D-cyclopropyl glycine for Boc-D-tert-leucine. N-Boc deprotection was achieved using 2,2,2-trifluoroethanol in a microwave reactor. MS: (M+H)$^+$=393.

Example 56

2-(1-Methyl-1H-pyrazol-4-yl)-5H-pyrrolo[2,3-b]pyrazine-7-carboxylic acid [(R)-2-(4-cyano-piperidin-1-yl)-1-cyclopropyl-2-oxo-ethyl]-amide

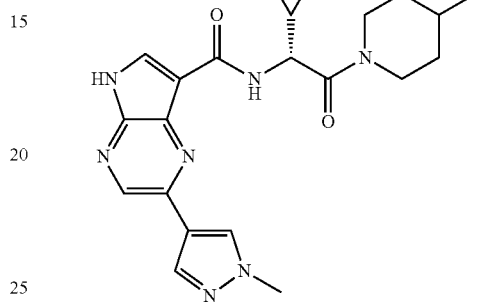

Prepared according to the procedure outlined in Example 1 substituting piperidine-4-carbonitrile for pyrrolidine, Boc-D-cyclopropyl glycine for Boc-D-tert-leucine, and 2-(1-methyl-1H-pyrazol-4-yl)-5-((2-(trimethylsilyl)ethoxy)methyl)-5H-pyrrolo[3,2-b]pyrazine-7-carboxylic acid for 2-cyclopropyl-5-(2-trimethylsilanyl-ethoxymethyl)-5H-pyrrolo[2,3-b]pyrazine-7-carboxylic acid. N-Boc deprotection was achieved using 2,2,2-trifluoroethanol in a microwave reactor. MS: (M+H)$^+$=433.

Example 57

2-(1-Ethyl-1H-pyrazol-4-yl)-5H-pyrrolo[2,3-b]pyrazine-7-carboxylic acid [(R)-2-(3-cyano-azetidin-1-yl)-1-methyl-2-oxo-ethyl]-amide

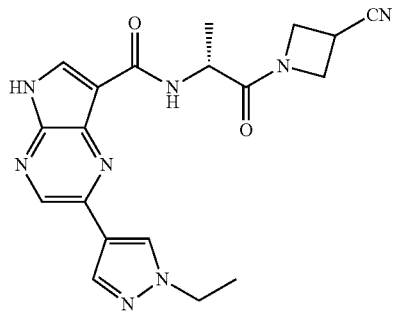 [SMILES: CCn1cc(-c2cnc3[nH]cc(C(=O)N[C@H](C)C(=O)N4CC(C#N)C4)c3n2)cn1]

Prepared according to the procedure outlined in Example 1 substituting 3-cyanoazetidine hydrochloride for pyrrolidine, Boc-D-alanine for Boc-D-tert-leucine, and 2-(1-ethyl-1H-pyrazol-4-yl)-5-((2-(trimethylsilyl)ethoxy)methyl)-5H-pyrrolo[3,2-b]pyrazine-7-carboxylic acid for 2-cyclopropyl-5-(2-trimethylsilanyl-ethoxymethyl)-5H-pyrrolo[2,3-b]

pyrazine-7-carboxylic acid. Trifluoroacetic acid was used in place of hydrochloric acid for all N-Boc deprotection steps. MS: (M+H)+=393.

Example 58

2-(1-Ethyl-1H-pyrazol-4-yl)-5H-pyrrolo[2,3-b]pyrazine-7-carboxylic acid [(R)-2-(4-cyano-piperidin-1-yl)-1-methyl-2-oxo-ethyl]-amide

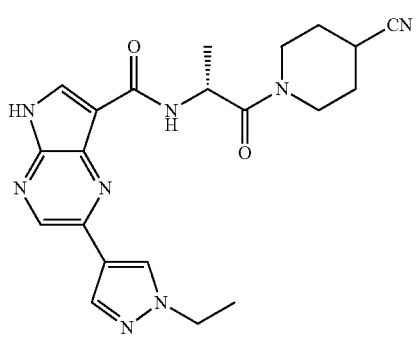 [SMILES: CCn1cc(-c2cnc3[nH]cc(C(=O)N[C@H](C)C(=O)N4CCC(C#N)CC4)c3n2)cn1]

Prepared according to the procedure outlined in Example 1 substituting piperidine-4-carbonitrile for pyrrolidine, Boc-D-alanine for Boc-D-tert-leucine, and 2-(1-ethyl-1H-pyrazol-4-yl)-5-((2-(trimethylsilyl)ethoxy)methyl)-5H-pyrrolo[3,2-b]pyrazine-7-carboxylic acid for 2-cyclopropyl-5-(2-trimethylsilanyl-ethoxymethyl)-5H-pyrrolo[2,3-b]pyrazine-7-carboxylic acid. Trifluoroacetic acid was used in place of hydrochloric acid for all N-Boc deprotection steps. MS: (M+H)+=421.

Example 59

2-Cyclopropyl-5H-pyrrolo[2,3-b]pyrazine-7-carboxylic acid ((R)-2-azetidin-1-yl-1-methyl-2-oxo-ethyl)-amide

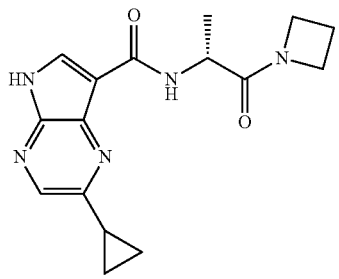 [SMILES: C[C@@H](NC(=O)c1c[nH]c2ncc(C3CC3)nc12)C(=O)N1CCC1]

Prepared according to the procedure outlined in Example 1 substituting azetidine hydrochloride for pyrrolidine and Boc-D-alanine for Boc-D-tert-leucine. Trifluoroacetic acid was used in place of hydrochloric acid for all N-Boc deprotection steps. MS: (M+H)+=314.

Example 60

2-Cyclopropyl-5H-pyrrolo[2,3-b]pyrazine-7-carboxylic acid [(R)-1-methyl-2-(2-oxa-6-aza-spiro[3.3]hept-6-yl)-2-oxo-ethyl]-amide

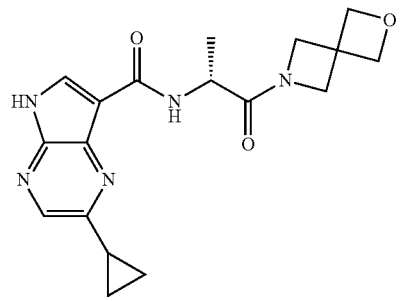 [SMILES: C[C@@H](NC(=O)c1c[nH]c2ncc(C3CC3)nc12)C(=O)N1CC2(COC2)C1]

Prepared according to the procedure outlined in Example 1 substituting 2-oxa-6-aza-spiro[3.3]heptane (*Angew. Chem. Int. Ed.* 2008, 47, 4512) for pyrrolidine and Boc-D-alanine for Boc-D-tert-leucine. N-Boc deprotection was achieved using 2,2,2-trifluoroethanol in a microwave reactor. MS: (M+H)+=356.

Example 61

2-(1-Ethyl-1H-pyrazol-4-yl)-5H-pyrrolo[2,3-b]pyrazine-7-carboxylic acid [(R)-1-(1-methyl-cyclopropyl)-2-oxo-2-pyrrolidin-1-yl-ethyl]-amide Step 1

To a solution of (1-methylcyclopropyl)methanol (2.0 g, 23.2 mmol) in CH₂Cl₂ (100 mL) was added PCC (5.51 g, 25.5 mmol) portionwise. The resulting dark brown reaction mixture was stirred at room temperature overnight. The reaction mixture was filtered over a pad of Celite, rinsing with CH₂Cl₂. The filtrate was concentrated at ambient temperature. The crude brown oily residue was passed through a 2" pad of SiO₂, rinsing with CH₂Cl₂. The filtrate was concentrated at ambient temperature to afford 2.4 g of 1-methyl-cyclopropanecarbaldehyde as a light yellow-green oil which was used without further purification.
Step 2

To a solution of 1-methyl-cyclopropanecarbaldehyde (1.85 g, 22.0 mmol) in CHCl₃ (30 mL) was added (S)-2-amino-2-phenylethanol (2.74 g, 20.0 mmol) and MgSO₄ (3 g). The cloudy reaction mixture was stirred at room temperature for 3 hr then filtered, rinsing with CHCl₃ (10 mL). Cooled to 0° C. and slowly added trimethylsilanecarbonitrile (5.0 ml, 39.9 mmol). The orange reaction mixture was stirred at 0° C. for 1 hr then allowed to warm to room temperature overnight. The reaction was quenched with 1.0 M HCl and stirred vigorously for 5 min then neutralized with 10% aqueous NaOH and extracted with CH₂Cl₂. The combined organics were dried over MgSO4 and concentrated to a light orange oil. NMR analysis showed that some TMS-ether remained. The crude product was treated with 10 mL of 3.0 M aqueous HCl for 10 min at which time TLC verified that the silyl group was removed. Extracted with CH₂Cl₂ (2×), dried over MgSO4 and concentrated. The residue was purified by SiO₂ chromatography (10-30% EtOAc/hexanes) to isolate 1.0 g (22%) of (R)-2-((S)-2-hydroxy-1-phenylethylamino)-2-(1-methylcyclopropyl)acetonitrile as a colorless oil and a single diastereomer.
Step 3

(R)-2-((S)-2-hydroxy-1-phenylethylamino)-2-(1-methylcyclopropyl)acetonitrile (1.0 g, 4.3 mmol was dissolved in aqueous 6 M HCl (10 mL, 60.0 mmol) and heated at 100° C. for 20 h. The reaction mixture was cooled to room temperature and slowly adjusted to pH=8 using 4 M NaOH. The resultant white precipitate was collected via filtration and dried on high vacuum to afford 0.34 g of product. The filtrate was evaporated to a white solid then triturated with a small amount of cold water to afford an additional 0.66 g of white solid after filtration and drying. Total yield was 1.0 g (92%) of (R)-2-((S)-2-hydroxy-1-phenylethylamino)-2-(1-methylcyclopropyl)acetic acid.
Step 4

(R)-2-((S)-2-hydroxy-1-phenylethylamino)-2-(1-methylcyclopropyl)acetic acid (1.0 g, 4.0 mmol) was suspended in MeOH (50 mL). Added 1.0 M HCl in MeOH (4.0 mL, 4.0 mmol) and all solids dissolved to provide a colorless solution. Added 10% Pd/C (100 mg) and stirred under H₂ balloon overnight. The reaction mixture was filtered over Celite, rinsing with MeOH. The filtrate was concentrated to a sticky white solid (1.0 g). Trituration with Et₂O afforded 700 mg of (R)-2-amino-2-(1-methylcyclopropyl)acetic acid hydrochloride as a white solid.
Step 5

To a suspension of (R)-2-amino-2-(1-methylcyclopropyl) acetic acid hydrochloride (664 mg, 4.0 mmol) in 1,4-dioxane (8 mL) was added 1.0 M aqueous NaOH (4.0 mL, 4.0 mmol). All solids dissolved to give a colorless solution. Added di-tert-butyl dicarbonate (875 mg, 4.0 mmol) and stirred vigorously at room temperature overnight. The reaction mixture was diluted with H₂O, neutralized with 1.0 M HCl, and extracted with CH₂Cl₂ (3×). The combined organics were dried over MgSO₄ and concentrated to a viscous colorless oil. Trituration with petroleum ether for several hours afforded 0.42 g (46%) of (R)-tert-butoxycarbonylamino-(1-methyl-cyclopropyl)-acetic acid as two crops of a white solid.
Step 6

2-(1-Ethyl-1H-pyrazol-4-yl)-5H-pyrrolo[2,3-b]pyrazine-7-carboxylic acid [(R)-1-(1-methyl-cyclopropyl)-2-oxo-2-pyrrolidin-1-yl-ethyl]-amide. Prepared according to the procedure outlined in Example 1 substituting (R)-tert-butoxycarbonylamino-(1-methyl-cyclopropyl)-acetic acid for Boc-D-tert-leucine and 2-(1-ethyl-1H-pyrazol-4-yl)-5-((2-(trimethylsilyl)ethoxy)methyl)-5H-pyrrolo[3,2-b]pyrazine-7-carboxylic acid for 2-cyclopropyl-5-(2-trimethylsilanyl-ethoxymethyl)-5H-pyrrolo[2, 3-1)]pyrazine-7-carboxylic acid. MS: (M+H)⁺=422.

Example 62

2-Cyclopropyl-5H-pyrrolo[2,3-b]pyrazine-7-carboxylic acid [(R)-1-(4-hydroxy-4-phenyl-piperidine-1-carbonyl)-2,2-dimethyl-propyl]-amide

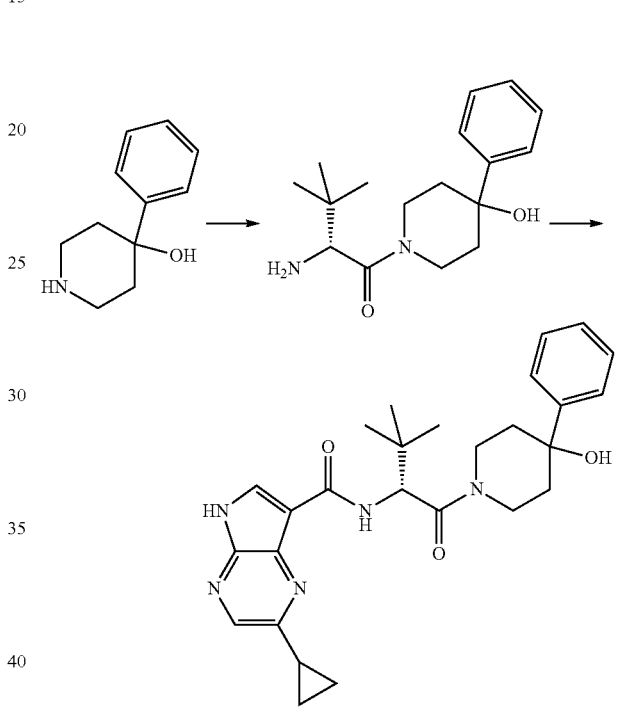

Step 1

A round-bottomed flask was charged with Boc-D-tert-leucine (0.30 g, 1.3 mmol, 4-hydroxy-4-phenylpiperidine (345 mg, 1.95 mmol), HOBT (218 mg, 1.43 mmol) and EDC (274 mg, 1.43 mmol). Then added DMF (6 mL) followed by N,N-diisopropylethylamine (0.34 mL, 1.95 mmol). The light yellow reaction mixture was stirred at room temperature overnight then quenched with water and extracted with diethyl ether (2×). The organic layers were combined and washed twice with water and once with brine then dried over sodium sulfate, filtered and concentrated. The residue was purified by chromatography over 24 g SiO₂ with 0-40% EtOAc/heptane to give 0.48 g (95%) of [(R)-1-(4-hydroxy-4-phenyl-piperidine-1-carbonyl)-2,2-dimethyl-propyl]-carbamic acid tert-butyl ester as an off-white foam.
Step 2

A 5 mL microwave vial was charged with [(R)-1-(4-hydroxy-4-phenyl-piperidine-1-carbonyl)-2,2-dimethyl-propyl]-carbamic acid tert-butyl ester (0.20 g, 0.51 mmol) and 2,2,2-trifluoroethanol (2.6 mL). The vial was flushed with Argon then sealed and heated at 150° C. for 4 h under microwave irradiation. The reaction mixture was concentrated to afford 0.19 g of (R)-2-amino-1-(4-hydroxy-4-phenyl-piperidin-1-yl)-3,3-dimethyl-butan-1-one as light yellow oil which was used without further purification.

Step 3

A round-bottomed flask was charged with 2-cyclopropyl-5-((2-(trimethylsilyl)ethoxy)methyl)-5H-pyrrolo[2,3-b]pyrazine-7-carboxylic acid (0.12 g, 0.36 mmol), (R)-2-amino-1-(4-hydroxy-4-phenylpiperidin-1-yl)-3,3-dimethylbutan-1-one (191 mg, 0.49 mmol), HOBT (61 mg, 0.40 mmol) and EDC (76 mg, 0.40 mmol). Then added DMF (1.6 mL) followed by N,N-diisopropylethylamine (0.12 mL, 0.68 mmol). The reaction mixture was stirred at room temperature over the weekend the quenched with water and extracted with diethyl ether (2×). The organic layers were combined and washed twice with water and once with brine then dried over sodium sulfate, filtered and concentrated. The residue was purified by chromatography over 12 g $SiO_2$ with 0-60% EtOAc/heptane to afford 0.21 g (94%) of 2-cyclopropyl-5-(2-trimethylsilanyl-ethoxymethyl)-5H-pyrrolo[2,3-b]pyrazine-7-carboxylic acid [(R)-1-(4-hydroxy-4-phenyl-piperidine-1-carbonyl)-2,2-dimethyl-propyl]-amide as a light yellow oil.

Step 4

In a round-bottomed flask, 2-cyclopropyl-5-(2-trimethylsilanyl-ethoxymethyl)-5H-pyrrolo[2,3-b]pyrazine-7-carboxylic acid [(R)-1-(4-hydroxy-4-phenyl-piperidine-1-carbonyl)-2,2-dimethyl-propyl]-amide (0.21 g, 0.33 mmol) was dissolved in acetonitrile (4.2 mL). 18-Crown-6 (89 mg, 0.33 mmol) and cesium fluoride (507 mg, 3.34 mmol) were added. The reaction mixture was stirred at 85° C. overnight and then at room temperature for 24 h. Silica Gel (~1 g) was added to the reaction mixture and the suspension was concentrated and purified by chromatography over 12 g $SiO_2$ with 0-100% EtOAc/heptane to 0-10% MeOH/EtOAc to afford an oil. Trituration with dichloromethane/hexanes afforded 45 mg (26%) of 2-cyclopropyl-5H-pyrrolo[2,3-b]pyrazine-7-carboxylic acid [(R)-1-(4-hydroxy-4-phenyl-piperidine-1-carbonyl)-2,2-dimethyl-propyl]-amide as a yellow powder. MS: $(M+H)^+$=476.

Example 63

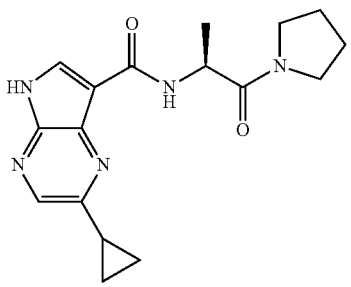 [SMILES: C[C@H](NC(=O)c1c[nH]c2ncc(C3CC3)nc12)C(=O)N1CCCC1]

2-Cyclopropyl-5H-pyrrolo[2,3-b]pyrazine-7-carboxylic acid ((S)-methyl-2-oxo-2-pyrrolidin-1-yl-ethyl)-amide. Prepared according to the procedure outlined in Example 1 substituting Boc-L-alanine for Boc-D-tert-leucine. N-Boc deprotection was achieved using 2,2,2-trifluoroethanol in a microwave reactor. MS: $(M+H)^+$=328.

Example 64

2-Cyclopropyl-5H-pyrrolo[2,3-b]pyrazine-7-carboxylic acid ((S)-1-methyl-2-oxo-2-piperidin-1-yl-ethyl)-amide

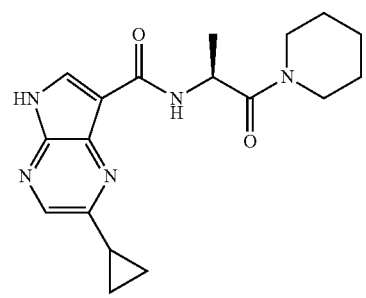 [SMILES: C[C@H](NC(=O)c1c[nH]c2ncc(C3CC3)nc12)C(=O)N1CCCCC1]

Prepared according to the procedure outlined in Example 1 substituting piperidine for pyrrolidine and Boc-L-alanine for Boc-D-tert-leucine. MS: $(M+H)^+$=342.

Example 65

2-Cyclopropyl-5H-pyrrolo[2,3-b]pyrazine-7-carboxylic acid [(R)-2-(3-cyano-azetidin-1-yl)-1-cyclopropyl-2-oxo-ethyl]-amide

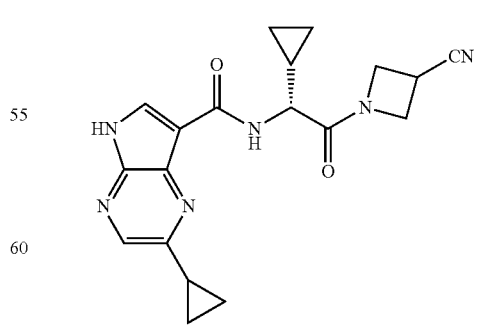

Prepared according to the procedure outlined in Example 1 substituting 3-cyanoazetidine hydrochloride for pyrrolidine and Boc-D-cyclopropyl glycine for Boc-D-tert-leucine.

Example 66

2-(1-Methyl-1H-pyrazol-4-yl)-5H-pyrrolo[2,3-b]pyrazine-7-carboxylic acid [(R)-2-(3-cyano-azetidin-1-yl)-1-cyclopropyl-2-oxo-ethyl]-amide

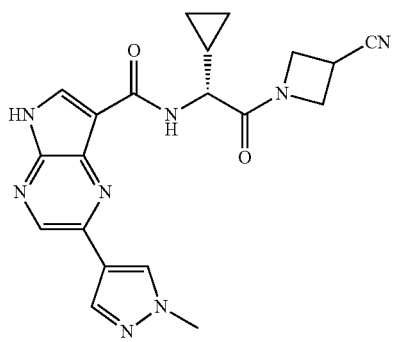 [SMILES: Cn1cc(-c2cnc3[nH]cc(C(=O)N[C@@H](C(=O)N4CC(C#N)C4)C4CC4)c3n2)cn1]

Prepared according to the procedure outlined in Example 1 substituting 3-cyanoazetidine hydrochloride for pyrrolidine, Boc-D-cyclopropyl glycine for Boc-D-tert-leucine, and 2-(1-methyl-1H-pyrazol-4-yl)-5-((2-(trimethylsilyl)ethoxy)methyl)-5H-pyrrolo[3,2-b]pyrazine-7-carboxylic acid for 2-cyclopropyl-5-(2-trimethylsilanyl-ethoxymethyl)-5H-pyrrolo[2,3-b]pyrazine-7-carboxylic acid. N-Boc deprotection was achieved using 2,2,2-trifluoroethanol in a microwave reactor. MS: (M+H)$^+$=405.

Example 67

2-(1-Methyl-1H-pyrazol-4-yl)-5H-pyrrolo[2,3-b]pyrazine-7-carboxylic acid [(R)-1-(3-cyano-azetidine-1-carbonyl)-3-methyl-butyl]-amide

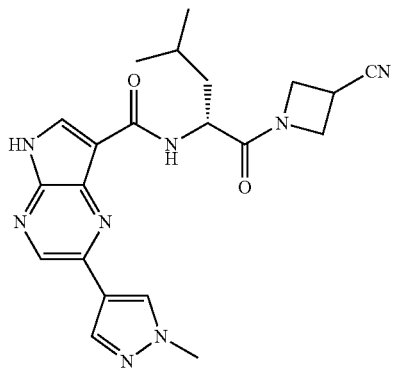 [SMILES: CC(C)C[C@@H](NC(=O)c1c[nH]c2ncc(-c3cnn(C)c3)nc12)C(=O)N1CC(C#N)C1]

Prepared according to the procedure outlined in Example 1 substituting 3-cyanoazetidine hydrochloride for pyrrolidine, Boc-D-leucine for Boc-D-tert-leucine, and 2-(1-methyl-1H-pyrazol-4-yl)-5-((2-(trimethylsilyl)ethoxy)methyl)-5H-pyrrolo[3,2-b]pyrazine-7-carboxylic acid for 2-cyclopropyl-5-(2-trimethylsilanyl-ethoxymethyl)-5H-pyrrolo[2,3-b]pyrazine-7-carboxylic acid. Trifluoroacetic acid was used in place of hydrochloric acid for all N-Boc deprotection steps. MS: (M+H)$^+$=421.

Example 68

2-(1-Ethyl-1H-pyrazol-4-yl)-5H-pyrrolo[2,3-b]pyrazine-7-carboxylic acid [(R)-2-(4-cyano-piperidin-1-yl)-1-cyclopropyl-2-oxo-ethyl]-amide

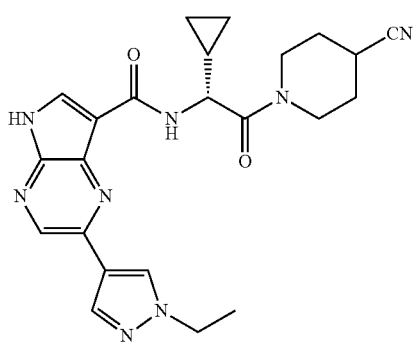 [SMILES: CCn1cc(-c2cnc3[nH]cc(C(=O)N[C@@H](C(=O)N4CCC(C#N)CC4)C4CC4)c3n2)cn1]

Prepared according to the procedure outlined in Example 1 substituting piperidine-4-carbonitrile for pyrrolidine, Boc-D-cyclopropyl glycine for Boc-D-tert-leucine, and 2-(1-ethyl-1H-pyrazol-4-yl)-5-((2-(trimethylsilyl)ethoxy)methyl)-5H-pyrrolo[3,2-b]pyrazine-7-carboxylic acid for 2-cyclopropyl-5-(2-trimethylsilanyl-ethoxymethyl)-5H-pyrrolo[2,3-b]pyrazine-7-carboxylic acid. Trifluoroacetic acid was used in place of hydrochloric acid for all N-Boc deprotection steps. MS: (M+H)$^+$=447.

Example 69

2-Cyclopropyl-5H-pyrrolo[2,3-b]pyrazine-7-carboxylic acid [(R)-1-(4-hydroxy-4-methyl-piperidine-1-carbonyl)-2,2-dimethyl-propyl]-amide

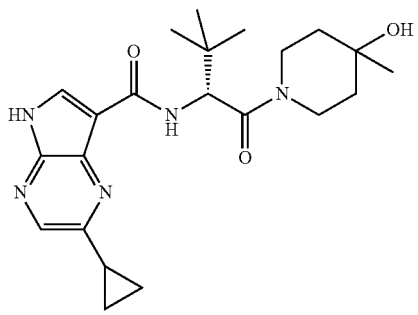 [SMILES: CC1(O)CCN(C(=O)[C@H](NC(=O)c2c[nH]c3ncc(C4CC4)nc23)C(C)(C)C)CC1]

Prepared according to the procedure outlined in Example 1 substituting 4-methyl-piperidin-4-ol for pyrrolidine. MS: (M+H)+=414.

Example 70

2-Cyclopropyl-5H-pyrrolo[2,3-b]pyrazine-7-carboxylic acid [(R)-1-(4-hydroxy-4-trifluoromethyl-piperidine-1-carbonyl)-2,2-dimethyl-propyl]-amide

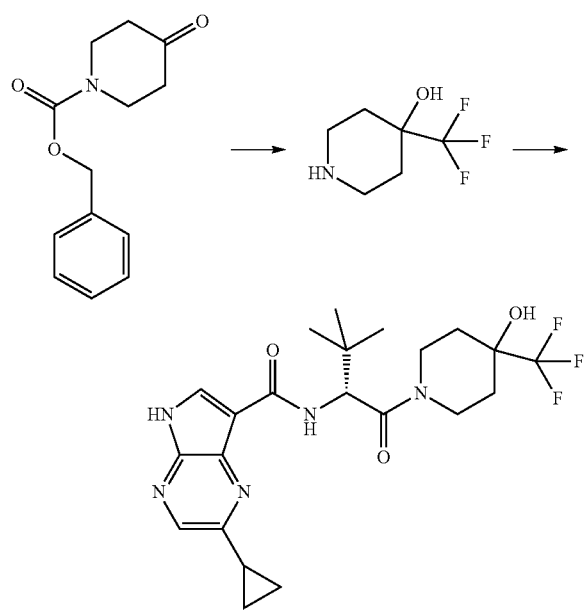

Step 1

In a 3-neck round-bottomed flask, benzyl 4-oxopiperidine-1-carboxylate (1.0 g, 4.3 mmol) was dissolved in THF (10 mL). The reaction mixture was cooled to 0° C. and trimethyl (trifluoromethyl)silane (0.78 mL, 5.3 mmol) was added. Then added TBAF (1.0M solution in THF, 0.05 mL, 0.05 mmol) which caused the internal temperature to rise to 30° C. The reaction mixture was stirred at room temperature overnight. Additional TBAF (1.0M solution in THF, 4.3 mL, 4.3 mmol) was added and the reaction mixture was stirred at room temperature for 4.25 h. The reaction mixture was quenched with water and extracted with CH$_2$Cl$_2$ (2×). The organic layers were combined, dried over sodium sulfate, filtered and concentrated. The residue was triturated with toluene to afford 0.82 g (63%) of 4-hydroxy-4-trifluoromethyl-piperidine-1-carboxylic acid benzyl ester as a light yellow solid.

Step 2

In a round-bottomed flask, 4-hydroxy-4-trifluoromethyl-piperidine-1-carboxylic acid benzyl ester (0.82 g, 2.7 mmol) was dissolved in EtOH (5 mL). 10% Palladium on carbon (Degussa type, 82 mg) was added and the flask was evacuated, flushed with argon, evacuated and flushed with hydrogen. The reaction mixture was stirred under hydrogen atmosphere (balloon) at room temperature overnight then filtered over Celite and rinsed with MeOH. The filtrate was concentrated to afford 0.44 g (97%) of 4-trifluoromethyl-piperidin-4-ol as a pale yellow solid.

Step 3

2-Cyclopropyl-5H-pyrrolo[2,3-b]pyrazine-7-carboxylic acid [(R)-1-(4-hydroxy-4-trifluoromethyl-piperidine-1-carbonyl)-2,2-dimethyl-propyl]-amide. Prepared according to the procedure outlined in Example 1 substituting 4-trifluoromethyl-piperidin-4-ol for pyrrolidine. MS: (M+H)+=468.

Example 71

2-(1-Ethyl-1H-pyrazol-4-yl)-5H-pyrrolo[2,3-b]pyrazine-7-carboxylic acid [(R)-2-(4-cyano-piperidin-1-yl)-2-oxo-1-(1-trifluoromethyl-cyclopropyl)-ethyl]-amide and 2-(1-Ethyl-1H-pyrazol-4-yl)-5H-pyrrolo[2,3-b]pyrazine-7-carboxylic acid [(S)-2-(4-cyano-piperidin-1-yl)-2-oxo-1-(1-trifluoromethyl-cyclopropyl)-ethyl]-amide

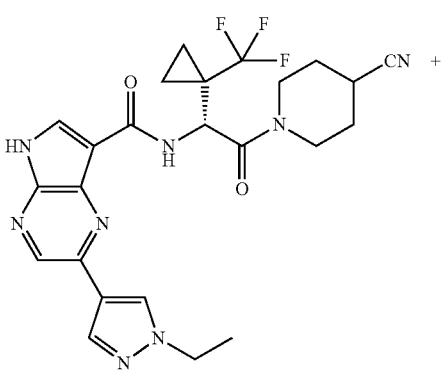

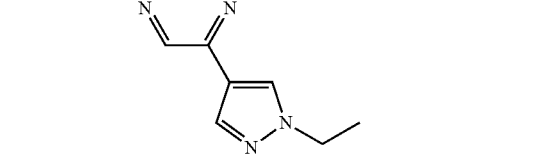

Prepared according to the procedure outlined in Example 1 substituting piperidine-4-carbonitrile for pyrrolidine, N-Boc-2-(1-trifluoromethylcyclopropyl)-DL-glycine for Boc-D-tert-leucine, and 2-(1-ethyl-1H-pyrazol-4-yl)-5-((2-(trimethylsilyl)ethoxy)methyl)-5H-pyrrolo[3,2-b]pyrazine-7-carboxylic acid for 2-cyclopropyl-5-(2-trimethylsilanylethoxymethyl)-5H-pyrrolo[2,3-b]pyrazine-7-carboxylic acid. Trifluoroacetic acid was used instead of hydrochloric acid for all N-Boc deprotection steps. The R and S enanti-

Example 72

2-(1-Methyl-1H-pyrazol-4-yl)-5H-pyrrolo[2,3-b]pyrazine-7-carboxylic acid [(R)-2-(3-cyano-azetidin-1-yl)-1-cyclohexyl-2-oxo-ethyl]-amide

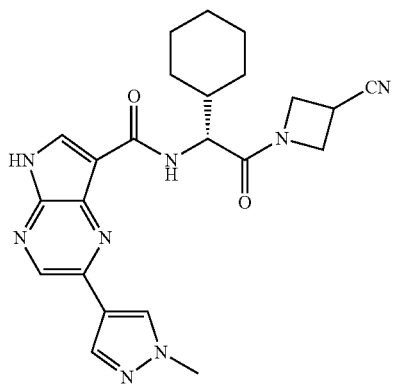 [SMILES: Cn1cc(-c2cnc3[nH]cc(C(=O)N[C@@H](C(=O)N4CC(C#N)C4)C4CCCCC4)c3n2)cn1]

Prepared according to the procedure outlined in Example 1 substituting 3-cyanoazetidine hydrochloride for pyrrolidine, Boc-D-cyclohexyl glycine for Boc-D-tert-leucine, and 2-(1-methyl-1H-pyrazol-4-yl)-5-((2-(trimethylsilyl)ethoxy)methyl)-5H-pyrrolo[3,2-b]pyrazine-7-carboxylic acid for 2-cyclopropyl-5-(2-trimethylsilanyl-ethoxymethyl)-5H-pyrrolo[2,3-b]pyrazine-7-carboxylic acid. Trifluoroacetic acid was used in place of hydrochloric acid for all N-Boc deprotection steps. MS: (M+H)$^+$=447.

Example 73

2-(1-Methyl-1H-imidazol-4-yl)-5H-pyrrolo[2,3-b]pyrazine-7-carboxylic acid [(R)-1-(4-cyano-piperidine-1-carbonyl)-2,2-dimethyl-propyl]-amide

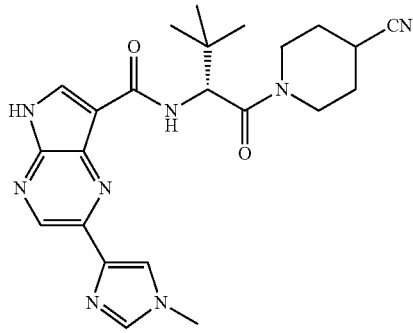 [SMILES: Cn1cnc(-c2cnc3[nH]cc(C(=O)N[C@@H](C(=O)N4CCC(C#N)CC4)C(C)(C)C)c3n2)c1]

Step 1
Methyl-4-tributylstannanyl-1H-imidazole was prepared according to WO 2007/062288.
Step 2
In a pressure tube 2-bromo-5-(2-trimethylsilanyl-ethoxymethyl)-5H-pyrrolo[2,3-]pyrazine-7-carboxylic acid [(R)-1-(4-cyano-piperidine-1-carbonyl)-2,2-dimethyl-propyl]-amide (125 mg, 0.22 mmol) and 1-methyl-4-tributylstannanyl-1H-imidazole (97 mg, 0.26 mmol) were dissolved in DMF (2 mL). Pd(PPh$_3$)$_4$ (12.5 mg, 0.01 mmol) and CuI (8 mg, 0.04 mmol) were added. The tube was sealed and heated at 80° C. for 1.5 h. The reaction mixture was cooled to room temperature, quenched with H$_2$O and extracted with EtOAc. The organic extracts were washed with saturated aqueous LiCl and brine, dried over MgSO$_4$, and concentrated. The residue was purified by SiO$_2$ chromatography (0-10% MeOH/EtOAc) to afford 121 mg (95%) of 2-(1-methyl-1H-imidazol-4-yl)-5-(2-trimethylsilanyl-ethoxymethyl)-5H-pyrrolo[2,3-b]pyrazine-7-carboxylic acid [(R)-1-(4-cyano-piperidine-1-carbonyl)-2,2-dimethyl-propyl]-amide as a light brown gum.

Step 3
2-(1-Methyl-1H-imidazol-4-yl)-5H-pyrrolo[2,3-b]pyrazine-7-carboxylic acid [(R)-1-(4-cyano-piperidine-1-carbonyl)-2,2-dimethyl-propyl]-amide. Prepared according to the procedure outlined in Example 1, Step 4 substituting 2-(1-methyl-1H-imidazol-4-yl)-5-(2-trimethylsilanyl-ethoxymethyl)-5H-pyrrolo[2,3-b]pyrazine-7-carboxylic acid [(R)-1-(4-cyano-piperidine-1-carbonyl)-2,2-dimethyl-propyl]-amide for (R)-2-cyclopropyl-N-(3,3-dimethyl-1-oxo-1-(pyrrolidin-1-yl)butan-2-yl)-5-((2-(trimethylsilyl)ethoxy)methyl)-5H-pyrrolo[2,3-b]pyrazine-7-carboxamide. MS: (M+H)$^+$=449.

Example 74

2-(1-Ethyl-1H-pyrazol-4-yl)-5H-pyrrolo[2,3-b]pyrazine-7-carboxylic acid {(R)-1-[3-(4,5-dihydro-1H-imidazol-2-yl)-3-fluoro-pyrrolidine-1-carbonyl]-2,2-dimethyl-propyl}-amide

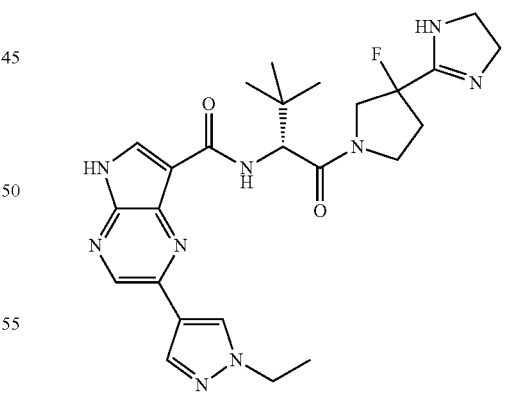

2-(1-Ethyl-1H-pyrazol-4-yl)-5H-pyrrolo[2,3-b]pyrazine-7-carboxylic acid {(R)-1-[3-(4,5-dihydro-1H-imidazol-2- yl)-3-fluoro-pyrrolidine-1-carbonyl]-2,2-dimethyl-propyl}-amide. Isolated as an additional product during Example 16, Step 4. MS: (M+H)⁺=510.

Example 75

2-Phenoxy-5H-pyrrolo[2,3-b]pyrazine-7-carboxylic acid [(R)-2-methyl-1-(pyrrolidine-1-carbonyl)-propyl]-amide

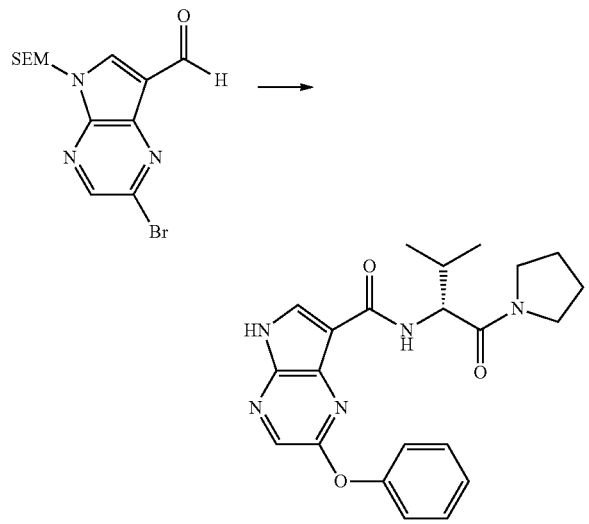

Step 1

A mixture of 2-bromo-5-(2-trimethylsilanyl-ethoxymethyl)-5H-pyrrolo[2,3-b]pyrazine-7-carbaldehyde (3.29 g, 9.23 mmol), phenol (1.04 g, 11.08 mmol), K₃PO₄ (3.92 g, 18.46 mmol), [2'-(di-tert-butyl-phosphanyl)-biphenyl-2-yl]-dimethyl-amine (0.157 g, 0.46 mmol), Pd(OAc)₂ (0.103 g, 0.46 mmol) and degassed toluene (50 mL) was stirred under nitrogen in a sealed tube at 150° C. overnight. The reaction mixture was cooled to room temperature and partitioned between ethyl acetate and water. The aqueous layer was extracted with ethyl acetate, and the combined organic layers were dried over MgSO₄, filtered and concentrated. The residue was purified by SiO₂ column chromatography (0-30% EtOAc/hexanes) to afford 2.09 g (61%) of 2-phenoxy-5-(2-trimethylsilanyl-ethoxymethyl)-5H-pyrrolo[2,3-b]pyrazine-7-carbaldehyde as a beige solid.

Step 2

A stock solution of Jones reagent (2.67 M) was prepared by carefully adding concentrated H₂SO₄ (2.3 mL) to CrO₃ (2.67 g) then diluting to 10 mL with H₂O. To a solution of 2-phenoxy-5-(2-trimethylsilanyl-ethoxymethyl)-5H-pyrrolo[2,3-b]pyrazine-7-carbaldehyde (2.35 g, 6.37 mmol) in acetone (75 mL) at 0° C. was added Jones reagent (5 mL, 13.4 mmol) dropwise. The reaction mixture was stirred at room temperature for 2 h then quenched with i-PrOH (2 mL), diluted with EtOAc, and filtered over Celite, rinsing with EtOAc. The filtrate was washed with cold water (3×) and brine then dried over MgSO₄ and concentrated. The residue was purified by SiO₂ column chromatography (30-70% EtOAc/hexanes) to provide 1.59 g (65%) of 2-phenoxy-5-(2-trimethylsilanyl-ethoxymethyl)-5H-pyrrolo[2,3-b]pyrazine-7-carboxylic acid as a light yellow solid.

Step 3

To a solution of 2-phenoxy-5-(2-trimethylsilanyl-ethoxymethyl)-5H-pyrrolo[2,3-b]pyrazine-7-carboxylic acid (0.10 g, 0.26 mmol), 4-dimethylaminopyridine (0.048 g, 0.39 mmol) and (3-dimethylamino-propyl)-ethyl-carbodiimide (0.075 g, 0.39 mmol) in CH₂Cl₂ (2 mL) was added (R)-2-amino-3-methyl-1-pyrrolidin-1-yl-butan-1-one (0.066 g, 0.39 mmol) in CH₂Cl₂ (0.5 mL). The reaction mixture was stirred at room temperature overnight, then quenched with water and extracted with ethyl acetate (3×). The organic layer was washed with water and saturated aqueous NaCl solution and dried over MgSO₄, filtered and concentrated. The residue was purified by SiO₂ column chromatography (0-100% EtOAc/hexanes) to afford 2-phenoxy-5-(2-trimethylsilanyl-ethoxymethyl)-5H-pyrrolo[2,3-b]pyrazine-7-carboxylic acid [(R)-2-methyl-1-(pyrrolidine-1-carbonyl)-propyl]-amide as a yellow oil.

Step 4

To a solution of 2-phenoxy-5-(2-trimethylsilanyl-ethoxymethyl)-5H-pyrrolo[2,3-b]pyrazine-7-carboxylic acid [(R)-2-methyl-1-(pyrrolidine-1-carbonyl)-propyl]-amide from Step 3 in dichloromethane (0.5 mL) was added trifluoroacetic acid (0.7 mL). The reaction mixture was stirred at room temperature overnight then concentrated. The residue was stirred with THF (1 mL), water (0.5 mL), and Et₃N (0.5 mL) for 2 h then concentrated. The residue was partitioned between ethyl acetate and water and the aqueous layer was extracted with ethyl acetate. The combined organic layers were dried over MgSO₄ and concentrated. The residue was purified by SiO₂ column chromatography (5% MeOH/CH₂Cl₂) to provide 0.049 g (46%, 2 steps) of 2-phenoxy-5H-pyrrolo[2,3-b]pyrazine-7-carboxylic acid [(R)-2-methyl-1-(pyrrolidine-1-carbonyl)-propyl]-amide as a white foam. MS: 408 (M+H)⁺.

Example 76

2-(1-Cyclopropyl-1H-pyrazol-4-yl)-5H-pyrrolo[2,3-b]pyrazine-7-carboxylic acid [(R)-1-(4-cyano-piperidine-1-carbonyl)-2,2-dimethyl-propyl]-amide

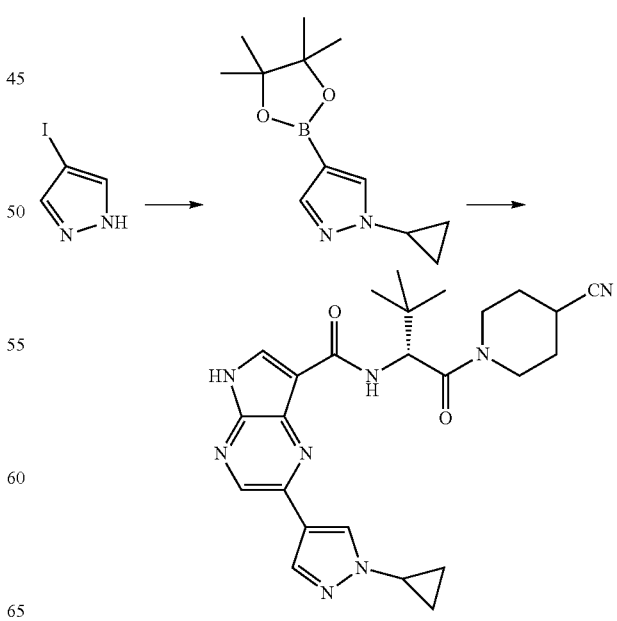

161

Step 1

In a flask were combined 4-iodo-1H-pyrazole (1.00 g, 5.16 mmol), cyclopropylboronic acid (886 mg, 10.3 mmol) and sodium carbonate (1.09 g, 10.3 mmol) and the mixture suspended in 1,2-dichloroethane (20 mL). A suspension of copper (II) acetate (936 mg, 5.16 mmol) and 2,2-bipyridine (805 mg, 5.16 mmol) in 1,2-dichloroethane (40 mL) was warmed to 50° C. and added and the resulting mixture heated at 70° C. overnight. The mixture was then cooled and filtered and the solids rinsed with EtOAc. The combined filtrates were concentrated and the residue taken up in EtOAc and 50% saturated aqueous $NH_4Cl$. The organic layer was washed with sat $NH_4Cl$, sat $NaHCO_3$ and sat NaCl and dried over $MgSO_4$. The solution was concentrated and the residue purified by $SiO_2$ chromatography (5-35% EtOAc/heptane) to afford 517 mg (43%) 1-cyclopropyl-4-iodo-1H-pyrazole as a colorless oil.

Step 2

In a flask 1-cyclopropyl-4-iodo-1H-pyrazole (405 mg, 1.73 mmol) was dissolved in THF (8.0 mL) and the solution cooled to 0° C. Isopropylmagnesium chloride (2.0 M in THF, 1.04 mL, 2.08 mmol) was added dropwise and the mixture stirred at 0° C. for 45 min, after which 2-isopropoxy-4,4,5,5-tetramethyl-1,3,2-dioxaborolane (0.53 mL, 2.60 mmol) was added and the mixture allowed to warm to room temperature over 1 h. The mixture was quenched with 50% sat aqueous $NH_4Cl$ and extracted with EtOAc. The organic extract was washed with sat. NaCl, dried over $MgSO_4$ and the solution was concentrated. The residue was purified by $SiO_2$ chromatography (20-50% EtOAc/heptane) to afford 405 mg (83%) of 1-cyclopropyl-1H-pyrazole-4-boronic acid pinacol ester as a colorless viscous oil.

Step 3

2-(1-Cyclopropyl-1H-pyrazol-4-yl)-5H-pyrrolo[2,3-b]pyrazine-7-carboxylic acid [(R)-1-(4-cyano-piperidine-1-carbonyl)-2,2-dimethyl-propyl]-amide. Prepared according to the procedure outlined in Example 2 substituting 1-((R)-2-amino-3,3-dimethyl-butyryl)-piperidine-4-carbonitrile trifluoroacetate for (R)-2-amino-3,3-dimethyl-1-pyrrolidin-1-yl-butan-1-one hydrochloride in Step 1 and 1-cyclopropyl-1H-pyrazole-4-boronic acid pinacol ester for 1-ethyl-1H-pyrazole-4-boronic acid pinacol ester in Step 2. MS: $(M+H)^+$=475.

Example 77

2-[1-(2,2,2-Trifluoro-ethyl)-1H-pyrazol-4-yl]-5H-pyrrolo[2,3-b]pyrazine-7-carboxylic acid [(R)-1-(4-cyano-piperidine-1-carbonyl)-2,2-dimethyl-propyl]-amide

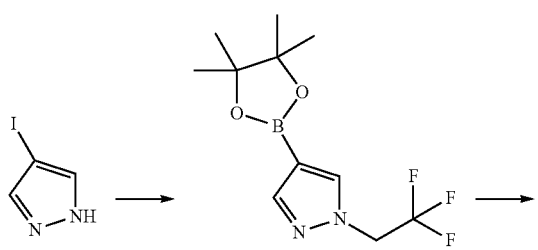

162

-continued

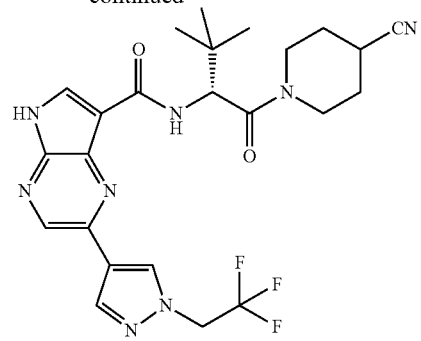

Step 1

In a microwave vial 4-iodo-1H-pyrazole (1.00 g, 5.16 mmol) and cesium carbonate (6.72 g, 20.6 mmol) were suspended in DMF (8.0 mL) and 1,1,1-trifluoro-2-iodoethane (2.06 mL, 20.6 mmol) was added. The mixture was heated at 90° C. by microwave for 60 minutes then the mixture was filtered and the filter cake rinsed with EtOAc. The filtrate was concentrated then taken up in EtOAc and 50% saturated aqueous $NH_4Cl$. The organic layer was washed with sat LiCl and sat NaCl then dried over $MgSO_4$. The solution was concentrated and the residue purified by $SiO_2$ chromatography (5-35% EtOAc/heptane) to afford 1.08 g (76%) of 4-iodo-1-(2,2,2-trifluoroethyl)-1H-pyrazole as a colorless oil.

Step 2

1-(2,2,2-Trifluoroethyl)-1H-pyrazole-4-boronic acid pinacol ester. Prepared according to the procedure outlined in Example 80, Step 2 substituting 4-iodo-1-(2,2,2-trifluoroethyl)-1H-pyrazole for 1-cyclopropyl-4-iodo-1H-pyrazole.

Step 3

2-[1-(2,2,2-Trifluoro-ethyl)-1H-pyrazol-4-yl]-5H-pyrrolo[2,3-b]pyrazine-7-carboxylic acid [(R)-1-(4-cyano-piperidine-1-carbonyl)-2,2-dimethyl-propyl]-amide. Prepared according to the procedure outlined in Example 2 substituting 1-((R)-2-amino-3,3-dimethyl-butyryl)-piperidine-4-carbonitrile trifluoroacetate for (R)-2-amino-3,3-dimethyl-1-pyrrolidin-1-yl-butan-1-one hydrochloride in Step 1 and 1-(2,2,2-trifluoroethyl)-1H-pyrazole-4-boronic acid pinacol ester for 1-ethyl-1H-pyrazole-4-boronic acid pinacol ester in Step 2. MS: $(M+H)^+$=517.

Example 78

2-(1-Ethyl-1H-pyrazol-4-yl)-5H-pyrrolo[2,3-b]pyrazine-7-carboxylic acid [(R)-1-(4,4-difluoro-piperidine-1-carbonyl)-2,2-dimethyl-propyl]-amide

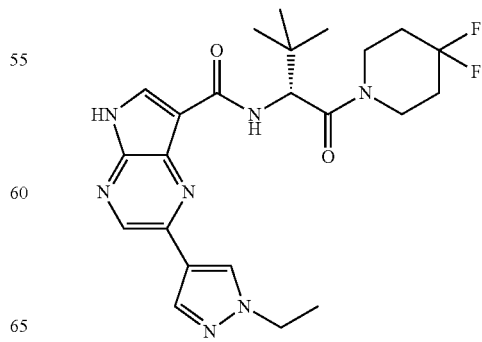

Prepared according to the procedure outlined in Example 1 substituting 4,4-difluoropiperidine hydrochloride for pyrrolidine and 2-(1-ethyl-1H-pyrazol-4-yl)-5-((2-(trimethylsilyl)ethoxy)methyl)-5H-pyrrolo[3,2-b]pyrazine-7-carboxylic acid for 2-cyclopropyl-5-(2-trimethylsilanyl-ethoxymethyl)-5H-pyrrolo[2, 3-1)]pyrazine-7-carboxylic acid. MS: (M+H)+= 474.

Example 79

2-Cyclopropyl-5H-pyrrolo[2,3-b]pyrazine-7-carboxylic acid [(R)-1-(7,8-dihydro-5H-[1,6]naphthyridine-6-carbonyl)-2,2-dimethyl-propyl]-amide

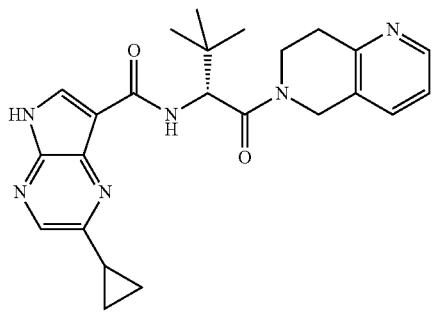 [SMILES: CC(C)(C)[C@@H](NC(=O)c1c[nH]c2ncc(C3CC3)nc12)C(=O)N1CCc2ncccc2C1]

Prepared according to the procedure outlined in Example 1 substituting 5,6,7,8-tetrahydro-1,6-naphthyridine dihydrochloride for pyrrolidine. MS: (M+H)+=433.

Example 80

2-Cyclopropyl-5H-pyrrolo[2,3-b]pyrazine-7-carboxylic acid [(R)-2-(3-cyano-azetidin-1-yl)-2-oxo-1-(tetrahydro-pyran-4-yl)-ethyl]-amide and 2-Cyclopropyl-5H-pyrrolo[2,3-b]pyrazine-7-carboxylic acid [(S)-2-(3-cyano-azetidin-1-yl)-2-oxo-1-(tetrahydro-pyran-4-yl)-ethyl]-amide

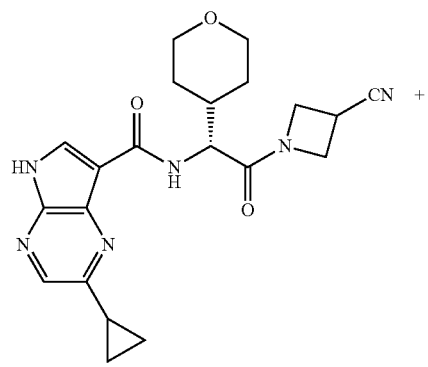

+

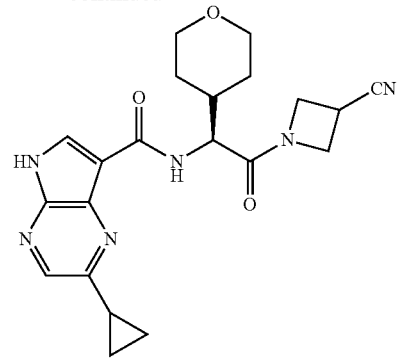

Prepared according to the procedure outlined in Example 1 substituting piperidine-4-carbonitrile for azetidine-3-carbonitrile hydrochloride and N-Boc-4'-tetrahydropyranylglycine for Boc-D-tert-leucine. Trifluoroacetic acid was used instead of hydrochloric acid for all N-Boc deprotection steps. The R and S enantiomers were separated at Step 3 via chiral preparative SFC chromatography. R enantiomer, (M+H)+=409; S enantiomer, (M+H)+=409.

Example 81

2-Cyclopropyl-5H-pyrrolo[2,3-b]pyrazine-7-carboxylic acid [(R)-1-(2,3-dihydro-indole-1-carbonyl)-2,2-dimethyl-propyl]-amide

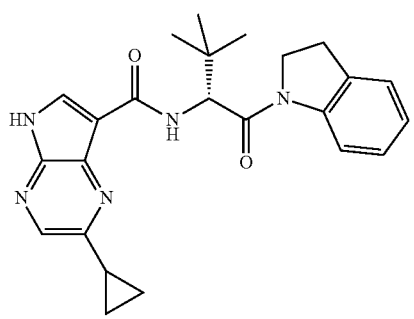 [SMILES: CC(C)(C)[C@@H](NC(=O)c1c[nH]c2ncc(C3CC3)nc12)C(=O)N1CCc2ccccc21]

Prepared according to the procedure outlined in Example 1 substituting indoline for pyrrolidine. MS: (M+H)+=418.

Example 82

2-(1-Ethyl-1H-pyrazol-4-yl)-5H-pyrrolo[2,3-b]pyrazine-7-carboxylic acid [(R)-1-cyclopropyl-2-(3,3-difluoro-pyrrolidin-1-yl)-2-oxo-ethyl]-amide

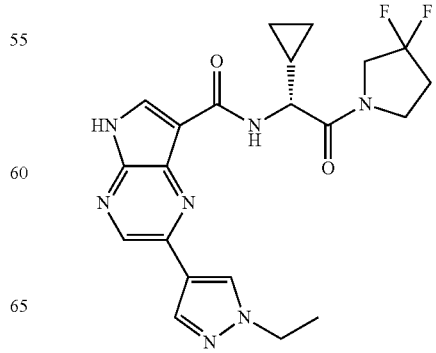

Prepared according to the procedure outlined in Example 1 substituting 3,3-difluoropyrrolidine hydrochloride for pyrrolidine, Boc-D-cyclopropyl glycine for Boc-D-tert-leucine, and 2-(1-ethyl-1H-pyrazol-4-yl)-5-((2-(trimethylsilyl)ethoxy)methyl)-5H-pyrrolo[3,2-b]pyrazine-7-carboxylic acid for 2-cyclopropyl-5-(2-trimethylsilanyl-ethoxymethyl)-5H-pyrrolo[2,3-b]pyrazine-7-carboxylic acid. MS: (M+H)$^+$=444.

Example 83

2-(1-Ethyl-1H-pyrazol-4-yl)-5H-pyrrolo[2,3-b]pyrazine-7-carboxylic acid [(R)-1-(4-hydroxy-4-methyl-piperidine-1-carbonyl)-2,2-dimethyl-propyl]-amide

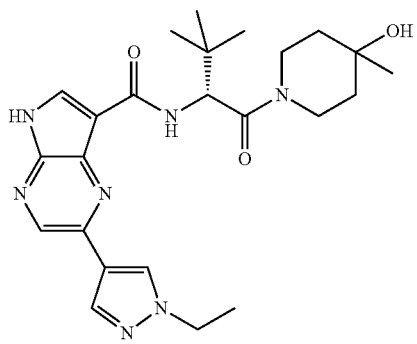

Prepared according to the procedure outlined in Example 1 substituting 4-methyl-piperidin-4-ol for pyrrolidine and 2-(1-ethyl-1H-pyrazol-4-yl)-5-((2-(trimethylsilyl)ethoxy)methyl)-5H-pyrrolo[3,2-b]pyrazine-7-carboxylic acid for 2-cyclopropyl-5-(2-trimethylsilanyl-ethoxymethyl)-5H-pyrrolo[2, 3-1)]pyrazine-7-carboxylic acid. MS: (M+H)$^+$=468.

Example 84

2-Cyclopropyl-5H-pyrrolo[2,3-b]pyrazine-7-carboxylic acid [(R)-2-((S)-3-cyano-pyrrolidin-1-yl)-1-cyclopropyl-2-oxo-ethyl]-amide

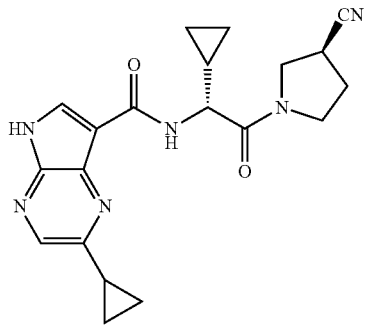 [SMILES: N#C[C@H]1CCN(C(=O)[C@H](NC(=O)c2c[nH]c3ncc(C4CC4)nc23)C2CC2)C1]

Prepared according to the procedure outlined in Example 1 substituting (S)-pyrrolidine-3-carbonitrile for pyrrolidine and Boc-D-cyclopropyl glycine for Boc-D-tert-leucine. N-Boc deprotection in step 2 was achieved using 2,2,2-trifluoroethanol in a microwave reactor. SEM deprotection in step 4 was achieved using CsF in refluxing acetonitrile. MS: (M+H)$^+$=379.

Example 85

2-(1-Methyl-1H-pyrazol-4-yl)-5H-pyrrolo[2,3-b]pyrazine-7-carboxylic acid [(R)-2-((S)-3-cyano-pyrrolidin-1-yl)-1-cyclopropyl-2-oxo-ethyl]-amide

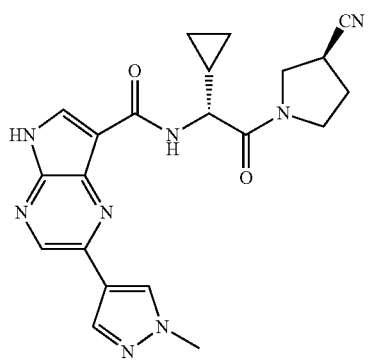 [SMILES: Cn1cc(-c2cnc3[nH]cc(C(=O)N[C@@H](C(=O)N4CC[C@H](C#N)C4)C4CC4)c3n2)cn1]

Prepared according to the procedure outlined in Example 1 substituting (S)-pyrrolidine-3-carbonitrile for pyrrolidine, Boc-D-cyclopropyl glycine for Boc-D-tert-leucine, and 2-(1-methyl-1H-pyrazol-4-yl)-5-((2-(trimethylsilyl)ethoxy)methyl)-5H-pyrrolo[3,2-b]pyrazine-7-carboxylic acid for 2-cyclopropyl-5-(2-trimethylsilanyl-ethoxymethyl)-5H-pyrrolo[2,3-b]pyrazine-7-carboxylic acid. N-Boc deprotection in step 2 was achieved using 2,2,2-trifluoroethanol in a microwave reactor. SEM deprotection in step 4 was achieved using CsF in refluxing acetonitrile. MS: (M+H)$^+$=419.

Example 86

2-Cyclopropyl-5H-pyrrolo[2,3-b]pyrazine-7-carboxylic acid [(R)-2-((R)-3-cyano-pyrrolidin-1-yl)-1-cyclopropyl-2-oxo-ethyl]-amide

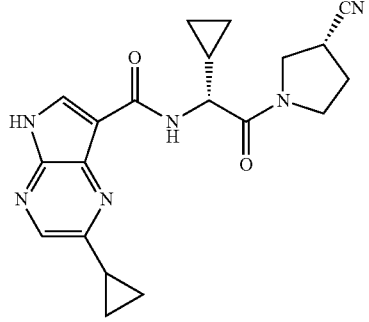 [SMILES: N#C[C@@H]1CCN(C(=O)[C@H](NC(=O)c2c[nH]c3ncc(C4CC4)nc23)C2CC2)C1]

Prepared according to the procedure outlined in Example 1 substituting (R)-pyrrolidine-3-carbonitrile for pyrrolidine and Boc-D-cyclopropyl glycine for Boc-D-tert-leucine. N-Boc deprotection in step 2 was achieved using 2,2,2-trifluoroethanol in a microwave reactor. SEM deprotection in step 4 was achieved using CsF in refluxing acetonitrile. MS: (M+H)⁺=379.

Example 87

2-(1-Methyl-1H-pyrazol-4-yl)-5H-pyrrolo[2,3-b]pyrazine-7-carboxylic acid [(R)-2-((R)-3-cyano-pyrrolidin-1-yl)-1-cyclopropyl-2-oxo-ethyl]-amide

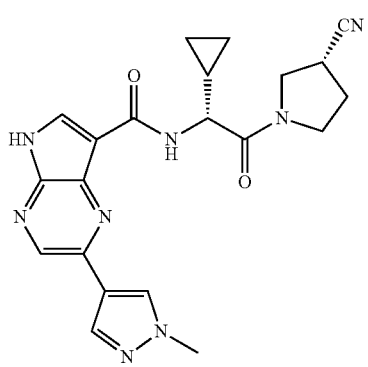 [SMILES: Cn1cc(-c2cnc3[nH]cc(C(=O)N[C@@H](C(=O)N4CC[C@@H](C#N)C4)C4CC4)c3n2)cn1]

Prepared according to the procedure outlined in Example 1 substituting (R)-pyrrolidine-3-carbonitrile for pyrrolidine, Boc-D-cyclopropyl glycine for Boc-D-tert-leucine, and 2-(1-methyl-1H-pyrazol-4-yl)-5-((2-(trimethylsilyl)ethoxy)methyl)-5H-pyrrolo[3,2-b]pyrazine-7-carboxylic acid for 2-cyclopropyl-5-(2-trimethylsilanyl-ethoxymethyl)-5H-pyrrolo[2,3-b]pyrazine-7-carboxylic acid. N-Boc deprotection in step 2 was achieved using 2,2,2-trifluoroethanol in a microwave reactor. SEM deprotection in step 4 was achieved using CsF in refluxing acetonitrile. MS: (M+H)⁺=419.

Example 88

2-Cyclopropyl-5H-pyrrolo[2,3-b]pyrazine-7-carboxylic acid [(R)-1-cyclopropyl-2-(2-oxa-6-aza-spiro[3.3]hept-6-yl)-2-oxo-ethyl]-amide

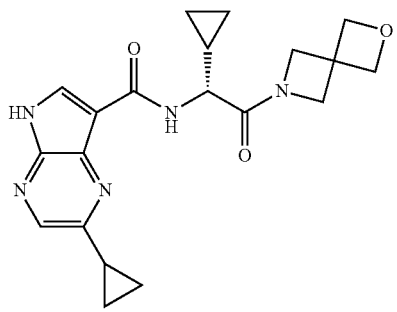 [SMILES: O=C(N[C@@H](C(=O)N1CC2(COC2)C1)C1CC1)c1c[nH]c2ncc(C3CC3)nc12]

Prepared according to the procedure outlined in Example 1 substituting 2-oxa-6-aza-spiro[3.3]heptane oxalate for pyrrolidine and Boc-D-cyclopropyl glycine for Boc-D-tert-leucine. N-Boc deprotection in step 2 was achieved using 2,2,2-trifluoroethanol in a microwave reactor. SEM deprotection in step 4 was achieved using CsF in refluxing acetonitrile. MS: (M+H)⁺=382.

Example 89

2-(1-Methyl-1H-pyrazol-4-yl)-5H-pyrrolo[2,3-b]pyrazine-7-carboxylic acid [(R)-1-cyclopropyl-2-(2-oxa-6-aza-spiro[3.3]hept-6-yl)-2-oxo-ethyl]-amide

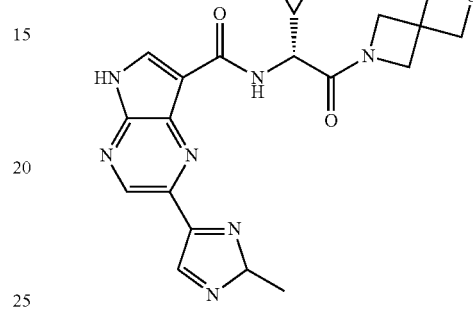

Prepared according to the procedure outlined in Example 1 substituting 2-oxa-6-aza-spiro[3.3]heptane oxalate for pyrrolidine, Boc-D-cyclopropyl glycine for Boc-D-tert-leucine, and 2-(1-methyl-1H-pyrazol-4-yl)-5-((2-(trimethylsilyl)ethoxy)methyl)-5H-pyrrolo[3,2-b]pyrazine-7-carboxylic acid for 2-cyclopropyl-5-(2-trimethylsilanyl-ethoxymethyl)-5H-pyrrolo[2,3-b]pyrazine-7-carboxylic acid. N-Boc deprotection in step 2 was achieved using 2,2,2-trifluoroethanol in a microwave reactor. SEM deprotection in step 4 was achieved using CsF in refluxing acetonitrile. MS: (M+H)⁺=422.

Example 90

2-Cyclopropyl-5H-pyrrolo[2,3-b]pyrazine-7-carboxylic acid [(R)-1-cyclopropyl-2-((1S,5R,6R)-6-hydroxymethyl-3-aza-bicyclo[3.1.0]hex-3-yl)-2-oxo-ethyl]-amide

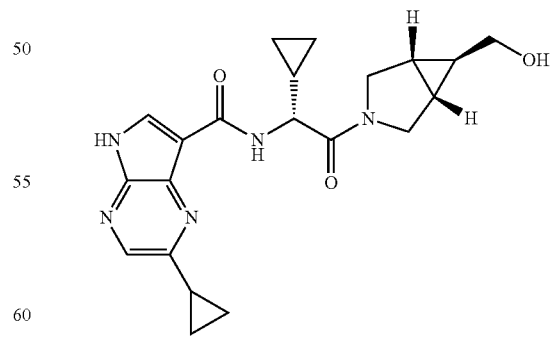

Prepared according to the procedure outlined in Example 1 substituting (1α,5α,6α)-3-azabicyclo[3.1.0]hexan-6-yl-methanol for pyrrolidine and Boc-D-cyclopropyl glycine for Boc-D-tert-leucine. N-Boc deprotection in step 2 was achieved using 2,2,2-trifluoroethanol in a microwave reactor.

SEM deprotection in step 4 was achieved using CsF in refluxing acetonitrile. MS: (M+H)⁺=396.

Example 91

2-(1-Methyl-1H-pyrazol-4-yl)-5H-pyrrolo[2,3-b]pyrazine-7-carboxylic acid [(R)-1-cyclopropyl-2-((1S,5R,6R)-6-hydroxymethyl-3-aza-bicyclo[3.1.0]hex-3-yl)-2-oxo-ethyl]-amide

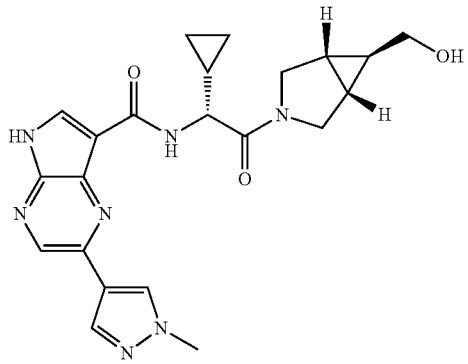 [SMILES: Cn1cc(-c2cnc3[nH]cc(C(=O)N[C@@H](C(=O)N4C[C@@H]5[C@@H](CO)[C@@H]5C4)C4CC4)c3n2)cn1]

Prepared according to the procedure outlined in Example 1 substituting (1α,5α,6α)-3-azabicyclo[3.1.0]hexan-6-yl-methanol for pyrrolidine, Boc-D-cyclopropyl glycine for Boc-D-tert-leucine, and 2-(1-methyl-1H-pyrazol-4-yl)-5-((2-(trimethylsilyl)ethoxy)methyl)-5H-pyrrolo[3,2-b]pyrazine-7-carboxylic acid for 2-cyclopropyl-5-(2-trimethylsilanyl-ethoxymethyl)-5H-pyrrolo[2,3-b]pyrazine-7-carboxylic acid. N-Boc deprotection in step 2 was achieved using 2,2,2-trifluoroethanol in a microwave reactor. SEM deprotection in step 4 was achieved using CsF in refluxing acetonitrile. MS: (M+H)⁺=436.

Example 92

2-Cyclopropyl-5H-pyrrolo[2,3-b]pyrazine-7-carboxylic acid [(R)-1-cyclopropyl-2-(1,1-dioxo-thiomorpholin-4-yl)-2-oxo-ethyl]-amide

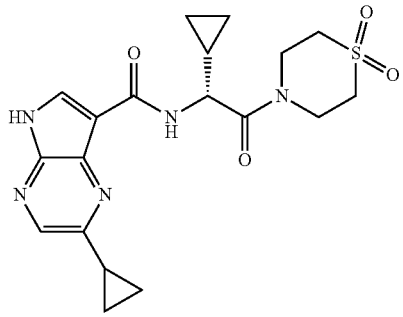 [SMILES: O=C(N[C@@H](C(=O)N1CCS(=O)(=O)CC1)C1CC1)c1c[nH]c2ncc(C3CC3)nc12]

Prepared according to the procedure outlined in Example 1 substituting thiomorpholine-1,1-dioxide for pyrrolidine and Boc-D-cyclopropyl glycine for Boc-D-tert-leucine. N-Boc deprotection in step 2 was achieved using 2,2,2-trifluoroethanol in a microwave reactor. SEM deprotection in step 4 was achieved using CsF in refluxing acetonitrile. MS: (M+H)⁺=418.

Example 93

2-(1-Methyl-1H-pyrazol-4-yl)-5H-pyrrolo[2,3-b]pyrazine-7-carboxylic acid [(R)-1-cyclopropyl-2-(1,1-dioxo-thiomorpholin-4-yl)-2-oxo-ethyl]-amide

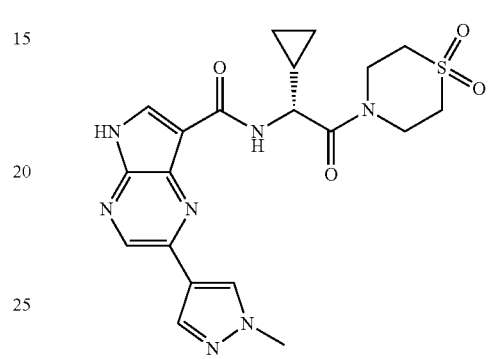

Prepared according to the procedure outlined in Example 1 substituting thiomorpholine-1,1-dioxide for pyrrolidine, Boc-D-cyclopropyl glycine for Boc-D-tert-leucine, and 2-(1-methyl-1H-pyrazol-4-yl)-5-((2-(trimethylsilyl)ethoxy)methyl)-5H-pyrrolo[3,2-b]pyrazine-7-carboxylic acid for 2-cyclopropyl-5-(2-trimethylsilanyl-ethoxymethyl)-5H-pyrrolo[2,3-b]pyrazine-7-carboxylic acid. N-Boc deprotection in step 2 was achieved using 2,2,2-trifluoroethanol in a microwave reactor. SEM deprotection in step 4 was achieved using CsF in refluxing acetonitrile. MS: (M+H)⁺=458.

Example 94

2-(1-Ethyl-1H-pyrazol-4-yl)-5H-pyrrolo[2,3-b]pyrazine-7-carboxylic acid [(R)-1-(4-cyano-piperidine-1-carbonyl)-3,3,3-trifluoro-propyl]-amide and 2-(1-Ethyl-1H-pyrazol-4-yl)-5H-pyrrolo[2,3-b]pyrazine-7-carboxylic acid [(S)-1-(4-cyano-piperidine-1-carbonyl)-3,3,3-trifluoro-propyl]-amide

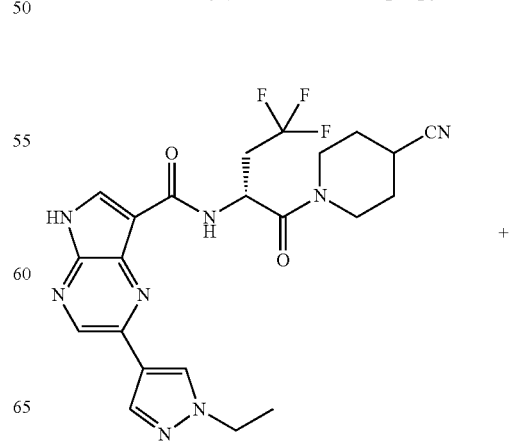

171
-continued

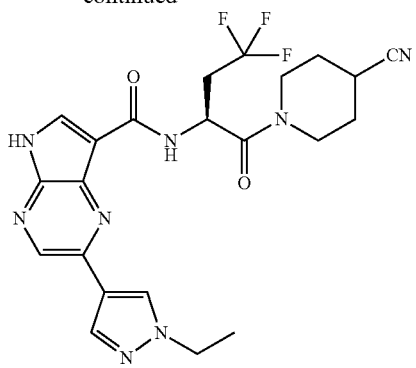

Step 1

To a suspension of 2-amino-4,4,4-trifluorobutanoic acid (0.50 g, 3.2 mmol) in 1,4-dioxane (8 mL) was added 1.0 M aqueous NaOH (6.37 mL, 6.4 mmol). Then added di-tert-butyldicarbonate (764 mg, 3.5 mmol) and stirred vigorously overnight at room temperature. The cloudy reaction mixture was diluted with water (5 mL), neutralized with 1.0 M HCl and extracted with EtOAc (2×). The combined organics were dried over MgSO$_4$ and concentrated to a colorless oil. Trituration with petroleum ether afforded 620 mg (76%) of 2-tert-butoxycarbonylamino-4,4,4-trifluoro-butyric acid as a white powdery solid.

Step 2

2-(1-Ethyl-1H-pyrazol-4-yl)-5H-pyrrolo[2,3-b]pyrazine-7-carboxylic acid [(R)-1-(4-cyano-piperidine-1-carbonyl)-3,3,3-trifluoro-propyl]-amide and 2-(1-Ethyl-1H-pyrazol-4-yl)-5H-pyrrolo[2,3-b]pyrazine-7-carboxylic acid [(S)-1-(4-cyano-piperidine-1-carbonyl)-3,3,3-trifluoro-propyl]-amide. Prepared according to the procedure outlined in Example 1 substituting piperidine-4-carbonitrile for pyrrolidine, 2-tert-butoxycarbonylamino-4,4,4-trifluoro-butyric acid for Boc-D-tert-leucine, and 2-(1-ethyl-1H-pyrazol-4-yl)-5-((2-(trimethylsilyl)ethoxy)methyl)-5H-pyrrolo[3,2-b]pyrazine-7-carboxylic acid for 2-cyclopropyl-5-(2-trimethylsilanyl-ethoxymethyl)-5H-pyrrolo[2,3-b]pyrazine-7-carboxylic acid. Trifluoroacetic acid was used instead of hydrochloric acid for all N-Boc deprotection steps. The R and S enantiomers were separated at Step 3 via chiral preparative SFC chromatography. R enantiomer, (M+H)$^+$=489; S enantiomer, (M+H)$^+$=489.

Example 95

2-Cyclopropyl-5H-pyrrolo[2,3-b]pyrazine-7-carboxylic acid [(R)-2-(3-cyano-3-methyl-azetidin-1-yl)-1-cyclopropyl-2-oxo-ethyl]-amide

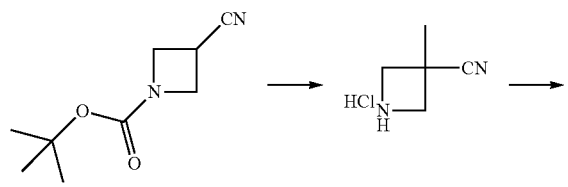

172
-continued

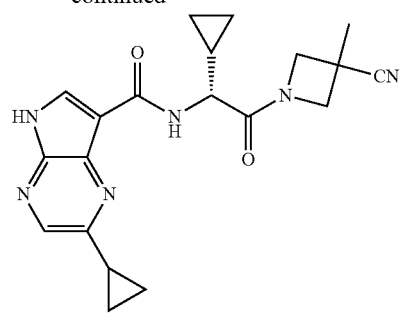

Step 1

In a 100 mL 2-neck round-bottomed flask, tert-butyl 3-cyanoazetidine-1-carboxylate (1.5 g, 8.2 mmol) was dissolved in THF (30 mL). The colorless solution was cooled to −76° C. and lithium bis(trimethylsilyl)amide (1.0M solution in THF, 9.0 mL, 9.0 mmol) was added dropwise over 25 min. The yellow solution was stirred at −76° C. for 30 min then iodomethane (0.78 mL, 12.5 mmol) was slowly added. The reaction mixture was stirred at −76° C. for 30 min and then warmed to room temperature over 1 h. The reaction mixture was quenched with 10 mL of saturated NH$_4$Cl and diluted with 10 mL of water then extracted with ~100 ml EtOAc (2×). The combined organic layers were washed with ~10 mL water and ~10 mL brine then dried over sodium sulfate, filtered and concentrated. The residue was chromatographed over 40 g silica gel with EtOAc/hexanes, (gradient: 0-30% EtOAc). All fractions containing product were combined and concentrated to afford 1.44 g (89%) of 3-cyano-3-methyl-azetidine-1-carboxylic acid tert-butyl ester as a yellow solid.

Step 2

A 20 mL microwave vial was charged with 3-cyano-3-methyl-azetidine-1-carboxylic acid tert-butyl ester (0.75 g, 3.82 mmol) and 2,2,2-trifluoroethanol (15.0 mL, 206 mmol). The vial was flushed with Argon and closed. The colorless solution was heated at 150° C. for 4 h under microwave irradiation. The reaction mixture was cooled to 0° C. and hydrogen chloride (1.0M solution in diethyl ether, 4.6 mL, 4.6 mmol) was added dropwise. The light yellow solution was concentrated and the residue was triturated with diethyl ether to afford 466 mg (92%) of 3-cyano-3-methyl-azetidine hydrochloride as a light yellow powder.

Step 3

2-Cyclopropyl-5H-pyrrolo[2,3-b]pyrazine-7-carboxylic acid [(R)-2-(3-cyano-3-methyl-azetidin-1-yl)-1-cyclopropyl-2-oxo-ethyl]-amide. Prepared according to the procedure outlined in Example 1 substituting 3-cyano-3-methyl-azetidine hydrochloride for pyrrolidine and Boc-D-cyclopropyl glycine for Boc-D-tert-leucine. N-Boc deprotection in step 2 was achieved using 2,2,2-trifluoroethanol in a microwave reactor. MS: (M+H)⁺=379.

Example 96

2-(1-Methyl-1H-pyrazol-4-yl)-5H-pyrrolo[2,3-b]pyrazine-7-carboxylic acid [(R)-2-(3-cyano-3-methyl-azetidin-1-yl)-1-cyclopropyl-2-oxo-ethyl]-amide

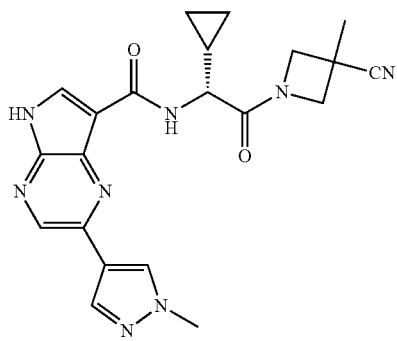 [SMILES: Cn1cc(-c2cnc3[nH]cc(C(=O)N[C@@H](C(=O)N4CC(C)(C#N)C4)C4CC4)c3n2)cn1]

Prepared according to the procedure outlined in Example 1 substituting 3-cyano-3-methyl-azetidine hydrochloride for pyrrolidine, Boc-D-cyclopropyl glycine for Boc-D-tert-leucine, and 2-(1-methyl-1H-pyrazol-4-yl)-5-((2-(trimethylsilyl)ethoxy)methyl)-5H-pyrrolo[3,2-b]pyrazine-7-carboxylic acid for 2-cyclopropyl-5-(2-trimethylsilanyl-ethoxymethyl)-5H-pyrrolo[2,3-b]pyrazine-7-carboxylic acid. N-Boc deprotection in step 2 was achieved using 2,2,2-trifluoroethanol in a microwave reactor. MS: (M+H)⁺=419.

Example 97

2-(1-Methyl-1H-pyrazol-4-yl)-5H-pyrrolo[2,3-b]pyrazine-7-carboxylic acid [(R)-1-(3-cyano-3-methyl-azetidine-1-carbonyl)-2,2-dimethyl-propyl]-amide

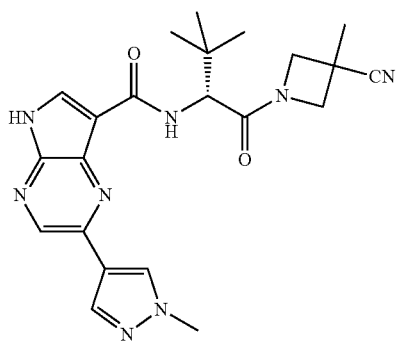 [SMILES: Cn1cc(-c2cnc3[nH]cc(C(=O)N[C@@H](C(=O)N4CC(C)(C#N)C4)C(C)(C)C)c3n2)cn1]

Prepared according to the procedure outlined in Example 1 substituting 3-cyano-3-methyl-azetidine hydrochloride for pyrrolidine and 2-(1-methyl-1H-pyrazol-4-yl)-5-((2-(trimethylsilyl)ethoxy)methyl)-5H-pyrrolo[3,2-b]pyrazine-7-carboxylic acid for 2-cyclopropyl-5-(2-trimethylsilanyl-ethoxymethyl)-5H-pyrrolo[2,3-b]pyrazine-7-carboxylic acid. N-Boc deprotection in step 2 was achieved using 2,2,2-trifluoroethanol in a microwave reactor. MS: (M+H)⁺=435.

Example 98

2-(1-Ethyl-1H-pyrazol-4-yl)-5H-pyrrolo[2,3-b]pyrazine-7-carboxylic acid [(R)-1-cyclopropyl-2-(4,4-difluoro-piperidin-1-yl)-2-oxo-ethyl]-amide

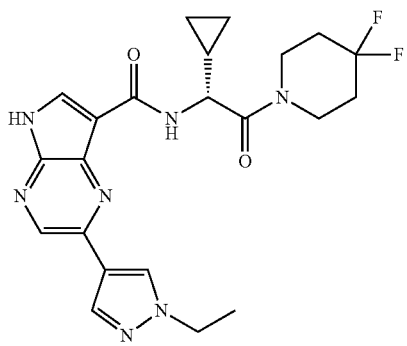 [SMILES: CCn1cc(-c2cnc3[nH]cc(C(=O)N[C@@H](C(=O)N4CCC(F)(F)CC4)C4CC4)c3n2)cn1]

Prepared according to the procedure outlined in Example 1 substituting 4,4-difluoropiperidine hydrochloride for pyrrolidine, Boc-D-cyclopropyl glycine for Boc-D-tert-leucine, and 2-(1-ethyl-1H-pyrazol-4-yl)-5-((2-(trimethylsilyl)ethoxy)methyl)-5H-pyrrolo[3,2-b]pyrazine-7-carboxylic acid for 2-cyclopropyl-5-(2-trimethylsilanyl-ethoxymethyl)-5H-pyrrolo[2,3-b]pyrazine-7-carboxylic acid. MS: (M+H)⁺=458.

Example 99

2-(1-Ethyl-1H-pyrazol-4-yl)-5H-pyrrolo[2,3-b]pyrazine-7-carboxylic acid [(R)-1-cyclopropyl-2-(4-hydroxy-4-trifluoromethyl-piperidin-1-yl)-2-oxo-ethyl]-amide

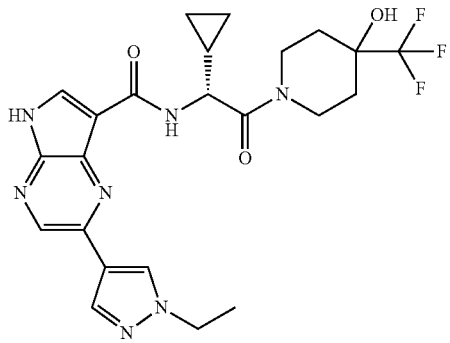 [SMILES: CCn1cc(-c2cnc3[nH]cc(C(=O)N[C@@H](C(=O)N4CCC(O)(C(F)(F)F)CC4)C4CC4)c3n2)cn1]

Prepared according to the procedure outlined in Example 1 substituting 4-trifluoromethyl-piperidin-4-ol (Example 74, step 2) for pyrrolidine, Boc-D-cyclopropyl glycine for Boc-D-tert-leucine, and 2-(1-ethyl-1H-pyrazol-4-yl)-5-((2-(trimethylsilyl)ethoxy)methyl)-5H-pyrrolo[3,2-b]pyrazine-7-carboxylic acid for 2-cyclopropyl-5-(2-trimethylsilanyl-ethoxymethyl)-5H-pyrrolo[2,3-b]pyrazine-7-carboxylic acid. MS: (M+H)⁺=506.

Example 100

2-(1-Ethyl-1H-pyrazol-4-yl)-5H-pyrrolo[2,3-b]pyrazine-7-carboxylic acid [(R)-1-cyclopropyl-2-(3-hydroxy-3-methyl-azetidin-1-yl)-2-oxo-ethyl]-amide

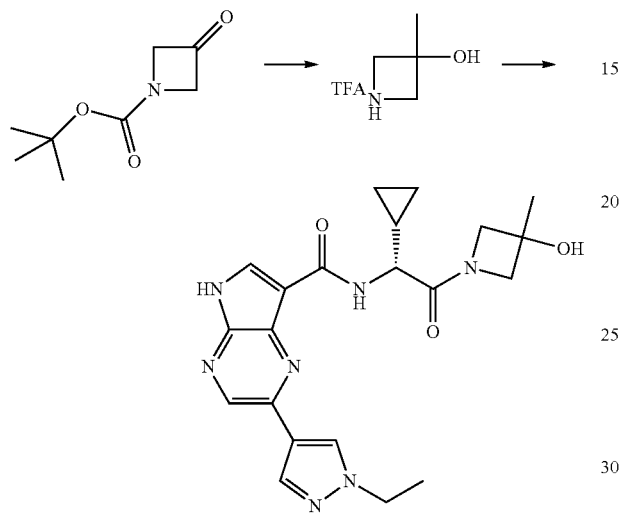

Step 1

In a dry round-bottomed flask, 1-Boc-3-azetidinone (0.70 g, 4.1 mmol) was dissolved in THF (20 mL). The solution was cooled to 0° C. and methylmagnesium chloride (3.0 M solution in THF, 2.0 mL, 6.0 mmol) was added dropwise. The reaction mixture was stirred at 0° C. for 1 h. The reaction mixture was quenched with 10 mL saturated NH₄Cl, diluted with 5 mL water and extracted with 100 mL EtOAc (2×). The combined organic layers were washed with 10 mL water and 10 mL brine then combined, dried over sodium sulfate, filtered and concentrated to afford 757 mg (99%) of 3-hydroxy-3-methyl-azetidine-1-carboxylic acid tert-butyl ester as an off-white solid.

Step 2

In a round-bottomed flask, 3-hydroxy-3-methyl-azetidine-1-carboxylic acid tert-butyl ester (0.40 g, 2.13 mmol) was dissolved in dichloromethane (20 mL). The colorless solution was cooled to 0° C. and trifluoroacetic acid (6.5 ml) was slowly added. After the addition was complete, the ice bath was removed and the reaction mixture was stirred at room temperature for 1.5 h. The reaction mixture was concentrated to afford 3-methyl-azetidin-3-ol trifluoroacetate as light brown oil which was used without further purification.

Step 3

2-(1-Ethyl-1H-pyrazol-4-yl)-5H-pyrrolo[2,3-b]pyrazine-7-carboxylic acid [(R)-1-cyclopropyl-2-(3-hydroxy-3-methyl-azetidin-1-yl)-2-oxo-ethyl]-amide. Prepared according to the procedure outlined in Example 1 substituting 3-methyl-azetidin-3-ol trifluoroacetate for pyrrolidine, Boc-D-cyclopropyl glycine for Boc-D-tert-leucine, and 2-(1-ethyl-1H-pyrazol-4-yl)-5-((2-(trimethylsilyl)ethoxy)methyl)-5H-pyrrolo[3,2-b]pyrazine-7-carboxylic acid for 2-cyclopropyl-5-(2-trimethylsilanyl-ethoxymethyl)-5H-pyrrolo[2,3-b] pyrazine-7-carboxylic acid. Trifluoroacetic acid was used instead of hydrochloric acid for all N-Boc deprotection steps. MS: (M+H)⁺=424.

Example 101

2-Cyclopropyl-5H-pyrrolo[2,3-b]pyrazine-7-carboxylic acid [(1R,2R)-1-(4-cyano-piperidine-1-carbonyl)-2-methyl-butyl]-amide

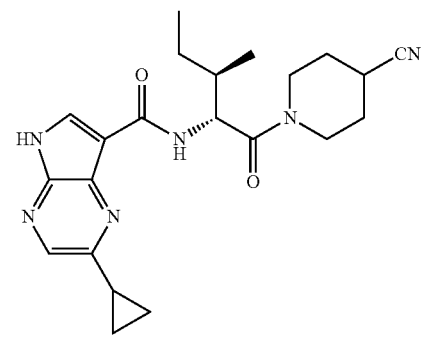 [SMILES: CC[C@@H](C)[C@@H](NC(=O)c1c[nH]c2ncc(C3CC3)nc12)C(=O)N1CCC(C#N)CC1]

Prepared according to the procedure outlined in Example 1 substituting piperidine-4-carbonitrile for pyrrolidine and Boc-D-isoleucine for Boc-D-tert-leucine and using trifluoroacetic acid instead of hydrochloric acid for all N-Boc deprotection steps. MS: (M+H)⁺=409.

Example 102

2-Cyclopropyl-5H-pyrrolo[2,3-b]pyrazine-7-carboxylic acid [(1R,2S)-1-(4-cyano-piperidine-1-carbonyl)-2-methyl-butyl]-amide

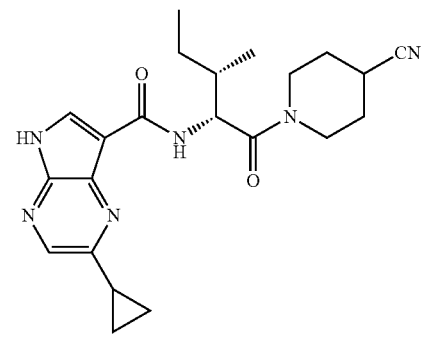 [SMILES: CC[C@H](C)[C@@H](NC(=O)c1c[nH]c2ncc(C3CC3)nc12)C(=O)N1CCC(C#N)CC1]

Prepared according to the procedure outlined in Example 1 substituting piperidine-4-carbonitrile for pyrrolidine and Boc-D-allo-isoleucine for Boc-D-tert-leucine and using trifluoroacetic acid instead of hydrochloric acid for all N-Boc deprotection steps. MS: (M+H)+=409.

Example 103

2-Cyclopropyl-5H-pyrrolo[2,3-b]pyrazine-7-carboxylic acid [(R)-2-(4-cyano-piperidin-1-yl)-1-cyclopropylmethyl-2-oxo-ethyl]-amide

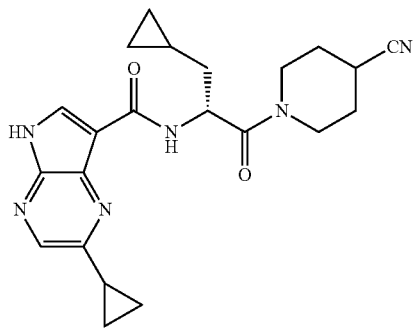 [SMILES: N#CC1CCN(C(=O)[C@@H](CC2CC2)NC(=O)c2c[nH]c3ncc(C4CC4)nc23)CC1]

Step 1

To a suspension of (R)-2-amino-3-cyclopropylpropionic acid (0.57 g, 4.4 mmol) in 1,4-dioxane (8 mL) was added 1.0 M aqueous NaOH (4.0 mL, 4.0 mmol). Then added di-tert-butyldicarbonate (0.96 g, 4.4 mmol) and stirred vigorously overnight at room temperature. The cloudy reaction mixture was diluted with water (5 mL), neutralized with 1.0 M HCl and extracted with EtOAc (2×). The combined organics were dried over MgSO4 and concentrated to afford (R)-2-tert-butoxycarbonylamino-3-cyclopropyl-propionic acid as a viscous colorless oil which was used without further purification.

Step 2

2-Cyclopropyl-5H-pyrrolo[2,3-b]pyrazine-7-carboxylic acid [(R)-2-(4-cyano-piperidin-1-yl)-1-cyclopropylmethyl-2-oxo-ethyl]-amide. Prepared according to the procedure outlined in Example 1 substituting piperidine-4-carbonitrile for pyrrolidine and (R)-2-tert-butoxycarbonylamino-3-cyclopropyl-propionic acid for Boc-D-tert-leucine and using trifluoroacetic acid instead of hydrochloric acid for all N-Boc deprotection steps. MS: (M+H)+=407.

Example 104

2-Cyclopropyl-5H-pyrrolo[2,3-b]pyrazine-7-carboxylic acid [(R)-2-(4-cyano-piperidin-1-yl)-2-oxo-1-phenyl-ethyl]-amide

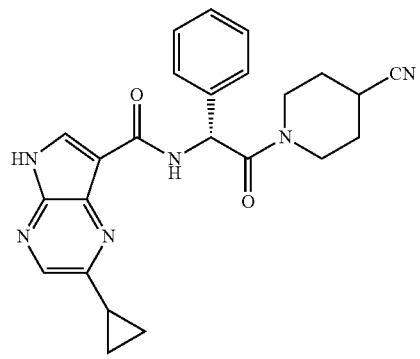 [SMILES: N#CC1CCN(C(=O)[C@H](NC(=O)c2c[nH]c3ncc(C4CC4)nc23)c2ccccc2)CC1]

Prepared according to the procedure outlined in Example 1 substituting piperidine-4-carbonitrile for pyrrolidine and Boc-D-phenylglycine for Boc-D-tert-leucine and using trifluoroacetic acid instead of hydrochloric acid for all N-Boc deprotection steps. MS: (M+H)+=429.

Example 105

2-(1-Methyl-1H-pyrazol-4-yl)-5H-pyrrolo[2,3-b]pyrazine-7-carboxylic acid [(R)-1-cyclopropyl-2-(3,3-difluoro-azetidin-1-yl)-2-oxo-ethyl]-amide

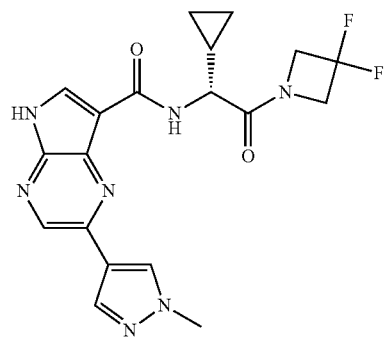 [SMILES: Cn1cc(-c2cnc3[nH]cc(C(=O)N[C@@H](C(=O)N4CC(F)(F)C4)C4CC4)c3n2)cn1]

Prepared according to the procedure outlined in Example 1 substituting 3,3-difluoroazetidine hydrochloride for pyrrolidine, Boc-D-cyclopropyl glycine for Boc-D-tert-leucine, and 2-(1-methyl-1H-pyrazol-4-yl)-5-((2-(trimethylsilyl)ethoxy)methyl)-5H-pyrrolo[3,2-b]pyrazine-7-carboxylic acid for 2-cyclopropyl-5-(2-trimethylsilanyl-ethoxymethyl)-5H-pyrrolo[2,3-b]pyrazine-7-carboxylic acid. Trifluoroacetic acid was used instead of hydrochloric acid for all N-Boc deprotection steps. MS: (M+H)+=416.

Example 106

2-(1-Methyl-1H-pyrazol-4-yl)-5H-pyrrolo[2,3-b]pyrazine-7-carboxylic acid [(R)-2-(3-cyano-3-ethyl-azetidin-1-yl)-1-cyclopropyl-2-oxo-ethyl]-amide

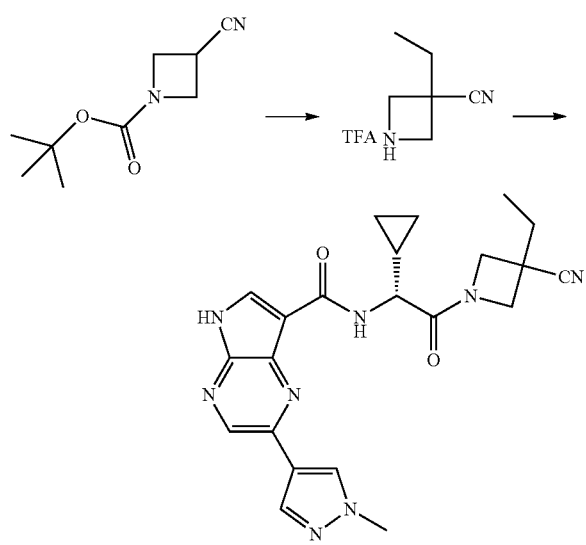

Step 1

In a 100 mL 2-neck round-bottomed flask, tert-butyl 3-cyanoazetidine-1-carboxylate (0.80 g, 4.4 mmol) was dissolved in THF (16 mL). The colorless solution was cooled to −76° C. and lithium bis(trimethylsilyl)amide (1.0M solution in THF, 4.8 mL, 4.8 mmol) was added dropwise over 20 min. The yellow solution was stirred at −76° C. for 30 min then iodoethane (0.50 mL, 6.2 mmol) was slowly added. The reaction mixture was stirred at −76° C. for 30 min and then warmed to room temperature and stirred for 3 h. The reaction mixture was quenched with 10 mL of saturated NH4Cl and diluted with 10 mL of water then extracted with ~100 ml EtOAc (2×). The combined organic layers were washed with ~10 mL water and ~10 mL brine then dried over sodium sulfate, filtered and concentrated. The residue was chromatographed over 40 g silica gel with EtOAc/hexanes, (gradient: 0-20% EtOAc). All fractions containing product were combined and concentrated to afford 0.84 g (91%) of 3-cyano-3-ethyl-azetidine-1-carboxylic acid tert-butyl ester as a light yellow oil.

Step 2

In a round-bottomed flask, 3-cyano-3-ethyl-azetidine-1-carboxylic acid tert-butyl ester (0.40 g, 1.9 mmol) was dissolved in dichloromethane (12 mL). The light yellow solution was cooled to 0° C. and trifluoroacetic acid (4.4 mL) was slowly added. After the addition was complete, the ice bath was removed and the reaction mixture was stirred at room temperature for 1.5 h. The reaction mixture was concentrated to afford 3-cyano-3-ethyl-azetidine trifluoroacetate as a light yellow oil which was used without further purification.

Step 3

2-(1-Methyl-1H-pyrazol-4-yl)-5H-pyrrolo[2,3-b]pyrazine-7-carboxylic acid [(R)-2-(3-cyano-3-ethyl-azetidin-1-yl)-1-cyclopropyl-2-oxo-ethyl]-amide. Prepared according to the procedure outlined in Example 1 substituting 3-cyano-3-ethyl-azetidine trifluoroacetate for pyrrolidine, Boc-D-cyclopropyl glycine for Boc-D-tert-leucine, and 2-(1-methyl-1H-pyrazol-4-yl)-5-((2-(trimethylsilyl)ethoxy)methyl)-5H-pyrrolo[3,2-b]pyrazine-7-carboxylic acid for 2-cyclopropyl-5-(2-trimethylsilanyl-ethoxymethyl)-5H-pyrrolo[2,3-b]pyrazine-7-carboxylic acid. Trifluoroacetic acid was used instead of hydrochloric acid for all N-Boc deprotection steps. MS: (M+H)+=433.

Example 107

2-(4-Trifluoromethyl-phenyl)-5H-pyrrolo[2,3-b]pyrazine-7-carboxylic acid [(R)-1-(4-cyano-piperidine-1-carbonyl)-2,2-dimethyl-propyl]-amide

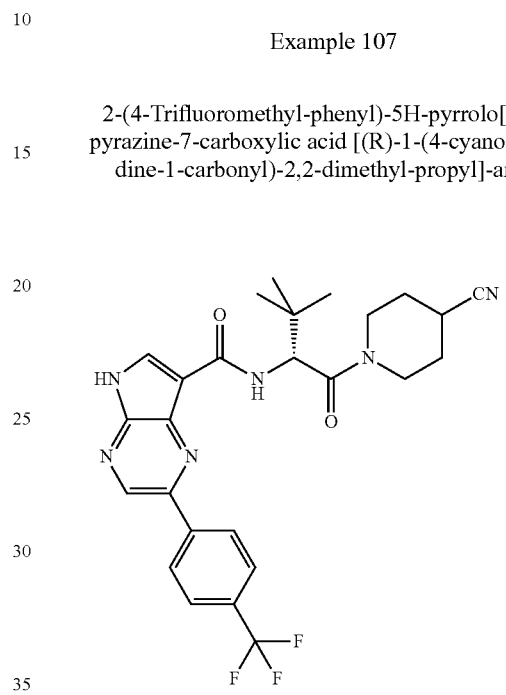

Prepared according to the procedure outlined in Example 2 substituting 1-((R)-2-amino-3,3-dimethyl-butyryl)-piperidine-4-carbonitrile trifluoroacetate for (R)-2-amino-3,3-dimethyl-1-pyrrolidin-1-yl-butan-1-one hydrochloride in Step 1 and 4-(trifluoromethyl)-phenylboronic acid for 1-ethyl-1H-pyrazole-4-boronic acid pinacol ester in Step 2. MS: (M+H)+= 513

Example 108

2-(3,4,5-Trimethoxy-phenyl)-5H-pyrrolo[2,3-b]pyrazine-7-carboxylic acid [(R)-2-(3-cyano-azetidin-1-yl)-1-methyl-2-oxo-ethyl]-amide

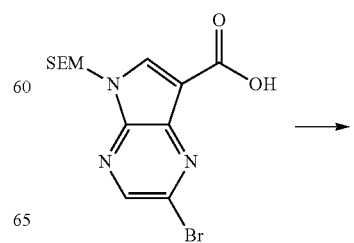

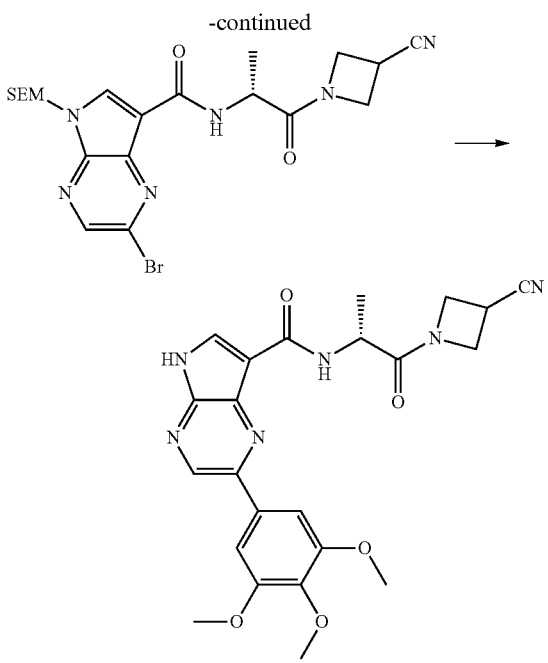

Step 1

In a round-bottomed flask were combined Boc-D-alanine (500 mg, 2.64 mmol), azetidine-3-carbonitrile hydrochloride (376 mg, 3.17 mmol), HOBT (445 mg, 2.91 mmol) and HATU (1.11 g, 2.91 mmol). Then added DMF (5 mL) followed by N,N-diisopropylethylamine (1.38 mL, 7.93 mmol). The yellow reaction mixture was stirred at room temperature for 3 h then quenched with water and extracted with EtOAc (3×). The combined organics were washed with water (3×) dried over MgSO$_4$ and concentrated. The residue was purified by SiO$_2$ chromatography (50% to 100% EtOAc/hexanes) to afford 493 mg (74%) of [(R)-2-(3-cyanoazetidin-1-yl)-1-methyl-2-oxo-ethyl]-carbamic acid tert-butyl ester as a white solid.

Step 2

To a solution of [(R)-2-(3-cyanoazetidin-1-yl)-1-methyl-2-oxo-ethyl]-carbamic acid tert-butyl ester (860 mg, 3.4 mmol) in CH$_2$Cl$_2$ (20 mL) was added trifluoroacetic acid (4.0 mL). The reaction mixture was stirred at room temperature for 2 h then concentrated to afford 1-((R)-2-amino-propionyl)-azetidine-3-carbonitrile trifluoroacetate as a pale yellow oil which was used without further purification.

Step 3

In a round-bottomed flask were combined 2-bromo-5-((2-(trimethylsilyl)ethoxy)methyl)-5H-pyrrolo[2,3-b]pyrazine-7-carboxylic acid (1.05 g, 2.82 mmol) (derived from Procedure 1, Method B; approx 3:1 Br:Cl), 1-((R)-2-amino-propionyl)-azetidine-3-carbonitrile trifluoroacetate (900 mg, 3.37 mmol), and HATU (1.18 g, 3.1 mmol). Then added DMF (10 mL) followed by N,N-diisopropylethylamine (1.48 mL, 8.46 mmol). The yellow reaction mixture was stirred at room temperature overnight then quenched with water and extracted with EtOAc (3×). The combined organics were washed with water (3×), dried over MgSO$_4$ and concentrated. The residue was purified by SiO$_2$ chromatography (30% to 100% EtOAc/hexanes) to afford 1.19 g (83%) of 2-bromo-5-(2-trimethylsilanyl-ethoxymethyl)-5H-pyrrolo[2,3-b]pyrazine-7-carboxylic acid [(R)-2-(3-cyano-azetidin-1-yl)-1-methyl-2-oxo-ethyl]-amide as a white foamy solid (approx 3:1 mixture of Br and Cl compounds).

Step 4

In a round-bottomed flask 2-bromo-5-(2-trimethylsilanyl-ethoxymethyl)-5H-pyrrolo[2,3-b]pyrazine-7-carboxylic acid [(R)-2-(3-cyano-azetidin-1-yl)-1-methyl-2-oxo-ethyl]-amide (125 mg, 0.25 mmol) and 3,4,5-trimethoxyphenylboronic acid (78 mg, 0.37 mmol) were dissolved in DME (2.0 mL). Aqueous K$_2$CO$_3$ (2.0 M, 0.37 mL, 0.74 mmol) and Pd(PPh$_3$)$_4$ (14 mg, 0.012 mmol) were added and the mixture degassed with a gentle stream of N$_2$ for 15 min. The reaction mixture was heated at 90° C. for 1.5 h then cooled to room temperature, quenched with H$_2$O and extracted with EtOAc. The organic extracts were washed with brine, dried over MgSO$_4$, and concentrated. The residue was purified by SiO$_2$ chromatography (50-100% EtOAc/heptane) to afford 146 mg (>100%) of 2-(3,4,5-trimethoxy-phenyl)-5-(2-trimethylsilanyl-ethoxymethyl)-5H-pyrrolo[2,3-b]pyrazine-7-carboxylic acid [(R)-2-(3-cyano-azetidin-1-yl)-1-methyl-2-oxo-ethyl]-amide as a viscous colorless oil.

Step 5

To a solution of the above 2-(3,4,5-trimethoxy-phenyl)-5-(2-trimethylsilanyl-ethoxymethyl)-5H-pyrrolo[2,3-b]pyrazine-7-carboxylic acid [(R)-2-(3-cyano-azetidin-1-yl)-1-methyl-2-oxo-ethyl]-amide in CH$_2$Cl$_2$ (2.25 mL) was added TFA (0.75 mL). The reaction mixture was stirred overnight and concentrated. The residue was dissolved in a mixture of ammonium hydroxide, MeOH and CH$_2$Cl$_2$ (1:10:60, 3.0 mL) and stirred at room temperature for 90 min. The reaction mixture was then concentrated and the residue purified by SiO$_2$ chromatography (0-10% MeOH/CH$_2$Cl$_2$) to afford 97 mg (85%, 2 steps) of 2-(3,4,5-trimethoxy-phenyl)-5H-pyrrolo[2,3-1)]pyrazine-7-carboxylic acid [(R)-2-(3-cyano-azetidin-1-yl)-1-methyl-2-oxo-ethyl]-amide as a white powder. MS: (M+H)$^+$=465.

Example 109

2-[3-(3,3-Dimethyl-pyrrolidin-1-yl)-phenyl]-5H-pyrrolo[2,3-b]pyrazine-7-carboxylic acid [(R)-2-(3-cyano-azetidin-1-yl)-1-methyl-2-oxo-ethyl]-amide

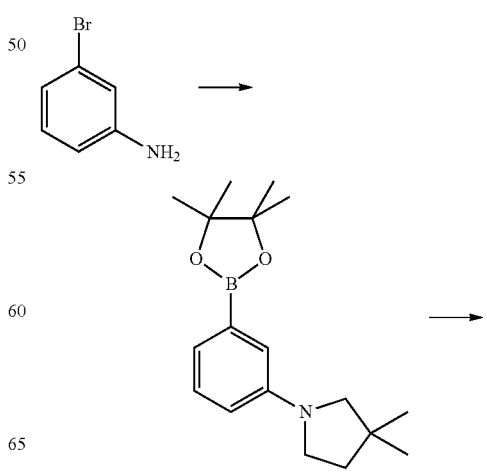

183

-continued

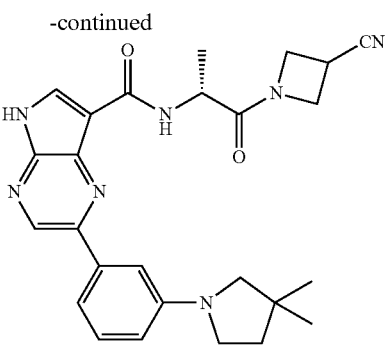

Step 1

3-Bromophenylamine (10.0 g, 58.1 mmol) and 3,3-dimethyl-dihydro-furan-2,5-dione (8.2 g, 63.9 mmol) were suspended in 300 ml DCM. The reaction was stirred at 50° C. for 3 h. The reaction was cooled to room temperature and 1,1'-carbonyldiimidazole (11.3 g, 69.7 mmol) was added in portions. The reaction was heated again to 50° C. and stirred overnight. The solvent was evaporated and the product was crystallized from isopropyl alcohol to give 9.3 g of 1-(3-bromophenyl)-3,3-dimethyl-pyrrolidine-2,5-dione. The mother liquor was concentrated and chromatographed using a gradient of 0% to 20% ethyl acetate in hexanes to give another 1.3 g of product for a combined yield of 10.6 g (65%).

Step 2

1-(3-Bromophenyl)-3,3-dimethyl-pyrrolidine-2,5-dione (10.6 g, 37.7 mmol) was suspended in 200 ml of THF. Borane dimethyl sulfide complex (33 ml of a 10.1 M solution) was added and the reaction was stirred at room temperature for 3 hrs. The reaction was cooled in an ice bath. Methanol (100 ml) was added dropwise, followed by 300 ml of water. This mixture was transferred to a separatory funnel and DCM was added. The organic phase was isolated, washed with brine, filtered through Celite and concentrated. The product was chromatographed using a gradient of 0% to 5% ethyl acetate in hexanes, concentrated, triturated with methanol and filtered to give 8.0 g (84%) of 1-(3-bromophenyl)-3,3-dimethyl-pyrrolidine.

Step 3

1-(3-Bromophenyl)-3,3-dimethyl-pyrrolidine (6.7 g, 26.4 mmol) was suspended in 132 ml of THF and cooled to −78° C. in a dry ice acetone bath. tert-Butyl lithium (1.7 M solution in pentane, 46.6 ml, 79.2 mmol) was added dropwise and the reaction was stirred at −78° C. for 15 min. 2-Isopropoxy-4,4,5,5-tetramethyl-[1,3,2]dioxaborolane (10.8 ml, 52.8 mmol) was added and the reaction was stirred at −78° C. for 2 h. The reaction was quenched with saturated aqueous ammonium chloride and warmed to room temperature. Water was added and the layers were separated. The aqueous layer was back extracted twice with ethyl acetate. The combined organic layers were dried, filtered and concentrated. The crude product was chromatographed using a gradient of 0% to 10% ethyl acetate in hexanes to give 6.0 g (75%) of 3,3-dimethyl-1-[3 (4,4,5,5-tetramethyl[1,3,2]dioxaborolan-2-yl)-phenyl]-pyrrolidine.

Step 4

2-[3-(3,3-Dimethyl-pyrrolidin-1-yl)-phenyl]-5H-pyrrolo[2,3-b]pyrazine-7-carboxylic acid [(R)-2-(3-cyano-azetidin-1-yl)-1-methyl-2-oxo-ethyl]-amide. Prepared according to the procedure outlined in Example 108, steps 4-5 substituting 3,3-dimethyl-1-[3(4,4,5,5-tetramethyl[1,3,2]dioxaborolan-

184

2-yl)-phenyl]-pyrrolidine for 3,4,5-trimethoxyphenylboronic acid. MS: (M+H)$^+$=472.

Example 110

2-[3-(3,3-Dimethyl-pyrrolidin-1-yl)-phenyl]-5H-pyrrolo[2,3-b]pyrazine-7-carboxylic acid [(R)-2-(3-cyano-azetidin-1-yl)-1-methyl-2-oxo-ethyl]-amide

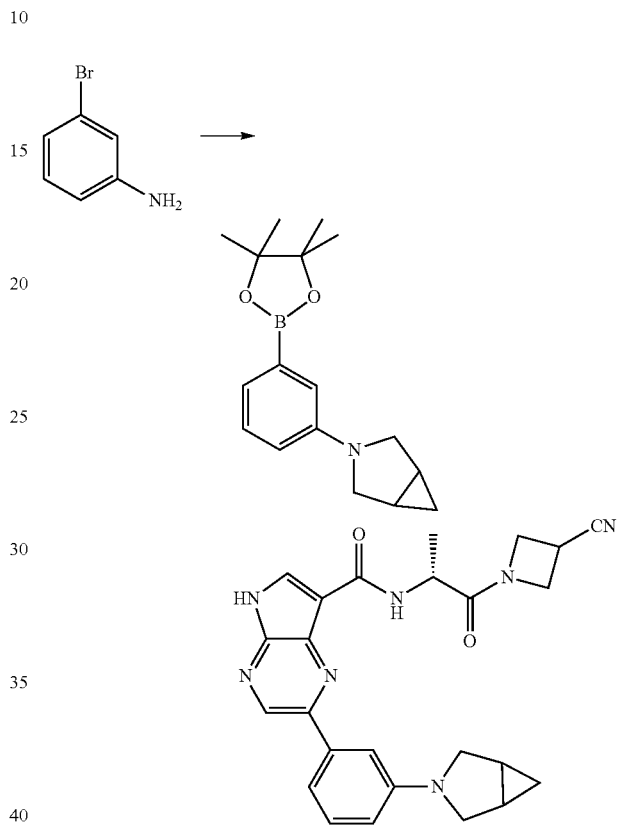

Step 1

3-Bromophenylamine (2.78 g, 16.2 mmol) and 3-oxabicyclo[3.1.0]hexane-2,4-dione (2.0 g, 17.8 mmol) were suspended in 90 mL dichloromethane. The reaction was stirred at 50° C. for 3 h. The reaction was cooled to room temperature and 1,1'-carbonyldiimidazole (3.14 g, 19.4 mmol) was added in portions. The reaction was heated again to 50° C. and stirred overnight then cooled to room temperature and the solvent was evaporated. The residue was redissolved in 90 mL 1,2-dichloroethane and additional 1,1'-carbonyldiimidazole (1.13 g, 7.0 mmol) was added. The reaction mixture was heated at reflux for 2.5 h then cooled to room temperature. The solvent was evaporated and the product was crystallized from isopropyl alcohol to give 4.25 g (99%) of 3-(3-bromophenyl)-3-aza-bicyclo[3.1.0]hexane-2,4-dione as a white solid.

Step 2

3-(3-Bromo-phenyl)-3-aza-bicyclo[3.1.0]hexane-2,4-dione (4.25 g, 16.0 mmol) was suspended in 80 mL of THF. Borane dimethyl sulfide complex (14.2 mL of a 10.1 M solution) was added and the reaction was heated at 50° C. for 1 h. The reaction was cooled in an ice bath. Methanol (65 mL) was slowly added, followed by 150 mL of water. This mixture was extracted with EtOAc (2×) and the combined organics were dried over MgSO$_4$ and concentrated. The residue was taken up in dichloromethane and the resulting suspension was filtered. The filtrate was concentrated and the residue was purified by SiO$_2$ chromatography using a gradient of 0% to 20% ethyl acetate/heptane to afford 3.63 g (95%) of 3-(3-bromophenyl)-3-aza-bicyclo[3.1.0]hexane as a white solid.
Step 3

3-(3-Bromo-phenyl)-3-aza-bicyclo[3.1.0]hexane (2.0 g, 8.4 mmol) was dissolved in 40 mL of THF and cooled to −78° C. in a dry ice acetone bath. tert-Butyl lithium (1.7 M solution in pentane, 14.8 mL, 25.2 mmol) was added dropwise and the reaction was stirred at −78° C. for 15 min. 2-Isopropoxy-4,4,5,5-tetramethyl-[1,3,2]dioxaborolane (3.4 mL, 16.8 mmol) was added and the reaction was stirred at −78° C. for 2 h. The reaction was quenched with saturated aqueous ammonium chloride and warmed to room temperature. Water was added and the layers were separated. The aqueous layer was extracted twice with ethyl acetate. The combined organic layers were dried, filtered and concentrated. The crude residue was chromatographed using a gradient of 0% to 10% ethyl acetate/heptane to give 1.93 g (81%) of 3-[3-(4,4,5,5-tetramethyl-[1,3,2]dioxaborolan-2-yl)-phenyl]-3-aza-bicyclo[3.1.0]hexane as a white solid.
Step 4

2-[3-(3,3-Dimethyl-pyrrolidin-1-yl)-phenyl]-5H-pyrrolo[2,3-b]pyrazine-7-carboxylic acid [(R)-2-(3-cyano-azetidin-1-yl)-1-methyl-2-oxo-ethyl]-amide. Prepared according to the procedure outlined in Example 108, steps 4-5 3-[3-(4,4,5,5-tetramethyl-[1,3,2]dioxaborolan-2-yl)-phenyl]-3-aza-bicyclo[3.1.0]hexane for 3,4,5-trimethoxyphenylboronic acid. MS: (M+H)$^+$=456.

Example 111

2-(4-tert-Butyl-pyridin-2-yl)-5H-pyrrolo[2,3-b]pyrazine-7-carboxylic acid [(R)-2-(4-cyano-piperidin-1-yl)-1-cyclopropyl-2-oxo-ethyl]-amide

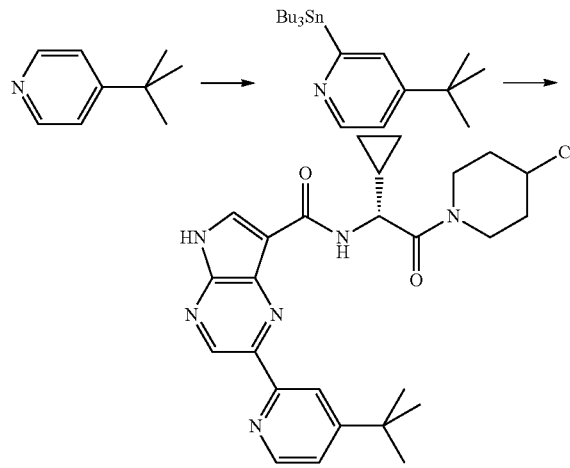

Step 1

In a round-bottomed flask, 4-tert-butylpyridine (1.5 g, 11.1 mmol) was dissolved in acetic acid (9 mL) and hydrogen peroxide (30 wt. % solution in water, 6.0 mL, 58.7 mmol) was added. The colorless solution was stirred at 90° C. overnight. The reaction mixture was cooled to room temperature and concentrated. The residue was poured onto ~40 mL saturated Na$_2$CO$_3$ solution and extracted with 100 mL dichloromethane (2×). The organic layers were combined, dried over sodium sulfate, filtered and concentrated to afford 1.75 g (99%) of 4-tert-butylpyridine N-oxide as light yellow solid.
Step 2

In a round-bottomed flask, phosphorous oxybromide (5.0 g, 17.4 mmol and 4-tert-butylpyridine N-oxide (0.85 g, 5.34 mmol) were dissolved in 1,2-dichloroethane (35 mL). The reaction mixture was stirred at 70° C. overnight then cooled to room temperature and slowly poured onto ice. Sodium hydroxide (50% solution in water) was added slowly until pH~10. The mixture was then extracted three times with ~100 mL dichloromethane. The organic layers were combined, dried over sodium sulfate, filtered and concentrated. The residue was absorbed on 4 g SiO$_2$ and chromatographed over 24 g SiO$_2$ with EtOAc/Hexanes (gradient: 0-10% EtOAc). All fractions containing product were combined and concentrated to give 157 mg (14%) of 2-bromo-4-tert-butyl pyridine as a colorless oil.
Step 3

In a round-bottomed flask, 2-bromo-4-tert-butylpyridine (149 mg, 0.70 mmol) was dissolved in THF (4 mL). The colorless solution was cooled to −76° C. and n-butyllithium (1.6M solution in hexanes, 0.57 mL, 0.91 mmol) was added dropwise. The brown solution was stirred at −76° C. for 30 min then tributylchlorostannane (0.23 mL, 0.85 mmol) was slowly added. The reaction mixture was stirred at −76° C. for 15 min and then warmed to room temperature and stirred for 1.5 h. The reaction mixture was quenched with saturated aqueous NH$_4$Cl and extracted with 50 mL EtOAc (2×). The combined organic layers were washed with 5 mL water and 5 mL brine then dried over sodium sulfate, filtered and concentrated. The residue was chromatographed over 24 g SiO$_2$ with EtOAc/Hexanes (gradient: 0-20% EtOAc). All fractions containing product were combined and concentrated to give 147 mg (30%, purity=60%) of 4-tert-butyl-2-(tributylstannyl)pyridine as a colorless oil.
Step 4

In a round-bottomed flask 2-bromo-5-(2-trimethylsilanyl-ethoxymethyl)-5H-pyrrolo[2,3-b]pyrazine-7-carboxylic acid [(R)-2-(4-cyano-piperidin-1-yl)-1-cyclopropyl-2-oxo-ethyl]-amide (95 mg, 0.17 mmol) and 4-tert-butyl-2-(tributylstannyl)pyridine (141 mg, 0.20 mmol) were dissolved in DMF (1.6 mL). The reaction mixture was evacuated and backfilled with Argon. Tetrakis(triphenylphosphine)palladium(0) (10 mg, 0.009 mmol) and copper (I) iodide (7 mg, 0.037 mmol) were added. The reaction mixture was stirred at 90° C. overnight. The reaction mixture was cooled to room temperature, quenched with 5 mL water and extracted with 50 mL diethyl ether (2×). The combined organic layers were washed twice with 5 mL water and once with 5 mL brine then dried over sodium sulfate, filtered and concentrated. The residue was chromatographed over 24 g SiO$_2$ with MeOH/CH$_2$Cl$_2$/0.5% NH$_4$OH (gradient: 0-2% MeOH). All fractions containing product were combined and concentrated to provide 68 mg (59%) of 2-(4-tert-butyl-pyridin-2-yl)-5-(2-trimethylsilanyl-ethoxymethyl)-5H-pyrrolo[2,3-b]pyrazine-7-carboxylic acid [(R)-2-(4-cyano-piperidin-1-yl)-1-cyclopropyl-2-oxo-ethyl]-amide.
Step 5

In a round-bottomed flask, 2-(4-tert-butyl-pyridin-2-yl)-5-(2-trimethylsilanyl-ethoxymethyl)-5H-pyrrolo[2,3-b]pyrazine-7-carboxylic acid [(R)-2-(4-cyano-piperidin-1-yl)-1-cyclopropyl-2-oxo-ethyl]-amide (62 mg, 0.091 mmol) was dissolved in dichloromethane (0.5 mL) and trifluoroacetic acid (0.28 mL) was added. The yellow reaction mixture was stirred at room temperature for 2.75 h then concentrated under reduced pressure. The residue was dissolved in dichloromethane (0.5 mL) and ethylenediamine (0.37 mL) was added. The reaction mixture was stirred at room temperature for 1.25 h then quenched with 5 mL water and extracted with EtOAc (2×). The combined organic layers were washed with 5 mL water and 5 mL brine then dried over sodium sulfate, filtered and concentrated. The residue was chromatographed over 8 g SiO₂ with MeOH/CH₂Cl₂/0.5% NH₄OH (gradient: 0-4% MeOH). All fractions containing product were combined and concentrated to afford 28 mg (61%) of 2-(4-tert-butyl-pyridin-2-yl)-5H-pyrrolo[2,3-b]pyrazine-7-carboxylic acid [(R)-2-(4-cyano-piperidin-1-yl)-1-cyclopropyl-2-oxo-ethyl]-amide as a yellow foamy solid. MS: (M+H)⁺=486.

Example 112

2-(4-Phenyl-pyridin-2-yl)-5H-pyrrolo[2,3-b]pyrazine-7-carboxylic acid [(R)-2-(4-cyano-piperidin-1-yl)-1-cyclopropyl-2-oxo-ethyl]-amide

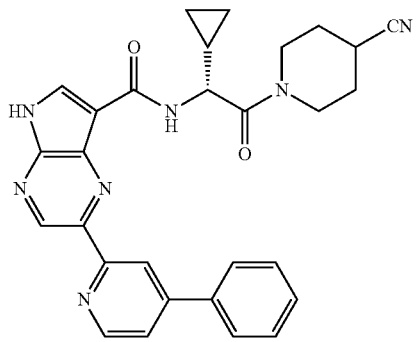 [SMILES: N#CC1CCN(C(=O)[C@H](NC(=O)c2c[nH]c3ncc(-c4cc(-c5ccccc5)ccn4)nc23)C2CC2)CC1]

Prepared according to the procedure outlined in Example 111, steps 3-5 substituting 2-bromo-4-phenylpyridine for 2-bromo-4-tert-butylpyridine. MS: (M+H)⁺=506.

Example 113

2-(4-Thiophen-2-yl-pyridin-2-yl)-5H-pyrrolo[2,3-b]pyrazine-7-carboxylic acid [(R)-2-(4-cyano-piperidin-1-yl)-1-cyclopropyl-2-oxo-ethyl]-amide

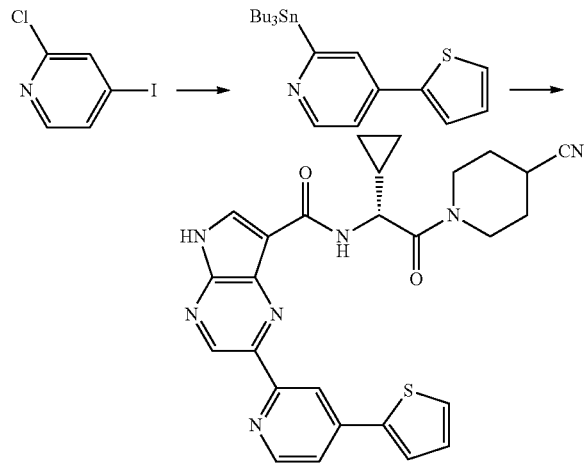

Step 1

A round-bottomed flask was charged with 2-chloro-4-iodopyridine (600 mg, 2.5 mmol), thiophen-2-ylboronic acid (385 mg, 3.0 mmol), trans-dichlorobis(triphenylphosphine) palladium (II) (176 mg, 0.251 mmol), THF (9 mL) and 2M aqueous sodium carbonate (3.0 mL, 6.0 mmol). The reaction mixture was stirred at 70° C. overnight. The reaction mixture was cooled to room temperature then diluted with 20 mL water and extracted with 100 mL EtOAc (2×). The combined organic layers were washed with 20 mL water and 20 mL brine then dried over sodium sulfate, filtered and concentrated. The residue was absorbed on ~2 g SiO₂ and chromatographed over 24 g SiO₂ with EtOAc/hexanes (gradient: 0-10% EtOAc). All fractions containing product were combined and concentrated to give 430 mg (88%) of 2-chloro-4-thiophen-2-yl-pyridine as a light yellow solid.

Step 2

A 20 mL microwave vial was charged with 2-chloro-4-thiophen-2-yl-pyridine (428 mg, 2.19 mmol), sodium iodide (3.28 g, 21.9 mmol) and acetonitrile (3.5 mL). Acetyl chloride (0.24 mL, 3.4 mmol) was added and the vial was flushed with Argon and closed. The reaction mixture was stirred at 80° C. overnight. The reaction mixture was cooled to room temperature and quenched with 10 mL saturated Na₂CO₃ solution then extracted with 50 mL dichloromethane. The organic layer was washed with 10 mL 10% Na₂S₂O₃ solution. The aqueous layers were extracted twice with 50 mL dichloromethane. The organic layers were combined, dried over sodium sulfate, filtered and concentrated. The residue was chromatographed over 24 g SiO₂ with EtOAc/hexanes (gradient: 0-10% EtOAc). All fractions containing product were combined and concentrated to afford 563 mg (90%) of 2-iodo-4-thiophen-2-yl-pyridine as a light yellow solid.

Step 3

In a round-bottomed flask, 2-iodo-4-thiophen-2-yl-pyridine (150 mg, 0.52 mmol) was dissolved in THF (3.2 mL). The light yellow solution was cooled to −16° C. (NaCl/ice bath) and isopropylmagnesium chloride (2.0M solution in THF, 0.30 mL, 0.60 mmol) was added dropwise. The reaction mixture was stirred at −16° C. for 20 min then tributylchlorostannane (0.17 mL, 0.63 mmol) was slowly added. After the addition, the reaction mixture was allowed to warm to room temperature and stirred for 1 h. The reaction mixture was quenched with saturated NH₄Cl solution and then extracted with 50 mL EtOAc (2×). The combined organic layers were washed with 5 mL water and once with 5 mL brine then dried over sodium sulfate, filtered and concentrated to afford 4-thiophen-2-yl-2-(tributylstannanyl)pyridine a light brown oil which was used without further purification.

Step 4

2-(4-Thiophen-2-yl-pyridin-2-yl)-5H-pyrrolo[2,3-b]pyrazine-7-carboxylic acid [(R)-2-(4-cyano-piperidin-1-yl)-1-cyclopropyl-2-oxo-ethyl]-amide. Prepared according to the procedure outlined in Example 111, steps 4-5 substituting 4-thiophen-2-yl-2-(tributylstannanyl)pyridine for 4-tert-butyl-2-(tributylstannyl)pyridine. MS: (M+H)+=512.

Example 114

2-Pyridin-2-yl-5H-pyrrolo[2,3-b]pyrazine-7-carboxylic acid [(R)-1-(4-cyano-piperidine-1-carbonyl)-2,2-dimethyl-propyl]-amide

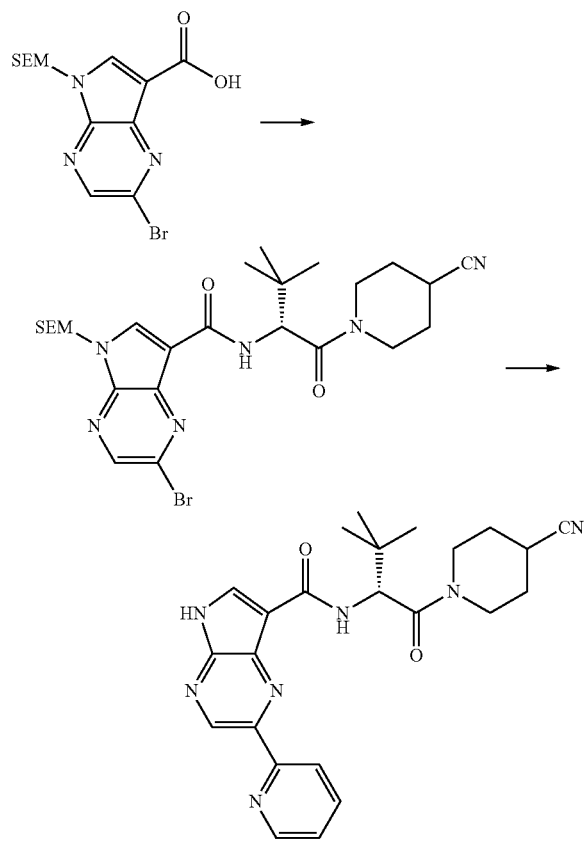

Step 1

A round-bottomed flask was charged with Boc-D-tert-leucine (2.5 g, 10.8 mmol), HOBT (4.2 g, 24.9 mmol), EDC (4.77 g, 24.9 mmol) and piperidine-4-carbonitrile (2.98 g, 27.0 mmol). Then added DMF (50 mL) followed by N,N-diisopropylethylamine (10.7 ml, 61.6 mmol). The yellow reaction mixture was stirred at room temperature overnight then quenched with 10% citric acid and extracted with EtOAc (2×). The combined organic layers were washed twice with 10% citric acid, twice with sat'd LiCl and once with brine then dried over MgSO$_4$, filtered and concentrated to give 3.4 g (97%) of [(R)-1-(4-cyano-piperidine-1-carbonyl)-2,2-dimethyl-propyl]-carbamic acid tert-butyl ester as a beige foamy solid.

Step 2

To a solution of [(R)-1-(4-cyano-piperidine-1-carbonyl)-2,2-dimethyl-propyl]-carbamic acid tert-butyl ester (3.4 g, 10.5 mmol) in CH$_2$Cl$_2$ (60 mL) was added trifluoroacetic acid (20 mL). The reaction mixture was stirred at room temperature overnight then concentrated to afford 1-((R)-2-amino-3,3-dimethyl-butyryl)-piperidine-4-carbonitrile trifluoroacetate as a light brown oil which was used without further purification.

Step 3

In a flask were combined 2-bromo-5-(2-trimethylsilanylethoxymethyl)-5H-pyrrolo[2,3-b]pyrazine-7-carboxylic acid (1.6 g, 4.3 mmol), 1-((R)-2-amino-3,3-dimethyl-butyryl)-piperidine-4-carbonitrile trifluoroacetate (crude from step 2), EDC (1.89 g, 9.9 mmol) and HOBt (1.67 g, 9.9 mmol). DMF (40 mL) was added followed by i-Pr$_2$NEt (5.2 mL, 30.1 mmol). The reaction mixture was stirred at room temperature for overnight and then concentrated. The residue was taken up in EtOAc and 10% citric acid and the organic layer washed with 10% citric acid, sat. NaHCO$_3$, sat LiCl and brine, dried over MgSO$_4$, and concentrated. The residue was purified by silica gel chromatography (40%-100% EtOAc/hexanes) to give 1.46 g (59%) of 2-bromo-5-(2-trimethylsilanyl-ethoxymethyl)-5H-pyrrolo[2,3-b]pyrazine-7-carboxylic acid [(R)-1-(4-cyano-piperidine-1-carbonyl)-2,2-dimethyl-propyl]-amide as a beige foamy solid.

Step 4

2-Pyridin-2-yl-5H-pyrrolo[2,3-b]pyrazine-7-carboxylic acid [(R)-1-(4-cyano-piperidine-1-carbonyl)-2,2-dimethyl-propyl]-amide. Prepared according to the procedure outlined in Example 111, steps 4-5 substituting 2-bromo-5-(2-trimethylsilanyl-ethoxymethyl)-5H-pyrrolo[2,3-b]pyrazine-7-carboxylic acid [(R)-1-(4-cyano-piperidine-1-carbonyl)-2,2-dimethyl-propyl]-amide for 2-bromo-5-(2-trimethylsilanyl-ethoxymethyl)-5H-pyrrolo[2,3-b]pyrazine-7-carboxylic acid [(R)-2-(4-cyano-piperidin-1-yl)-1-cyclopropyl-2-oxoethyl]-amide and 2-(tributylstannanyl)pyridine for 4-tert-butyl-2-(tributylstannyl)pyridine. MS: (M+H)+=446.

Example 115

2-(4-Trifluoromethyl-pyridin-2-yl)-5H-pyrrolo[2,3-b]pyrazine-7-carboxylic acid [(R)-1-(4-cyano-piperidine-1-carbonyl)-2,2-dimethyl-propyl]-amide

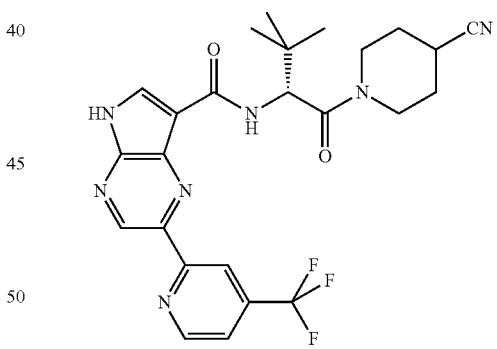

Step 1

In a microwave vial 2-bromo-4-(trifluoromethyl)pyridine (330 mg, 1.46 mmol), bis(tributylyln) (1.44 mL, 2.85 mmol), and PdCl$_2$(PPh$_3$)$_2$ (51 mg, 0.073 mmol) were suspended in 1,4-dioxane (15 mL). The mixture was degassed with a gentle stream of N$_2$ for 15 min then the vial was then sealed and heated in a microwave reactor at 140° C. for 3 h. The reaction mixture was cooled to room temperature and concentrated. The residue was purified by SiO$_2$ chromatography (5-20% EtOAc/hexane) to give 229 mg (36%) of 2-tributylstannanyl-4-trifluoromethyl-pyridine.

Step 2

2-(4-Trifluoromethyl-pyridin-2-yl)-5H-pyrrolo[2,3-b]pyrazine-7-carboxylic acid [(R)-1-(4-cyano-piperidine-1- carbonyl)-2,2-dimethyl-propyl]-amide. Prepared according to the procedure outlined in Example 111, steps 4-5 substituting 2-bromo-5-(2-trimethylsilanyl-ethoxymethyl)-5H-pyrrolo[2,3-b]pyrazine-7-carboxylic acid [(R)-1-(4-cyano-piperidine-1-carbonyl)-2,2-dimethyl-propyl]-amide for 2-bromo-5-(2-trimethylsilanyl-ethoxymethyl)-5H-pyrrolo[2,3-b]pyrazine-7-carboxylic acid [(R)-2-(4-cyano-piperidin-1-yl)-1-cyclopropyl-2-oxo-ethyl]-amide and 2-tributylstannanyl-4-trifluoromethyl-pyridine for 4-tert-butyl-2-(tributylstannyl)pyridine. MS: (M+H)+=514.

Example 116

2-(4-Methoxy-pyridin-2-yl)-5H-pyrrolo[2,3-b]pyrazine-7-carboxylic acid [(R)-1-(4-cyano-piperidine-1-carbonyl)-2,2-dimethyl-propyl]-amide

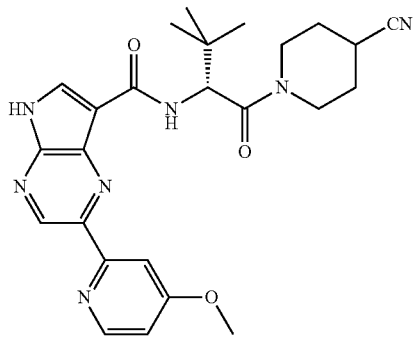 [SMILES: COc1ccnc(-c2cnc3[nH]cc(C(=O)N[C@@H](C(=O)N4CCC(C#N)CC4)C(C)(C)C)c3n2)c1]

Example 117

2-(4-Cyclopentyloxy-pyridin-2-yl)-5H-pyrrolo[2,3-b]pyrazine-7-carboxylic acid [(R)-1-(4-cyano-piperidine-1-carbonyl)-2,2-dimethyl-propyl]-amide

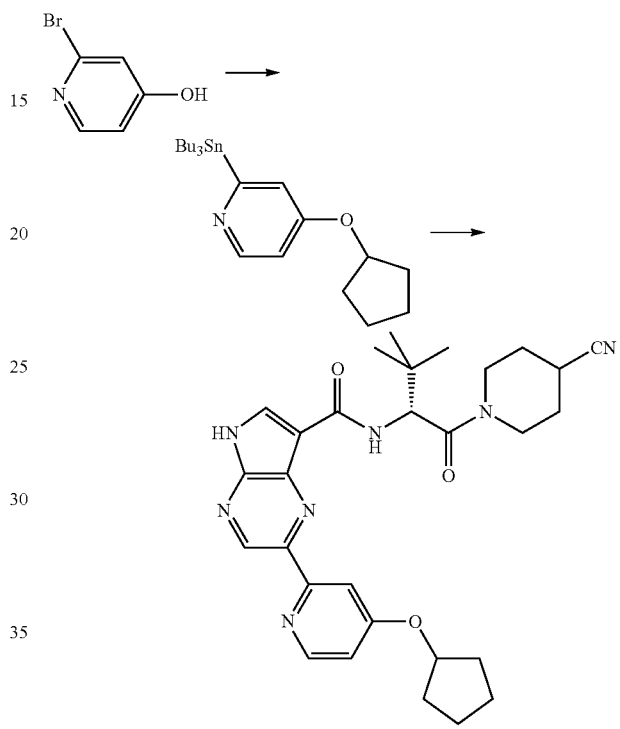

Step 1

In a round bottomed flask 2-bromo-4-methoxypyridine (315 mg, 1.68 mmol) was dissolved in THF (6 mL). The solution was cooled to 0° C. and isopropylmagnesium chloride lithium chloride complex (1.3 M in THF, 1.35 mL, 1.76 mmol) was added dropwise. The reaction mixture was stirred at 0° C. for 30 min then at room temperature for 1.5 h. An additional portion of isopropylmagnesium chloride lithium chloride complex (1.3 M in THF, 0.15 mL, 0.20 mmol) was added and stirring was continued at room temperature for 30 min. Tributyltin chloride (0.50 mL, 1.84 mmol) was added and the reaction mixture was stirred at room temperature for 2 h. The reaction mixture was concentrated to give 4-methoxy-2-tributylstannanyl-pyridine as a white paste which was used without further purification.

Step 2

2-(4-Methoxy-pyridin-2-yl)-5H-pyrrolo[2,3-b]pyrazine-7-carboxylic acid [(R)-1-(4-cyano-piperidine-1-carbonyl)-2,2-dimethyl-propyl]-amide. Prepared according to the procedure outlined in Example 111, steps 4-5 substituting 2-bromo-5-(2-trimethylsilanyl-ethoxymethyl)-5H-pyrrolo[2,3-b]pyrazine-7-carboxylic acid [(R)-1-(4-cyano-piperidine-1-carbonyl)-2,2-dimethyl-propyl]-amide for 2-bromo-5-(2-trimethylsilanyl-ethoxymethyl)-5H-pyrrolo[2,3-b]pyrazine-7-carboxylic acid [(R)-2-(4-cyano-piperidin-1-yl)-1-cyclopropyl-2-oxo-ethyl]-amide and 4-methoxy-2-tributylstannanyl-pyridine for 4-tert-butyl-2-(tributylstannyl)pyridine. MS: (M+H)+=476.

Step 1

To a solution of 2-bromopyridin-4-ol (1.6 g, 9.2 mmol) and bromocyclopentane (1.28 mL, 12.0 mmol) in DMF (12 mL) in a microwave vial was added cesium carbonate (4.19 g, 12.9 mmol). The vial was sealed and heated in a microwave reactor at 120° C. for 2 h. The reaction mixture was cooled to room temperature, quenched with water and extracted with EtOAc (3×). The combined organics were washed with sat'd LiCl and sat'd NaCl then dried over MgSO4 and concentrated. The residue was purified by SiO2 chromatography (20-30% EtOAc/heptane) to give 1.83 g (73%) of 2-bromo-4-cyclopentyloxy-pyridine as a yellow oil.

Step 2

In a round bottomed flask 2-bromo-4-cyclopentyloxy-pyridine (339 mg, 1.40 mmol) was dissolved in THF (6 mL). The solution was cooled to 0° C. and isopropylmagnesium chloride lithium chloride complex (1.3 M in THF, 1.1 mL, 1.47 mmol) was added dropwise. The reaction mixture was stirred at 0° C. for 15 min then at room temperature for 2 h. An additional portion of isopropylmagnesium chloride lithium chloride complex (1.3 M in THF, 0.27 mL, 0.35 mmol) was added and stirring was continued at room temperature for 30 min. Tributyltin chloride (0.42 mL, 1.54 mmol) was added and the reaction mixture was stirred at room temperature for 2 h. The reaction mixture was quenched with water and extracted with ethyl acetate. The organic phase was washed with brine, dried over MgSO4 and concentrated to give 4-cyclopentyloxy-2-tributylstannanyl-pyridine as a light brown oil which was used without further purification.

Step 3

2-(4-Cyclopentyloxy-pyridin-2-yl)-5H-pyrrolo[2,3-b]pyrazine-7-carboxylic acid [(R)-1-(4-cyano-piperidine-1-carbonyl)-2,2-dimethyl-propyl]-amide. Prepared according to the procedure outlined in Example 111, steps 4-5 substituting 2-bromo-5-(2-trimethylsilanyl-ethoxymethyl)-5H-pyrrolo[2,3-b]pyrazine-7-carboxylic acid [(R)-1-(4-cyano-piperidine-1-carbonyl)-2,2-dimethyl-propyl]-amide for 2-bromo-5-(2-trimethylsilanyl-ethoxymethyl)-5H-pyrrolo[2,3-b]pyrazine-7-carboxylic acid [(R)-2-(4-cyano-piperidin-1-yl)-1-cyclopropyl-2-oxo-ethyl]-amide and 4-cyclopentyloxy-2-tributylstannanyl-pyridine for 4-tert-butyl-2-(tributylstannyl)pyridine. MS: (M+H)$^+$=530.

Example 118

2-(4-Cyclopropylmethoxy-pyridin-2-yl)-5H-pyrrolo[2,3-b]pyrazine-7-carboxylic acid [(R)-2-(4-cyano-piperidin-1-yl)-1-cyclopropyl-2-oxo-ethyl]-amide

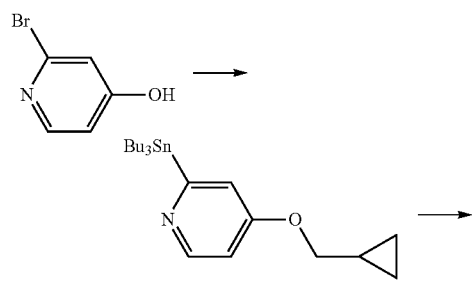

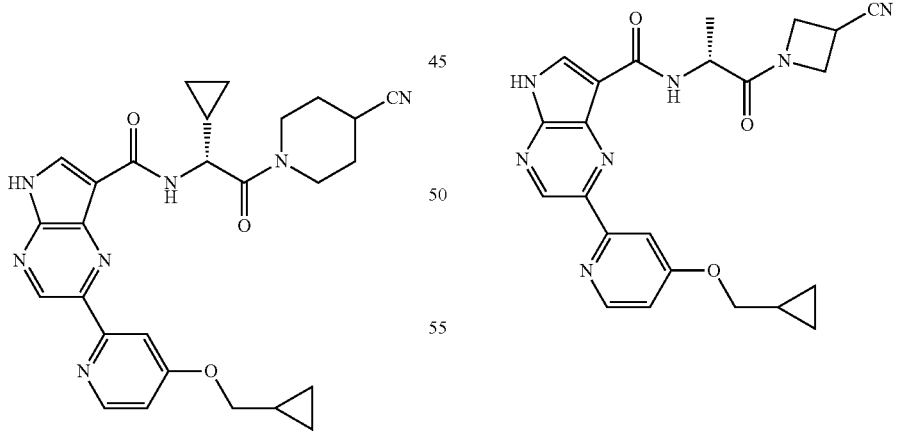

Step 1

To a solution of 2-bromopyridin-4-ol (1.6 g, 9.2 mmol) and (bromomethyl)cyclopropane (1.61 g, 12.0 mmol) in DMF (12 mL) in a microwave vial was added cesium carbonate (4.19 g, 12.9 mmol). The vial was sealed and heated in a microwave reactor at 120° C. for 4 h. The reaction mixture was cooled to room temperature, quenched with water and extracted with EtOAc (2×). The combined organics were washed with sat'd NaCl then dried over MgSO$_4$ and concentrated. The residue was purified by SiO$_2$ chromatography (20-50% EtOAc/heptane) to give 1.45 g (69%) of 2-bromo-4-cyclopropylmethoxy-pyridine as a yellow oil.

Step 2

In a round bottomed flask 2-bromo-4-cyclopropylmethoxy-pyridine (315 mg, 1.38 mmol) was dissolved in THF (6 mL). The solution was cooled to 0° C. and isopropylmagnesium chloride lithium chloride complex (1.3 M in THF, 1.1 mL, 1.45 mmol) was added dropwise. The reaction mixture was stirred at 0° C. for 30 min then at room temperature for 1.5 h. Tributyltin chloride (0.42 mL, 1.52 mmol) was added and the reaction mixture was stirred at room temperature for 2 h. The reaction mixture was quenched with water and extracted with ethyl acetate. The organic phase was washed with brine, dried over MgSO$_4$ and concentrated to give 4-cyclopropylmethoxy-2-tributylstannanyl-pyridine as a yellow oil which was used without further purification.

Step 3

2-(4-Cyclopropylmethoxy-pyridin-2-yl)-5H-pyrrolo[2,3-1)]pyrazine-7-carboxylic acid [(R)-2-(4-cyano-piperidin-1-yl)-1-cyclopropyl-2-oxo-ethyl]-amide. Prepared according to the procedure outlined in Example 111, steps 4-5 substituting 4-cyclopropylmethoxy-2-tributylstannanyl-pyridine for 4-tert-butyl-2-(tributylstannyl)pyridine. MS: (M+H)$^+$=500.

Example 119

2-(4-Cyclopropylmethoxy-pyridin-2-yl)-5H-pyrrolo[2,3-b]pyrazine-7-carboxylic acid [(R)-2-(3-cyano-azetidin-1-yl)-1-methyl-2-oxo-ethyl]-amide Prepared according to the procedure outlined in Example 111, steps 4-5 substituting 2-bromo-5-(2-trimethylsilanyl-ethoxymethyl)-5H-pyrrolo[2,3-b]pyrazine-7-carboxylic acid [(R)-2-(3-cyano-azetidin-1-yl)-1-methyl-2-oxo-ethyl]-amide for 2-bromo-5-(2-trimethylsilanyl-ethoxymethyl)-5H-pyrrolo[2,3-b]pyrazine-7-carboxylic acid [(R)-2-(4-cyano-piperidin-1-yl)-1-cyclopropyl-2-oxo-ethyl]-amide and 4-cyclopropylmethoxy-2-tributylstannanyl-pyridine for 4-tert-butyl-2-(tributylstannyl)pyridine. MS: (M+H)⁺=446.

tributylstannanyl-pyridine for 4-tert-butyl-2-(tributylstannyl)pyridine. MS: (M+H)⁺=442.

Example 120

2-(4-Pyrazol-1-yl-pyridin-2-yl)-5H-pyrrolo[2,3-b]pyrazine-7-carboxylic acid [(R)-2-(3-cyano-azetidin-1-yl)-1-methyl-2-oxo-ethyl]-amide

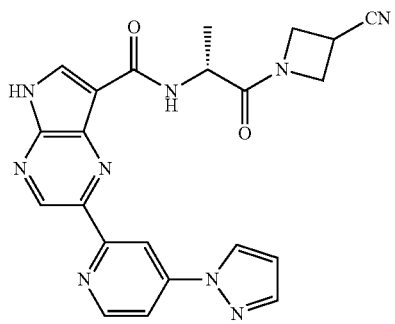 [SMILES: C[C@@H](NC(=O)c1c[nH]c2ncc(-c3cc(-n4cccn4)ccn3)nc12)C(=O)N1CC(C#N)C1]

Example 121

2-(4-Pyrrol-1-yl-pyridin-2-yl)-5H-pyrrolo[2,3-b]pyrazine-7-carboxylic acid [(R)-2-(3-cyano-azetidin-1-yl)-1-methyl-2-oxo-ethyl]-amide

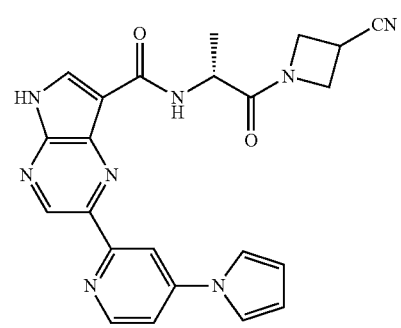 [SMILES: C[C@@H](NC(=O)c1c[nH]c2ncc(-c3cc(-n4cccc4)ccn3)nc12)C(=O)N1CC(C#N)C1]

Step 1

In a round-bottomed flask, 2-bromo-4-(1H-pyrazol-1-yl)pyridine (0.15 g, 0.67 mmol) was dissolved in THF (4.4 mL). The light yellow solution was cooled to 0° C. and isopropylmagnesium chloride lithium chloride complex (1.3 M solution in THF, 0.57 mL, 0.74 mmol) was added dropwise. The reaction mixture was stirred at 0° C. for 25 min and at room temperature for 1.5 h. Additional isopropylmagnesium chloride lithium chloride complex (1.3 M solution in THF, 0.29 mL, 0.38 mmol) was added and the reaction mixture was stirred at room temperature for 30 min. The reaction mixture was cooled to 0° C. and tributyltin chloride (0.21 mL, 0.77 mmol) was slowly added. After the addition was complete, the ice bath was removed and the reaction mixture was stirred at room temperature for 1 h. The reaction mixture was quenched with saturated NH₄Cl solution and then extracted with 50 mL EtOAc (2×). The combined organic layers were washed with ~5 mL water and ~5 mL brine then dried over sodium sulfate, filtered and concentrated to provide 4-pyrazol-1-yl-2-tributylstannanyl-pyridine as a light brown oil which was used without further purification.

Step 2

2-(4-Pyrazol-1-yl-pyridin-2-yl)-5H-pyrrolo[2,3-b]pyrazine-7-carboxylic acid [(R)-2-(3-cyano-azetidin-1-yl)-1-methyl-2-oxo-ethyl]-amide. Prepared according to the procedure outlined in Example 111, steps 4-5 substituting 2-bromo-5-(2-trimethylsilanyl-ethoxymethyl)-5H-pyrrolo[2,3-b]pyrazine-7-carboxylic acid [(R)-2-(3-cyano-azetidin-1-yl)-1-methyl-2-oxo-ethyl]-amide for 2-bromo-5-(2-trimethylsilanyl-ethoxymethyl)-5H-pyrrolo[2,3-b]pyrazine-7-carboxylic acid [(R)-2-(4-cyano-piperidin-1-yl)-1-cyclopropyl-2-oxo-ethyl]-amide and 4-pyrazol-1-yl-2-

Step 1

In a round-bottomed flask, 2-bromo-4-(1H-pyrrol-1-yl)pyridine (0.20 g, 0.90 mmol) was dissolved in THF (6 mL). The light yellow solution was cooled to 0° C. and isopropylmagnesium chloride lithium chloride complex (1.3 M solution in THF, 0.78 mL, 1.0 mmol) was added dropwise. The reaction mixture was stirred at 0° C. for 40 min and at room temperature for 2 h. The reaction mixture was cooled to 0° C. and tributyltin chloride (0.28 mL, 1.03 mmol) was slowly added. After the addition was complete, the ice bath was removed and the reaction mixture was stirred at room temperature for 1.5 h. The reaction mixture was quenched with saturated NH₄Cl solution and then extracted with 50 mL EtOAc (2×). The combined organic layers were washed with ~5 mL water and ~5 mL brine then dried over sodium sulfate, filtered and concentrated to provide 4-pyrrol-1-yl-2-tributylstannanyl-pyridine as a light brown oil which was used without further purification.

Step 2

2-(4-Pyrrol-1-yl-pyridin-2-yl)-5H-pyrrolo[2,3-b]pyrazine-7-carboxylic acid [(R)-2-(3-cyano-azetidin-1-yl)-1-methyl-2-oxo-ethyl]-amide. Prepared according to the procedure outlined in Example 111, steps 4-5 substituting 2-bromo-5-(2-trimethylsilanyl-ethoxymethyl)-5H-pyrrolo[2,3-b]pyrazine-7-carboxylic acid [(R)-2-(3-cyano-azetidin-1-yl)-1-methyl-2-oxo-ethyl]-amide for 2-bromo-5-(2-trimethylsilanyl-ethoxymethyl)-5H-pyrrolo[2,3-b]pyrazine-7-carboxylic acid [(R)-2-(4-cyano-piperidin-1-yl)-1-cyclopropyl-2-oxo-ethyl]-amide and 4-pyrrol-1-yl-2-

Example 122

2-(4-Cyclopent-1-enyl-pyridin-2-yl)-5H-pyrrolo[2,3-b]pyrazine-7-carboxylic acid [(R)-2-(3-cyano-azetidin-1-yl)-1-methyl-2-oxo-ethyl]-amide

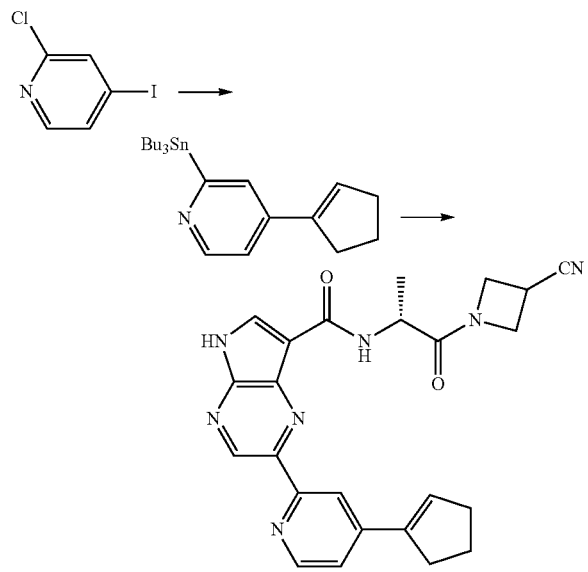

Step 1

To a solution of 2-cyclopentenyl-4,4,5,5-tetramethyl-1,3,2-dioxaborolane (681 mg, 3.51 mmol) and 2-chloro-4-iodopyridine (700 mg, 2.92 mmol) in 1,4-dioxane (12 mL) was added 2.0 M aqueous $Na_2CO_3$ (4.39 mL, 8.77 mmol) and tetrakis(triphenylphosphine)palladium(0) (67.6 mg, 0.059 mmol). The reaction mixture was heated at 90° C. for 3.5 h then cooled to room temperature, diluted with water and extracted with EtOAc (2×). The combined organics were dried over $MgSO_4$ and concentrated. The residue was purified by silica gel chromatography (0% to 10% EtOAc/hexanes) to afford 450 mg (86%) of 2-chloro-4-cyclopent-1-enyl-pyridine as a white solid.

Step 2

A flask was charged with sodium iodide (3.75 g, 25.0 mmol), 2-chloro-4-cyclopent-1-enyl-pyridine (450 mg, 2.5 mmol) and acetonitrile (8 mL). Acetyl chloride (0.27 mL, 3.76 mmol) was slowly added and the reaction mixture was heated at reflux overnight. The reaction mixture was cooled to room temperature and quenched with water. Saturated $Na_2CO_3$ and 10% $Na_2S_2O_3$ were added and the mixture was extracted with EtOAc (3×). The combined organics were dried over $MgSO_4$ and concentrated. The residue was purified by chromatography (0% to 10% EtOAc/hexanes) to afford 2-iodo-4-cyclopent-1-enyl-pyridine as a white solid.

Step 3

To a solution of 2-iodo-4-cyclopent-1-enyl-pyridine (150 mg, 0.55 mmol) in THF (3 mL) at −78° C. was added n-BuLi (1.6 M in hexanes, 0.38 mL, 0.61 mmol). The resulting deep orange-brown solution was stirred at −78° C. for 15 min then tributylchlorostannane (0.17 mL, 61 mmol) was added dropwise. The reaction mixture was stirred at −78° C. for 30 min then warmed to room temperature over 30 min, quenched with water and extracted with EtOAc (2×). The combined organics were dried over $MgSO_4$ and concentrated to provide 4-cyclopent-1-enyl-2-tributylstannanyl-pyridine as an orange oil which was used without further purification.

Step 4

2-(4-Cyclopent-1-enyl-pyridin-2-yl)-5H-pyrrolo[2,3-b]pyrazine-7-carboxylic acid [(R)-2-(3-cyano-azetidin-1-yl)-1-methyl-2-oxo-ethyl]-amide. Prepared according to the procedure outlined in Example 111, steps 4-5 substituting 2-bromo-5-(2-trimethylsilanyl-ethoxymethyl)-5H-pyrrolo[2,3-b]pyrazine-7-carboxylic acid [(R)-2-(3-cyano-azetidin-1-yl)-1-methyl-2-oxo-ethyl]-amide for 2-bromo-5-(2-trimethylsilanyl-ethoxymethyl)-5H-pyrrolo[2,3-b]pyrazine-7-carboxylic acid [(R)-2-(4-cyano-piperidin-1-yl)-1-cyclopropyl-2-oxo-ethyl]-amide and 4-cyclopent-1-enyl-2-tributylstannanyl-pyridine for 4-tert-butyl-2-(tributylstannyl)pyridine. MS: $(M+H)^+=442$.

Example 123

2-(3-Pyrrolidin-1-yl-phenyl)-5H-pyrrolo[2,3-b]pyrazine-7-carboxylic acid [(R)-2-(3-cyano-azetidin-1-yl)-1-methyl-2-oxo-ethyl]-amide

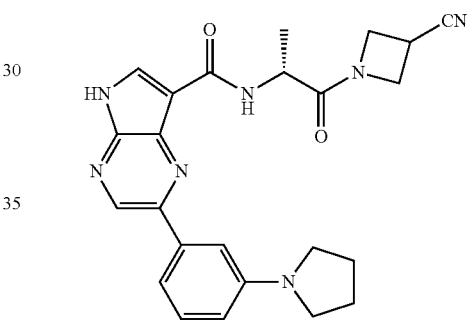

Prepared according to the procedure outlined in Example 108, steps 4-5 substituting 3-(pyrrolidin-1-yl)phenylboronic acid hydrochloride for 3,4,5-trimethoxyphenylboronic acid. MS: $(M+H)^+=444$.

Example 124

2-(1-Cyclopentyl-1H-[1,2,3]triazol-4-yl)-5H-pyrrolo[2,3-b]pyrazine-7-carboxylic acid [(R)-2-(4-cyano-piperidin-1-yl)-1-cyclopropyl-2-oxo-ethyl]-amide

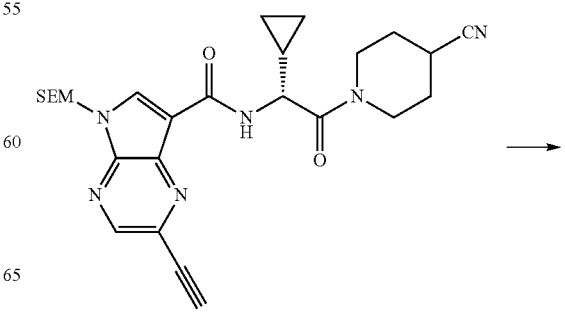

-continued

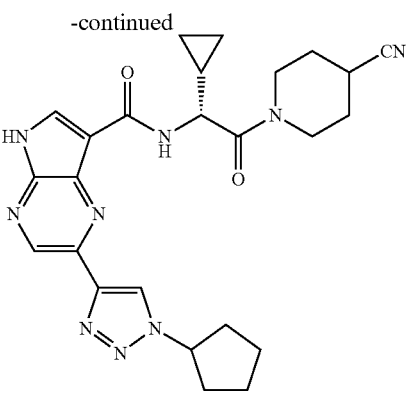

Step 1

To a solution of 2-bromo-5-(2-trimethylsilanyl-ethoxymethyl)-5H-pyrrolo[2,3-b]pyrazine-7-carboxylic acid [(R)-2-(4-cyano-piperidin-1-yl)-1-cyclopropyl-2-oxo-ethyl]-amide (0.50 g, 0.89 mmol) (5:1 mix of 5-Br and 5-Cl) in DMF (3 mL) were added sequentially triethylamine (0.50 mL, 3.56 mmol), ethynyltrimethylsilane (0.15 mL, 1.07 mmol), Pd(PPh$_3$)$_2$Cl$_2$ (31.2 mg, 0.045 mmol), and copper (I) iodide (8.5 mg, 0.045 mmol). Upon the addition of CuI all solids dissolved. The reaction mixture was stirred at room temperature for 30 min then heated at 50° C. for 1 h. The reaction mixture was cooled to room temperature, quenched with water and extracted with EtOAc (3×). The combined organics were washed with water (3×) and brine then dried over MgSO$_4$ and concentrated. The residue was purified by silica gel chromatography (50% to 100% EtOAc/hexanes) to isolate 430 mg (83%) of 5-(2-trimethylsilanyl-ethoxymethyl)-2-trimethylsilanylethynyl-5H-pyrrolo[2,3-b]pyrazine-7-carboxylic acid [(R)-2-(4-cyano-piperidin-1-yl)-1-cyclopropyl-2-oxo-ethyl]-amide as a brown foamy solid. NMR showed a trace of unreacted 5-Cl pyrrolopyrazine present.

Step 2

To a solution of 5-(2-trimethylsilanyl-ethoxymethyl)-2-trimethylsilanylethynyl-5H-pyrrolo[2,3-b]pyrazine-7-carboxylic acid [(R)-2-(4-cyano-piperidin-1-yl)-1-cyclopropyl-2-oxo-ethyl]-amide (400 mg, 0.69 mmol) in MeOH (8 mL) at room temp was added K$_2$CO$_3$ (10 mg, 0.072 mmol). The reaction mixture was stirred at room temp for 30 min then concentrated. The residue was dissolved in CH$_2$Cl$_2$ and washed with water. The organic layer was dried over MgSO$_4$ and concentrated. The residue was purified by silica gel chromatography (50% to 100% EtOAc/hexanes) to afford 310 mg (89%) of 2-ethynyl-5-(2-trimethylsilanyl-ethoxymethyl)-5H-pyrrolo[2,3-b]pyrazine-7-carboxylic acid [(R)-2-(4-cyano-piperidin-1-yl)-1-cyclopropyl-2-oxo-ethyl]-amide as a light brown foamy solid. NMR showed a trace of 5-Cl pyrrolopyrazine present.

Step 3

Azidocyclopentane was prepared according to the procedure outlined in *Synthesis* 1997, 413: To a solution of bromocyclopentane (0.40 g, 2.68 mmol) in DMSO (6 mL) at room temp was added solid sodium azide (192 mg, 2.95 mmol) with stirring. The sodium azide gradually dissolved over about 1 h. The reaction mixture was stirred at room temp overnight then quenched with water and extracted with Et2O (2×). The combined organics were washed with water (3×) then dried over MgSO$_4$ and carefully concentrated at 300 torr and ambient temperature to afford azidocyclopentane as a colorless oil which was used without further purification.

Step 4

A microwave vial was charged with 2-ethynyl-5-(2-trimethylsilanyl-ethoxymethyl)-5H-pyrrolo[2,3-b]pyrazine-7-carboxylic acid [(R)-2-(4-cyano-piperidin-1-yl)-1-cyclopropyl-2-oxo-ethyl]-amide (100 mg, 0.20 mmol), azidocyclopentane (32.9 mg, 0.3 mmol), t-BuOH (0.6 mL), and H$_2$O (0.6 mL). To this sticky mixture was added 1.0 M aqueous copper (II) sulfate (39.5 µL, 0.04 mmol) and copper powder (10.0 mg, 0.16 mmol). The vial was sealed and the heterogeneous reaction mixture was heated in a microwave reactor at 125° C. for 5 min. The reaction mixture was cooled to room temperature and filtered, rinsing with EtOAc. The filtrate was washed with water, dried over MgSO$_4$, and concentrated. The residue was purified by silica gel chromatography (50% to 100% EtOAc/hexanes) to afford 85 mg (70%) of 2-(1-cyclopentyl-1H-[1,2,3]triazol-4-yl)-5-(2-trimethylsilanyl-ethoxymethyl)-5H-pyrrolo[2,3-b]pyrazine-7-carboxylic acid [(R)-2-(4-cyano-piperidin-1-yl)-1-cyclopropyl-2-oxo-ethyl]-amide as an off-white foamy solid.

Step 5

To a solution of 2-(1-cyclopentyl-1H-[1,2,3]triazol-4-yl)-5-(2-trimethylsilanyl-ethoxymethyl)-5H-pyrrolo[2,3-b]pyrazine-7-carboxylic acid [(R)-2-(4-cyano-piperidin-1-yl)-1-cyclopropyl-2-oxo-ethyl]-amide (85 mg, 0.14 mmol) in CH$_2$Cl$_2$ (4 mL) was added TFA (2.0 mL). The reaction mixture was stirred at room temp for 3 h then concentrated. The residue was redissolved in CH$_2$Cl$_2$ (4 mL) and ethylenediamine (0.5 mL) was added. The reaction mixture was stirred at room temp for 0.5 h then concentrated. The residue was purified twice by silica gel chromatography (50% to 100% EtOAc/hexanes to 5% MeOH/EtOAc then 0% to 5% MeOH/CH$_2$Cl$_2$ (0.5% NH$_4$OH)) then triturated with Et$_2$O to isolate 35 mg (52%) of 2-(1-cyclopentyl-1H-[1,2,3]triazol-4-yl)-5H-pyrrolo[2,3-b]pyrazine-7-carboxylic acid [(R)-2-(4-cyano-piperidin-1-yl)-1-cyclopropyl-2-oxo-ethyl]-amide as a white powder. MS: (M+H)$^+$=488.

Example 125

2-(1-Phenyl-1H-[1,2,3]triazol-4-yl)-5H-pyrrolo[2,3-b]pyrazine-7-carboxylic acid [(R)-2-(4-cyano-piperidin-1-yl)-1-cyclopropyl-2-oxo-ethyl]-amide

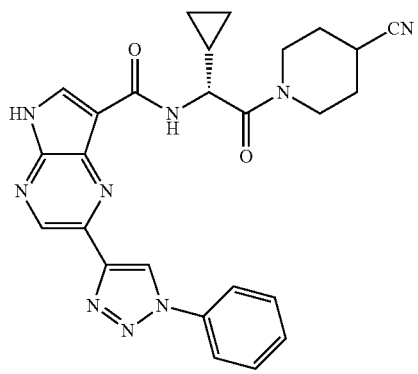 [SMILES: N#CC1CCN(C(=O)[C@H](NC(=O)c2c[nH]c3ncc(-c4cn(-c5ccccc5)nn4)nc23)C2CC2)CC1]

Step 1

To a solution of aniline (300 mg, 3.22 mmol) in water (2 mL) and conc. HCl (1 mL) at 0° C. was slowly added a solution of sodium nitrite (289 mg, 4.19 mmol) in water (1 mL). The reaction mixture was stirred at 0° C. for 10 min then a solution of sodium azide (251 mg, 3.87 mmol) in water (1 mL) was slowly added. The reaction mixture was stirred at room temp for 1 h then extracted with Et₂O (2×). The combined organics were washed with water, dried over MgSO₄, and carefully concentrated at 300 torr and ambient temperature to afford 350 mg (91%) of azidobenzene as a light orange oil.

Step 2

2-(1-Phenyl-1H-[1,2,3]triazol-4-yl)-5H-pyrrolo[2,3-b]pyrazine-7-carboxylic acid [(R)-2-(4-cyano-piperidin-1-yl)-1-cyclopropyl-2-oxo-ethyl]-amide. Prepared according to the procedure outlined in Example 124, steps 4-5 substituting azidobenzene for azidocyclopentane. MS: (M+H)⁺=496.

Example 126

2-(3-Methylcarbamoyl-phenyl)-5H-pyrrolo[2,3-b]pyrazine-7-carboxylic acid [(R)-2-(3-cyano-azetidin-1-yl)-1-methyl-2-oxo-ethyl]-amide

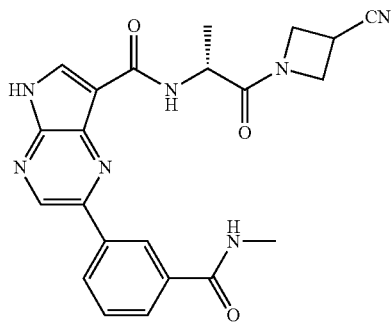 [SMILES: CNC(=O)c1cccc(-c2cnc3[nH]cc(C(=O)N[C@H](C)C(=O)N4CC(C#N)C4)c3n2)c1]

Prepared according to the procedure outlined in Example 108, steps 4-5 substituting 3-(methylcarbamoyl)phenylboronic acid for 3,4,5-trimethoxyphenylboronic acid. MS: (M+H)⁺=432.

Example 127

2-(3-Isopropylcarbamoyl-phenyl)-5H-pyrrolo[2,3-b]pyrazine-7-carboxylic acid [(R)-2-(3-cyano-azetidin-1-yl)-1-methyl-2-oxo-ethyl]-amide

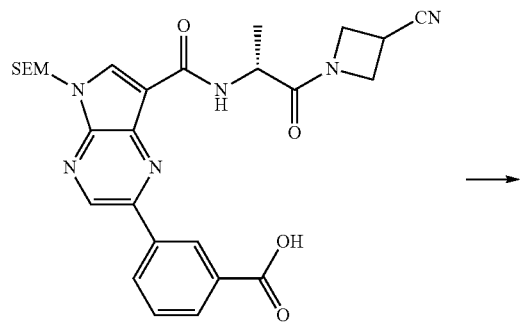

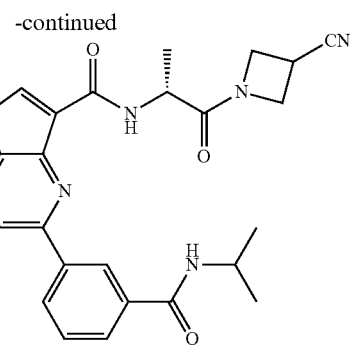

Step 1

To a solution of 2-bromo-5-(2-trimethylsilanyl-ethoxymethyl)-5H-pyrrolo[2,3-b]pyrazine-7-carboxylic acid [(R)-2-(3-cyano-azetidin-1-yl)-1-methyl-2-oxo-ethyl]-amide (200 mg, 0.39 mmol) (approx 3:1 mix of 5-Br & 5-Cl) and 3-carboxyphenylboronic acid (85.0 mg, 0.51 mmol) in 1,2-DME (4 mL) were added Pd(Ph₃P)₄ (22.8 mg, 0.02 mmol) and 2.0 M aqueous Na₂CO₃ (0.8 mL, 1.6 mmol). The reaction mixture was heated at 90° C. overnight then cooled to room temp and diluted with water. The pH was adjusted to 6 with 1.0 M HCl before extracting with EtOAc (2×). The combined organics were dried over MgSO₄ and concentrated. The residue was purified by silica gel chromatography (0% to 4% MeOH/CH₂Cl₂ (0.5% NH4OH)) to afford 145 mg (67%) of 3-[7-[(R)-2-(3-cyano-azetidin-1-yl)-1-methyl-2-oxo-ethylcarbamoyl]-5-(2-trimethylsilanyl-ethoxymethyl)-5H-pyrrolo[2,3-b]pyrazin-2-yl]-benzoic acid as a white foamy solid.

Step 2

To a solution of 3-[7-[(R)-2-(3-cyano-azetidin-1-yl)-1-methyl-2-oxo-ethylcarbamoyl]-5-(2-trimethylsilanyl-ethoxymethyl)-5H-pyrrolo[2,3-b]pyrazin-2-yl]-benzoic acid (70 mg, 0.13 mmol) and HATU (53.4 mg, 0.14 mmol) in DMF (1.5 mL) was added isopropylamine (44 µL, 0.51 mmol). The reaction mixture was stirred at room temp for 4 h then quenched with water and extracted with EtOAc (2×). The combined organics were washed with water (3×) and brine then dried over MgSO₄ and concentrated. The residue was chromatographed with 50% to 100% EtOAc/hexanes to isolate 52 mg (69%) of 2-(3-isopropylcarbamoyl-phenyl)-5-(2-trimethylsilanyl-ethoxymethyl)-5H-pyrrolo[2,3-b]pyrazine-7-carboxylic acid [(R)-2-(3-cyano-azetidin-1-yl)-1-methyl-2-oxo-ethyl]-amide as an off-white foamy solid.

Step 3

To a solution of 2-(3-isopropylcarbamoyl-phenyl)-5-(2-trimethylsilanyl-ethoxymethyl)-5H-pyrrolo[2,3-b]pyrazine-7-carboxylic acid [(R)-2-(3-cyano-azetidin-1-yl)-1-methyl-2-oxo-ethyl]-amide (52 mg, 0.088 mmol) in CH₂Cl₂ (4 mL) was added TFA (1.5 mL). The reaction mixture was stirred at room temp for 3 h then concentrated. The residue was redissolved in CH₂Cl₂ (4 mL) and ethylenediamine (0.5 mL) was added. The reaction mixture was stirred at room temp for 0.5 h then concentrated. The residue was purified by silica gel chromatography (50% to 100% EtOAc/hexanes to 5% MeOH) then triturated with Et₂O to isolate 30 mg (70%) of 2-(3-isopropylcarbamoyl-phenyl)-5H-pyrrolo[2,3-b]pyrazine-7-carboxylic acid [(R)-2-(3-cyano-azetidin-1-yl)-1-methyl-2-oxo-ethyl]-amide as a white powder. MS: (M+H)⁺= 460.

Example 128

2-[3-(Cyclopropylmethyl-carbamoyl)-phenyl]-5H-pyrrolo[2,3-b]pyrazine-7-carboxylic acid [(R)-2-(3-cyano-azetidin-1-yl)-1-methyl-2-oxo-ethyl]-amide

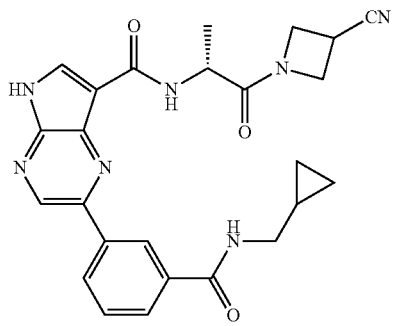 [SMILES: C[C@@H](NC(=O)c1c[nH]c2ncc(-c3cccc(C(=O)NCC4CC4)c3)nc12)C(=O)N1CC(C#N)C1]

Prepared according to the procedure outlined in Example 127, steps 2-3 substituting cyclopropylmethylamine for isopropylamine. MS: (M+H)⁺=472.

Example 129

2-(4-Methylcarbamoyl-pyridin-2-yl)-5H-pyrrolo[2,3-b]pyrazine-7-carboxylic acid [(R)-2-(3-cyano-azetidin-1-yl)-1-methyl-2-oxo-ethyl]-amide

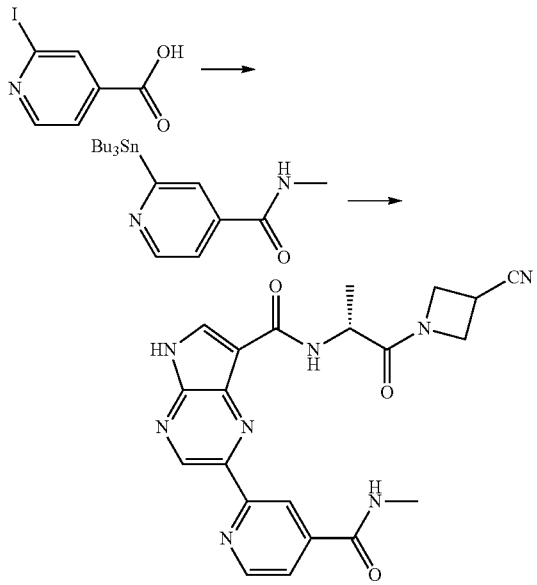

Step 1

A round-bottomed flask was charged with 2-iodoisonicotinic acid (0.70 g, 2.81 mmol), HOBt (474 mg, 3.09 mmol) and EDC (593 mg, 3.09 mmol). DMF (4 mL) was added followed by methylamine (2.0M solution in THF, 8.0 mL, 16.0 mmol) and the resultant suspension was stirred at room temperature overnight. The reaction mixture was quenched with water and extracted with 70 mL diethyl ether (2×). The combined organic layers were washed twice with ~5 mL water and once with ~5 mL brine then dried over sodium sulfate, filtered and concentrated. The residue was chromatographed over 24 g silica gel with EtOAc/Hexanes (gradient: 0-60% EtOAc). All fractions containing product were combined and concentrated to give 410 mg (56%) of 2-iodo-N-methyl-isonicotinamide as a white solid.

Step 2

In a round-bottomed flask, 2-iodo-N-methylisonicotinamide (0.18 g, 0.69 mmol) was dissolved in THF (3.9 mL) and sodium hydride (60% dispersion in mineral oil, 33 mg, 0.83 mmol) was added. The reaction mixture was stirred at room temperature for 10 min then cooled to −16° C. (NaCl/ice bath) and isopropylmagnesium chloride (2.0M solution in THF, 0.39 mL, 0.780 mmol) was added dropwise. The reaction mixture was stirred at −16° C. for 40 min then tributylchlorostannane (0.22 mL, 0.81 mmol) was slowly added. The reaction mixture was allowed to warm to room temperature and stirred for 2 h then quenched with saturated NH₄Cl solution and then extracted with 50 mL EtOAc (2×). The combined organic layers were washed with 5 mL water and 5 mL brine then dried over sodium sulfate, filtered and concentrated. The residue was chromatographed over 12 g silica gel with EtOAc/Hexanes (contains 1% Triethylamine) (gradient: 0-30% EtOAc). All fractions containing product were combined and concentrated to afford 89 mg (31%) of N-methyl-2-tributylstannanyl-isonicotinamide as a colorless oil.

Step 3

2-(4-Methylcarbamoyl-pyridin-2-yl)-5H-pyrrolo[2,3-b]pyrazine-7-carboxylic acid [(R)-2-(3-cyano-azetidin-1-yl)-1-methyl-2-oxo-ethyl]-amide. Prepared according to the procedure outlined in Example 111, steps 4-5 substituting 2-bromo-5-(2-trimethylsilanyl-ethoxymethyl)-5H-pyrrolo[2,3-b]pyrazine-7-carboxylic acid [(R)-2-(3-cyano-azetidin-1-yl)-1-methyl-2-oxo-ethyl]-amide for 2-bromo-5-(2-trimethylsilanyl-ethoxymethyl)-5H-pyrrolo[2,3-b]pyrazine-7-carboxylic acid [(R)-2-(4-cyano-piperidin-1-yl)-1-cyclopropyl-2-oxo-ethyl]-amide and N-methyl-2-tributylstannanyl-isonicotinamide for 4-tert-butyl-2-(tributylstannyl)pyridine. MS: (M+H)⁺=433.

Example 130

2-[1-(4-Fluorophenyl)-1H-pyrazol-4-yl]-5H-pyrrolo[2,3-b]pyrazine-7-carboxylic acid [(R)-1-(4-cyano-piperidine-1-carbonyl)-2,2-dimethyl-propyl]-amide

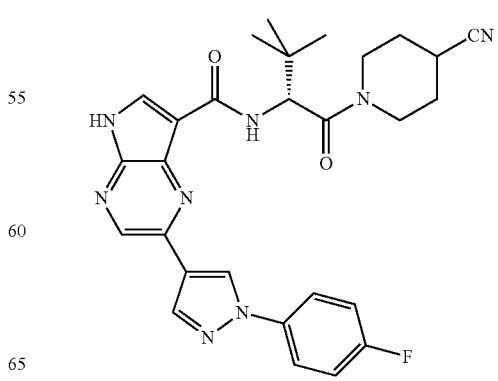

Prepared according to the procedure outlined in Example 2 substituting 1-((R)-2-amino-3,3-dimethyl-butyryl)-piperidine-4-carbonitrile trifluoroacetate for (R)-2-amino-3,3-dimethyl-1-pyrrolidin-1-yl-butan-1-one hydrochloride in Step 1 and 1-(4-fluorophenyl)-1H-pyrazole-4-boronic acid for 1-ethyl-1H-pyrazole-4-boronic acid pinacol ester in Step 2. MS: $(M+H)^+ = 529$.

Example 131

2-(1-Cyclopropylmethyl-1H-imidazol-4-yl)-5H-pyrrolo[2,3-b]pyrazine-7-carboxylic acid [(R)-1-(4-cyano-piperidine-1-carbonyl)-2,2-dimethyl-propyl]-amide

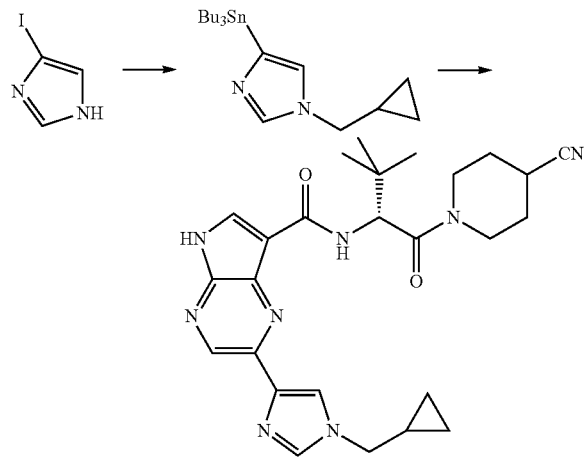

Step 1

To a solution of 4-iodo-1H-imidazole (800 mg, 4.12 mmol) in DMF (50 mL) was added cesium carbonate (5.37 g, 16.5 mmol) and (bromomethyl)cyclopropane (1.6 mL, 16.5 mmol). The reaction mixture was stirred at room temperature for 3 h then concentrated under reduced pressure. The residue was dissolved in EtOAc and washed sequentially with water, sat'd LiCl and sat'd NaCl. The organic layer was dried over MgSO$_4$ and concentrated. The residue was purified by silica gel chromatography (50% to 100% EtOAc/heptane) to isolate first 590 mg (58%) of 1-cyclopropylmethyl-4-iodo-1H-imidazole as a pale yellow oil followed by 227 mg (22%) of 1-cyclopropylmethyl-5-iodo-1H-imidazole as a pale yellow oil.

Step 2

In a round bottomed flask 1-cyclopropylmethyl-4-iodo-1H-imidazole (570 mg, 2.3 mmol) was dissolved in THF (10 mL). The solution was cooled to 0° C. and isopropylmagnesium chloride (2.0 M in THF, 1.15 mL, 2.3 mmol) was added dropwise. The reaction mixture was warmed to room temperature and stirred for 1.5 h. Tributylchlorostannane (0.62 mL, 2.3 mmol) was added and the reaction mixture was stirred at room temperature for 1 h. The reaction mixture was quenched with saturated NH$_4$Cl solution and extracted with ethyl acetate (3×). The combined organics were washed with brine, dried over MgSO$_4$ and concentrated. The residue was purified by silica gel chromatography with 20% to 50% EtOAc/heptane (containing 0.5% triethylamine) to isolate 740 mg (78%) of 1-cyclopropylmethyl-4-tributylstannanyl-1H-imidazole as a light yellow oil.

Step 3

In a round bottomed flask 2-bromo-5-(2-trimethylsilanyl-ethoxymethyl)-5H-pyrrolo[2,3-]pyrazine-7-carboxylic acid [(R)-1-(4-cyano-piperidine-1-carbonyl)-2,2-dimethyl-propyl]-amide (150 mg, 0.26 mmol) and 1-cyclopropylmethyl-4-tributylstannanyl-1H-imidazole (160 mg, 0.39 mmol) were dissolved in DMF (2 mL). Pd(PPh$_3$)$_4$ (15 mg, 0.013 mmol) and CuI (10 mg, 0.052 mmol) were added. The reaction mixture was heated at 80° C. for 1 h then cooled to room temperature, quenched with H$_2$O and extracted with EtOAc. The organic extracts were washed with saturated aqueous LiCl and brine, dried over MgSO$_4$, and concentrated. The residue was purified by SiO$_2$ chromatography (0-5% MeOH/EtOAc) to afford 162 mg (99%) of 2-(1-cyclopropylmethyl-1H-imidazol-4-yl)-5-(2-trimethylsilanyl-ethoxymethyl)-5H-pyrrolo[2,3-b]pyrazine-7-carboxylic acid [(R)-1-(4-cyano-piperidine-1-carbonyl)-2,2-dimethyl-propyl]-amide as a viscous colorless oil.

Step 4

To a solution of 2-(1-cyclopropylmethyl-1H-imidazol-4-yl)-5-(2-trimethylsilanyl-ethoxymethyl)-5H-pyrrolo[2,3-b]pyrazine-7-carboxylic acid [(R)-1-(4-cyano-piperidine-1-carbonyl)-2,2-dimethyl-propyl]-amide (160 mg, 0.26 mmol) in CH$_2$Cl$_2$ (2.25 mL) was added trifluoroacetic acid (0.75 mL). The reaction mixture was stirred at room temperature for 2 h and concentrated. The residue was dissolved in a mixture of ammonium hydroxide, MeOH and CH$_2$Cl$_2$ (1:10:60, 3.0 mL) and stirred at room temperature for 30 min. The reaction mixture was then concentrated and the residue purified twice by SiO$_2$ chromatography (0-5% MeOH/EtOAc then 0-10% MeOH/CH$_2$Cl$_2$) to afford 27 mg (21%) of 2-(1-cyclopropylmethyl-1H-imidazol-4-yl)-5H-pyrrolo[2,3-b]pyrazine-7-carboxylic acid [(R)-1-(4-cyano-piperidine-1-carbonyl)-2,2-dimethyl-propyl]-amide as a white powder. MS: $(M+H)^+ = 489$.

Example 132

2-[1-(2,2,2-Trifluoro-ethyl)-1H-imidazol-4-yl]-5H-pyrrolo[2,3-b]pyrazine-7-carboxylic acid [(R)-1-(4-cyano-piperidine-1-carbonyl)-2,2-dimethyl-propyl]-amide

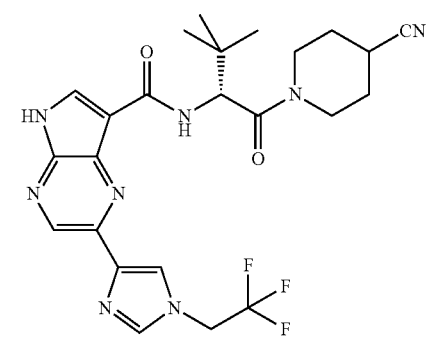 [SMILES: CC(C)(C)[C@@H](NC(=O)c1c[nH]c2ncc(-c3cn(CC(F)(F)F)cn3)nc12)C(=O)N1CCC(C#N)CC1]

Prepared according to the procedure outlined in Example 131 substituting 2,2,2-trifluoroethyl 4-methylbenzenesulfonate for (bromomethyl)cyclopropane in Step 1. MS: (M+H)+=517.

Example 133

2-(1-Cyclopentyl-1H-imidazol-4-yl)-5H-pyrrolo[2,3-b]pyrazine-7-carboxylic acid [(R)-1-(4-cyano-piperidine-1-carbonyl)-2,2-dimethyl-propyl]-amide

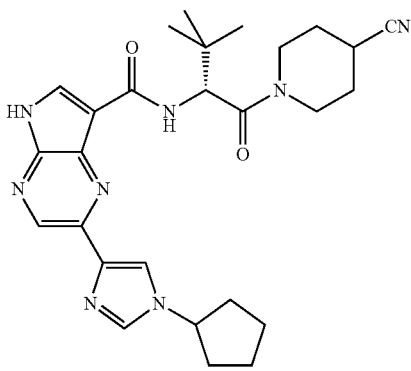 [SMILES: CC(C)(C)[C@@H](NC(=O)c1c[nH]c2ncc(-c3cn(C4CCCC4)cn3)nc12)C(=O)N1CCC(C#N)CC1]

Prepared according to the procedure outlined in Example 131 substituting bromocyclopentane for (bromomethyl)cyclopropane in Step 1. MS: (M+H)+=503.

Example 134

2-(1-Cyclopentyl-1H-imidazol-4-yl)-5H-pyrrolo[2,3-b]pyrazine-7-carboxylic acid [(R)-2-(4-cyano-piperidin-1-yl)-1-cyclopropyl-2-oxo-ethyl]-amide

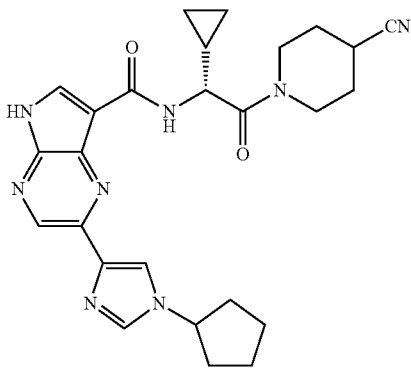 [SMILES: N#CC1CCN(C(=O)[C@H](NC(=O)c2c[nH]c3ncc(-c4cn(C5CCCC5)cn4)nc23)C2CC2)CC1]

Prepared according to the procedure outlined in Example 131 substituting bromocyclopentane for (bromomethyl)cyclopropane in Step 1 and 2-bromo-5-(2-trimethylsilanyl-ethoxymethyl)-5H-pyrrolo[2,3-b]pyrazine-7-carboxylic acid [(R)-2-(4-cyano-piperidin-1-yl)-1-cyclopropyl-2-oxo-ethyl]-amide for 2-bromo-5-(2-trimethylsilanyl-ethoxymethyl)-5H-pyrrolo[2,3-]pyrazine-7-carboxylic acid [(R)-1-(4-cyano-piperidine-1-carbonyl)-2,2-dimethyl-propyl]-amide in Step 3. MS: (M+H)+=487.

Example 135

2-(2-Methyl-1-phenyl-1H-imidazol-4-yl)-5H-pyrrolo[2,3-b]pyrazine-7-carboxylic acid [(R)-2-(3-cyano-azetidin-1-yl)-1-cyclopropyl-2-oxo-ethyl]-amide

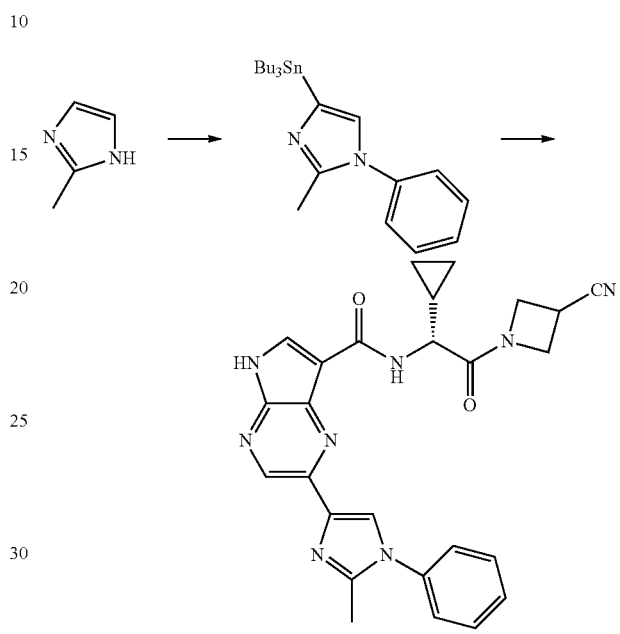

Step 1

(R)-2-(tert-butoxycarbonylamino)-2-cyclopropylacetic acid (2.25 g, 10.5 mmol) and O-benzotriazol-1-yl-N,N,N',N'-tetramethyluronium tetrafluoroborate (3.69 g, 11.5 mmol) were dissolved in dichloromethane (105 mL). 3-Cyanoazetidine hydrochloride (1.36 g, 11.5 mmol) and then N,N-diisopropylethylamine (4.5 mL, 26.1 mmol) were added and the mixture was stirred at room temperature for 5 h. Water, dilute HCl and more dichloromethane were added, the layers were separated and the aqueous layer was extracted once more with dichloromethane. The combined organic layers were washed with sodium chloride solution, dried over sodium sulfate and concentrated. The residue was purified by silica gel chromatography (methanol/dichloromethane) to give 2.45 g (83%) of [(R)-2-(3-cyano-azetidin-1-yl)-1-cyclopropyl-2-oxo-ethyl]-carbamic acid tert-butyl ester.

Step 2

[(R)-2-(3-cyano-azetidin-1-yl)-1-cyclopropyl-2-oxo-ethyl]-carbamic acid tert-butyl ester (0.99 g, 3.54 mmol) was dissolved in 24 mL of dichloromethane and cooled in an ice bath. Trifluoroacetic acid (10.6 mL) was added slowly and the reaction was then stirred at room temperature. After 3 h., the reaction was judged complete by TLC and was then evaporated under high vacuum. The residue was dissolved in 34 mL of acetonitrile to which was then added 2-bromo-5-(2-trimethylsilanyl-ethoxymethyl)-5H-pyrrolo[2,3-b]pyrazine-7-carboxylic acid (1.28 g, 3.44 mmol), O-benzotriazol-1-yl-N,N,N',N'-tetramethyluronium tetrafluoroborate (1.21 g, 3.78 mmol) and N,N-diisopropylethylamine (2.1 mL, 12 mmol). The reaction was stirred for 18 h and then water and ethyl acetate were added. The layers were separated and the aqueous layer was extracted once more with ethyl acetate. The combined organic layers were washed with brine and dried over sodium sulfate. After evaporation, the residue was purified by silica gel chromatography (methanol/dichloromethane). The resultant viscous oil was triturated with hexanes to provide 0.93 g (50%) of 2-bromo-5-(2-trimethylsilanyl-ethoxymethyl)-5H-pyrrolo[2,3-b]pyrazine-7-carboxylic acid [(R)-2-(3-cyano-azetidin-1-yl)-1-cyclopropyl-2-oxo-ethyl]-amide as a white solid.
Step 3a
Iodine (18.5 g, 73.1 mmol) was dissolved in 90 mL of chloroform. 2-Methylimidazole (3.0 g, 36.5 mmol) in 90 mL of 2M NaOH solution was added slowly. The cloudy mixture cleared to two phases by 2.5 h. The layers were separated and acetic acid (10.5 mL, 183 mmol) was added to the organic layer to neutralize the reaction (to pH~5-6). A solid appeared which was filtered off and recrystallized from warm acetonitrile to afford 8.5 g (69%) of 4,5-diiodo-2-methyl-1H-imidazole. $(M+H)^+=334$.
Step 3b
4,5-Diiodo-2-methyl-1H-imidazole (8.5 g, 25.5 mmol) was dissolved in 430 mL of 3:7 ethanol:water. Sodium sulfite (25.7 g, 204 mmol) was added and the reaction was brought to reflux (~100° C.) for 24 h. The reaction mixture was concentrated to about half its volume. The solids which appeared were filtered off and rinsed with water to isolate 5.3 g (66%) of 4-iodo-2-methyl-1H-imidazole. $(M+H)^+=209$.
Step 4
4-Iodo-2-methyl-1H-imidazole (1.0 g, 4.8 mmol) was dissolved in 30 mL of THF. Copper TMEDA catalyst (447 mg, 0.96 mmol, Aldrich) and then phenylboronic acid (0.41 g, 3.35 mmol) were added. Oxygen gas was bubbled into the reaction mixture for 20 min, then the mixture was stirred at room temperature for 90 min. An additional 0.21 g of phenylboronic acid was added followed by an additional 20 min of oxygen gas bubbling and 75 min of stirring at room temperature. An additional 0.21 g of phenylboronic acid was added followed by an additional 20 min of oxygen gas bubbling and then stirring at room temperature for 20 h. The reaction mixture was filtered through a bed of neutral alumina, concentrated and purified by silica gel chromatography (ethyl acetate/hexanes) to give 0.55 g (40%) of 4-iodo-2-methyl-1-phenyl-1H-imidazole (($M+H)^+=285$) and 0.47 g (35%) of 5-iodo-2-methyl-1-phenyl-1H-imidazole.
Step 5
4-Iodo-2-methyl-1-phenyl-1H-imidazole (0.55 g, 1.94 mmol) was dissolved in 9 mL of anhydrous THF and isopropylmagnesium chloride (2 M THF solution, 1.2 mL, 2.4 mmol) was added dropwise. The reaction was stirred for more than 1 h at room temperature. Tributylstannyl chloride (0.55 mL, 2.03 mmol) was slowly added. After the reaction was judged to be complete by TLC, NH₄Cl solution and ethyl acetate were added. The layers were separated and the aqueous layer was extracted twice more with ethyl acetate. The combined organic layers were washed with brine, dried over sodium sulfate and concentrated. The residue was purified by silica gel chromatography (triethylamine/ethyl acetate/hexanes) to give 0.2 g (23%) of 2-methyl-1-phenyl-4-tributylstannanyl-1H-imidazole.
Step 6
2-Bromo-5-(2-trimethylsilanyl-ethoxymethyl)-5H-pyrrolo[2,3-b]pyrazine-7-carboxylic acid [(R)-2-(3-cyano-azetidin-1-yl)-1-cyclopropyl-2-oxo-ethyl]-amide (115 mg, 0.188 mmol) and 2-methyl-1-phenyl-4-tributylstannanyl-1H-imidazole (101 mg, 0.225 mmol) were dissolved in 1.9 mL of DMF and the mixture was purged with Ar gas. Tetrakis(triphenylphosphine)palladium (10.8 mg, 0.0094 mmol) and then copper (I) iodide (7.1 mg, 0.038 mmol) were added and the reaction was sealed and stirred in an 80° C. oil bath for 18 h. The reaction was cooled and water, dichloromethane, and sodium bicarbonate solution were added. The layers were separated, and the aqueous layer was extracted twice more with dichloromethane. The combined organic layers were washed with water and then brine, and dried over sodium sulfate. After evaporation, the residue was purified by silica gel chromatography (methanol/dichloromethane) to provide 68 mg (59%) of 2-(2-methyl-1-phenyl-1H-imidazol-4-yl)-5-(2-trimethylsilanyl-ethoxymethyl)-5H-pyrrolo[2,3-b]pyrazine-7-carboxylic acid [(R)-2-(3-cyano-azetidin-1-yl)-1-cyclopropyl-2-oxo-ethyl]-amide. $(M+H)^+=611$.
Step 7
2-(2-Methyl-1-phenyl-1H-imidazol-4-yl)-5-(2-trimethylsilanyl-ethoxymethyl)-5H-pyrrolo[2,3-b]pyrazine-7-carboxylic acid [(R)-2-(3-cyano-azetidin-1-yl)-1-cyclopropyl-2-oxo-ethyl]-amide (68 mg, 0.111 mmol) was dissolved in 0.6 mL of dichloromethane and then stirred in an ice bath. Trifluoroacetic acid (0.4 mL) was added slowly and the ice bath was removed. The reaction was stirred for 3 h and then cooled in ice bath. Sodium bicarbonate solution was added and the mixture was extracted three times with ethyl acetate. The combined organic layers were washed with brine and dried over sodium sulfate. After evaporation, the residue was dissolved in 4 mL of absolute ethanol, sodium acetate (183 mg) was added and the mixture was stirred for 20 h at 60° C. The reaction was cooled, and water and ethyl acetate were added. The layers were separated and the aqueous layer was extracted twice more with ethyl acetate. The combined organic layers were washed with brine, dried over sodium sulfate and evaporated. The residue was purified by silica gel chromatography (methanol/dichloromethane) to give 33 mg (62%) of 2-(2-methyl-1-phenyl-1H-imidazol-4-yl)-5H-pyrrolo[2,3-b]pyrazine-7-carboxylic acid [(R)-2-(3-cyano-azetidin-1-yl)-1-cyclopropyl-2-oxo-ethyl]-amide. MS: $(M+H)^+=481$; mp=175-179° C.

Example 136

2-[1-(3,5-Difluoro-phenyl)-2-methyl-1H-imidazol-4-yl]-5H-pyrrolo[2,3-b]pyrazine-7-carboxylic acid [(R)-1-(3-cyano-azetidine-1-carbonyl)-2,2-dimethyl-propyl]-amide

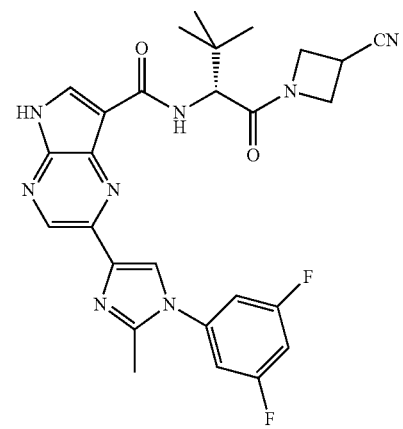 [SMILES: Cc1nc(-c2cnc3[nH]cc(C(=O)N[C@@H](C(=O)N4CC(C#N)C4)C(C)(C)C)c3n2)cn1-c1cc(F)cc(F)c1]

Prepared according to the procedure outlined in Example 135 substituting (R)-2-tert-butoxycarbonylamino-3,3-dimethyl-butyric acid for (R)-2-(tert-butoxycarbonylamino)-2-cyclopropylacetic acid in Step 1, and substituting 1-(3,5- difluoro-phenyl)-4-iodo-2-methyl-1H-imidazole for 4-iodo-2-methyl-1-phenyl-1H-imidazole in Step 5. MS: (M+H)⁺=533; mp=187-190° C.

Example 137

2-[1-(3-Fluorophenyl)-2-methyl-1H-imidazol-4-yl]-5H-pyrrolo[2,3-b]pyrazine-7-carboxylic acid [(R)-1-(3-cyano-azetidine-1-carbonyl)-2,2-dimethyl-propyl]-amide

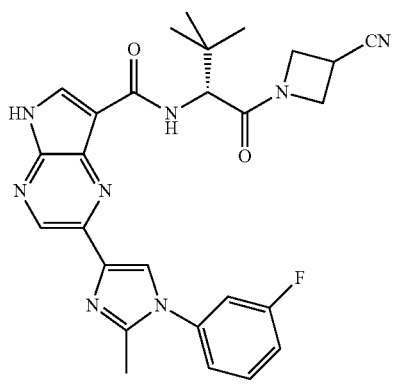 [SMILES: Cc1nc(-c2cnc3[nH]cc(C(=O)N[C@@H](C(=O)N4CC(C#N)C4)C(C)(C)C)c3n2)cn1-c1cccc(F)c1]

Prepared according to the procedure outlined in Example 135 substituting (R)-2-tert-butoxycarbonylamino-3,3-dimethyl-butyric acid for (R)-2-(tert-butoxycarbonylamino)-2-cyclopropylacetic acid in Step 1, and substituting 3-fluorophenylboronic acid for phenylboronic acid in Step 4. MS: (M+H)⁺=515; mp=171-176° C.

Example 138

2-[2-Methyl-1-(2,2,2-trifluoro-ethyl)-1H-imidazol-4-yl]-5H-pyrrolo[2,3-b]pyrazine-7-carboxylic acid [(R)-2-(3-cyano-azetidin-1-yl)-1-cyclopropyl-2-oxo-ethyl]amide

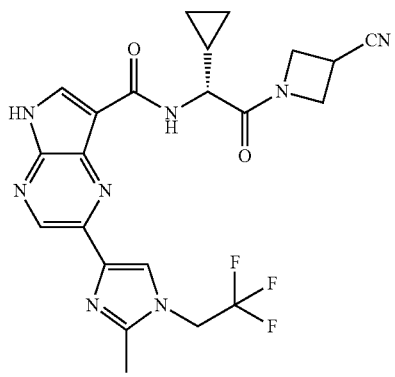 [SMILES: Cc1nc(-c2cnc3[nH]cc(C(=O)N[C@@H](C(=O)N4CC(C#N)C4)C4CC4)c3n2)cn1CC(F)(F)F]

Step 1

4-Iodo-2-methyl-1H-imidazole (1.0 g, 4.8 mmol) was dissolved in 10 mL of DMF. Trifluoroethyl p-toluenesulfonate (4.89 g, 19.2 mmol) and cesium carbonate (1.57 g, 4.8 mmol) were added and the mixture was stirred for 18 h in a 50° C. oil bath. The reaction was cooled and taken up in ethyl acetate and water. The layers were separated, and the aqueous layer was extracted twice more with ethyl acetate. The combined organic layers were washed with water and brine, and dried over sodium sulfate. After evaporation, the residue was purified by silica gel chromatography (ethyl acetate/hexanes) to give 0.6 g (43%) of 4-iodo-2-methyl-1-(2,2,2-trifluoro-ethyl)-1H-imidazole. (M+H)⁺=291.

Step 2

2-[2-Methyl-1-(2,2,2-trifluoro-ethyl)-1H-imidazol-4-yl]-5H-pyrrolo[2,3-b]pyrazine-7-carboxylic acid [(R)-2-(3-cyano-azetidin-1-yl)-1-cyclopropyl-2-oxo-ethyl]-amide. Prepared according to the procedure outlined in Example 135 substituting 4-iodo-2-methyl-1-(2,2,2-trifluoro-ethyl)-1H-imidazole for 4-iodo-2-methyl-1-phenyl-1H-imidazole in Step 5. MS: (M+H)⁺=487; mp=255-256° C.

Example 139

2-[1-(2,5-Difluoro-phenyl)-1H-imidazol-4-yl]-5H-pyrrolo[2,3-b]pyrazine-7-carboxylic acid [(R)-2-(3-cyano-azetidin-1-yl)-1-cyclopropyl-2-oxo-ethyl] amide

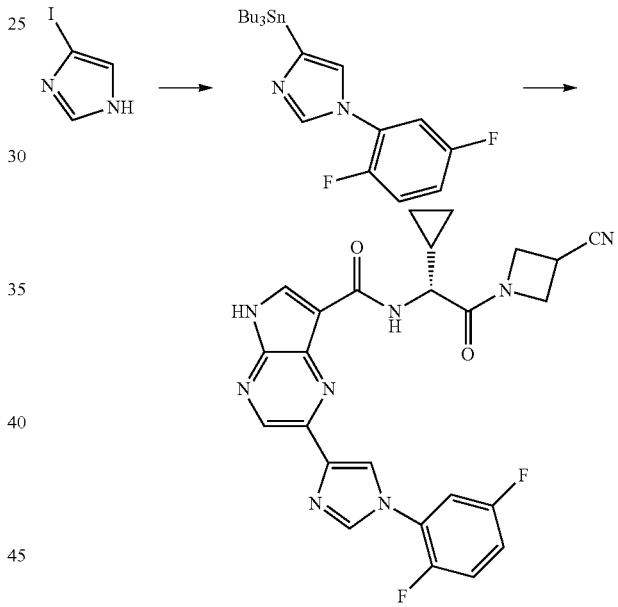

Step 1

Following a procedure similar to that outlined in *Chem. Comm.* 2004, 188-189: A solution of 2,5-difluorophenylboronic acid (47 mg, 0.30 mmol), 4-iodo-1H-imidazole (46 mg, 0.24 mmol), copper(I) chloride (1.8 mg, 0.018 mmol), and 1 mL of methanol was stirred under air at 60° C. for 3 h, then concentrated. Column chromatography (0-33% EtOAc/hexanes) afforded 14.5 mg (20%) of 1-(2,5-difluorophenyl)-4-iodo-1H-imidazole as a white solid.

Step 2

A solution of 1-(2,5-difluorophenyl)-4-iodo-1H-imidazole (0.115 g, 0.38 mmol) in 2 mL of tetrahydrofuran was chilled in an ice/water bath 5 min. Isopropylmagnesium chloride solution (2.0 M in tetrahydrofuran, 0.190 mL, 0.38 mmol) was added all at once. The bath was removed, and the pale yellow solution stirred 1.5 h. Tributyltin chloride (0.105 mL, 0.39 mmol) was added all at once, and the pale yellow solution was stirred 1.5 h. A sat. aq. NH₄Cl solution (10 mL) was added, and the mixture was extracted with two 10 mL portions of ethyl acetate. The combined organic layers were washed with 20 mL of a sat. aq. NaCl solution, dried over Na$_2$SO$_4$, filtered and concentrated to provide 0.198 g of 1-(2,5-difluoro-phenyl)-4-tributylstannanyl-1H-imidazole as a yellow oil which was used without further purification. MS: (M+H)$^+$=471.

Step 3

A pressure tube was charged with 2-bromo-5-(2-trimethylsilanyl-ethoxymethyl)-5H-pyrrolo[2,3-b]pyrazine-7-carbaldehyde (0.110 g, 0.31 mmol), Pd(PPh$_3$)$_4$ (0.020 g, 0.017 mmol), CuI (0.012 g, 0.063 mmol) and the above-prepared crude 1-(2,5-difluorophenyl)-4-(tributylstannyl)-1H-imidazole (0.198 g) in 3 mL of DMF. The tube was capped under Ar and the orange yellow mixture stirred at 80° C. for 1.5 h, then allowed to cool. The mixture was partitioned between 20 mL of ethyl acetate and 20 mL of water+20 mL of a sat. aq. NH$_4$Cl solution. The organic layer was washed with 20 mL of a sat. aq. NaCl solution, dried over Na$_2$SO$_4$, filtered and concentrated. Column chromatography (20-100% EtOAc/hexanes) of the residue afforded 0.087 g (62%) of 2-[1-(2,5-difluoro-phenyl)-1H-imidazol-4-yl]-5-(2-trimethylsilanyl-ethoxymethyl)-5H-pyrrolo[2,3-b]pyrazine-7-carbaldehyde as a slightly impure yellow oil, which was used without further purification. MS: (M+Na)$^+$=478.

Step 4

A mixture of 2-[1-(2,5-difluoro-phenyl)-1H-imidazol-4-yl]-5-(2-trimethylsilanyl-ethoxymethyl)-5H-pyrrolo[2,3-b]pyrazine-7-carbaldehyde (0.087 g, 0.19 mmol) and sulfamic acid (0.127 g, 1.30 mmol) in 2 mL of 1,4-dioxane and 0.2 mL of water was treated dropwise with a mixture of sodium chlorite (0.031 g, 0.27 mmol) and KH$_2$PO$_4$ (0.335 g, 2.46 mmol)) in 1 mL of water, rinsing with 1 mL of water. The pale yellow solution was stirred 1.25 h as a white precipitate formed. The mixture was partitioned between 10 mL of water and 10 mL of ethyl acetate. The organic layer was washed with 10 mL of a sat. aq. NaCl solution, dried over Na$_2$SO$_4$, filtered and concentrated to afford 0.067 g (74%) of 2-[1-(2,5-difluoro-phenyl)-1H-imidazol-4-yl]-5-(2-trimethylsilanyl-ethoxymethyl)-5H-pyrrolo[2,3-b]pyrazine-7-carboxylic acid as a pale yellow solid, which was used without further purification. MS: (M+H)$^+$=472.

Step 5

A solution of 2-[1-(2,5-difluoro-phenyl)-1H-imidazol-4-yl]-5-(2-trimethylsilanyl-ethoxymethyl)-5H-pyrrolo[2,3-b]pyrazine-7-carboxylic acid (0.067 g, 0.14 mmol), (R)-1-(2-amino-2-cyclopropylacetyl)azetidine-3-carbonitrile (0.038 g, 0.21 mmol), DMAP (0.021 g, 0.17 mmol) and EDC (0.036 g, 0.19 mmol) in 2 mL dichloromethane was stirred for 13.5 h. Dichloromethane (10 mL) was added, and the solution was sequentially washed with 10 mL of a 1 M citric acid solution, 10 mL of water, and 10 mL of a sat. aq. NaCl solution then dried over Na$_2$SO$_4$, filtered and concentrated. The residue was purified using column chromatography (80% EtOAc/hexanes) to afford 0.044 g (48%) of 2-[1-(2,5-difluoro-phenyl)-1H-imidazol-4-yl]-5-(2-trimethylsilanyl-ethoxymethyl)-5H-pyrrolo[2,3-b]pyrazine-7-carboxylic acid [(R)-2-(3-cyano-azetidin-1-yl)-1-cyclopropyl-2-oxo-ethyl]-amide as a foamy pale yellow solid. MS: (M+Na)$^+$=655.

Step 6

A solution of 2-[1-(2,5-difluoro-phenyl)-1H-imidazol-4-yl]-5-(2-trimethylsilanyl-ethoxymethyl)-5H-pyrrolo[2,3-b]pyrazine-7-carboxylic acid [(R)-2-(3-cyano-azetidin-1-yl)-1-cyclopropyl-2-oxo-ethyl]-amide (0.037 g, 0.058 mmol), 18-crown-6 (0.016 g, 0.058 mmol) and cesium fluoride (0.093 g, 0.58 mmol) in 1 mL of acetonitrile was stirred at 75° C. for 5 d, then concentrated. The resulting residue was partitioned between 5 mL of a 1 M citric acid solution and 5 mL of dichloromethane. The aqueous layer was extracted with two 5 mL portions of dichloromethane. The combined organic layers were dried over Na$_2$SO$_4$, filtered and concentrated. Dichloromethane (1 mL) and 1 mL of trifluoroacetic acid were added, and the yellow solution was stirred 2 h, then concentrated. Dichloromethane (0.5 mL) and 0.5 mL of ethylene diamine were added, and the yellow-orange solution was stirred 1 h. The solution was partitioned between 10 mL of ethyl acetate and 5 mL of water, and the aqueous layer was extracted with 10 mL of ethyl acetate. The combined organic layers were dried over Na$_2$SO$_4$, filtered and concentrated. Column chromatography (0->10% MeOH/EtOAc) afforded 0.0055 g (19%) of 2-[1-(2,5-difluoro-phenyl)-1H-imidazol-4-yl]-5H-pyrrolo[2,3-b]pyrazine-7-carboxylic acid [(R)-2-(3-cyano-azetidin-1-yl)-1-cyclopropyl-2-oxo-ethyl]-amide as a pale yellow solid. MS: (M–H)$^-$=501.

Example 140

2-[1-(2,3,5-Trifluoro-phenyl)-1H-imidazol-4-yl]-5H-pyrrolo[2,3-b]pyrazine-7-carboxylic acid [(R)-2-(3-cyano-azetidin-1-yl)-1-cyclopropyl-2-oxo-ethyl]-amide

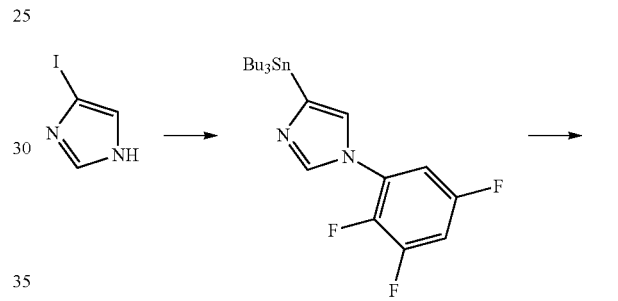

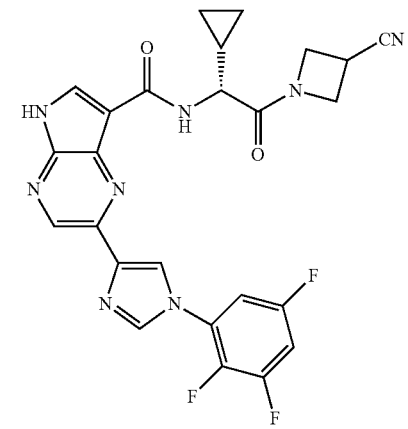

Step 1

A solution of 2-bromo-5-(2-trimethylsilanyl-ethoxymethyl)-5H-pyrrolo[2,3-b]pyrazine-7-carboxylic acid [(R)-2-(3-cyano-azetidin-1-yl)-1-cyclopropyl-2-oxo-ethyl]-amide (0.104 g, 0.195 mmol, contains some 2-chloro impurity), 1 mL of dichloromethane and 1 mL of TFA was stirred for 3 h, then concentrated to a pale yellow oil. The oil was dissolved in 0.5 mL of dichloromethane and 0.5 mL of ethylene diamine, and the yellow solution was stirred for 1.25 h, then partitioned between 5 mL of water and 10 mL of ethyl acetate. The aqueous layer was extracted with 10 mL of ethyl acetate. The combined organic layers were dried over $Na_2SO_4$, filtered and concentrated to give 0.087 g of 2-bromo-5H-pyrrolo[2,3-b]pyrazine-7-carboxylic acid [(R)-2-(3-cyano-azetidin-1-yl)-1-cyclopropyl-2-oxo-ethyl]-amide as a pale yellow residue, which was used without further purification. MS: $(M+Na)^+=427$. A major impurity is 2-chloro-5H-pyrrolo[2,3-b]pyrazine-7-carboxylic acid [(R)-2-(3-cyano-azetidin-1-yl)-1-cyclopropyl-2-oxo-ethyl]-amide. MS: $(M+Na)^+=381$. Approximate 3:1 ratio of Br:Cl.

Step 2

Following a procedure similar to that outlined in *Synthesis* 2008, 795-799: A mixture of 2,3,5-trifluorophenylboronic acid (0.302 g, 1.72 mmol), 4-iodo-1H-imidazole (0.498 g, 2.57 mmol), 2 mL of methanol, and $Cu_2O$ (0.049 g, 0.34 mmol) was stirred under air for 21 h, then filtered through Celite and concentrated to an oily white solid. Column chromatography (0->33% EtOAc/hexanes) afforded 0.150 g (27%) of 4-iodo-1-(2,3,5-trifluorophenyl)-1H-imidazole as a white solid. MS: $(M+H)^+=325$.

Step 3

A solution of 4-iodo-1-(2,3,5-trifluorophenyl)-1H-imidazole (0.140 g, 0.43 mmol) in 2 mL of THF under Ar was chilled in an ice/water bath 5 min. Isopropylmagnesium chloride (2.0 M in tetrahydrofuran, 0.225 mL, 0.45 mmol) was added, the bath was removed, and the pale yellow solution was stirred for 1.5 h. Tributyltin chloride (0.055 mL, 0.20 mmol) was added all at once, and the pale yellow solution was stirred 1 h. A sat. aq. NH4Cl solution (10 mL) was added, and the mixture was extracted with two 10 mL portions of EtOAc. The combined organic layers were washed with 10 mL of a sat. aq. NaCl solution, dried over $Na_2SO_4$, filtered and concentrated to give 4-tributylstannanyl-1-(2,3,5-trifluoro-phenyl)-1H-imidazole as a yellow oil which was used without further purification.

Step 4

To the crude 4-tributylstannanyl-1-(2,3,5-trifluoro-phenyl)-1H-imidazole from Step 3 was added crude 2-bromo-5H-pyrrolo[2,3-b]pyrazine-7-carboxylic acid [(R)-2-(3-cyano-azetidin-1-yl)-1-cyclopropyl-2-oxo-ethyl]-amide (0.087 g, from Step 1) in 3 mL of DMF, $Pd(PPh_3)_4$ (0.032 g, 0.027 mmol) and CuI (0.021 g, 0.110 mmol). The dark yellow mixture was stirred at 80° C. for 16 h, then allowed to cool. The mixture was partitioned between 20 mL of ethyl acetate and 20 mL of a sat. aq. $NH_4Cl$ solution. The organic layer was washed with 20 mL of water+20 mL of a sat. aq. NaCl. The organic layer was dried over $Na_2SO_4$, filtered and concentrated. Column chromatography (0-10% MeOH/EtOAc) of the residue afforded 0.005 g (5%) of 2-[1-(2,3,5-trifluoro-phenyl)-1H-imidazol-4-yl]-5H-pyrrolo[2,3-b]pyrazine-7-carboxylic acid [(R)-2-(3-cyano-azetidin-1-yl)-1-cyclopropyl-2-oxo-ethyl]-amide as a yellow solid, ca. 85% pure. MS: $(M+Na)^+=543$.

Example 141

2-(2-Chlorothiazol-5-yl)-5H-pyrrolo[2,3-b]pyrazine-7-carboxylic acid [(R)-1-(4-cyano-piperidine-1-carbonyl)-2,2-dimethyl-propyl]-amide

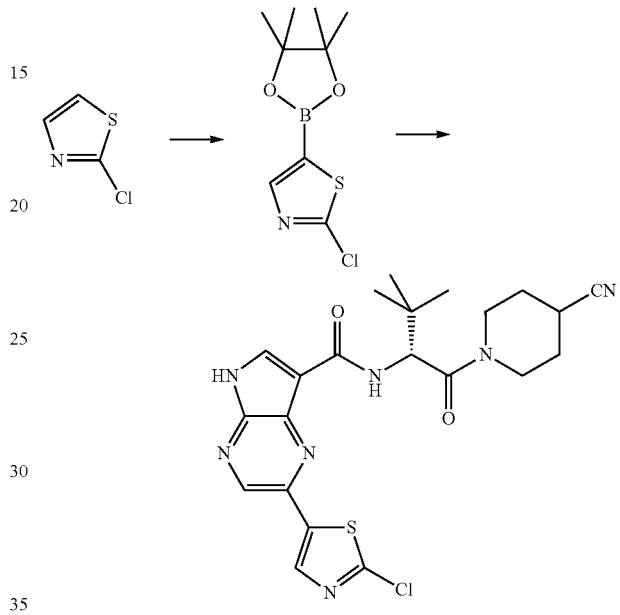

Step 1

Diisopropylamine (0.66 mL, 4.6 mmol) and triisopropylborate (1.26 mL, 5.44 mmol) were dissolved in 52 mL of anhydrous diethyl ether and then cooled to −90° C. n-Butyllithium (2.6 M in toluene, 1.77 mL, 4.6 mmol) was added slowly to the reaction and the mixture was stirred for 30 min. 2-Chlorothiazole (0.5 g, 4.18 mmol) was added and the reaction was allowed to gradually reach room temperature over 3 h. A solution of pinacol (0.69 g, 5.85 mmol) in 5 mL of diethyl ether was added. After 15 min, acetic acid (0.26 mL, 4.6 mmol) was added and the mixture was then filtered through Celite, rinsing with more diethyl ether. The filtrate was evaporated and the residue was distilled using a Kugelrohr apparatus at a temperature of 120-130° C. to give 0.84 g (82%) of 2-chloro-5-(4,4,5,5-tetramethyl-[1,3,2]dioxaborolan-2-yl)-thiazole.

Step 2

In a microwave vial, 1,4-dioxane (3 mL) was purged with argon gas. 2-Bromo-5-(2-trimethylsilanyl-ethoxymethyl)-5H-pyrrolo[2,3-b]pyrazine-7-carboxylic acid [(R)-1-(4-cyano-piperidine-1-carbonyl)-2,2-dimethyl-propyl]-amide (100 mg, 0.173 mmol), 2-chloro-5-(4,4,5,5-tetramethyl-[1,3,2]dioxaborolan-2-yl)-thiazole (128 mg, 0.519 mmol), palladium tetrakis(triphenylphosphine) (10 mg, 0.009 mmol), and then cesium carbonate (113 mg, 0.346 mmol) were added. The reaction vessel was sealed and heated in a microwave reactor at 170° C. for 1 h. Additional 2-chloro-5-(4,4,5,5-tetramethyl-[1,3,2]dioxaborolan-2-yl)-thiazole (90 mg, 0.366 mmol) and palladium tetrakis(triphenylphosphine) (6 mg, 0.005 mmol) were added and the reaction was resubjected at 170° C. for 2 h. The reaction was cooled and water and ethyl acetate were added. The layers were separated and the aqueous layer was extracted twice more with ethyl acetate. The combined organic layers were washed with brine and dried over sodium sulfate. After evaporation, the residue was purified by silica gel chromatography (methanol/dichloromethane) to yield 39 mg (36%) of 2-(2-chlorothiazol-5-yl)-5-(2-trimethylsilanyl-ethoxymethyl)-5H-pyrrolo[2,3-b]pyrazine-7-carboxylic acid [(R)-1-(4-cyano-piperidine-1-carbonyl)-2,2-dimethyl-propyl]-amide. (M+Na)⁺=638.

Step 3

2-(2-Chlorothiazol-5-yl)-5-(2-trimethylsilanyl-ethoxymethyl)-5H-pyrrolo[2,3-b]pyrazine-7-carboxylic acid [(R)-1-(4-cyano-piperidine-1-carbonyl)-2,2-dimethyl-propyl]-amide (39 mg, 0.063 mmol) was dissolved in 0.8 mL of dichloromethane and then stirred in an ice bath. Trifluoroacetic acid (0.4 mL) was added slowly and the ice bath was removed. The reaction was stirred for 2.5 h and then cooled in ice bath. Sodium bicarbonate solution was added and the mixture was extracted three times with ethyl acetate. The combined organic layers were washed with brine and dried over sodium sulfate. After evaporation, the residue was dissolved in 4 mL of absolute ethanol, sodium acetate (104 mg, 1.27 mmol) was added and the mixture was stirred at 60° C. for 20 h. The reaction was cooled, and water and ethyl acetate were added. The layers were separated and the aqueous layer was extracted twice more with ethyl acetate. The combined organic layers were washed with brine, dried over sodium sulfate and evaporated. Purification by reverse phase chromatography afforded 8 mg (26%) of 2-(2-chlorothiazol-5-yl)-5H-pyrrolo[2,3-b]pyrazine-7-carboxylic acid [(R)-1-(4-cyano-piperidine-1-carbonyl)-2,2-dimethyl-propyl]-amide. MS: (M+Na)⁺=509.

Example 142

2-(4-Trifluoromethyl-phenyl)-5H-pyrrolo[2,3-b]pyrazine-7-carboxylic acid [(R)-2-(3-cyano-azetidin-1-yl)-1-cyclopropyl-2-oxo-ethyl]-amide

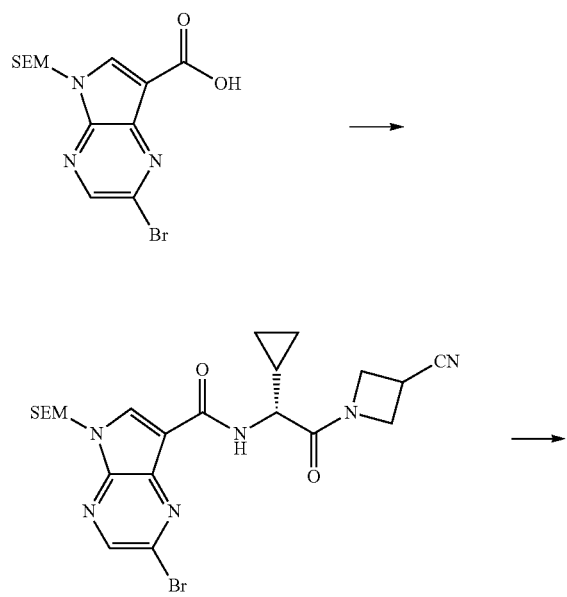

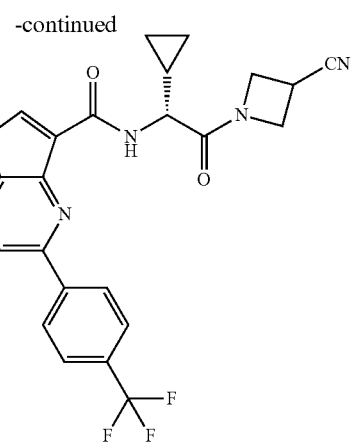

Step 1

(R)-2-(tert-butoxycarbonylamino)-2-cyclopropylacetic acid (2.25 g, 10.5 mmol) and O-benzotriazol-1-yl-N,N,N',N'-tetramethyluronium tetrafluoroborate (3.69 g, 11.5 mmol) were dissolved in dichloromethane (105 mL). 3-Cyanoazetidine hydrochloride (1.36 g, 11.5 mmol) and then N,N-diisopropylethylamine (4.5 mL, 26.1 mmol) were added and the mixture was stirred at room temperature for 5 h. Water, dilute HCl and more dichloromethane were added, the layers were separated and the aqueous layer was extracted once more with dichloromethane. The combined organic layers were washed with sodium chloride solution, dried over sodium sulfate and concentrated. The residue was purified by silica gel chromatography (methanol/dichloromethane) to give 2.45 g (83%) of [(R)-2-(3-cyano-azetidin-1-yl)-1-cyclopropyl-2-oxo-ethyl]-carbamic acid tert-butyl ester.

Step 2

[(R)-2-(3-cyano-azetidin-1-yl)-1-cyclopropyl-2-oxo-ethyl]-carbamic acid tert-butyl ester (0.99 g, 3.54 mmol) was dissolved in 24 mL of dichloromethane and cooled in an ice bath. Trifluoroacetic acid (10.6 mL) was added slowly and the reaction was then stirred at room temperature. After 3 h., the reaction was judged complete by TLC and was then evaporated under high vacuum. The residue was dissolved in 34 mL of acetonitrile to which was then added 2-bromo-5-(2-trimethylsilanyl-ethoxymethyl)-5H-pyrrolo[2,3-b]pyrazine-7-carboxylic acid (1.28 g, 3.44 mmol), O-benzotriazol-1-yl-N,N,N',N'-tetramethyluronium tetrafluoroborate (1.21 g, 3.78 mmol) and N,N-diisopropylethylamine (2.1 mL, 12 mmol). The reaction was stirred for 18 h and then water and ethyl acetate were added. The layers were separated and the aqueous layer was extracted once more with ethyl acetate. The combined organic layers were washed with brine and dried over sodium sulfate. After evaporation, the residue was purified by silica gel chromatography (methanol/dichloromethane). The resultant viscous oil was triturated with hexanes to provide 0.93 g (50%) of 2-bromo-5-(2-trimethylsilanyl-ethoxymethyl)-5H-pyrrolo[2,3-b]pyrazine-7-carboxylic acid [(R)-2-(3-cyano-azetidin-1-yl)-1-cyclopropyl-2-oxo-ethyl]-amide as a white solid.

Step 3

In a microwave vial, 2-bromo-5-(2-trimethylsilanyl-ethoxymethyl)-5H-pyrrolo[2,3-b]pyrazine-7-carboxylic acid [(R)-2-(3-cyano-azetidin-1-yl)-1-cyclopropyl-2-oxo-ethyl]-amide (80 mg, 0.15 mmol) was dissolved in 1.5 mL of 1,4-dioxane and 0.35 mL of water. The solution was purged with Ar gas then 4-(trifluoromethyl)phenylboronic acid (31 mg, 0.165 mmol), palladium bis-(diphenylphosphino)ferrocene dichloride, dichloromethane complex (6.1 mg, 0.008 mmol) and potassium carbonate (62 mg, 0.45 mmol) were added. The reaction vessel was sealed and heated in a microwave reactor at 150° C. for 30 min. The reaction was cooled and water and ethyl acetate were added. The mixture was poured into ethyl acetate and sodium bicarbonate solution. The layers were separated and the aqueous layer was extracted twice more with ethyl acetate. The combined organic layers were washed with brine and dried over sodium sulfate. After evaporation, the residue was purified by silica gel chromatography (methanol/dichloromethane) to give 60 mg (66%) of 2-(4-trifluoromethylphenyl)-5-(2-trimethylsilanyl-ethoxymethyl)-5H-pyrrolo[2,3-b]pyrazine-7-carboxylic acid [(R)-2-(3-cyano-azetidin-1-yl)-1-cyclopropyl-2-oxo-ethyl]-amide.

Step 4

2-(4-Trifluoromethylphenyl)-5-(2-trimethylsilanyl-ethoxymethyl)-5H-pyrrolo[2,3-b]pyrazine-7-carboxylic acid [(R)-2-(3-cyano-azetidin-1-yl)-1-cyclopropyl-2-oxo-ethyl]-amide (62 mg, 0.104 mmol) was dissolved in 0.8 mL of dichloromethane and then stirred in an ice bath. Trifluoroacetic acid (0.4 mL) was added slowly and the ice bath was removed. The reaction was stirred for 2.5 h and then cooled in ice bath. Sodium bicarbonate solution was added and the mixture was extracted three times with ethyl acetate. The combined organic layers were washed with brine and dried over sodium sulfate. After evaporation, the residue was dissolved in 4 mL of absolute ethanol, sodium acetate (170 mg, 2.07 mmol) was added and the mixture was stirred at 60° C. for overnight. The reaction was cooled, and water and ethyl acetate were added. The layers were separated and the aqueous layer was extracted twice more with ethyl acetate. The combined organic layers were washed with brine, dried over sodium sulfate and evaporated. The residue was purified by silica gel chromatography (methanol/dichloromethane) to give 34 mg (70%) of 2-(4-trifluoromethyl-phenyl)-5H-pyrrolo[2,3-b]pyrazine-7-carboxylic acid [(R)-2-(3-cyano-azetidin-1-yl)-1-cyclopropyl-2-oxo-ethyl]-amide. MS: (M+H)$^+$= 469; mp=207-209° C.

Example 143

2-[4-(4-Acetyl-piperazin-1-yl)-phenyl]-5H-pyrrolo[2,3-b]pyrazine-7-carboxylic acid [(R)-2-(3-cyano-azetidin-1-yl)-1-cyclopropyl-2-oxo-ethyl]-amide

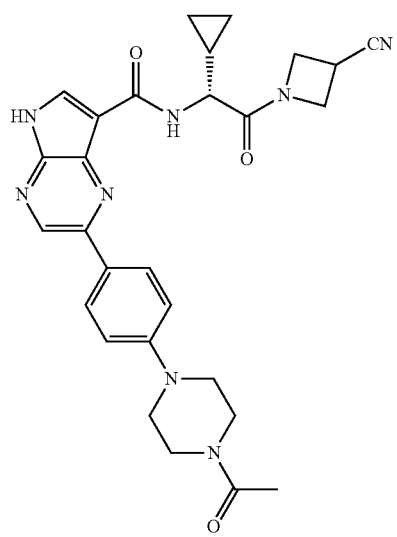 [SMILES: CC(=O)N1CCN(c2ccc(-c3cnc4[nH]cc(C(=O)N[C@@H](C(=O)N5CC(C#N)C5)C5CC5)c4n3)cc2)CC1]

Prepared according to the procedure outlined in Example 142 substituting 1-{4-[4-(4,4,5,5-tetramethyl-[1,3,2]diox-aborolan-2-yl)-phenyl]-piperazin-1-yl}-ethanone for 4-(trifluoromethyl)phenylboronic acid in Step 3. MS: (M+H)$^+$= 527; mp=185-188° C.

Example 144

2-[4-(4-Methyl-piperazin-1-yl)-phenyl]-5H-pyrrolo[2,3-b]pyrazine-7-carboxylic acid [(R)-2-(3-cyano-azetidin-1-yl)-1-cyclopropyl-2-oxo-ethyl]-amide

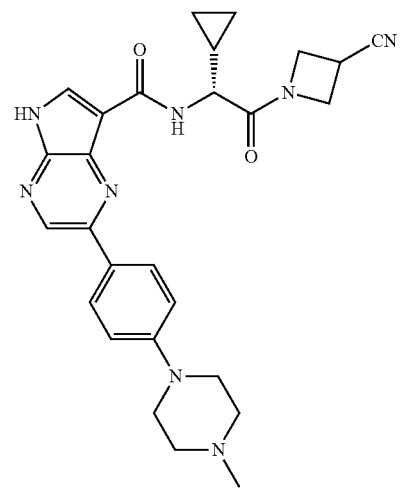 [SMILES: CN1CCN(c2ccc(-c3cnc4[nH]cc(C(=O)N[C@@H](C(=O)N5CC(C#N)C5)C5CC5)c4n3)cc2)CC1]

Prepared according to the procedure outlined in Example 142 substituting 1-methyl-4-[4-(4,4,5,5-tetramethyl-[1,3,2]dioxaborolan-2-yl)-phenyl]-piperazine for 4-(trifluoromethyl)phenylboronic acid in Step 3. MS: (M+H)$^+$=499; mp=178-185° C.

Example 145

2-(4-Morpholin-4-yl-phenyl)-5H-pyrrolo[2,3-b]pyrazine-7-carboxylic acid [(R)-2-(3-cyano-azetidin-1-yl)-1-cyclopropyl-2-oxo-ethyl]-amide

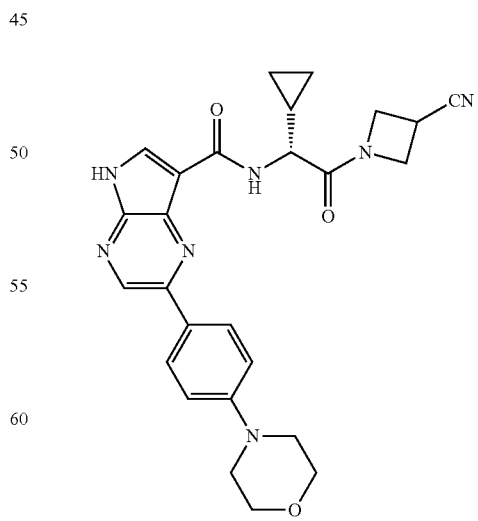

Prepared according to the procedure outlined in Example 142 substituting 4-[4-(4,4,5,5-tetramethyl-[1,3,2]dioxaborolan-2-yl)-phenyl]-morpholine for 4-(trifluoromethyl)phenylboronic acid in Step 3. MS: (M+H)$^+$=486; mp=186-192° C.

Example 146

2-(4-Dimethylamino-phenyl)-5H-pyrrolo[2,3-b]pyrazine-7-carboxylic acid [(R)-2-(3-cyano-azetidin-1-yl)-1-cyclopropyl-2-oxo-ethyl]-amide

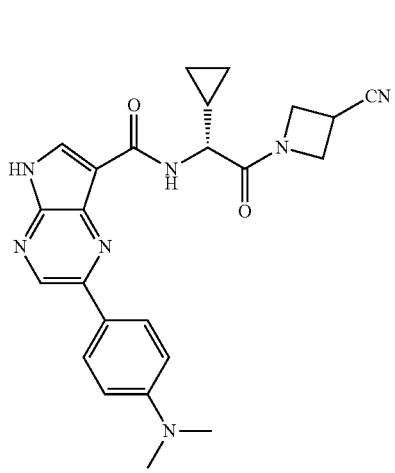 [SMILES: CN(C)c1ccc(-c2cnc3[nH]cc(C(=O)N[C@@H](C(=O)N4CC(C#N)C4)C4CC4)c3n2)cc1]

Prepared according to the procedure outlined in Example 142 substituting dimethyl-[4-(4,4,5,5-tetramethyl-[1,3,2]dioxaborolan-2-yl)-phenyl]-amine for 4-(trifluoromethyl)phenylboronic acid in Step 3. MS: (M+H)$^+$=444; mp=175-180° C.

Example 147

2-Phenyl-5H-pyrrolo[2,3-b]pyrazine-7-carboxylic acid [(R)-2-(3-cyano-azetidin-1-yl)-1-cyclopropyl-2-oxo-ethyl]-amide

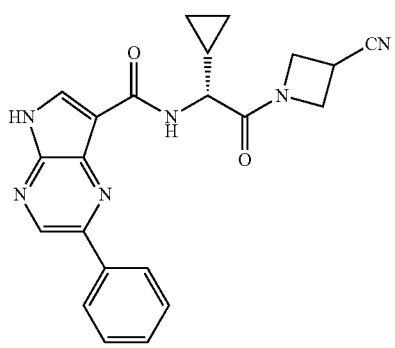 [SMILES: N#CC1CN(C(=O)[C@H](NC(=O)c2c[nH]c3ncc(-c4ccccc4)nc23)C2CC2)C1]

Prepared according to the procedure outlined in Example 142 substituting phenylboronic acid for 4-(trifluoromethyl)phenylboronic acid in Step 3. MS: (M+H)$^+$=401; mp=200-202° C.

Example 148

2-Cyclohexyloxy-5H-pyrrolo[2,3-b]pyrazine-7-carboxylic acid [(R)-1-(4-cyano-piperidine-1-carbonyl)-2,2-dimethyl-propyl]-amide

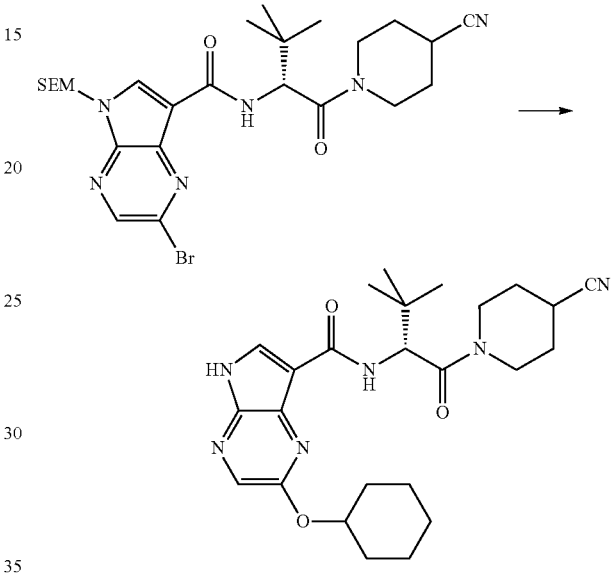

Step 1

A 10 mL flask was charged with 2-bromo-5-(2-trimethylsilanyl-ethoxymethyl)-5H-pyrrolo[2,3-b]pyrazine-7-carboxylic acid [(R)-1-(4-cyano-piperidine-1-carbonyl)-2,2-dimethyl-propyl]-amide (100 mg, 0.17 mmol, copper(I) iodide (1.7 mg, 0.009 mmol), 8-hydroxyquinoline (2.5 mg, 0.017 mmol) and potassium phosphate tribasic (74 mg, 0.34 mmol) under argon atmosphere. Cyclohexanol (1.82 mL, 17.3 mmol) was added and the reaction mixture was heated at 120° C. for 24 h. The reaction mixture was allowed to reach room temperature and then diluted with EtOAc (10 mL). The slurry was filtered over a celite pad and the filtrate was evaporated under vacuum. The crude residue was purified by preparative TLC (SiO$_2$, Hex:EtOAc, 1:1×2) to give 52 mg (50%) of 2-cyclohexyloxy-5-(2-trimethylsilanyl-ethoxymethyl)-5H-pyrrolo[2,3-b]pyrazine-7-carboxylic acid [(R)-1-(4-cyano-piperidine-1-carbonyl)-2,2-dimethyl-propyl]-amide. (M+Na)$^+$=619.

Step 2

To a solution of 2-cyclohexyloxy-5-(2-trimethylsilanyl-ethoxymethyl)-5H-pyrrolo[2, 3-1)]pyrazine-7-carboxylic acid [(R)-1-(4-cyano-piperidine-1-carbonyl)-2,2-dimethyl-propyl]-amide (84 mg, 0.14 mmol) in acetonitrile (30 mL) at room temperature was added 18-crown-6 (37 mg, 0.14 mmol) and cesium fluoride (214 mg, 1.41 mmol). The reaction mixture was heated at reflux for 72 h then cooled to room temperature and filtered over a celite pad. The filtrate was evaporated under vacuum and the crude residue was purified by column chromatography (SiO2-24 g, CH$_2$Cl$_2$, MeOH, NH$_4$OH/100:0:0 to 94:5.7:0.3 in 30 min) to afford 36 mg (55%) of 2-cyclohexyloxy-5H-pyrrolo[2,3-b]pyrazine-7- carboxylic acid [(R)-1-(4-cyano-piperidine-1-carbonyl)-2,2-dimethyl-propyl]-amide. MS: (M+H)⁺=467.

Example 149

2-(2,2,2-Trifluoro-ethoxy)-5H-pyrrolo[2,3-b]pyrazine-7-carboxylic acid [(R)-1-(4-cyano-piperidine-1-carbonyl)-2,2-dimethyl-propyl]-amide

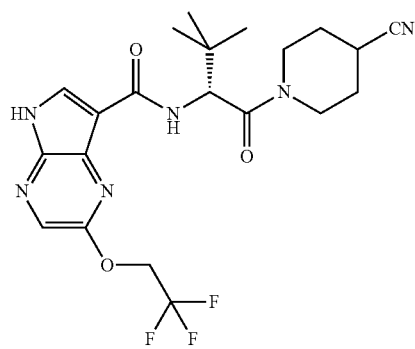 [SMILES: CC(C)(C)[C@@H](NC(=O)c1c[nH]c2ncc(OCC(F)(F)F)nc12)C(=O)N1CCC(C#N)CC1]

Prepared according to the procedure outlined in Example 148 substituting 2,2,2-trifluoroethanol for cyclohexanol in Step 1. MS: (M+Na)⁺=489.

Example 150

2-(3,3,3-Trifluoro-propoxy)-5H-pyrrolo[2,3-b]pyrazine-7-carboxylic acid [(R)-1-(4-cyano-piperidine-1-carbonyl)-2,2-dimethyl-propyl]-amide

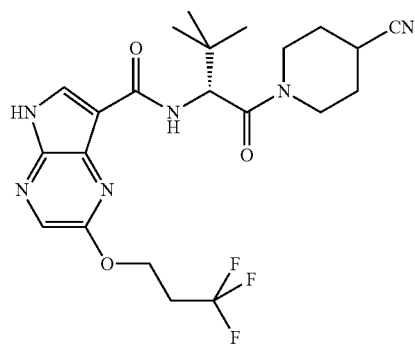 [SMILES: CC(C)(C)[C@@H](NC(=O)c1c[nH]c2ncc(OCCC(F)(F)F)nc12)C(=O)N1CCC(C#N)CC1]

Prepared according to the procedure outlined in Example 148 substituting 3,3,3-trifluoropropanol for cyclohexanol in Step 1. MS: (M+H)⁺=481.

Example 151

2-Cyclopentyloxy-5H-pyrrolo[2,3-b]pyrazine-7-carboxylic acid [(R)-1-(4-cyano-piperidine-1-carbonyl)-2,2-dimethyl-propyl]-amide

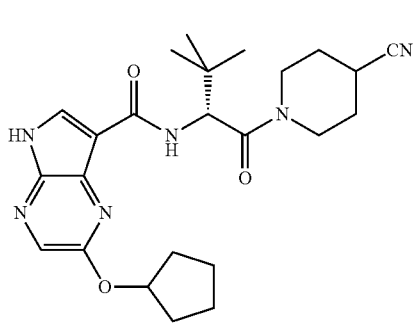 [SMILES: CC(C)(C)[C@@H](NC(=O)c1c[nH]c2ncc(OC3CCCC3)nc12)C(=O)N1CCC(C#N)CC1]

Prepared according to the procedure outlined in Example 148 substituting cyclopentanol for cyclohexanol in Step 1. MS: (M+Na)⁺=475.

Example 152

2-Isopropoxy-5H-pyrrolo[2,3-b]pyrazine-7-carboxylic acid [(R)-1-(4-cyano-piperidine-1-carbonyl)-2,2-dimethyl-propyl]-amide

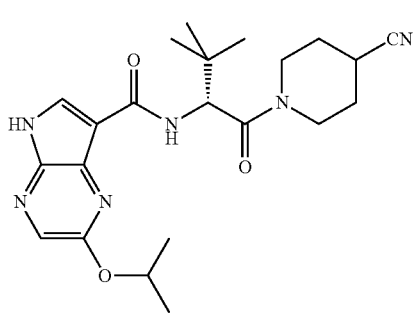 [SMILES: CC(C)Oc1cnc2[nH]cc(C(=O)N[C@@H](C(=O)N3CCC(C#N)CC3)C(C)(C)C)c2n1]

Prepared according to the procedure outlined in Example 148 substituting isopropanol for cyclohexanol in Step 1. MS: (M+H)+=427.

Example 153

2-(4-Chloro-1-oxo-1,3-dihydro-isoindol-2-yl)-5H-pyrrolo[2,3-b]pyrazine-7-carboxylic acid [(R)-2-(3-cyano-azetidin-1-yl)-1-cyclopropyl-2-oxo-ethyl]-amide

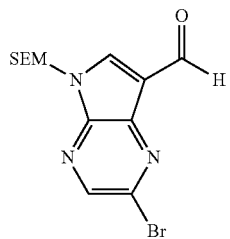

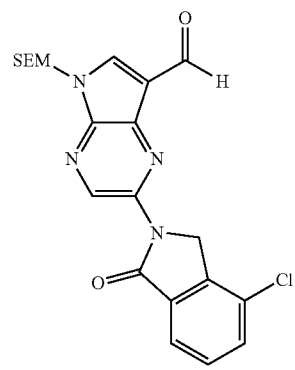

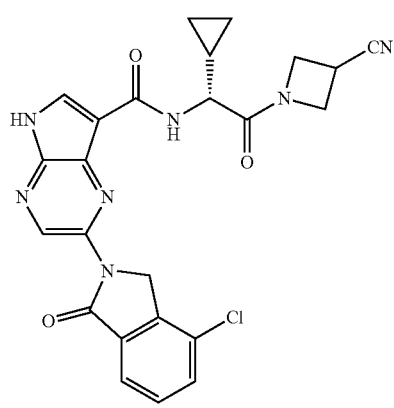

Step 1

A 10 mL flask was charged with 2-bromo-5-(2-trimethyl-silanyl-ethoxymethyl)-5H-pyrrolo[2,3-b]pyrazine-7-carbaldehyde (700 mg, 1.96 mmol), 4-chloro-2,3-dihydro-isoindol-1-one (395 mg, 2.36 mmol), N,N'-dimethylethylenediamine (42 µL, 0.39 mmol) and potassium carbonate (543 mg, 3.93 mmol) under argon atmosphere. Copper(I) iodide (37 mg, 0.20 mmol) was added and the reaction mixture was heated at 100° C. for 24 h. The reaction mixture was allowed to reach room temperature and then diluted with EtOAc (50 mL). The slurry was filtered over a celite pad and the filtrate was evaporated under vacuum. The crude residue was purified by column chromatography (SiO$_2$, 100 g, EtOAc:hexanes, 0-70% in 30 min) to provide 170 mg (20%) of 2-(4-chloro-1-oxo-1,3-dihydro-isoindol-2-yl)-5-(2-trimethylsilanyl-ethoxymethyl)-5H-pyrrolo[2,3-b]pyrazine-7-carbaldehyde as an off-white solid and 400 mg of recovered starting material.

Step 2

To a solution of 2-(4-chloro-1-oxo-1,3-dihydro-isoindol-2-yl)-5-(2-trimethylsilanyl-ethoxymethyl)-5H-pyrrolo[2,3-b]pyrazine-7-carbaldehyde (265 mg, 0.60 mmol) in 1,4-dioxane (35 mL) at 0° C. was added a solution of sulfamic acid (349 mg, 3.59 mmol) in water (4.35 mL. Then a solution of NaClO$_2$ (88 mg, 0.78 mmol) and KH$_2$PO$_4$ (977 mg, 7.18 mmol) in water (8.7 mL) was added via dropping funnel over 15 min. The ice bath was removed and the yellow cloudy reaction mixture was stirred at r.t. for 18 h. The reaction mixture was diluted with water and extracted with EtOAc (2×). The combined organic layers were dried over MgSO$_4$ and concentrated to give 269 mg (98%) of 2-(4-chloro-1-oxo-1,3-dihydro-isoindol-2-yl)-5-(2-trimethylsilanyl-ethoxymethyl)-5H-pyrrolo[2,3-b]pyrazine-7-carboxylic acid which was used without further purification.

Step 3

To a solution of 2-(4-chloro-1-oxo-1,3-dihydro-isoindol-2-yl)-5-(2-trimethylsilanyl-ethoxymethyl)-5H-pyrrolo[2,3-b]pyrazine-7-carboxylic acid (80 mg, 0.17 mmol) in DMF (2.4 mL) was added triethylamine (73 µl, 0.52 mmol), 1-((R)-2-amino-2-cyclopropyl-acetyl)-azetidine-3-carbonitrile (31.2 mg, 0.17 mmol) and PyBOP (109 mg, 0.21 mmol) at room temperature. The reaction mixture was stirred for 16 h at the same temperature then poured into EtOAc (50 mL) and washed with water (4×50 mL). The organic extracts were dried (Na$_2$SO$_4$) and evaporated under vacuum. The crude residue was purified by column chromatography (SiO$_2$, 23 g, Hex:EtOAc, 0% to 6:4, in 35 min) to afford 42 mg (39%) of 2-(4-chloro-1-oxo-1,3-dihydro-isoindol-2-yl)-5-(2-trimethylsilanyl-ethoxymethyl)-5H-pyrrolo[2,3-b]pyrazine-7-carboxylic acid [(R)-2-(3-cyano-azetidin-1-yl)-1-cyclopropyl-2-oxo-ethyl]-amide.

Step 4

To a solution of 2-(4-chloro-1-oxo-1,3-dihydro-isoindol-2-yl)-5-(2-trimethylsilanyl-ethoxymethyl)-5H-pyrrolo[2,3-b]pyrazine-7-carboxylic acid [(R)-2-(3-cyano-azetidin-1-yl)-1-cyclopropyl-2-oxo-ethyl]-amide (40 mg, 0.065 mmol) in dichloromethane (1 mL) at r.t. was added trifluoroacetic acid (0.30 mL, 3.87 mmol). The solution was stirred for 3 h at room temperature then concentrated under vacuum. The residue was dissolved in dichloromethane (1 mL) and ethylenediamine (0.43 mL, 6.45 mmol) was added. The reaction mixture was stirred at room temperature for 2 h then concentrated under vacuum. The crude residue was suspended in water: EtOAc (2 mL: 5 mL) and the resultant solid was collected by filtration, washing with EtOAc, to afford 23 mg (73%) of 2-(4-chloro-1-oxo-1,3-dihydro-isoindol-2-yl)-5H-pyrrolo[2, 3-b]pyrazine-7-carboxylic acid [(R)-2-(3-cyano-azetidin-1-yl)-1-cyclopropyl-2-oxo-ethyl]-amide as a white solid. MS: (M+Na)$^+$=512.

Example 154

2-(7-Chloro-thieno[3,2-b]pyridin-2-yl)-5H-pyrrolo[2,3-b]pyrazine-7-carboxylic acid [(R)-2-(3-cyano-azetidin-1-yl)-1-cyclopropyl-2-oxo-ethyl]-amide

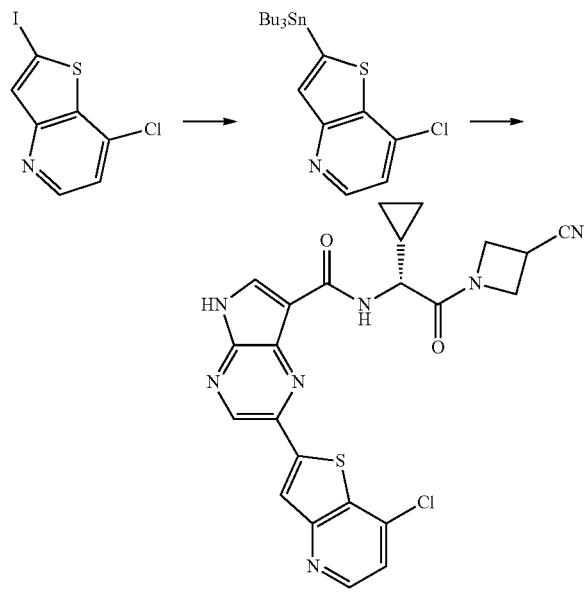

Step 1

In a round bottom flask, 7-chloro-2-iodothieno[3,2-b]pyridine (200 mg, 0.68 mmol) was suspended in THF (6 mL). The reaction mixture was cooled with a NaCl-ice bath (−12 to −8° C. internal temp) and isopropylmagnesium chloride (2.0 M in THF, 0.406 mL, 0.812 mmol) was added dropwise. The reaction mixture was stirred for 1 h at the same temperature, and then tributyltin chloride (0.29 mL, 1.08 mmol) was slowly added. The reaction mixture was allowed to warm to room temperature over ~1 h then quenched with an aqueous solution of NH$_4$Cl (20 mL) and extracted with EtOAc (30 mL). The organic layer was dried over Na$_2$SO$_4$ and evaporated to dryness. The crude residue was purified by column chromatography (SiO$_2$-11 g-Et$_3$N 2%, hexanes 100% 5 min, to hexanes:EtOAc, 9:1 in 15 min) to isolate 162 mg (52%) of 7-chloro-2-tributylstannanyl-thieno[3,2-b]pyridine as a colorless oil.

Step 2

To a solution of 2-bromo-5-(2-trimethylsilanyl-ethoxymethyl)-5H-pyrrolo[2,3-b]pyrazine-7-carboxylic acid [(R)-2-(3-cyano-azetidin-1-yl)-1-cyclopropyl-2-oxo-ethyl]-amide (180 mg, 0.34 mmol) and 7-chloro-2-tributylstannanyl-thieno[3,2-b]pyridine (162 mg, 0.35 mmol) in DMF (3 mL) were added copper(I) iodide (13.5 mg, 0.071 mmol) and tetrakis(triphenylphosphine)palladium(0) (20.4 mg, 0.018 mmol) under argon atmosphere. The reaction mixture was stirred for 16 h at 90° C. then poured into EtOAc (25 mL) and washed with water (4×30 mL). The organic extracts were dried over Na$_2$SO$_4$ and evaporated under vacuum. The crude residue was purified by column chromatography (SiO$_2$, 11 g, CH$_2$Cl$_2$ 100% to CH$_2$Cl$_2$:EtOAc 4:6 in 25 min) to afford 180 mg (82%) of 2-(7-chloro-thieno[3,2-b]pyridin-2-yl)-5-(2-trimethylsilanyl-ethoxymethyl)-5H-pyrrolo[2,3-b]pyrazine-7-carboxylic acid [(R)-2-(3-cyano-azetidin-1-yl)-1-cyclopropyl-2-oxo-ethyl]-amide.

Step 3

To a solution of 2-(7-chloro-thieno[3,2-b]pyridin-2-yl)-5-(2-trimethylsilanyl-ethoxymethyl)-5H-pyrrolo[2,3-b]pyrazine-7-carboxylic acid [(R)-2-(3-cyano-azetidin-1-yl)-1-cyclopropyl-2-oxo-ethyl]-amide (30 mg, 0.048 mmol) in dichloromethane (2 mL) was added trifluoroacetic acid (0.37 mL, 4.82 mmol). The reaction mixture was stirred for 3 h at room temperature then concentrated and dried under high vacuum for 1 h. The residue was dissolved in 3 mL of CH$_2$Cl$_2$:MeOH:NH$_4$OH (80:19:1) and stirred at room temperature for 18 h then evaporated to dryness under vacuum. The crude residue was washed with MeOH (3×3 mL) to give 17 mg (72%) of 2-(7-chloro-thieno[3,2-b]pyridin-2-yl)-5H-pyrrolo[2,3-b]pyrazine-7-carboxylic acid [(R)-2-(3-cyano-azetidin-1-yl)-1-cyclopropyl-2-oxo-ethyl]-amide. MS: (M+H)$^+$=492.

Example 155

2-(7-Pyrrolidin-1-yl-thieno[3,2-b]pyridin-2-yl)-5H-pyrrolo[2,3-b]pyrazine-7-carboxylic acid [(R)-2-(3-cyano-azetidin-1-yl)-1-cyclopropyl-2-oxo-ethyl] amide

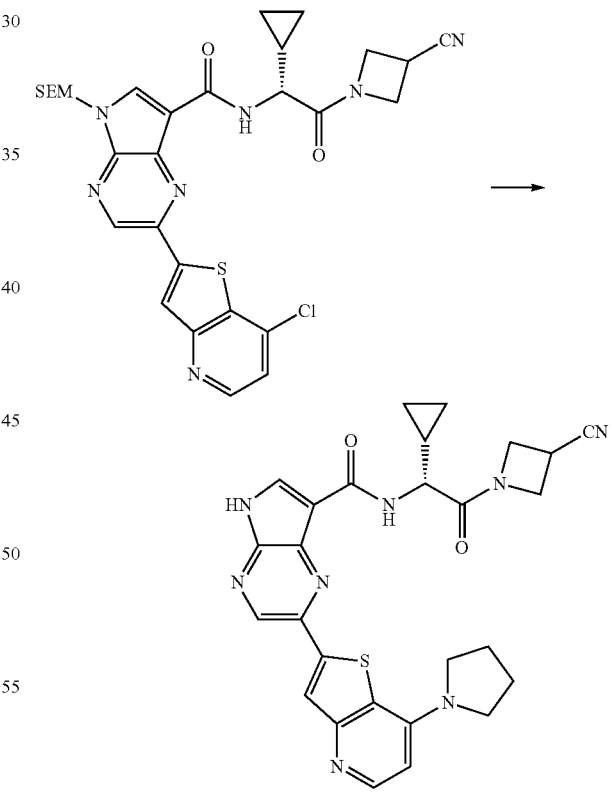

Step 1

A solution of 2-(7-chloro-thieno[3,2-b]pyridin-2-yl)-5-(2-trimethylsilanyl-ethoxymethyl)-5H-pyrrolo[2,3-b]pyrazine-7-carboxylic acid [(R)-2-(3-cyano-azetidin-1-yl)-1-cyclopropyl-2-oxo-ethyl]-amide (40 mg, 0.064 mmol) in pyrrolidine (5.32 ml, 64.3 mmol) was heated in a microwave reactor at 100° C. for 2 h. The reaction mixture was evaporated to dryness under vacuum. The crude residue was suspended in MeOH (0.5 mL) and the resultant solid collected by filtration, washing with MeOH, to give 36 mg (85%) 2-(7-pyrrolidin-1-yl-thieno[3,2-b]pyridin-2-yl)-5-(2-trimethylsilanyl-ethoxymethyl)-5H-pyrrolo[2,3-b]pyrazine-7-carboxylic acid [(R)-2-(3-cyano-azetidin-1-yl)-1-cyclopropyl-2-oxo-ethyl]-amide.

Step 2

2-(7-Pyrrolidin-1-yl-thieno[3,2-b]pyridin-2-yl)-5H-pyrrolo[2,3-b]pyrazine-7-carboxylic acid [(R)-2-(3-cyano-azetidin-1-yl)-1-cyclopropyl-2-oxo-ethyl]-amide. Prepared according to the procedure outlined in Example 154, step 3 substituting 2-(7-pyrrolidin-1-yl-thieno[3,2-b]pyridin-2-yl)-5-(2-trimethylsilanyl-ethoxymethyl)-5H-pyrrolo[2,3-b]pyrazine-7-carboxylic acid [(R)-2-(3-cyano-azetidin-1-yl)-1-cyclopropyl-2-oxo-ethyl]-amide for 2-(7-chloro-thieno[3,2-b]pyridin-2-yl)-5-(2-trimethylsilanyl-ethoxymethyl)-5H-pyrrolo[2,3-b]pyrazine-7-carboxylic acid [(R)-2-(3-cyano-azetidin-1-yl)-1-cyclopropyl-2-oxo-ethyl]-amide. The free base was treated with 1.0 M HCl in MeOH to isolate the hydrochloride salt. MS: $(M+H)^+=527$.

Example 156

2-[7-(2,2,2-Trifluoroethoxy)-thieno[3,2-b]pyridin-2-yl]-5H-pyrrolo[2,3-b]pyrazine-7-carboxylic acid [(R)-2-(3-cyano-azetidin-1-yl)-1-cyclopropyl-2-oxo-ethyl]-amide

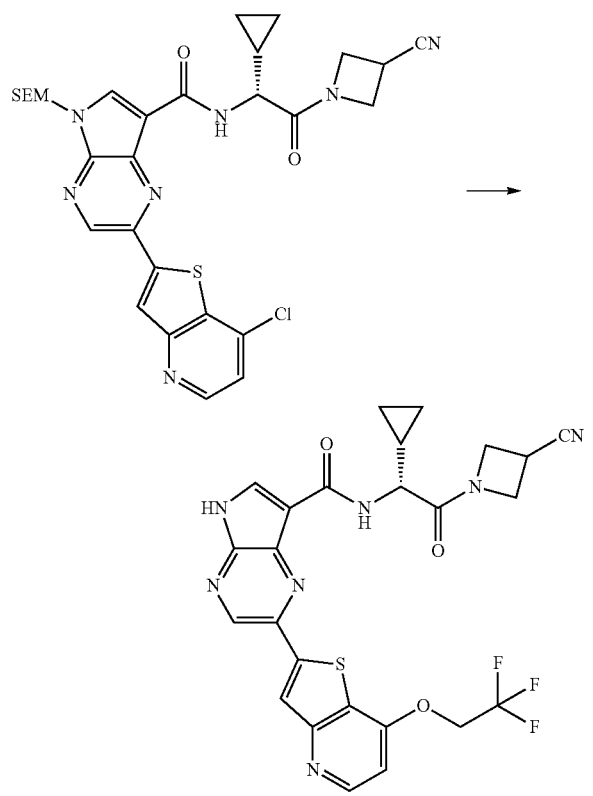 [SMILES: C[Si](C)(C)CCOCn1cc(C(=O)N[C@@H](C(=O)N2CC(C#N)C2)C2CC2)c2nc(-c3cc4nccc(Cl)c4s3)cnc21 ; N#CC1CN(C(=O)[C@H](NC(=O)c2c[nH]c3ncc(-c4cc5nccc(OCC(F)(F)F)c5s4)nc23)C2CC2)C1]

Step 1

To a suspension of sodium hydride (60% dispersion, 9.6 mg, 0.24 mmol) in DMF (3 mL) was added 2,2,2-trifluoroethanol (59 μL, 0.80 mmol) and then 2-(7-chloro-thieno[3,2-b]pyridin-2-yl)-5-(2-trimethylsilanyl-ethoxymethyl)-5H-pyrrolo[2,3-b]pyrazine-7-carboxylic acid [(R)-2-(3-cyano-azetidin-1-yl)-1-cyclopropyl-2-oxo-ethyl]-amide (50 mg, 0.08 mmol). The reaction mixture was stirred at 100° C. for 1 h under microwave assisted conditions then poured into EtOAc (20 mL) and washed with water (5×20 mL). The organic phase was evaporated under vacuum and the crude residue was purified by preparative TLC (CH$_2$Cl$_2$:MeOH:NH$_4$OH, 94:5.7:0.3) to give 47 mg (85%) of 2-[7-(2,2,2-trifluoroethoxy)-thieno[3,2-b]pyridin-2-yl]-5-(2-trimethylsilanyl-ethoxymethyl)-5H-pyrrolo[2,3-b]pyrazine-7-carboxylic acid [(R)-2-(3-cyano-azetidin-1-yl)-1-cyclopropyl-2-oxo-ethyl]-amide.

Step 2

2-[7-(2,2,2-Trifluoroethoxy)-thieno[3,2-b]pyridin-2-yl]-5H-pyrrolo[2,3-b]pyrazine-7-carboxylic acid [(R)-2-(3-cyano-azetidin-1-yl)-1-cyclopropyl-2-oxo-ethyl]-amide. Prepared according to the procedure outlined in Example 154, step 3 substituting 2-[7-(2,2,2-trifluoroethoxy)-thieno[3,2-b]pyridin-2-yl]-5-(2-trimethylsilanyl-ethoxymethyl)-5H-pyrrolo[2,3-b]pyrazine-7-carboxylic acid [(R)-2-(3-cyano-azetidin-1-yl)-1-cyclopropyl-2-oxo-ethyl]-amide for 2-(7-chloro-thieno[3,2-b]pyridin-2-yl)-5-(2-trimethylsilanyl-ethoxymethyl)-5H-pyrrolo[2,3-b]pyrazine-7-carboxylic acid [(R)-2-(3-cyano-azetidin-1-yl)-1-cyclopropyl-2-oxo-ethyl]-amide. MS: $(M+H)^+=556$.

Example 157

2-(7-Methoxy-thieno[3,2-b]pyridin-2-yl)-5H-pyrrolo[2,3-b]pyrazine-7-carboxylic acid [(R)-2-(3-cyano-azetidin-1-yl)-1-cyclopropyl-2-oxo-ethyl]-amide

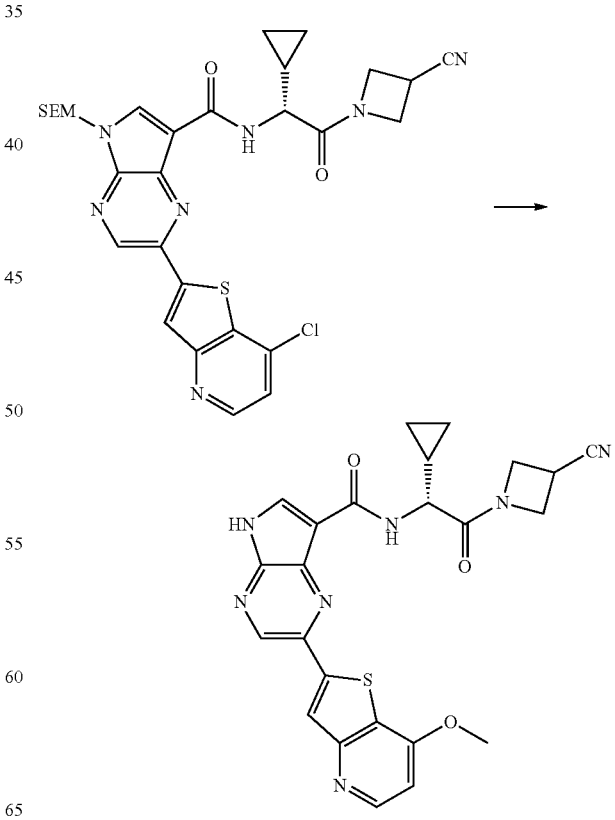

Step 1

To a solution of sodium methoxide in MeOH (0.5 M, 0.97 mL, 0.49 mmol) was added 2-(7-chloro-thieno[3,2-b]pyridin-2-yl)-5-(2-trimethylsilanyl-ethoxymethyl)-5H-pyrrolo[2,3-b]pyrazine-7-carboxylic acid [(R)-2-(3-cyano-azetidin-1-yl)-1-cyclopropyl-2-oxo-ethyl]-amide (35 mg, 0.056 mmol) and reaction mixture was stirred at 100° C. for 1 h under microwave assisted conditions. The reaction mixture was evaporated to dryness and the crude residue was purified by preparative TLC (CH$_2$Cl$_2$:MeOH:NH$_4$OH, 80:19:1) to give 18 mg (57%) of (R)-cyclopropyl-{[2-(7-methoxy-thieno[3,2-b]pyridin-2-yl)-5-(2-trimethylsilanyl-ethoxymethyl)-5H-pyrrolo[2,3-b]pyrazine-7-carbonyl]-amino}-acetic acid. MS: (M+H)$^+$=554; (M−H])$^-$=552.

Step 2

To a solution of (R)-cyclopropyl-{[2-(7-methoxy-thieno[3,2-b]pyridin-2-yl)-5-(2-trimethylsilanyl-ethoxymethyl)-5H-pyrrolo[2,3-b]pyrazine-7-carbonyl]-amino}-acetic acid (27 mg, 0.049 mmol) in DMF (2 mL) at room temperature was added triethylamine (34.0 µL, 0.24 mmol), azetidine-3-carbonitrile hydrochloride (6 mg, 0.049 mmol and PyBOP (31 mg, 0.059 mmol). The reaction mixture was stirred for 16 h at the same temperature then poured into EtOAc (25 mL) and washed with water (4×30 mL). The organic phase was dried over Na$_2$SO$_4$ and evaporated under vacuum. The crude residue was purified by column chromatography (SiO$_2$, 23 g, hex:EtOAc, 9:1 to 100% in 30 min) to give 26 mg (64%) of 2-(7-methoxy-thieno[3,2-b]pyridin-2-yl)-5-(2-trimethylsilanyl-ethoxymethyl)-5H-pyrrolo[2,3-b]pyrazine-7-carboxylic acid [(R)-2-(3-cyano-azetidin-1-yl)-1-cyclopropyl-2-oxo-ethyl]-amide.

Step 3

2-(7-Methoxy-thieno[3,2-b]pyridin-2-yl)-5H-pyrrolo[2,3-b]pyrazine-7-carboxylic acid [(R)-2-(3-cyano-azetidin-1-yl)-1-cyclopropyl-2-oxo-ethyl]-amide. Prepared according to the procedure outlined in Example 154, step 3 substituting 2-(7-methoxy-thieno[3,2-b]pyridin-2-yl)-5-(2-trimethylsilanyl-ethoxymethyl)-5H-pyrrolo[2,3-b]pyrazine-7-carboxylic acid [(R)-2-(3-cyano-azetidin-1-yl)-1-cyclopropyl-2-oxo-ethyl]-amide for 2-(7-chloro-thieno[3,2-b]pyridin-2-yl)-5-(2-trimethylsilanyl-ethoxymethyl)-5H-pyrrolo[2,3-b]pyrazine-7-carboxylic acid [(R)-2-(3-cyano-azetidin-1-yl)-1-cyclopropyl-2-oxo-ethyl]-amide. MS: (M+H)$^+$=488.

Example 158

2-(7-Chloro-thieno[3,2-b]pyridin-2-yl)-5H-pyrrolo[2,3-b]pyrazine-7-carboxylic acid [(R)-2-(3-cyano-azetidin-1-yl)-1-methyl-2-oxo-ethyl]-amide

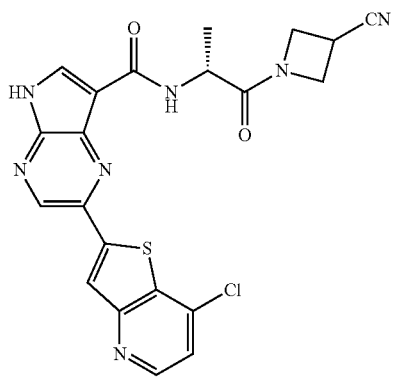 [SMILES: C[C@@H](NC(=O)c1c[nH]c2ncc(-c3cc4nccc(Cl)c4s3)nc12)C(=O)N1CC(C#N)C1]

Prepared according to the procedure outlined in Example 154 substituting 2-bromo-5-(2-trimethylsilanyl-ethoxymethyl)-5H-pyrrolo[2,3-1)]pyrazine-7-carboxylic acid [(R)-2-(3-cyano-azetidin-1-yl)-1-methyl-2-oxo-ethyl]-amide for 2-bromo-5-(2-trimethylsilanyl-ethoxymethyl)-5H-pyrrolo[2,3-b]pyrazine-7-carboxylic acid [(R)-2-(3-cyano-azetidin-1-yl)-1-cyclopropyl-2-oxo-ethyl]-amide in step 2. MS: (M+H)$^+$=467.

Example 159

2-(7-Pyrrolidin-1-yl-thieno[3,2-b]pyridin-2-yl)-5H-pyrrolo[2,3-b]pyrazine-7-carboxylic acid [(R)-2-(3-cyano-azetidin-1-yl)-1-methyl-2-oxo-ethyl]-amide

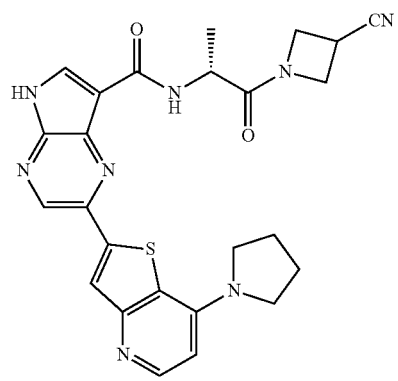 [SMILES: C[C@@H](NC(=O)c1c[nH]c2ncc(-c3cc4nccc(N5CCCC5)c4s3)nc12)C(=O)N1CC(C#N)C1]

Prepared according to the procedure outlined in Example 155 substituting 2-(7-chloro-thieno[3,2-b]pyridin-2-yl)-5-(2-trimethylsilanyl-ethoxymethyl)-5H-pyrrolo[2,3-b]pyrazine-7-carboxylic acid [(R)-2-(3-cyano-azetidin-1-yl)-1-methyl-2-oxo-ethyl]-amide for 2-(7-chloro-thieno[3,2-b]pyridin-2-yl)-5-(2-trimethylsilanyl-ethoxymethyl)-5H-pyrrolo[2,3-b]pyrazine-7-carboxylic acid [(R)-2-(3-cyano-azetidin-1-yl)-1-cyclopropyl-2-oxo-ethyl]-amide in step 1. MS: (M+H)$^+$=501.

Example 160

2-[7-(2,2,2-Trifluoro-ethoxy)-thieno[3,2-b]pyridin-2-yl]-5H-pyrrolo[2,3-b]pyrazine-7-carboxylic acid [(R)-2-(3-cyano-azetidin-1-yl)-1-methyl-2-oxo-ethyl]-amide

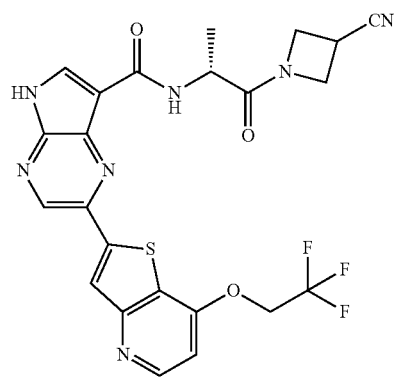 [SMILES: C[C@@H](NC(=O)c1c[nH]c2ncc(-c3cc4nccc(OCC(F)(F)F)c4s3)nc12)C(=O)N1CC(C#N)C1]

Prepared according to the procedure outlined in Example 156 substituting 2-(7-chloro-thieno[3,2-b]pyridin-2-yl)-5-(2-trimethylsilanyl-ethoxymethyl)-5H-pyrrolo[2,3-b]pyrazine-7-carboxylic acid [(R)-2-(3-cyano-azetidin-1-yl)-1-methyl-2-oxo-ethyl]-amide for 2-(7-chloro-thieno[3,2-b]pyridin-2-yl)-5-(2-trimethylsilanyl-ethoxymethyl)-5H-pyrrolo[2,3-b]pyrazine-7-carboxylic acid [(R)-2-(3-cyano-azetidin-1-yl)-1-cyclopropyl-2-oxo-ethyl]-amide in step 1. MS: (M+H)⁺=530.

Example 161

2-(7-Methoxy-thieno[3,2-b]pyridin-2-yl)-5H-pyrrolo[2,3-b]pyrazine-7-carboxylic acid [(R)-2-(3-cyano-azetidin-1-yl)-1-methyl-2-oxo-ethyl]-amide

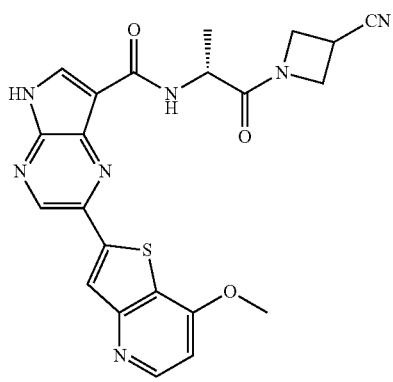 [SMILES: COc1ccnc2cc(-c3cnc4[nH]cc(C(=O)N[C@H](C)C(=O)N5CC(C#N)C5)c4n3)sc12]

Prepared according to the procedure outlined in Example 157 substituting 2-(7-chloro-thieno[3,2-b]pyridin-2-yl)-5-(2-trimethylsilanyl-ethoxymethyl)-5H-pyrrolo[2,3-b]pyrazine-7-carboxylic acid [(R)-2-(3-cyano-azetidin-1-yl)-1-methyl-2-oxo-ethyl]-amide for 2-(7-chloro-thieno[3,2-b]pyridin-2-yl)-5-(2-trimethylsilanyl-ethoxymethyl)-5H-pyrrolo[2,3-b]pyrazine-7-carboxylic acid [(R)-2-(3-cyano-azetidin-1-yl)-1-cyclopropyl-2-oxo-ethyl]-amide in step 1. MS: (M+H)⁺=462.

Example 162

2-(1,3-Dimethyl-1H-pyrazol-4-yl)-5H-pyrrolo[2,3-b]pyrazine-7-carboxylic acid [(R)-2-(3-cyano-azetidin-1-yl)-1-methyl-2-oxo-ethyl]-amide

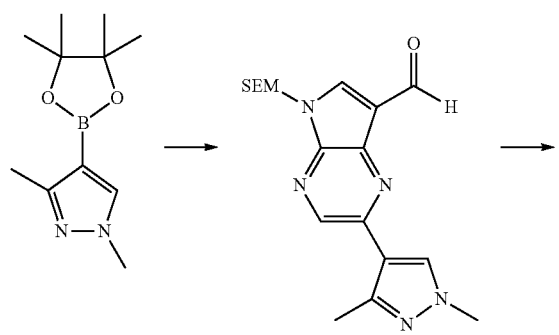

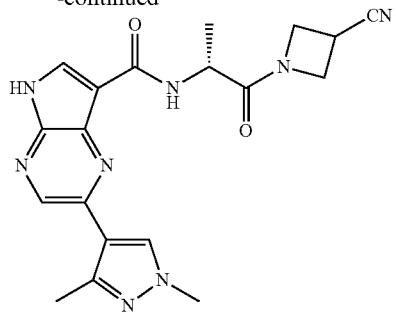

Step 1

In a 25 mL pressure vessel, 1,3-dimethyl-4-(4,4,5,5-tetramethyl-1,3,2-dioxaborolan-2-yl)-1H-pyrazole (439 mg, 1.98 mmol), lithium chloride (52 mg, 1.23 mmol) and 2-bromo-5-(2-trimethylsilanyl-ethoxymethyl)-5H-pyrrolo[2,3-b]pyrazine-7-carbaldehyde (440 mg, 1.23 mmol) were combined with ethanol (7 mL) and toluene (7 mL) and the mixture was purged with $N_2$. Potassium phosphate tribasic (917 mg, 4.32 mmol) was dissolved in 4 mL water and added to the mixture. After more purging with $N_2$ bis(triphenylphosphine)palladium (II) dichloride (87 mg, 0.12 mmol) was added, the vessel capped and stirred at 60-65° C. for 20 h. The reaction was cooled, then diluted with ethyl acetate and water. The organic layer was washed with brine, dried and evaporated. The crude material was purified by flash chromatography (silica gel, 80 g, 100% EtOAc to 20% THF/EtOAc) to give 360 mg (71% yield; 90% purity) of 2-(1,3-dimethyl-1H-pyrazol-4-yl)-5-(2-trimethylsilanyl-ethoxymethyl)-5H-pyrrolo[2,3-b]pyrazine-7-carbaldehyde.

Step 2

2-(1,3-Dimethyl-1H-pyrazol-4-yl)-5H-pyrrolo[2,3-b]pyrazine-7-carboxylic acid [(R)-2-(3-cyano-azetidin-1-yl)-1-methyl-2-oxo-ethyl]-amide. Prepared according to the procedure outlined in Example 153, steps 2-4 substituting 2-(1,3-dimethyl-1H-pyrazol-4-yl)-5-(2-trimethylsilanyl-ethoxymethyl)-5H-pyrrolo[2,3-b]pyrazine-7-carbaldehyde for 2-(4-chloro-1-oxo-1,3-dihydro-isoindol-2-yl)-5-(2-trimethylsilanyl-ethoxymethyl)-5H-pyrrolo[2,3-b]pyrazine-7-carbaldehyde in step 2, 1-((R)-2-aminopropionyl)-azetidine-3-carbonitrile trifluoroacetate for 1-((R)-2-amino-2-cyclopropyl-acetyl)-azetidine-3-carbonitrile in step 3, and HATU for PyBOP in step 3. MS: (M+H)⁺=393.

Biological Examples

JAK Assay Information

Determination of $IC_{50}$ of Janus Kinase (JAK) Inhibition:
Enzymes and peptide substrate used are described below:
JAK1: Recombinant human kinase domain from Invitrogen (Cat # PV4774)
JAK3: Recombinant human kinase domain from Millipore (Cat # 14-629) or prepared.
JAK2: Recombinant human kinase domain from Millipore (Cat # 14-640)
Substrate: N-terminally biotinylated 14-mer peptide derived from activation loop of JAK1 with sequence of the peptide substrate: Biotin-KAIETDKEYYTVKD
Assay conditions__ used are described below:
Assay Buffer: JAK Kinase Buffer: 50 mM Hepes [pH 7.2], 10 mM $MgCl_2$, 1 mM DTT, 1 mg/ml BSA. The assay was carried out in this buffer.

Assay Format The kinase activity of all three JAK kinases was measured using a radioactive, end-point assay and with trace amounts of $^{33}$P-ATP. The assays were carried out in 96-well polypropylene plates.

Experimental Method:

All concentrations were final in the reaction mixture and all incubations were carried at room temperature. Assay steps are described below:

1) Compounds were serially diluted in 100% DMSO typically at a 10× starting concentration of 1 mM. Final concentration of DMSO in the reaction was 10%.
2) Compounds were preincubated with enzyme (0.5 nM JAK3 (commercially available), 0.2 nM JAK3 (prepared), 1 nM JAK2, 5 nM JAK1) for 10 minutes.
3) Reactions were initiated by the addition of a cocktail of the two substrates (ATP and peptide premixed in the JAK Kinase Buffer). In the JAK2/JAK3 assays, ATP and the peptide were used at concentrations of 1.5 uM and 50 uM, respectively. JAK1 assay was carried out at an ATP concentration of 10 uM and a peptide concentration of 50 uM.
4) The duration of the assay for JAK2 and JAK3 is 20 minutes. JAK1 assay was carried out for 40 minutes. With all three enzymes, reactions were terminated by the addition of 0.5M EDTA to a final concentration of 100 mM.
5) 25 ul of terminated reactions were transferred to 150 ul of a 7.5% (v/v) slurry of streptavidin-coated sepharose beads in MgCl$_2$- and CaCl$_2$-free 1× Phosphate Buffered Saline containing 50 mM of EDTA in 96-well, 1.2 um MultiScreen-BV filter plates.
6) After a 30-minute incubation, the beads were washed under vacuum with the following buffers:
   a. 3 to 4 washes with 200 ul of 2M NaCl.
   b. 3 to 4 washes with 200 ul of 2M NaCl plus 1% (v/v) phosphoric acid.
   c. 1 wash with water.
7) Washed plates were dried in a 60° C. oven for between 1 to 2 hours.
8) 70 ul of Microscint 20 scintillation fluid was added to each well of filter plates and after at least 30 minutes of incubation, radioactive counts were measured in a Perkinelmer microplate scintillation counter.

Representative IC$_{50}$ results are in Table II below:

TABLE II

| Compound | Ic50 h-jak3(810-1124)-sf9-c: no additive |
|---|---|
| I-1 | 0.05159 |
| I-2 | 0.04579 |
| I-3 | 0.01171 |
| I-4 | 0.00486 |
| I-5 | 0.00172 |
| I-6 | 3.03651 |
| I-7 | 0.00656 |
| I-8 | 0.01234 |
| I-9 | 0.05294 |
| I-10 | 0.00218 |
| I-11 | 0.09151 |
| I-12 | 0.99241 |
| I-13 | 0.00453 |
| I-14 | 0.00802 |
| I-15 | 0.05495 |
| I-16 | 0.07248 |
| I-17 | 0.14793 |
| I-18 | 0.44311 |
| I-19 | 0.02700 |
| I-20 | 0.00705 |
| I-21 | 0.01494 |
| I-22 | 0.00534 |
| I-23 | 0.00953 |
| I-24 | 0.07276 |
| I-25 | 0.01612 |
| I-26 | 0.00398 |
| I-27 | 0.00194 |
| I-28 | 0.00051 |
| I-29 | 0.01362 |
| I-30 | 0.00124 |
| I-31 | 0.00080 |
| I-32 | 0.00098 |
| I-33 | 0.00032 |
| I-34 | 0.00087 |
| I-35 | 0.00068 |
| I-36 | 0.00032 |
| I-37 | 0.00180 |
| I-38 | 0.00279 |
| I-45 | 0.00070 |
| I-46 | 0.00429 |
| I-47 | 0.00104 |
| I-48 | 0.00060 |
| I-49 | 0.00101 |
| I-50 | 0.00040 |
| I-51 | 0.11095 |
| I-52 | 0.44049 |
| I-53 | 0.27888 |
| I-54 | 0.01491 |
| I-55 | 0.00152 |
| I-56 | 0.00077 |
| I-57 | 0.00032 |
| I-58 | 0.00049 |
| I-60 | 0.00079 |
| I-61 | 0.00042 |
| I-64 | 0.09493 |
| I-65 | 0.00087 |
| I-68 | 0.00058 |
| I-69 | 0.00032 |
| I-71 | 0.00392 |
| I-73 | 0.00334 |
| I-74 | 0.00113 |
| I-76 | 0.01182 |
| I-77 | 0.00032 |
| I-78 | 0.00032 |
| I-79 | 0.00032 |
| I-81 | 0.00032 |
| I-82 | 0.00032 |
| I-83 | 0.00032 |
| I-84 | 0.00075 |
| I-85 | 0.00085 |
| I-86 | 0.00402 |
| I-87 | 0.00449 |
| I-88 | 0.00123 |
| I-89 | 0.00423 |
| I-90 | 0.00973 |
| I-91 | 0.01701 |
| I-92 | 0.01091 |
| I-93 | 0.01635 |
| I-94 | 0.00366 |
| I-95 | 0.00273 |
| I-96 | 0.00069 |
| I-97 | 0.00391 |
| I-98 | 0.00216 |
| I-99 | 0.00078 |
| I-100 | 0.01605 |
| I-101 | 0.03700 |
| I-102 | 0.04312 |
| I-103 | 0.00834 |
| I-105 | 2.26468 |
| I-106 | 0.00261 |
| I-107 | 0.00657 |
| I-108 | 0.00605 |
| I-109 | 0.00061 |
| I-110 | 0.00122 |

TABLE II-continued

| Compound | Ic50 h-jak3(810-1124)-sf9-c: no additive |
|---|---|
| I-111 | 0.00571 |
| I-112 | 0.00097 |
| I-113 | 0.00371 |
| I-114 | 0.01628 |
| I-115 | 0.00292 |
| I-116 | 0.00273 |
| I-117 | 0.00101 |
| I-118 | 0.00605 |
| I-119 | 0.00274 |
| I-120 | 0.00370 |
| I-121 | 0.00167 |
| I-122 | 0.00405 |
| I-123 | 0.00062 |
| I-124 | 0.00137 |
| I-125 | 0.00035 |
| I-126 | 0.00057 |
| I-127 | 0.00356 |
| I-128 | 0.00281 |
| I-129 | 0.00118 |
| I-130 | 0.11280 |
| I-131 | 0.00258 |
| I-132 | 0.00049 |
| I-133 | 0.00167 |
| I-135 | 0.00611 |
| I-136 | 0.00711 |
| I-137 | 0.53864 |
| I-138 | 0.01905 |
| I-139 | 0.00032 |
| I-140 | 0.00068 |
| I-142 | 0.00047 |
| I-143 | 0.00042 |
| I-144 | 0.00062 |
| I-145 | 0.01520 |
| I-146 | 0.00038 |
| I-147 | 0.00446 |
| I-148 | 0.00198 |
| I-149 | 0.00127 |
| I-150 | 0.00200 |
| I-151 | 0.00032 |
| I-152 | 0.00952 |
| I-153 | 0.00902 |
| I-154 | 0.00306 |
| I-155 | 0.01051 |
| I-156 | 0.00597 |
| I-157 | 0.00328 |
| I-158 | 0.00234 |
| I-159 | 0.00266 |
| I-160 | 0.00038 |
| I-161 | 0.00032 |
| I-163 | 0.00032 |
| I-164 | 0.00032 |
| I-165 | 0.00068 |
| I-166 | 0.00032 |

SYK Assay Information
Determination of $IC_{50}$ of Spleen Tyrosine Kinase (SYK) Inhibition:

SYK kinase assay is a standard kinase assay adapted to a 96 well plate format. This assay is performed in 96-well format for $IC_{50}$ determination with 8 samples which represented 10 half log dilutions and a 40 µL reaction volume. The assay measures the incorporation of radiolabeled $^{33}$P γATP into an N-terminally biotinylated peptide substrate, derived from naturally occurring phosphoacceptor consensus sequence (Biotin-11aa DY*E). Phosphorylated products were detected upon termination of reactions with EDTA and the addition of Streptavidin coated beads.

Assay plates: 96-well MultiScreen 0.65 um filter plates (Millipore Cat. No.: MADVNOB10)
Streptavidin coated beads: Streptavidin Sepharose TM, suspension 5.0 mL, in 50 mM EDTA/PBS diluted (1:100), (Amersham, Cat. No.: 17-5113-01)
Compounds: 10 mM in 100% dimethylsulfoxide (DMSO), final conc.: compound 0.003-100 uM in 10% DMSO
Enzyme: SYK RPA purified, truncated construct of Spleen Tyrosine Kinase aa 360-635, stock solution 1 mg/mL, MW: 31.2 KDa, final conc.: 0.0005 µM.
Peptide 1: biotinylated peptide is derived from a naturally occurring phosphor-acceptor consensus sequence (Biotin-EPEGDYEEVLE), special order from QCB, stock solution 20 mM, final conc.: 5.0 µM.
ATP: Adenosine-5'-triphosphate 20 mM, (ROCHE Cat. No.: 93202720), final concentration: 20 µM
Buffer: HEPES: 2-Hydroxyethyl piperazine-2-ethane-sulfonic acid (Sigma, Cat. No.: H-3375) final concentration: 50 mM HEPES pH7.5
BSA: Bovine Serum Albumin Fraction V, fatty acid free (Roche Diagnostics GmbH, Cat. No. 9100221) diluted to a final concentration of 0.1%
EDTA: EDTA stock solution 500 mM, (GIBCO, Cat. No.: 15575-038) final concentration: 0.1 mM
DTT: 1,4-Dithiothreitol (Roche Diagnostics GmbH, Cat. No.: 197777), final conc.: 1 mM
$MgCl_2 \times 6H_2O$: MERCK, Cat. No.: 105833.1000, final concentration: 10 mM
Assay Dilution Buffer (ADB): 50 mM HEPES, 0.1 mM EGTA, 0.1 mM Na Vanadate, 0.1 mM β-glycerophosphate, 10 mM $MgCl_2$, 1 mM DTT, 0.1% BSA, pH 7.5
Bead wash buffer: 10 g/L PBS (Phosphate buffered saline) with 2M NaCl+1% phosphoric acid.

Experimental Method:

In 40 µL volume, 26 µL of ADB diluted, purified recombinant human SYK360-635 [0.5 nM] was mixed with 4 µL of 10× concentrations of the test compounds, [usually 100 µM-0.003 µM] in [10%] DMSO and the mixture was incubated for 10 min at RT.

The kinase reaction was initiated by the addition of 10 µL 4× substrate cocktail containing the DYE peptide substrate [0 or 5 µM], ATP [20 µM] and $^{33}$PγATP [2 µCi/rxn]. After incubation at 30° C. for 15 min, the reaction was terminated by the transfer of 25 µL pf the reaction sample to a 96 well 0.65 µm Millipore MADVNOB membrane/plate containing 200 µL, 5 mM EDTA and 20% Streptavidine coated beads in PBS.

The unbound radionucleotides were washed under vacuum with 3×250 µL 2M NaCl; 2×250 µL 2M NaCl+1% phosphoric acid; 1×250 µL $H_2O$. After the last wash membrane/plates were transferred to an adaptor plate, heat dried for 15 min at 60° C., and 50 µL scintillation cocktail was added to each well and 4 h later the amount of radioactivity was counted in a top counter.

The percent inhibition was calculated based on the uninhibited enzyme rate:

$$\% \text{ Inhibition} = 100/(1+(IC_{50}/\text{Inhibitor conc})^n)$$

The $IC_{50}$ was calculated using a non-linear curve fit with XLfit software (ID Business Solution Ltd., Guilford, Surrey, UK).

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

We claim:

1. A compound of Formula I

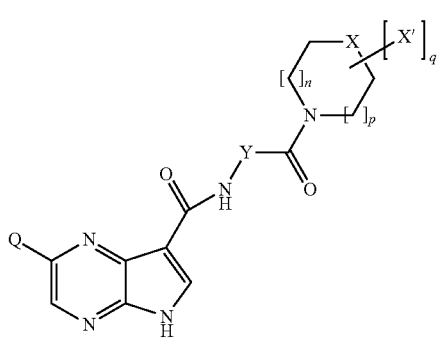

wherein:
Y is CH(R¹);
R¹ is H or R¹ᵃ;
R¹ᵃ is lower alkyl, lower alkoxy, phenyl, benzyl, heteroaryl, cycloalkyl, heterocycloalkyl, or cycloalkylalkyl, optionally substituted with one or more R¹ᵃ';
R¹ᵃ' is halogen, lower alkyl, lower haloalkyl, lower alkoxy, lower hydroxyalkyl, oxo, hydroxy, or —CN;
X is C(R²)(R³), N(R²), S(=O)₂, or O;
each R² is independently H or R²ᵃ;
each R²ᵃ is independently lower alkyl, lower haloalkyl, halogen, lower alkoxy, lower hydroxyalkyl, cyano, cyano lower alkyl, hydroxy, C(=O)R²ᵃ' or S(=O)₂R²ᵃ';
each R²ᵃ' is independently H or lower alkyl;
each X' is independently halogen, lower alkyl, cyano, hydroxy, lower haloalkyl, lower hydroxyalkyl, heteroaryl, spiroheterocycloalkyl, spirocycloalkyl, lower alkoxy, lower alkylamino, or lower dialkylamino;
or X' and R² come together to form a bicyclic ring system, optionally substituted with one or more R²';
R²' is halogen, lower alkyl, lower alkoxy, hydroxy, lower hydroxyalkyl, lower haloalkyl, lower hydroxyalkylcyano, or —S(O)₂CH₃;
R³ is H, hydroxy, halogen or lower alkyl;
or R² and R³ come together to form a spirocyclic ring system, optionally substituted with one or more R²';
q is 0, 1, 2, 3, or 4;
n is 0 or 1;
p is 0 or 1;
Q is H, halogen, hydroxy, cyano or Q';
Q' is lower alkyl, lower alkenyl, lower alkynyl, lower alkoxy, cycloalkyl, cycloalkyloxy, phenyl, phenyloxy, cycloalkenyl, heterocycloalkyl, or heteroaryl, optionally substituted with one or more Qᵃ;
Qᵃ is Qᵇ or Qᶜ;
Qᵇ is halogen, oxo, hydroxy, —CN, —SCH₃, —S(O)₂CH₃, or —S(=O)CH₃;
Qᶜ is Qᵈ or Qᵉ;
or two Qᵃ come together to form a bicyclic ring system, optionally substituted with one or more Qᵇ or Qᶜ;
Qᵈ is —O(Qᵉ), —S(=O)₂(Qᵉ), —C(=O)N(Qᵉ)₂, —S(O)₂(Qᵉ), —C(=O)(Qᵉ), —C(=O)O(Qᵉ), —N(Qᵉ)₂; —N(Qᵉ)C(=O)(Qᵉ), —N(Qᵉ)C(=O)O(Qᵉ), or —N(Qᵉ)C(=O)N(Qᵉ)₂;
each Qᵉ is independently H or Qᵉ';
each Qᵉ' is independently lower alkyl, phenyl, benzyl, lower haloalkyl, lower alkoxy, cycloalkyl, cycloalkyl lower alkyl, cycloalkenyl, heterocycloalkyl, or heteroaryl, optionally substituted with one or more Qᶠ;
Qᶠ is Qᵍ or Qʰ;
Qᵍ is halogen, hydroxy, cyano, oxo, or —C(=O)(Qʰ);
Qʰ is lower alkyl, lower haloalkyl, lower alkoxy, amino, phenyl, benzyl, cycloalkyl, heterocycloalkyl, or heteroaryl, optionally substituted with one or more Qⁱ; and
Qⁱ is halogen, hydroxy, cyano, lower alkyl, lower haloalkyl, or lower alkoxy;
or a pharmaceutically acceptable salt thereof.

2. The compound of claim 1, wherein Q is cycloalkyl, phenyl or heteroaryl, optionally substituted with one or more Qᵃ.

3. The compound of claim 2, wherein X is C(R²)(R³).

4. The compound of claim 3, wherein R² is lower alkyl, cyano, halogen, lower alkoxy, lower haloalkyl, or hydroxy.

5. The compound of claim 4, wherein n is 0 and p is 0.

6. The compound of claim 4, wherein n is 1 and p is 0.

7. The compound of claim 4, wherein n is 1 and p is 1.

8. The compound of claim 4, wherein q is 0.

9. The compound of claim 4 wherein R² is cyano.

10. The compound of claim 9, wherein q is 0.

11. The compound of claim 10, wherein R¹ is lower alkyl, lower alkoxy, cycloalkyl, lower haloalkyl, or lower haloalkyl cycloalkyl.

12. The compound of claim 11, wherein R¹ is lower alkyl or cycloalkyl.

13. The compound of claim 12, wherein R³ is H.

14. The compound of claim 12, wherein R³ is lower alkyl.

15. A pharmaceutical composition comprising the compound of claim 1, admixed with at least one pharmaceutically acceptable carrier, excipient or diluent.

16. A compound selected from the group consisting of:
2-Cyclopropyl-5H-pyrrolo[2,3-b]pyrazine-7-carboxylic acid ((R)-1-methyl-2-oxo-2-pyrrolidin-1-yl-ethyl)-amide;
2-Cyclopropyl-5H-pyrrolo[2,3-b]pyrazine-7-carboxylic acid ((R)-1-methyl-2-oxo-2-piperidin-1-yl-ethyl)-amide;
2-Cyclopropyl-5H-pyrrolo[2,3-b]pyrazine-7-carboxylic acid [(R)-1-(pyrrolidine-1-carbonyl)-propyl]-amide;
2-Cyclopropyl-5H-pyrrolo[2,3-b]pyrazine-7-carboxylic acid [(R)-2-methyl-1-(pyrrolidine-1-carbonyl)-propyl]-amide;
2-Cyclopropyl-5H-pyrrolo[2,3-b]pyrazine-7-carboxylic acid ((R)-1-cyclopropyl-2-oxo-2-pyrrolidin-1-yl-ethyl)-amide;
2-Cyclopropyl-5H-pyrrolo[2,3-b]pyrazine-7-carboxylic acid ((S)-1-methyl-2-oxo-2-pyrrolidin-1-yl-ethyl)-amide;
2-Cyclopropyl-5H-pyrrolo[2,3-b]pyrazine-7-carboxylic acid [(R)-2-methyl-1-(piperidine-1-carbonyl)-propyl]-amide;

2-Cyclopropyl-5H-pyrrolo[2,3-b]pyrazine-7-carboxylic acid [(R)-2-methyl-1-(morpholine-4-carbonyl)-propyl]-amide;
2-Cyclopropyl-5H-pyrrolo[2,3-b]pyrazine-7-carboxylic acid [(R)-2-(3-methoxy-pyrrolidin-1-yl)-1-methyl-2-oxo-ethyl]-amide;
2-Cyclopropyl-5H-pyrrolo[2,3-b]pyrazine-7-carboxylic acid [(R)-2,2-dimethyl-1-(pyrrolidine-1-carbonyl)-propyl]-amide;
2-Cyclopropyl-5H-pyrrolo[2,3-b]pyrazine-7-carboxylic acid [(R)-2-(3-hydroxy-pyrrolidin-1-yl)-1-methyl-2-oxo-ethyl]-amide;
2-Cyclopropyl-5H-pyrrolo[2,3-b]pyrazine-7-carboxylic acid ((S)-1-methyl-2-oxo-2-piperidin-1-yl-ethyl)-amide;
2-(1-Ethyl-1H-pyrazol-4-yl)-5H-pyrrolo[2,3-b]pyrazine-7-carboxylic acid [(R)-2,2-dimethyl-1-(pyrrolidine-1-carbonyl)-propyl]-amide;
2-Cyclopropyl-5H-pyrrolo[2,3-b]pyrazine-7-carboxylic acid [(R)-2-(3-cyano-pyrrolidin-1-yl)-1-methyl-2-oxo-ethyl]-amide;
2-Cyclopropyl-5H-pyrrolo[2,3-b]pyrazine-7-carboxylic acid [(R)-1-methyl-2-(3-methyl-pyrrolidin-1-yl)-2-oxo-ethyl]-amide;
2-Cyclopropyl-5H-pyrrolo[2,3-b]pyrazine-7-carboxylic acid [(R)-1-methyl-2-(2-methyl-pyrrolidin-1-yl)-2-oxo-ethyl]-amide;
2-Cyclopropyl-5H-pyrrolo[2,3-b]pyrazine-7-carboxylic acid ((R)-2-azetidin-1-y1-1-methyl-2-oxo-ethyl)-amide;
2-Phenoxy-5H-pyrrolo[2,3-b]pyrazine-7-carboxylic acid [(R)-2-methyl-1-(pyrrolidine-1-carbonyl)-propyl]-amide;
2-Cyclopropyl-5H-pyrrolo[2,3-b]pyrazine-7-carboxylic acid [2,2,2-trifluoro-1-(pyrrolidine-1-carbonyl)-ethyl]-amide;
2-Cyclopropyl-5H-pyrrolo[2,3-b]pyrazine-7-carboxylic acid [(R)-2-(3-cyano-azetidin-1-yl)-1-methyl-2-oxo-ethyl]-amide;
2-Cyclopropyl-5H-pyrrolo[2,3-b]pyrazine-7-carboxylic acid [(R)-2-(3,3-difluoro-pyrrolidin-1-yl)-1-methyl-2-oxo-ethyl]-amide;
2-Cyclopropyl-5H-pyrrolo[2,3-b]pyrazine-7-carboxylic acid [(R)-2-((S)-3-fluoro-pyrrolidin-1-yl)-1-methyl-2-oxo-ethyl]-amide;
2-Cyclopropyl-5H-pyrrolo[2,3-b]pyrazine-7-carboxylic acid [(R)-2-((R)-3-fluoro-pyrrolidin-1-yl)-1-methyl-2-oxo-ethyl]-amide;
2-Cyclopropyl-5H-pyrrolo[2,3-b]pyrazine-7-carboxylic acid [(R)-1-methyl-2-(2-oxa-6-aza-spiro[3.3]hept-6-yl)-2-oxo-ethyl]-amide;
2-Cyclopropyl-5H-pyrrolo[2,3-b]pyrazine-7-carboxylic acid [(R)-1-methyl-2-oxo-2-(3-trifluoromethyl-pyrrolidin-1-yl)-ethyl]-amide;
2-Cyclopropyl-5H-pyrrolo[2,3-b]pyrazine-7-carboxylic acid ((R)-1-cyclopentyl-2-oxo-2-pyrrolidin-1-yl-ethyl)-amide;
2-(1-Ethyl-1H-pyrazol-4-yl)-5H-pyrrolo[2,3-b]pyrazine-7-carboxylic acid ((R)-1-cyclopropyl-2-oxo-2-pyrrolidin-1-yl-ethyl)-amide;
2-(1-Ethyl-1H-pyrazol-4-yl)-5H-pyrrolo[2,3-b]pyrazine-7-carboxylic acid [(R)-1-(3-cyano-3-methyl-pyrrolidine-1-carbonyl)-2,2-dimethyl-propyl]-amide;
2-Cyclopropyl-5H-pyrrolo[2,3-b]pyrazine-7-carboxylic acid [(R)-1-(3-cyano-piperidine-1-carbonyl)-2,2-dimethyl-propyl]-amide;
2-Cyclopropyl-5H-pyrrolo[2,3-b]pyrazine-7-carboxylic acid [(R)-1-((S)-3-cyano-pyrrolidine-1-carbonyl)-2,2-dimethyl-propyl]-amide;
2-Cyclopropyl-5H-pyrrolo[2,3-b]pyrazine-7-carboxylic acid [(R)-1-((R)-3-cyano-pyrrolidine-1-carbonyl)-2,2-dimethyl-propyl]-amide;
2-Cyclopropyl-5H-pyrrolo[2,3-b]pyrazine-7-carboxylic acid [(R)-2,2-dimethyl-1-(piperidine-1-carbonyl)-propyl]-amide;
2-Cyclopropyl-5H-pyrrolo[2,3-b]pyrazine-7-carboxylic acid [(R)-1-(3-cyano-azetidine-1-carbonyl)-2,2-dimethyl-propyl]-amide;
2-(1-Ethyl-1H-pyrazol-4-yl)-5H-pyrrolo[2,3-b]pyrazine-7-carboxylic acid [(R)-1-(1-methyl-cyclopropyl)-2-oxo-2-pyrrolidin-1-yl-ethyl]-amide;
2-Cyclopropyl-5H-pyrrolo[2,3-b]pyrazine-7-carboxylic acid [(R)-1-(4-cyano-piperidine-1-carbonyl)-2,2-dimethyl-propyl]-amide;
2-(1-Ethyl-1H-pyrazol-4-yl)-5H-pyrrolo[2,3-b]pyrazine-7-carboxylic acid [(R)-1-(3-cyano-3-fluoro-pyrrolidine-1-carbonyl)-2,2-dimethyl-propyl]-amide;
2-Cyclopropyl-5H-pyrrolo[2,3-b]pyrazine-7-carboxylic acid ((R)-1-cyclohexyl-2-oxo-2-pyrrolidin-1-yl-ethyl)-amide;
2-(1-Ethyl-1H-pyrazol-4-yl)-5H-pyrrolo[2,3-b]pyrazine-7-carboxylic acid {(R)-1-[3-(4,5-dihydro-1H-imidazol-2-yl)-3-fluoro-pyrrolidine-1-carbonyl]-2,2-dimethyl-propyl}-amide;
2-Cyclopropyl-5H-pyrrolo[2,3-b]pyrazine-7-carboxylic acid [(R)-1-(3-cyano-3-methyl-azetidine-1-carbonyl)-2,2-dimethyl-propyl]-amide;
2-Cyclopropyl-5H-pyrrolo[2,3-b]pyrazine-7-carboxylic acid [(R)-2-(3-cyano-azetidin-1-yl)-1-cyclopentyl-2-oxo-ethyl]-amide;
2-Cyclopropyl-5H-pyrrolo[2,3-b]pyrazine-7-carboxylic acid [(R)-1-(3,3-difluoro-pyrrolidine-1-carbonyl)-2,2-dimethyl-propyl]-amide;
2-Cyclopropyl-5H-pyrrolo[2,3-b]pyrazine-7-carboxylic acid [(R)-1-(3,4-dihydro-1H-isoquinoline-2-carbonyl)-2,2-dimethyl-propyl]-amide;
2-Cyclopropyl-5H-pyrrolo[2,3-b]pyrazine-7-carboxylic acid [(R)-1-(4-cyano-piperidine-1-carbonyl)-3-methyl-butyl]-amide;
2-Cyclopropyl-5H-pyrrolo[2,3-b]pyrazine-7-carboxylic acid [(R)-1-(4-cyano-4-methyl-piperidine-1-carbonyl)-2,2-dimethyl-propyl]-amide;
2-Cyclopropyl-5H-pyrrolo[2,3-b]pyrazine-7-carboxylic acid [(R)-2-(4-cyano-piperidin-1-yl)-1-cyclopentyl-2-oxo-ethyl]-amide;
2-Cyclopropyl-5H-pyrrolo[2,3-b]pyrazine-7-carboxylic acid [(S)-2-(4-cyano-piperidin-1-yl)-2-oxo-1-(1-trifluoromethyl-cyclopropyl)-ethyl]-amide;
2-Cyclopropyl-5H-pyrrolo[2,3-b]pyrazine-7-carboxylic acid [(R)-2-(4-cyano-piperidin-1-yl)-2-oxo-1-(1-trifluoromethyl-cyclopropyl)-ethyl]-amide;
2-Cyclopropyl-5H-pyrrolo[2,3-b]pyrazine-7-carboxylic acid [(R)-1-benzyl-2-(4-cyano-piperidin-1-yl)-2-oxo-ethyl]-amide;
2-Cyclopropyl-5H-pyrrolo[2,3-b]pyrazine-7-carboxylic acid [(R)-1-(4-cyano-piperidine-1-carbonyl)-3,3-dimethyl-butyl]-amide;
2-(3,5-Bis-trifluoromethyl-phenyl)-5H-pyrrolo[2,3-b]pyrazine-7-carboxylic acid [(R)-1-(4-cyano-piperidine-1-carbonyl)-2,2-dimethyl-propyl]-amide;
2-(3-Pyrrolidin-1-yl-phenyl)-5H-pyrrolo[2,3-b]pyrazine-7-carboxylic acid [(R)-1-(4-cyano-piperidine-1-carbonyl)-2,2-dimethyl-propyl]-amide;

2-Cyclopropyl-5H-pyrrolo[2,3-b]pyrazine-7-carboxylic acid [(R)-1-(4,4-difluoro-piperidine-1-carbonyl)-2,2-dimethyl-propyl]-amide;

2-(1-Methyl-1H-pyrazol-4-yl)-5H-pyrrolo[2,3-b]pyrazine-7-carboxylic acid [(R)-1-(3-cyano-azetidine-1-carbonyl)-2,2-dimethyl-propyl]-amide;

2-(1H-Pyrazol-4-yl)-5H-pyrrolo[2,3-b]pyrazine-7-carboxylic acid [(R)-1-(4-cyano-piperidine-1-carbonyl)-2,2-dimethyl-propyl]-amide;

2-(1-Methyl-1H-pyrazol-4-yl)-5H-pyrrolo[2,3-b]pyrazine-7-carboxylic acid [(R)-1-(4-cyano-piperidine-1-carbonyl)-2,2-dimethyl-propyl]-amide;

2-(1-Ethyl-1H-pyrazol-4-yl)-5H-pyrrolo[2,3-b]pyrazine-7-carboxylic acid [(R)-1-(4-cyano-piperidine-1-carbonyl)-2,2-dimethyl-propyl]-amide;

2-Cyclopropyl-5H-pyrrolo[2,3-b]pyrazine-7-carboxylic acid [(R)-1-(4-acetyl-piperazine-1-carbonyl)-2,2-dimethyl-propyl]-amide;

2-Cyclopropyl-5H-pyrrolo[2,3-b]pyrazine-7-carboxylic acid [(R)-2,2-dimethyl-1-(4-trifluoromethyl-piperidine-1-carbonyl)-propyl]-amide;

2-(1-Methyl-1H-pyrazol-4-yl)-5H-pyrrolo[2,3-b]pyrazine-7-carboxylic acid [(R)-1-((S)-3-cyano-pyrrolidine-1-carbonyl)-2,2-dimethyl-propyl]-amide;

2-(1-Methyl-1H-pyrazol-4-yl)-5H-pyrrolo[2,3-b]pyrazine-7-carboxylic acid [(R)-1-((R)-3-cyano-pyrrolidine-1-carbonyl)-2,2-dimethyl-propyl]-amide;

2-Cyclopropyl-5H-pyrrolo[2,3-b]pyrazine-7-carboxylic acid [(R)-2-(4-cyano-piperidin-1-yl)-1-cyclopropyl-2-oxo-ethyl]-amide;

2-(1-Ethyl-1H-pyrazol-4-yl)-5H-pyrrolo[2,3-b]pyrazine-7-carboxylic acid [(R)-2-(3-cyano-azetidin-1-yl)-1-methyl-2-oxo-ethyl]-amide;

2-(1-Methyl-1H-pyrazol-4-yl)-5H-pyrrolo[2,3-b]pyrazine-7-carboxylic acid [(R)-2-(4-cyano-piperidin-1-yl)-1-cyclopropyl-2-oxo-ethyl]-amide;

2-(3,4,5-Trimethoxy-phenyl)-5H-pyrrolo[2,3-b]pyrazine-7-carboxylic acid [(R)-1-(4-cyano-piperidine-1-carbonyl)-2,2-dimethyl-propyl]-amide;

2-Cyclopropyl-5H-pyrrolo[2,3-b]pyrazine-7-carboxylic acid [(R)-1-(4-hydroxy-4-phenyl-piperidine-1-carbonyl)-2,2-dimethyl-propyl]-amide;

2-(2,5-Dimethoxy-phenyl)-5H-pyrrolo[2,3-b]pyrazine-7-carboxylic acid [(R)-1-(4-cyano-piperidine-1-carbonyl)-2,2-dimethyl-propyl]-amide;

2-(1-Ethyl-1H-pyrazol-4-yl)-5H-pyrrolo[2,3-b]pyrazine-7-carboxylic acid [(R)-2-(4-cyano-piperidin-1-yl)-1-methyl-2-oxo-ethyl]-amide;

2-Cyclopropyl-5H-pyrrolo[2,3-b]pyrazine-7-carboxylic acid [(R)-2-(3-cyano-azetidin-1-yl)-1-cyclopropyl-2-oxo-ethyl]-amide;

2-(1-Methyl-1H-pyrazol-4-yl)-5H-pyrrolo[2,3-b]pyrazine-7-carboxylic acid [(R)-1-(3-cyano-azetidine-1-carbonyl)-3-methyl-butyl]-amide;

2-(1-Methyl-1H-pyrazol-4-yl)-5H-pyrrolo[2,3-b]pyrazine-7-carboxylic acid [(R)-2-(3-cyano-azetidin-1-yl)-1-cyclopropyl-2-oxo-ethyl]-amide;

2-(1-Ethyl-1H-pyrazol-4-yl)-5H-pyrrolo[2,3-b]pyrazine-7-carboxylic acid [(R)-2-(4-cyano-piperidin-1-yl)-1-cyclopropyl-2-oxo-ethyl]-amide;

2-Cyclopropyl-5H-pyrrolo[2,3-b]pyrazine-7-carboxylic acid [(R)-1-(4-hydroxy-4-trifluoromethyl-piperidine-1-carbonyl)-2,2-dimethyl-propyl]-amide;

2-Cyclopropyl-5H-pyrrolo[2,3-b]pyrazine-7-carboxylic acid [(R)-1-(4-hydroxy-4-methyl-piperidine-1-carbonyl)-2,2-dimethyl-propyl]-amide;

2-(1-Ethyl-1H-pyrazol-4-yl)-5H-pyrrolo[2,3-b]pyrazine-7-carboxylic acid [(S)-2-(4-cyano-piperidin-1-yl)-2-oxo-1-(1-trifluoromethyl-cyclopropyl)-ethyl]-amide;

2-(1-Ethyl-1H-pyrazol-4-yl)-5H-pyrrolo[2,3-b]pyrazine-7-carboxylic acid [(R)-2-(4-cyano-piperidin-1-yl)-2-oxo-1-(1-trifluoromethyl-cyclopropyl)-ethyl]-amide;

2-(1-Methyl-1H-pyrazol-4-yl)-5H-pyrrolo[2,3-b]pyrazine-7-carboxylic acid [(R)-2-(3-cyano-azetidin-1-yl)-1-cyclohexyl-2-oxo-ethyl]-amide;

2-(1-Methyl-1H-imidazol-4-yl)-5H-pyrrolo[2,3-b]pyrazine-7-carboxylic acid [(R)-1-(4-cyano-piperidine-1-carbonyl)-2,2-dimethyl-propyl]-amide;

2-(1-Cyclopropyl-1H-pyrazol-4-yl)-5H-pyrrolo[2,3-b]pyrazine-7-carboxylic acid [(R)-1-(4-cyano-piperidine-1-carbonyl)-2,2-dimethyl-propyl]-amide;

2-[1-(2,2,2-Trifluoro-ethyl)-1H-pyrazol-4-yl]-5H-pyrrolo[2,3-b]pyrazine-7-carboxylic acid [(R)-1-(4-cyano-piperidine-1-carbonyl)-2,2-dimethyl-propyl]-amide;

2-Cyclopropyl-5H-pyrrolo[2,3-b]pyrazine-7-carboxylic acid [(R)-2-((S)-3-cyano-pyrrolidin-1-yl)-1-cyclopropyl-2-oxo-ethyl]-amide;

2-(1-Methyl-1H-pyrazol-4-yl)-5H-pyrrolo[2,3-b]pyrazine-7-carboxylic acid [(R)-2-((S)-3-cyano-pyrrolidin-1-yl)-1-cyclopropyl-2-oxo-ethyl]-amide;

2-(1-Methyl-1H-pyrazol-4-yl)-5H-pyrrolo[2,3-b]pyrazine-7-carboxylic acid [(R)-2-((R)-3-cyano-pyrrolidin-1-yl)-1-cyclopropyl-2-oxo-ethyl]-amide;

2-Cyclopropyl-5H-pyrrolo[2,3-b]pyrazine-7-carboxylic acid [(R)-2-((R)-3-cyano-pyrrolidin-1-yl)-1-cyclopropyl-2-oxo-ethyl]-amide;

2-Cyclopropyl-5H-pyrrolo[2,3-b]pyrazine-7-carboxylic acid [(R)-1-cyclopropyl-2-(2-oxa-6-aza-spiro[3.3]hept-6-yl)-2-oxo-ethyl]-amide;

2-(1-Methyl-1H-pyrazol-4-yl)-5H-pyrrolo[2,3-b]pyrazine-7-carboxylic acid [(R)-1-cyclopropyl-2-(2-oxa-6-aza-spiro[3.3]hept-6-yl)-2-oxo-ethyl]-amide;

2-Cyclopropyl-5H-pyrrolo[2,3-b]pyrazine-7-carboxylic acid [(R)-1-cyclopropyl-2-((1S,5R,6R)-6-hydroxymethyl-3-aza-bicyclo[3.1.0]hex-3-yl)-2-oxo-ethyl]-amide;

2-(1-Methyl-1H-pyrazol-4-yl)-5H-pyrrolo[2,3-b]pyrazine-7-carboxylic acid [(R)-1-cyclopropyl-2-((1S,5R,6R)-6-hydroxymethyl-3-aza-bicyclo[3.1.0]hex-3-yl)-2-oxo-ethyl]-amide;

2-Cyclopropyl-5H-pyrrolo[2,3-b]pyrazine-7-carboxylic acid [(R)-1-cyclopropyl-2-(1,1-dioxo-1$\lambda^6$-thiomorpholin-4-yl)-2-oxo-ethyl]-amide;

2-(1-Methyl-1H-pyrazol-4-yl)-5H-pyrrolo[2,3-b]pyrazine-7-carboxylic acid [(R)-1-cyclopropyl-2-(1,1-dioxo-1$\lambda^6$-thiomorpholin-4-yl)-2-oxo-ethyl]-amide;

2-Cyclohexyloxy-5H-pyrrolo[2,3-b]pyrazine-7-carboxylic acid [(R)-1-(4-cyano-piperidine-1-carbonyl)-2,2-dimethyl-propyl]-amide;

2-(3,3,3-Trifluoro-propoxy)-5H-pyrrolo[2,3-b]pyrazine-7-carboxylic acid [(R)-1-(4-cyano-piperidine-1-carbonyl)-2,2-dimethyl-propyl]-amide;

2-Cyclopentyloxy-5H-pyrrolo[2,3-b]pyrazine-7-carboxylic acid [(R)-1-(4-cyano-piperidine-1-carbonyl)-2,2-dimethyl-propyl]-amide;

2-(2,2,2-Trifluoro-ethoxy)-5H-pyrrolo[2,3-b]pyrazine-7-carboxylic acid [(R)-1-(4-cyano-piperidine-1-carbonyl)-2,2-dimethyl-propyl]-amide;

2-Isopropoxy-5H-pyrrolo[2,3-b]pyrazine-7-carboxylic acid [(R)-1-(4-cyano-piperidine-1-carbonyl)-2,2-dimethyl-propyl]-amide;

2-(4-Chloro-1-oxo-1,3-dihydro-isoindol-2-yl)-5H-pyrrolo[2,3-b]pyrazine-7-carboxylic acid [(R)-2-(3-cyano-azetidin-1-yl)-1-cyclopropyl-2-oxo-ethyl]-amide;
2-(7-Chloro-thieno[3,2-b]pyridin-2-yl)-5H-pyrrolo[2,3-b]pyrazine-7-carboxylic acid [(R)-2-(3-cyano-azetidin-1-yl)-1-cyclopropyl-2-oxo-ethyl]-amide;
2-(7-Pyrrolidin-1-yl-thieno[3,2-b]pyridin-2-yl)-5H-pyrrolo[2,3-b]pyrazine-7-carboxylic acid [(R)-2-(3-cyano-azetidin-1-yl)-1-cyclopropyl-2-oxo-ethyl]-amide;
2-[7-(2,2,2-Trifluoro-ethoxy)-thieno[3,2-b]pyridin-2-yl]-5H-pyrrolo [2,3-b]pyrazine-7-carboxylic acid [(R)-2-(3-cyano-azetidin-1-yl)-1-cyclopropyl-2-oxo-ethyl]-amide;
2-(7-Methoxy-thieno[3,2-b]pyridin-2-yl)-5H-pyrrolo[2,3-b]pyrazine-7-carboxylic acid [(R)-2-(3-cyano-azetidin-1-yl)-1-cyclopropyl-2-oxo-ethyl]-amide;
2-(7-Chloro-thieno[3,2-b]pyridin-2-yl)-5H-pyrrolo[2,3-b]pyrazine-7-carboxylic acid [(R)-2-(3-cyano-azetidin-1-yl)-1-methyl-2-oxo-ethyl]-amide;
2-(7-Pyrrolidin-1-yl-thieno[3,2-b]pyridin-2-yl)-5H-pyrrolo[2,3-b]pyrazine-7-carboxylic acid [(R)-2-(3-cyano-azetidin-1-yl)-1-methyl-2-oxo-ethyl]-amide;
2-[7-(2,2,2-Trifluoro-ethoxy)-thieno[3,2-b]pyridin-2-yl]-5H-pyrrolo[2,3-b]pyrazine-7-carboxylic acid [(R)-2-(3-cyano-azetidin-1-yl)-1-methyl-2-oxo-ethyl]-amide;
2-(7-Methoxy-thieno[3,2-b]pyridin-2-yl)-5H-pyrrolo[2,3-b]pyrazine-7-carboxylic acid [(R)-2-(3-cyano-azetidin-1-yl)-1-methyl-2-oxo-ethyl]-amide;
2-(1,3-Dimethyl-1H-pyrazol-4-yl)-5H-pyrrolo[2,3-b]pyrazine-7-carboxylic acid [(R)-2-(3-cyano-azetidin-1-yl)-1-methyl-2-oxo-ethyl]-amide;
2-(1-Ethyl-1H-pyrazol-4-yl)-5H-pyrrolo[2,3-b]pyrazine-7-carboxylic acid [(S)-1-(4-cyano-piperidine-1-carbonyl)-3,3,3-trifluoro-propyl]-amide;
2-(1-Ethyl-1H-pyrazol-4-yl)-5H-pyrrolo[2,3-b]pyrazine-7-carboxylic acid [(R)-1-(4-cyano-piperidine-1-carbonyl)-3,3,3-trifluoro-propyl]-amide;
2-(1-Cyclopentyl-1H-[1,2,3]triazol-4-yl)-5H-pyrrolo[2,3-b]pyrazine-7-carboxylic acid [(R)-2-(4-cyano-piperidin-1-yl)-1-cyclopropyl-2-oxo-ethyl]-amide;
2-(1-Phenyl-1H-[1,2,3]triazol-4-yl)-5H-pyrrolo[2,3-b]pyrazine-7-carboxylic acid [(R)-2-(4-cyano-piperidin-1-yl)-1-cyclopropyl-2-oxo-ethyl]-amide;
2-(3-Pyrrolidin-1-yl-phenyl)-5H-pyrrolo[2,3-b]pyrazine-7-carboxylic acid [(R)-2-(3-cyano-azetidin-1-yl)-1-methyl-2-oxo-ethyl]-amide;
2-(3-Methylcarbamoyl-phenyl)-5H-pyrrolo[2,3-b]pyrazine-7-carboxylic acid [(R)-2-(3-cyano-azetidin-1-yl)-1-methyl-2-oxo-ethyl]-amide;
2-(3-Isopropylcarbamoyl-phenyl)-5H-pyrrolo[2,3-b]pyrazine-7-carboxylic acid [(R)-2-(3-cyano-azetidin-1-yl)-1-methyl-2-oxo-ethyl]-amide;
2-[3-(Cyclopropylmethyl-carbamoyl)-phenyl]-5H-pyrrolo[2,3-b]pyrazine-7-carboxylic acid [(R)-2-(3-cyano-azetidin-1-yl)-1-methyl-2-oxo-ethyl]-amide;
2-(4-Cyclopent-1-enyl-pyridin-2-yl)-5H-pyrrolo[2,3-b]pyrazine-7-carboxylic acid [(R)-2-(3-cyano-azetidin-1-yl)-1-methyl-2-oxo-ethyl]-amide;
2-Cyclopropyl-5H-pyrrolo[2,3-b]pyrazine-7-carboxylic acid [(R)-2-(4-cyano-piperidin-1-yl)-2-oxo-1-phenyl-ethyl]-amide;
2-Pyridin-2-yl-5H-pyrrolo[2,3-b]pyrazine-7-carboxylic acid [(R)-1-(4-cyano-piperidine-1-carbonyl)-2,2-dimethyl-propyl]-amide;
2-Cyclopropyl-5H-pyrrolo[2,3-b]pyrazine-7-carboxylic acid [(R)-2-(4-cyano-piperidin-1-yl)-1-cyclopropylmethyl-2-oxo-ethyl]-amide;
2-[1-(4-Fluoro-phenyl)-1H-pyrazol-4-yl]-5H-pyrrolo[2,3-b]pyrazine-7-carboxylic acid [(R)-1-(4-cyano-piperidine-1-carbonyl)-2,2-dimethyl-propyl]-amide;
2-(4-Trifluoromethyl-pyridin-2-yl)-5H-pyrrolo[2,3-b]pyrazine-7-carboxylic acid [(R)-1-(4-cyano-piperidine-1-carbonyl)-2,2-dimethyl-propyl]-amide;
2-(1-Cyclopropylmethyl-1H-imidazol-4-yl)-5H-pyrrolo[2,3-b]pyrazine-7-carboxylic acid [(R)-1-(4-cyano-piperidine-1-carbonyl)-2,2-dimethyl-propyl]-amide;
2-(1-Cyclopentyl-1H-imidazol-4-yl)-5H-pyrrolo[2,3-b]pyrazine-7-carboxylic acid [(R)-1-(4-cyano-piperidine-1-carbonyl)-2,2-dimethyl-propyl]-amide;
2-(1-Cyclopentyl-1H-imidazol-4-yl)-5H-pyrrolo[2,3-b]pyrazine-7-carboxylic acid [(R)-2-(4-cyano-piperidin-1-yl)-1-cyclopropyl-2-oxo-ethyl]-amide;
2-[1-(2,2,2-Trifluoro-ethyl)-1H-imidazol-4-yl]-5H-pyrrolo[2,3-b]pyrazine-7-carboxylic acid [(R)-1-(4-cyano-piperidine-1-carbonyl)-2,2-dimethyl-propyl]-amide;
2-[3-(3,3-Dimethyl-pyrrolidin-1-yl)-phenyl]-5H-pyrrolo[2,3-b]pyrazine-7-carboxylic acid [(R)-2-(3-cyano-azetidin-1-yl)-1-methyl-2-oxo-ethyl]-amide;
2-Cyclopropyl-5H-pyrrolo[2,3-b]pyrazine-7-carboxylic acid [(1R,2S)-1-(4-cyano-piperidine-1-carbonyl)-2-methyl-butyl]-amide;
2-(3,4,5-Trimethoxy-phenyl)-5H-pyrrolo[2,3-b]pyrazine-7-carboxylic acid [(R)-2-(3-cyano-azetidin-1-yl)-1-methyl-2-oxo-ethyl]-amide;
2-[(1S,5R)-3-(3-Aza-bicyclo[3.1.0]hex-3-yl)-phenyl]-5H-pyrrolo[2,3-b]pyrazine-7-carboxylic acid [(R)-2-(3-cyano-azetidin-1-yl)-1-methyl-2-oxo-ethyl]-amide;
2-(4-Methoxy-pyridin-2-yl)-5H-pyrrolo[2,3-b]pyrazine-7-carboxylic acid [(R)-1-(4-cyano-piperidine-1-carbonyl)-2,2-dimethyl-propyl]-amide;
2-(4-Trifluoromethyl-phenyl)-5H-pyrrolo[2,3-b]pyrazine-7-carboxylic acid [(R)-1-(4-cyano-piperidine-1-carbonyl)-2,2-dimethyl-propyl]-amide;
2-(4-Cyclopropylmethoxy-pyridin-2-yl)-5H-pyrrolo[2,3-b]pyrazine-7-carboxylic acid [(R)-2-(4-cyano-piperidin-1-yl)-1-cyclopropyl-2-oxo-ethyl]-amide;
2-(4-Cyclopentyloxy-pyridin-2-yl)-5H-pyrrolo[2,3-b]pyrazine-7-carboxylic acid [(R)-1-(4-cyano-piperidine-1-carbonyl)-2,2-dimethyl-propyl]-amide;
2-(4-Cyclopropylmethoxy-pyridin-2-yl)-5H-pyrrolo[2,3-b]pyrazine-7-carboxylic acid [(R)-2-(3-cyano-azetidin-1-yl)-1-methyl-2-oxo-ethyl]-amide;
2-[1-(2,5-Difluoro-phenyl)-1H-imidazol-4-yl]-5H-pyrrolo[2,3-b]pyrazine-7-carboxylic acid [(R)-2-(3-cyano-azetidin-1-yl)-1-cyclopropyl-2-oxo-ethyl]-amide;
2-[1-(2,3,5-Trifluoro-phenyl)-1H-imidazol-4-yl]-5H-pyrrolo[2,3-b]pyrazine-7-carboxylic acid [(R)-2-(3-cyano-azetidin-1-yl)-1-cyclopropyl-2-oxo-ethyl]-amide;
2-(1-Ethyl-1H-pyrazol-4-yl)-5H-pyrrolo[2,3-b]pyrazine-7-carboxylic acid [(R)-1-(4,4-difluoro-piperidine-1-carbonyl)-2,2-dimethyl-propyl]-amide;
2-Cyclopropyl-5H-pyrrolo[2,3-b]pyrazine-7-carboxylic acid [(R)-1-(7,8-dihydro-5H-[1,6]naphthyridine-6-carbonyl)-2,2-dimethyl-propyl]-amide;
2-Cyclopropyl-5H-pyrrolo[2,3-b]pyrazine-7-carboxylic acid [(R)-2-(3-cyano-azetidin-1-yl)-2-oxo-1-(tetrahydro-pyran-4-yl)-ethyl]-amide;
2-Cyclopropyl-5H-pyrrolo[2,3-b]pyrazine-7-carboxylic acid [(S)-2-(3-cyano-azetidin-1-yl)-2-oxo-1-(tetrahydro-pyran-4-yl)-ethyl]-amide;
2-Cyclopropyl-5H-pyrrolo[2,3-b]pyrazine-7-carboxylic acid [(R)-1-(2,3-dihydro-indole-1-carbonyl)-2,2-dimethyl-propyl]-amide;

2-(1-Ethyl-1H-pyrazol-4-yl)-5H-pyrrolo[2,3-b]pyrazine-7-carboxylic acid [(R)-1-cyclopropyl-2-(3,3-difluoro-pyrrolidin-1-yl)-2-oxo-ethyl]-amide;

2-(1-Ethyl-1H-pyrazol-4-yl)-5H-pyrrolo[2,3-b]pyrazine-7-carboxylic acid [(R)-1-(4-hydroxy-4-methyl-piperidine-1-carbonyl)-2,2-dimethyl-propyl]-amide;

2-Cyclopropyl-5H-pyrrolo[2,3-b]pyrazine-7-carboxylic acid [(R)-2-(3-cyano-3-methyl-azetidin-1-yl)-1-cyclopropyl-2-oxo-ethyl]-amide;

2-(1-Methyl-1H-pyrazol-4-yl)-5H-pyrrolo[2,3-b]pyrazine-7-carboxylic acid [(R)-2-(3-cyano-3-methyl-azetidin-1-yl)-1-cyclopropyl-2-oxo-ethyl]-amide;

2-(1-Methyl-1H-pyrazol-4-yl)-5H-pyrrolo[2,3-b]pyrazine-7-carboxylic acid [(R)-1-(3-cyano-3-methyl-azetidine-1-carbonyl)-2,2-dimethyl-propyl]-amide;

2-(1-Ethyl-1H-pyrazol-4-yl)-5H-pyrrolo[2,3-b]pyrazine-7-carboxylic acid [(R)-1-cyclopropyl-2-(4,4-difluoro-piperidin-1-yl)-2-oxo-ethyl]-amide;

2-(4-tert-Butyl-pyridin-2-yl)-5H-pyrrolo[2,3-b]pyrazine-7-carboxylic acid [(R)-2-(4-cyano-piperidin-1-yl)-1-cyclopropyl-2-oxo-ethyl]-amide;

2-(1-Ethyl-1H-pyrazol-4-yl)-5H-pyrrolo[2,3-b]pyrazine-7-carboxylic acid [(R)-1-cyclopropyl-2-(4-hydroxy-4-trifluoromethyl-piperidin-1-yl)-2-oxo-ethyl]-amide;

2-(4-Phenyl-pyridin-2-yl)-5H-pyrrolo[2,3-b]pyrazine-7-carboxylic acid [(R)-2-(4-cyano-piperidin-1-yl)-1-cyclopropyl-2-oxo-ethyl]-amide;

2-(1-Ethyl-1H-pyrazol-4-yl)-5H-pyrrolo[2,3-b]pyrazine-7-carboxylic acid [(R)-1-cyclopropyl-2-(3-hydroxy-3-methyl-azetidin-1-yl)-2-oxo-ethyl]-amide;

2-Cyclopropyl-5H-pyrrolo[2,3-b]pyrazine-7-carboxylic acid [(1R,2R)-1-(4-cyano-piperidine-1-carbonyl)-2-methyl-butyl]-amide;

2-(1-Methyl-1H-pyrazol-4-yl)-5H-pyrrolo[2,3-b]pyrazine-7-carboxylic acid [(R)-1-cyclopropyl-2-(3,3-difluoro-azetidin-1-yl)-2-oxo-ethyl]-amide;

2-(1-Methyl-1H-pyrazol-4-yl)-5H-pyrrolo[2,3-b]pyrazine-7-carboxylic acid [(R)-2-(3-cyano-3-ethyl-azetidin-1-yl)-1-cyclopropyl-2-oxo-ethyl]-amide;

2-(4-Pyrazol-1-yl-pyridin-2-yl)-5H-pyrrolo[2,3-b]pyrazine-7-carboxylic acid [(R)-2-(3-cyano-azetidin-1-yl)-1-methyl-2-oxo-ethyl]-amide;

2-(4-Pyrrol-1-yl-pyridin-2-yl)-5H-pyrrolo[2,3-b]pyrazine-7-carboxylic acid [(R)-2-(3-cyano-azetidin-1-yl)-1-methyl-2-oxo-ethyl]-amide;

2-(4-Thiophen-2-yl-pyridin-2-yl)-5H-pyrrolo[2,3-b]pyrazine-7-carboxylic acid [(R)-2-(4-cyano-piperidin-1-yl)-1-cyclopropyl-2-oxo-ethyl]-amide;

2-(4-Methylcarbamoyl-pyridin-2-yl)-5H-pyrrolo[2,3-b]pyrazine-7-carboxylic acid [(R)-2-(3-cyano-azetidin-1-yl)-1-methyl-2-oxo-ethyl]-amide;

2-(2-Chloro-thiazol-5-yl)-5H-pyrrolo[2,3-b]pyrazine-7-carboxylic acid [(R)-1-(4-cyano-piperidine-1-carbonyl)-2,2-dimethyl-propyl]-amide;

2-[1-(3,5-Difluoro-phenyl)-2-methyl-1H-imidazol-4-yl]-5H-pyrrolo[2,3-b]pyrazine-7-carboxylic acid [(R)-1-(3-cyano-azetidine-1-carbonyl)-2,2-dimethyl-propyl]-amide;

2-[1-(3-Fluoro-phenyl)-2-methyl-1H-imidazol-4-yl]-5H-pyrrolo[2,3-b]pyrazine-7-carboxylic acid [(R)-1-(3-cyano-azetidine-1-carbonyl)-2,2-dimethyl-propyl]-amide;

2-(2-Methyl-1-phenyl-1H-imidazol-4-yl)-5H-pyrrolo[2,3-b]pyrazine-7-carboxylic acid [(R)-2-(3-cyano-azetidin-1-yl)-1-cyclopropyl-2-oxo-ethyl]-amide;

2-(4-Trifluoromethyl-phenyl)-5H-pyrrolo[2,3-b]pyrazine-7-carboxylic acid [(R)-2-(3-cyano-azetidin-1-yl)-1-cyclopropyl-2-oxo-ethyl]-amide;

2-[4-(4-Acetyl-piperazin-1-yl)-phenyl]-5H-pyrrolo[2,3-b]pyrazine-7-carboxylic acid [(R)-2-(3-cyano-azetidin-1-yl)-1-cyclopropyl-2-oxo-ethyl]-amide;

2-[4-(4-Methyl-piperazin-1-yl)-phenyl]-5H-pyrrolo[2,3-b]pyrazine-7-carboxylic acid [(R)-2-(3-cyano-azetidin-1-yl)-1-cyclopropyl-2-oxo-ethyl]-amide;

2-(4-Morpholin-4-yl-phenyl)-5H-pyrrolo[2,3-b]pyrazine-7-carboxylic acid [(R)-2-(3-cyano-azetidin-1-yl)-1-cyclopropyl-2-oxo-ethyl]-amide;

2-(4-Dimethylamino-phenyl)-5H-pyrrolo[2,3-b]pyrazine-7-carboxylic acid [(R)-2-(3-cyano-azetidin-1-yl)-1-cyclopropyl-2-oxo-ethyl]-amide;

2-[2-Methyl-1-(2,2,2-trifluoro-ethyl)-1H-imidazol-4-yl]-5H-pyrrolo[2,3-b]pyrazine-7-carboxylic acid [(R)-2-(3-cyano-azetidin-1-yl)-1-cyclopropyl-2-oxo-ethyl]-amide; and 2-Phenyl-5H-pyrrolo[2,3-b]pyrazine-7-carboxylic acid [(R)-2-(3-cyano-azetidin-1-yl)-1-cyclopropyl-2-oxo-ethyl]-amide.

\* \* \* \* \*